(12) United States Patent
Takahashi et al.

(10) Patent No.: US 11,950,498 B2
(45) Date of Patent: Apr. 2, 2024

(54) COMPOUND, MATERIAL FOR ORGANIC ELECTROLUMINESCENCE ELEMENT USING SAME, ORGANIC ELECTROLUMINESCENCE ELEMENT, AND ELECTRONIC DEVICE

(71) Applicant: IDEMITSU KOSAN CO., LTD., Tokyo (JP)

(72) Inventors: Ryota Takahashi, Sodegaura (JP); Keita Seda, Sodegaura (JP); Yuki Nakano, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 646 days.

(21) Appl. No.: 16/622,198

(22) PCT Filed: Jun. 22, 2018

(86) PCT No.: PCT/JP2018/023868
§ 371 (c)(1),
(2) Date: Dec. 12, 2019

(87) PCT Pub. No.: WO2018/235953
PCT Pub. Date: Dec. 27, 2018

(65) Prior Publication Data
US 2021/0151687 A1 May 20, 2021

(30) Foreign Application Priority Data
Jun. 23, 2017 (JP) ................. 2017-123734

(51) Int. Cl.
| H01L 51/00 | (2006.01) |
| C07D 307/77 | (2006.01) |
| C07D 307/91 | (2006.01) |
| C09K 11/06 | (2006.01) |
| H10K 85/60 | (2023.01) |
| H10K 50/11 | (2023.01) |

(52) U.S. Cl.
CPC ......... *H10K 85/636* (2023.02); *C07D 307/77* (2013.01); *C07D 307/91* (2013.01); *C09K 11/06* (2013.01); *C09K 2211/1018* (2013.01); *H10K 50/11* (2023.02); *H10K 85/6574* (2023.02)

(58) Field of Classification Search
None
See application file for complete search history.

(56) References Cited

U.S. PATENT DOCUMENTS

| 2016/0351816 A1 | 12/2016 | Kim et al. |
| 2016/0351817 A1 | 12/2016 | Kim et al. |
| 2018/0083197 A1 | 3/2018 | Park et al. |

FOREIGN PATENT DOCUMENTS

| CN | 106206964 A | 12/2016 |
| KR | 2016-0141361 A | 12/2016 |
| KR | 20170056425 A | 5/2017 |
| WO | WO-2013/125599 A1 | 8/2013 |
| WO | WO-2014/104144 A1 | 7/2014 |
| WO | WO-2016/190600 A1 | 12/2016 |

OTHER PUBLICATIONS

International Searching Authority, "International Search Report," issued in connection with International Patent Application No. PCT/JP2018/023868, dated Sep. 18, 2018.
International Searching Authority, "Written Opinion," issued in connection with International Patent Application No. PCT/JP2018/023868, dated Sep. 18, 2018.
International Preliminary Report on Patentability issued in connection with International Patent Application No. PCT/JP2018/023868, dated Dec. 24, 2019.
Korean Intellectual Property Office, "Request for the Submission of an Opinion," issued in connection with Korean Patent Application No. 10-2019-7035914, dated Mar. 2, 2023.
Chinese Office Action issued in connection with CN Appl. Ser. No. 201880041941.6 dated Oct. 17, 2022.

*Primary Examiner* — Jay Yang
(74) *Attorney, Agent, or Firm* — Foley & Lardner LLP

(57) ABSTRACT

This compound is represented by formula (1)

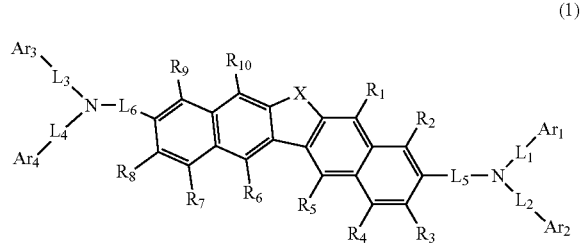

20 Claims, 1 Drawing Sheet

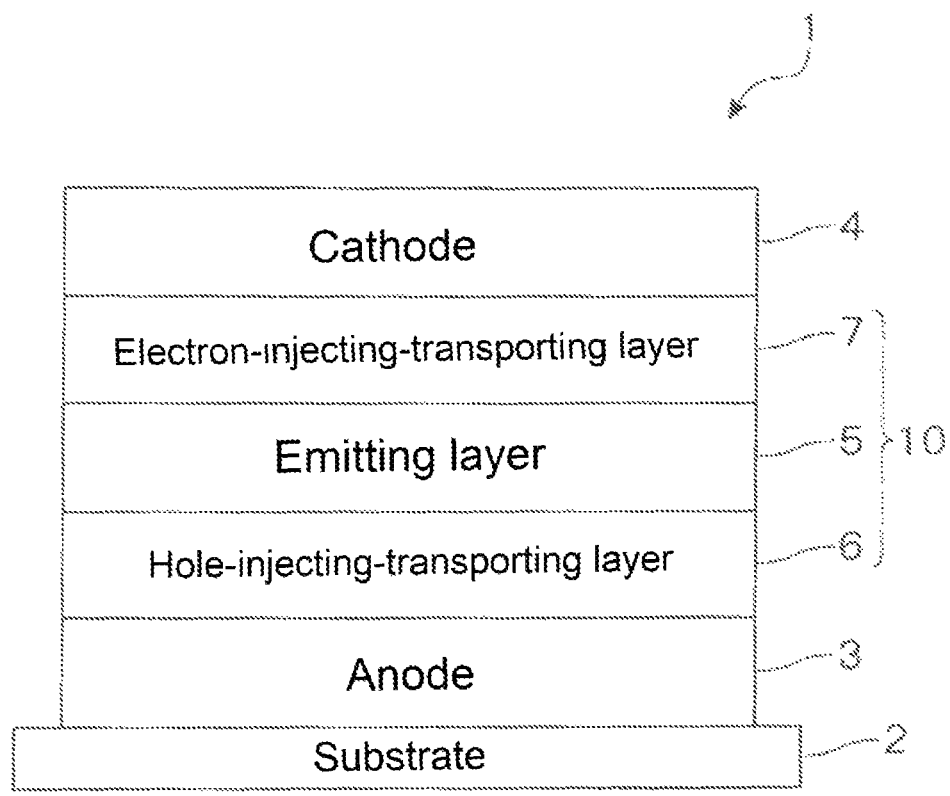

COMPOUND, MATERIAL FOR ORGANIC ELECTROLUMINESCENCE ELEMENT USING SAME, ORGANIC ELECTROLUMINESCENCE ELEMENT, AND ELECTRONIC DEVICE

RELATED APPLICATIONS

The present application claims priority under 37 U.S.C. § 371 to International Patent Application No. PCT/JP2018/023868, filed Jun. 22, 2018, which claims priority to and the benefit of Japanese Patent Application No. 2017-123734, filed on Jun. 23, 2017. The contents of these applications are hereby incorporated by reference in their entireties.

TECHNICAL FIELD

The invention relates to a novel compound, materials for organic electroluminescence device, an organic electroluminescence device and an electronic appliance, in which the novel compound is used.

BACKGROUND ART

When a voltage is applied to an organic electroluminescence device (hereinafter referred to as "organic EL device"), holes from an anode and electrons from a cathode are injected into an emitting layer, respectively. In the emitting layer, the injected holes and electrons are recombined to form excitons.

The organic EL device comprises emitting layer between anode and cathode. It may also have a stacked structure including organic layers such as: a hole-injecting layer, a hole-transporting layer, an electron-injecting layer, and an electron-transporting layer.

In Patent Document 1, a compound used in an organic EL device is disclosed.

In Patent Documents 2 and 3, a compound used in an organic light emitting device is disclosed.

In Patent Document 4, a compound used in an organic electric device is disclosed.

In Patent Document 5, a chalcogen-containing organic compound is disclosed.

RELATED ART DOCUMENTS

Patent Documents

[Patent Document 1] WO 2014/104144 A1
[Patent Document 2] US 2016/0351816 A1
[Patent Document 3] US 2016/0351817A1
[Patent Document 4] WO 2016/190600 A1
[Patent Document 5] WO 2013/125599 A1

SUMMARY OF THE INVENTION

It is an object of the invention to provide a compound having a high photoluminescence quantum yield of the fluorescence and a narrow half-width, and a material for an organic electroluminescence device, an organic electroluminescence device and an electronic appliance, in which the compound is used.

According to an aspect of the invention, the following compound is provided.

A compound represented by the following formula (1):

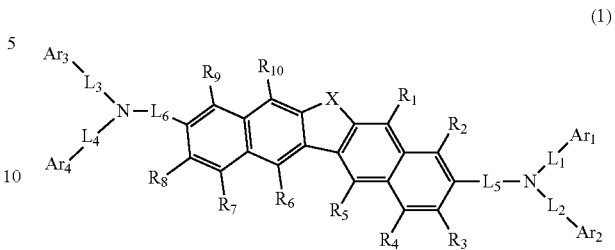

(1)

wherein in the formula (1), $R_1$ to $R_{10}$ is independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 carbon atoms that form a ring (hereinafter referred to as "ring carbon atoms"), a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{21}$)($R_{22}$)($R_{23}$), —C(=O)$R_{24}$, —COO$R_{25}$, —N($R_{26}$)($R_{27}$), a halogen atom, a cyano group, a nitro group, a substituted or unsubstituted aryl group including 6 to 50 ring carbon atoms, or a substituted or unsubstituted heterocyclic group including 5 to 50 atoms that form a ring (hereinafter referred to as "ring atoms");

$R_{21}$ to $R_{27}$ is independently a hydrogen atom, a substituted or unsubstituted alkyl group including 1 to 50 carbon atoms, a substituted or unsubstituted aryl group including 6 to 50 ring carbon atoms, or a substituted or unsubstituted heterocyclic group including 5 to 50 ring atoms;

X is an oxygen atom or a sulfur atom;

$Ar_1$ to $Ar_4$ is independently a substituted or unsubstituted aryl group including 6 to 50 ring carbon atoms, or a substituted or unsubstituted heterocyclic group including 5 to 50 ring atom; $Ar_1$ and $Ar_2$ may be bonded to each other via a single bond; $Ar_3$ and $Ar_4$ may be bonded to each other via a single bond;

$L_1$ to $L_6$ is independently a single bond, a substituted or unsubstituted alkylene group including 1 to 30 carbon atoms, a substituted or unsubstituted arylene group including 6 to 30 ring carbon atoms, or a substituted or unsubstituted heteroarylene group including 5 to 30 ring atoms; and when two or more $R_{21}$s to $R_{27}$s are present, each of two or more $R_{21}$s to $R_{27}$s can be the same as or different from each other.

According to another aspect of the invention, a material for an organic electroluminescence device comprising the above compound is provided.

According to another aspect of the invention, the following organic EL device is provided.

An organic electroluminescence device comprising:
a cathode;
an anode; and
an organic layer disposed between the cathode and the anode,
wherein the organic layer comprises the above-mentioned compound.

According to another aspect of the invention, the following organic EL device is provided.

An organic electroluminescence device comprising:
a cathode;
an anode; and
an emitting layer disposed between the cathode and the anode,
wherein the emitting layer comprises the compound.

According to another aspect of the invention, an electronic appliance comprising the organic EL device is provided.

According to the invention, a compound having a high photoluminescence quantum yield of the fluorescence and a narrow half-width, and a material for an organic electroluminescence device, an organic electroluminescence device and an electronic apparatus using the same can be provided.

BRIEF DESCRIPTION OF THE DRAWINGS

The FIGURE is a diagram showing a schematic configuration of one embodiment of an organic EL device of the invention.

DETAILED DESCRIPTION OF THE INVENTION

In this specification, a hydrogen atom means an atom including isotopes different in the number of neutrons, namely, a protium, a deuterium and a tritium.

In the specification, the term "the number of ring carbon atoms" represents the number of carbon atoms among the atoms which forms a subject ring itself of a compound having a structure in which atoms are bonded in a ring form (for example, a monocyclic compound, a fused ring compound, a cross-linked compound, a carbocyclic compound or a heterocyclic compound). When the subject ring is substituted by a substituent, the carbon contained in the substituent is not included in the number of ring carbon atoms. The same shall apply to "the number of ring carbon atoms" described below, unless otherwise noted. For example, a benzene ring has 6 ring carbon atoms; a naphthalene ring has 10 ring carbon atoms; a pyridinyl group has 5 ring carbon atoms; and a furanyl group has 4 ring carbon atoms. Further, when the benzene ring or the naphthalene ring is substituted by, for example, an alkyl group as a substituent, the number of carbon atoms of the alkyl group is not included in the number of ring carbon atoms. When a fluorene ring is bonded to, for example, a fluorene ring as a substituent (including a spirofluorene ring), the number of carbon atoms of the fluorene ring as a substituent is not included in the number of ring carbon atoms.

In the specification, a term "ring atoms" represents the number of atoms forming a subject ring itself of a compound having a structure in which atoms are bonded in a ring form (for example, a monocycle, a fused ring and a ring assembly) (for example, a monocyclic compound, a fused ring compound, a cross-linked compound, a carbocyclic compound or a heterocyclic compound). The atoms that do not form the ring (e.g., a hydrogen atom that terminates the atomic bonding of the atoms that form the ring) or the atoms contained in a substituent where the ring is substituted by the substituent is not included in the ring atom. The same shall apply to "the number of ring atoms" described below, unless otherwise noted. For example: the ring atom number of the pyridine ring is 6; the quinazoline ring has 10 ring atom atoms; and the ring atom number of the furan ring is 5. Each of hydrogen atoms bonded to carbon atoms of the pyridine ring or the quinazoline ring or atoms forming the substituent are not included in the number of ring atoms. When a fluorene ring is bonded to, for example, a fluorene ring as a substituent (including a spirofluorene ring), the number of atoms of the fluorene ring as the substituent is not included in the number of ring atoms.

In the specification, "XX to YY carbon atoms" in the expression "a substituted or unsubstituted ZZ group including XX to YY carbon atoms" represents the number of carbon atoms when the ZZ group is unsubstituted, and does not include the number of carbon atoms of the substituent when the ZZ group is substituted. Here, "YY" is larger than "XX", and "XX" and "YY" independently mean an integer of 1 or more.

In the specification, "XX to YY atoms" in the expression "a substituted or unsubstituted ZZ group including XX to YY atoms" represents the number of atoms when the ZZ group is unsubstituted, and does not include the number of atoms of the substituent when the ZZ group is substituted. Here, "YY" is larger than "XX", and "XX" and "YY" independently mean an integer of 1 or more.

The term "unsubstituted" in the context of "substituted or unsubstituted" means that there is no substitution by the substituent and a hydrogen atoms are bonded.

In the specification, the following groups are also included in a heterocyclic group. The heteroarylene group also includes a group in which the following groups are made into a divalent one.

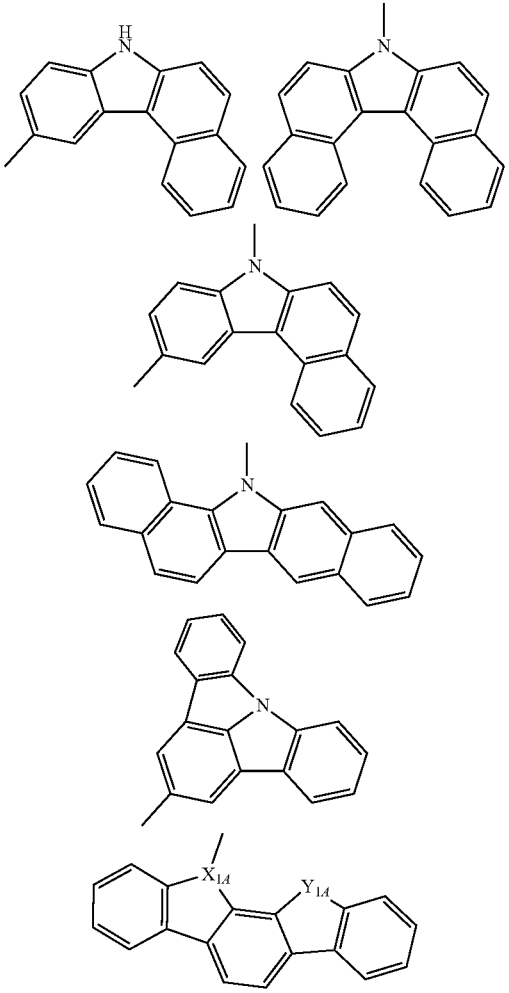

-continued

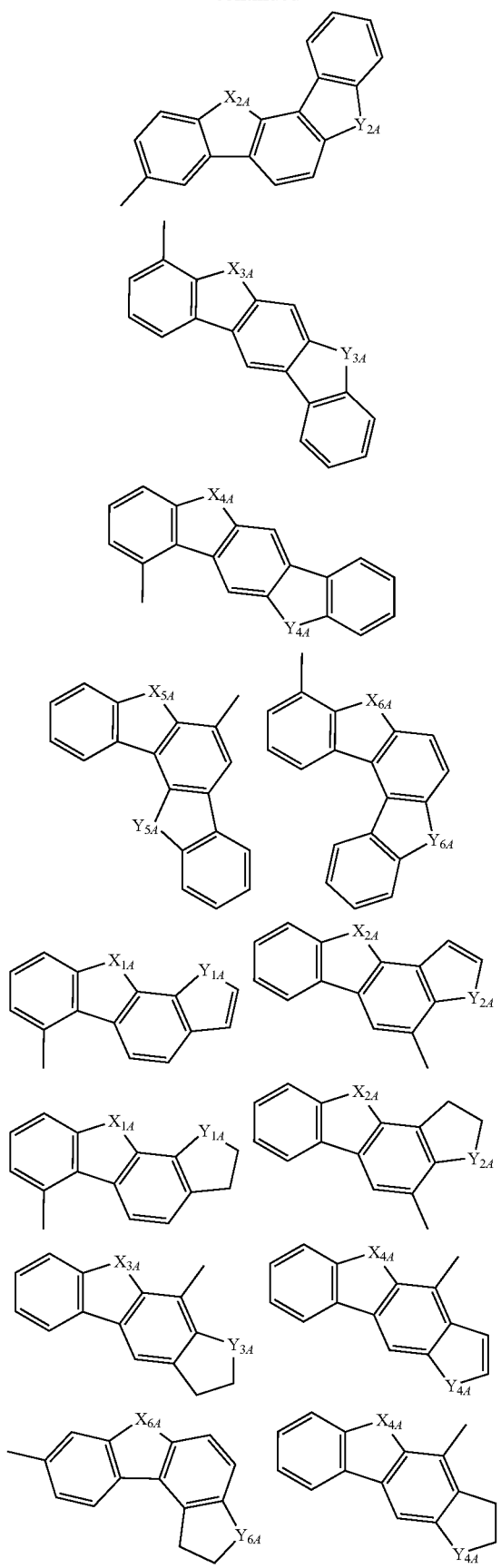

-continued

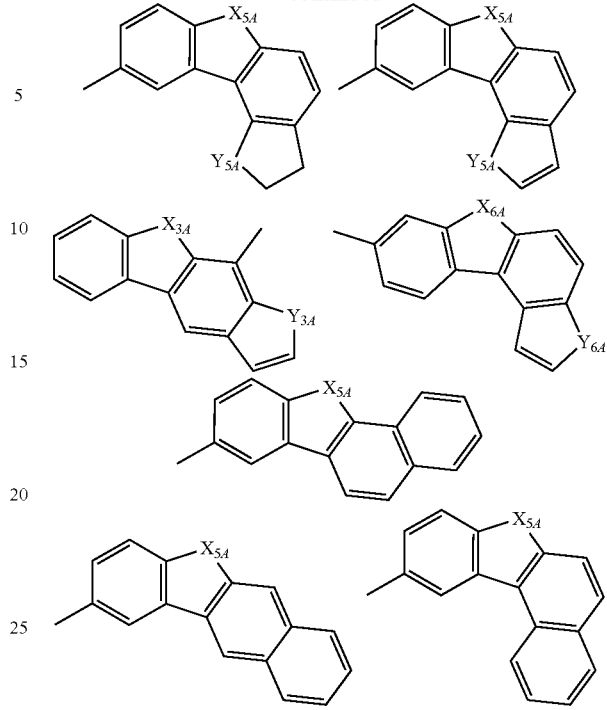

In the formulas, $X_{1A}$ to $X_{6A}$ and $Y_{1A}$ to $Y_{6A}$ are independently an oxygen atom, an sulfur atom, a —NZ-group or a —NH-group; Z is a substituted or unsubstituted aryl group including 6 to 50 ring carbon atoms, a substituted or unsubstituted heterocyclic group including 5 to 50 ring atom, or a substituted or unsubstituted alkyl group including 1 to 50 carbon atoms; and when two or more Zs are present, two or more Zs may be the same as or different from each other.

Examples of the aryl group including 6 to 50 ring carbon atoms for Z include the same as the aryl group including 6 to 50 ring carbon atoms, such as $R_1$ to $R_{10}$, described below.

Examples of the heterocyclic group including 5 to 50 ring atoms for Z include the same as the heterocyclic group including 5 to 50 ring atoms, such as $R_1$ to $R_{10}$, described below.

Examples of the alkyl group including 1 to 50 carbon atoms for Z include the same as the alkyl group including 1 to 50 carbon atoms, such as $R_1$ to $R_{10}$, described below.

An aspect of the compound of the invention is represented by the following formula (1):

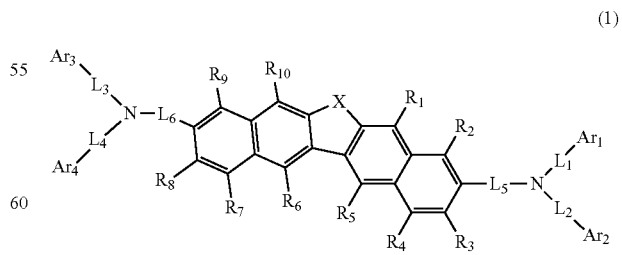

(1)

wherein in the formula (1), $R_1$ to $R_{10}$ are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, $-Si(R_{21})(R_{22})(R_{23})$, $-C(=O)R_{24}$, $-COOR_{25}$, $-N(R_{26})(R_{27})$, a halogen atom, a cyano group, a nitro group, a substituted or unsubstituted aryl group including 6 to 50 ring carbon atoms, or a substituted or substituted heterocyclic group including 5 to 50 ring atoms;

$R_{21}$ to $R_{27}$ are independently a hydrogen atom, a substituted or unsubstituted alkyl group including 1 to 50 carbon atoms, a substituted or unsubstituted aryl group including 6 to 50 ring carbon atoms, or a substituted or unsubstituted heterocyclic group including 5 to 50 ring atoms;

X is an oxygen atom or a sulfur atom;

$Ar_1$ to $Ar_4$ are independently a substituted or unsubstituted aryl group including 6 to 50 ring carbon atoms, or substituted or unsubstituted heterocyclic group including 5 to 50 ring atoms; $Ar_1$ and $Ar_2$ may be bonded to each other via a single bond; $Ar_3$ and $Ar_4$ may be bonded to each other via single bond;

$L_1$ to $L_6$ are independently a single bond, a substituted or unsubstituted alkylene group including 1 to 30 carbon atoms, a substituted or unsubstituted arylene group including 6 to 30 ring carbon atoms, or a substituted or unsubstituted heteroarylene group including 5 to 30 ring atoms; and when two or more $R_{21}$s to $R_{27}$s are present, each of two or more $R_{21}$s to $R_{27}$s can be the same as or different from each other.

By this, a photoluminescence quantum yield of the fluorescence can be improved and a narrow half-width can be obtained.

As an arbitrary effect, a blue color purity of a fluorescence spectrum can be improved.

The compound represented by the formula (1) is preferably represented by the following formula (2):

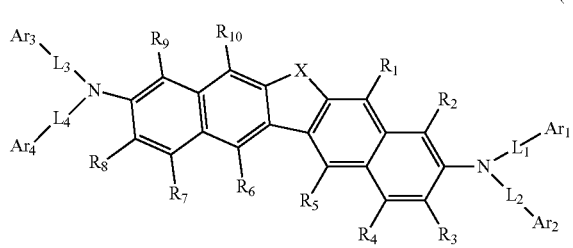

(2)

wherein in the formula (2), $R_1$ to $R_{10}$, X, $Ar_1$ to $Ar_4$ and $L_1$ to $L_4$ are as defined in the formula (1).

The compound represented by the formula (1) is preferably represented by the following formula (3):

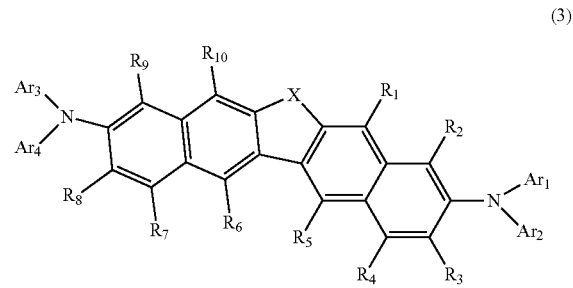

(3)

wherein in the formula (3), $R_1$ to $R_{10}$, X and $Ar_1$ to $Ar_4$ are as defined in the formula (1).

$R_1$ to $R_{10}$ are preferably independently selected from the group consisting of a hydrogen atom, a substituted or unsubstituted alkyl group including 1 to 50 carbon atoms, a substituted or unsubstituted aryl group including 6 to 50 ring carbon atoms, and a substituted or unsubstituted heterocyclic group including 5 to 50 ring atoms.

$R_1$ to $R_{10}$ are preferably independently selected from the group consisting of a hydrogen atom, a substituted or unsubstituted aryl group including 6 to 50 ring carbon atoms, and a substituted or unsubstituted heterocyclic group including 5 to 50 ring atoms.

$R_1$ to $R_{10}$ are preferably independently selected from the group consisting of a hydrogen atom, a substituted or unsubstituted aryl group including 6 to 18 ring carbon atoms, and a substituted or unsubstituted heterocyclic group including 5 to 18 ring atoms.

The compound represented by the formula (1) is preferably represented by the following formula (4):

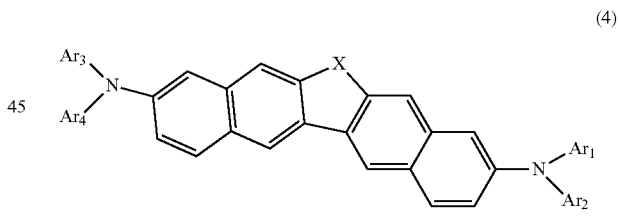

(4)

wherein in the formula (4), X and $Ar_1$ to $Ar_4$ are as defined in the formula (1).

X is preferably an oxygen atom.

$Ar_1$ to $Ar_4$ are preferably independently a substituted or unsubstituted aryl group including 6 to 18 ring carbon atoms, or a substituted or unsubstituted heterocyclic group including 5 to 18 ring atoms.

$Ar_1$ and $Ar_2$ are preferably not bonded to each other via a single bond. $Ar_3$ and $Ar_4$ are preferably not bonded to each other via a single bond.

$Ar_1$ to $Ar_4$ are preferably independently selected from the group consisting of a substituted or unsubstituted phenyl group, a substituted or unsubstituted biphenylyl group, a substituted or unsubstituted naphthyl group, and a group represented by the following formula (5):

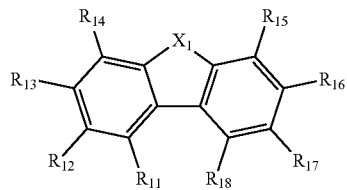

(5)

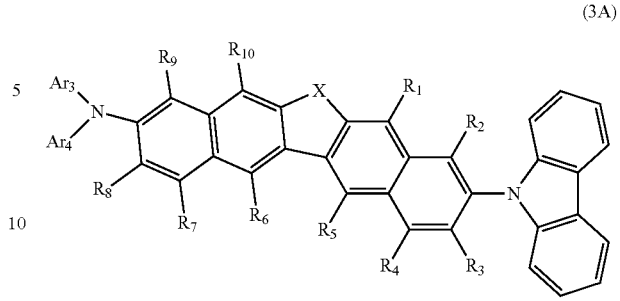

(3A)

wherein in the formula (5), $R_1$ to $R_{18}$ are independently a hydrogen atom, an alkyl group including 1 to 50 carbon atoms, an alkenyl group including 2 to 50 carbon atoms, an alkynyl group including 2 to 50 carbon atoms, a cycloalkyl group including 3 to 50 ring carbon atoms, an alkoxy group including 1 to 50 carbon atoms, an alkylthio group including 1 to 50 carbon atoms, an aryloxy group including 6 to 50 ring carbon atoms, an arylthio group including 6 to 50 ring carbon atoms, an aralkyl group including 7 to 50 carbon atoms, —Si($R_{51}$)($R_{52}$)($R_{53}$), —C(=O)$R_{54}$, —COO$R_{55}$, —N($R_{56}$)($R_{57}$), —S(=O)$_2R_{58}$, —P(=O)($R_{59}$)($R_{60}$), —Ge($R_{61}$)($R_{62}$)($R_{63}$), a halogen atom, a cyano group, a nitro group, an aryl group including 6 to 50 ring carbon atoms, a heterocyclic group including 5 to 50 ring atoms, or an atomic bonding; one of $R_{11}$ to $R_{18}$ is an atomic bonding;

wherein $R_{51}$ to $R_{63}$ are independently a hydrogen atom, an alkyl group including 1 to 50 carbon atoms, an aryl group including 6 to 50 ring carbon atoms, or a heterocyclic group including 5 to 50 ring atoms;

$X_1$ is an oxygen atom or a sulfur atom (preferably an oxygen atom); and when two or more $R_{51}$s to $R_{63}$s are present, each of two or more $R_{51}$s to $R_{53}$s may be the same as or different from each other.

The atomic bonding in $R_{11}$ to $R_{18}$ is bonded to the nitrogen atom to which $L_1$ to $L_4$ or $L_5$ is bonded or the nitrogen atom to which $L_6$ is bonded. For example, in the case where $Ar_1$ is a group represented by the formula (5) in the formula (1), when $L_1$ is not a single bond, the atomic bonding in $R_{11}$ to $R_{18}$ is bonded to $L_1$. For example, in the case where $Ar_1$ is a group represented by the formula (5) in the formula (1), when $L_1$ is a single bond, the atomic bonding in $R_{11}$ to $R_{18}$ is bonded to the nitrogen atom to which the $L_5$ is bonded.

$Ar_1$ to $Ar_4$ is preferably independently selected from the group consisting of a substituted or unsubstituted phenyl group, a substituted or unsubstituted biphenylyl group, and a substituted or unsubstituted naphthyl group.

$Ar_1$ to $Ar_4$ is preferably independently a substituted or unsubstituted phenyl group.

$Ar_1$ and $Ar_2$ may be bonded to each other via a single bond. $Ar_3$ and $Ar_4$ may be bonded to each other via a single bond.

For example, in the formula (3), when $Ar_1$ and $Ar_2$ are phenyl groups and $Ar_1$ and $Ar_2$ are bonded to each other via a single bond, a compound represented by the following formula (3A) is obtained, for example.

The substituent when referring to "substituted or unsubstituted" will be described later.

An aspect of the compound of the invention is preferably a material for an organic electroluminescence device.

Examples of the alkyl group of $R_1$ to $R_{10}$, $R_{11}$ to $R_{18}$, $R_{21}$ to $R_{27}$, after-mentioned $R_{31}$ to $R_{43}$, $R_{51}$ to $R_{63}$, after-mentioned $R_{101}$ to $R_{110}$, and after-mentioned $R_{121}$ to $R_{127}$ including 1 to 50 (preferably 1 to 18, more preferably 1 to 5) include, for example, a methyl group, an ethyl group, a propyl group, an isopropyl group, an n-butyl group, a s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, and the like.

Examples of the alkenyl group including 2 to 50 (preferably 2 to 18) carbon atoms of $R_1$ to $R_{10}$, $R_{11}$ to $R_{18}$, and after-mentioned $R_{101}$ to $R_{110}$ include a vinyl group, an allyl group, a 1-butenyl group, a 2-butenyl group, a 3-butenyl group, a 1,3-butanedienyl group, a 1-methylvinyl group, a 1-methylallyl group, a 1,1-dimethylallyl group, a 2-methylallyl group, a 1,2-dimethylallyl group, and the like.

Examples of the alkynyl group including 2 to 50 (preferably 2 to 18) carbon atoms of $R_1$ to $R_{10}$, $R_{11}$ to $R_{18}$, and after-mentioned $R_{101}$ to $R_{110}$ include an ethynyl group and the like.

Examples of the cycloalkyl group including 3 to 50 (preferably 3 to 18, more preferably 3 to 6) ring carbon atoms of $R_1$ to $R_{10}$, $R_{11}$ to $R_{18}$, and after-mentioned $R_{101}$ to $R_{110}$ include a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, and the like.

Examples of the alkoxy group including 1 to 50 (preferably 1 to 18) carbon atoms of $R_1$ to $R_{10}$, $R_{11}$ to $R_{18}$, and after-mentioned $R_{101}$ to $R_{110}$ include a group in which an oxygen atom is bonded to the above-mentioned alkyl group including 1 to 50 carbon atoms.

Examples of the alkylthio group including 1 to 50 (preferably 1 to 18) carbon atoms of $R_1$ to $R_{10}$, $R_{11}$ to $R_{18}$, and after-mentioned $R_{101}$ to $R_{110}$ include a group in which a sulfur atom is bonded to the above-mentioned alkyl group including 1 to 50 carbon atoms.

Examples of the aryl group including 6 to 50 (preferably 6 to 18) ring carbon atoms of $R_1$ to $R_{10}$, $R_{11}$ to $R_{18}$, $R_{21}$ to $R_{27}$, $R_{31}$ to $R_{43}$, $R_{51}$ to $R_{63}$, after-mentioned $R_{101}$ to $R_{110}$, after-mentioned $R_{121}$ to $R_{127}$, $Ar_1$ to $Ar_4$, and after-mentioned $Ar_{101}$ include, for example, a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a para-isopropylphenyl group, a meta-isopropylphenyl group, an ortho-isopropylphenyl group, a p-t-butylphenyl group, a meta-t-butylphenyl group, an ortho-t-butylphenyl group, a 3,4,5-trimethylphenyl group, a 4-phenoxyphenyl group, a 4-methoxyphenyl group, a 3,4-dimethoxyphenyl group, a 3,4,5-trimethoxyphenyl group, a 4-(phenylsulfanyl)phenyl group, a 4-(methylsulfanyl)phenyl group, an N',N'-dimethyl-N-phenyl group, an N',N'-dimethyl-N-phenyl group, a 2,6-dimethylphenyl group, a (2-phenylpropyl)phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group, a 9,9-dimethylfluorenyl group, a 9,9-diphenylfluorenyl group, a 9,9'-spirobifluorenyl group, a 9,9-di(4-methylphenyl)fluorenyl group, a 9,9-di(4-isopropylphenyl)fluorenyl group, 9,9-di(4-t-butylphenyl) fluorenyl group, a chrysenyl group, a fluoranthenyl group, and the like.

Among these, a phenyl group, a naphthyl group, a biphenylyl group, a terphenyl group, a pyrenyl group, a phenanthryl group, and a fluorenyl group are preferable, and a phenyl group, a naphthyl group, a biphenylyl group, a terphenyl group, a pyrenyl group, and a fluorenyl group are more preferable.

Examples of the heterocyclic group including 5 to 50 (preferably 5 to 18) ring atoms of $R_1$ to $R_{10}$, $R_{11}$ to $R_{18}$, $R_{21}$ to $R_{27}$, after-mentioned $R_{31}$ to $R_{43}$, $R_{51}$ to $R_{63}$, after-mentioned $R_{101}$ to $R_{110}$, after-mentioned $R_{121}$ to $R_{127}$, $Ar_1$ to $Ar_4$, and after-mentioned $Ar_{101}$ include a pyrrolyl group, a pyrazinyl group, a pyridinyl group, an indolyl group, an isoindolyl group, a furyl group, a benzofuranyl group, a isobenzofuranyl group, a dibenzofuranyl group, a dibenzothiophenyl group, a quinolyl group, an isoquinolyl group, a quinoxalinyl group, a carbazolyl group, a phenanthridinyl group, an acridinyl group, a phenanthrolinyl group, a thienyl group; and a monovalent group formed from a ring selected from the group consisting of a pyridine ring, a pyrazine ring, a pyrimidine ring, a pyridadine ring, a triazine ring, an indole ring, a quinoline ring, an acridine ring, a pyrrolidine ring, a dioxane ring, a piperidine ring, a morpholine ring, a piperazine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, a benzo[a]dibenzofuran ring, a benzo[b]dibenzofuran ring, a benzo[c]dibenzofuran ring, a 1,3-benzodioxole ring, a 2,3-dihydro-1,4-benzodioxin ring, a phenanthro[4,5-bcd]furan ring, and a benzophenoxazine ring; and the like.

Examples of the aryloxy group including 6 to 50 (preferably 6 to 18) ring carbon atoms of $R_1$ to $R_{10}$, $R_{11}$ to $R_{18}$, and after-mentioned $R_{101}$ to $R_{110}$ include, for example, a group in which an oxygen atom is bonded to the above-mentioned aryl group including 6 to 50 ring carbon atoms.

Examples of the arylthio group including 6 to 50 (preferably 6 to 18) ring carbon atoms of $R_1$ to $R_{10}$, $R_{11}$ to $R_{18}$, and after-mentioned $R_{101}$ to $R_{110}$ include, for example, a group in which a sulfur atom is bonded to the above-mentioned aryl group including 6 to 50 ring carbon atoms.

Examples of the aralkyl group including 7 to 50 (preferably 7 to 18) carbon atoms of $R_1$ to $R_{10}$, $R_1$ to $R_{18}$, and after-mentioned $R_{101}$ to $R_{110}$ include, for example, a benzyl group, a 1-phenylethyl group, a 2-phenylethyl group, a 1-phenylisopropyl group, a 2-phenylisopropyl group, a phenyl-t-butyl group, a α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, a m-methylbenzyl group, an o-methylbenzyl group, a p-chlorobenzyl group, a m-chlorobenzyl group, an o-chlorobenzyl group, a p-bromobenzyl group, a m-bromobenzyl group, an o-bromobenzyl group, a p-iodobenzyl group, a m-iodobenzyl group, an o-iodobenzyl group, a p-hydroxybenzyl group, a m-hydroxybenzyl group, an o-hydroxybenzyl group, a p-aminobenzyl group, a m-aminobenzyl group, an o-aminobenzyl group, a p-nitrobenzyl group, a m-nitrobenzyl group, an o-nitrobenzyl group, a p-cyanobenzyl group, a m-cyanobenzyl group, an o-cyanobenzyl group, a 1-hydroxy-2-phenylisopropyl group, a 1-chloro-2-phenylisopropyl group, and the like.

Examples of the halogen atom of $R_1$ to $R_{10}$, $R_{11}$ to $R_{18}$, and after-mentioned $R_{101}$ to $R_{110}$ include a fluorine atom, a chlorine atom, a bromine atom, a iodine atom; and the like.

Examples of the alkylene group including 1 to 30 (preferably 1 to 18, more preferably 1 to 5) carbon atoms of $L_1$ to $L_6$ include a methylene group, an ethylene group, and the like.

Examples of the arylene group including 6 to 30 (preferably 6 to 18, more preferably 6 to 12) ring carbon atoms of $L_1$ to $L_6$ and after-mentioned $L_{101}$ include a phenylene group (e.g., m-phenylene group), a naphthylene group, a biphenylene group, an anthranilene group, a pyrenylene group, and the like.

Examples of the heteroarylene group including 5 to 30 (preferably 5 to 18) ring atoms of $L_1$ to $L_3$ and after-mentioned $L_{101}$ include a non-fused heteroarylene group and a fused heteroarylene group, and more specifically, a divalent group based on a pyrrolyl group, a pyrazinyl group, a pyridinyl group, an indolyl group, an isoindolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthridinyl group, an acridinyl group, a phenanthrolinyl group, or a thienyl group; and a divalent group formed from a ring selected from the group consisting of
a pyridine ring, a pyrazine ring, a pyrimidine ring, a pyridazine ring, a triazine ring, an indole ring, a quinoline ring, an acridine ring, a pyrrolidine ring, a dioxane ring, a piperidine ring, a morpholine ring, a piperazine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, a benzo[a]dibenzofuran ring, a benzo[b]dibenzofuran ring, and benzo[c]dibenzofuran ring.

In the present specification, Examples of the substituent in the case of "substituted or unsubstituted" (hereinafter also referred to as an arbitrary substituent) include, for example, an alkyl group including 1 to 50 carbon atoms, an alkenyl group including 2 to 50 carbon atoms, an alkynyl group including 2 to 50 carbon atoms, a cycloalkyl group including 3 to 50 ring carbon atoms, an alkoxy group including 1 to 50 carbon atoms, an alkylthio group including 1 to 50 carbon atoms, an aryloxy group including 6 to 50 ring carbon atoms, an arylthio group including 6 to 50 ring carbon atoms, an aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), —S(=O)$_2R_{38}$, —P(=O)($R_{39}$)($R_{40}$), —Ge($R_{41}$)($R_{42}$)($R_{43}$) (where $R_{31}$ to $R_{43}$ are independently a hydrogen atom, an alkyl group including 1 to 50 carbon atoms, an aryl group including 6 to 50 ring carbon atoms, or a heterocyclic group including 5 to 50 ring atoms), a halogen atom, a cyano group, a nitro group, an aryl group including 6 to 50 ring carbon atoms, a heterocyclic group including 5 to 50 ring atoms, and the like. Among these, an alkyl group including 1 to 50 carbon atoms, an aryl group including 6 to 50 ring carbon atoms, and a heterocyclic group including 5 to 50 ring atoms are preferable, and an alkyl group including 1 to 18 carbon atoms, an aryl group including 6 to 18 ring carbon atoms, and an heterocyclic group including 5 to 18 ring atoms are more preferable.

When two or more $R_{31}$s to $R_{43}$s are present, each of two or more $R_{51}$s to $R_{63}$s may be the same as or different from each other.

Specific examples of these substituents and halogen atoms are the same as those described above for the substituents and the halogen atoms of $R_1$ to $R_{10}$, and the like, respectively.

In the specification, a saturated or unsaturated ring (preferably a saturated or unsaturated, substituted or unsubstituted, 5-membered ring, 6-membered ring or 7 or more-membered ring, and more preferably a benzene ring) may be formed between adjacent arbitrary substituents (or between non-adjacent ring formable arbitrary substituents).

In the specification, the arbitrary substituent may further be substituted by a substituent. Examples of the substituent further substituted on the arbitrary substituent include the same as those of the arbitrary substituent described above.

Specific examples of an aspect of the compound of the invention include, for example, the following compounds. Me represents a methyl group.

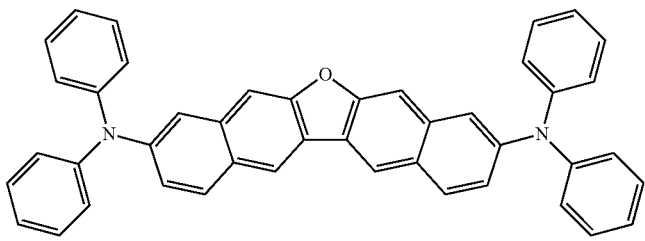

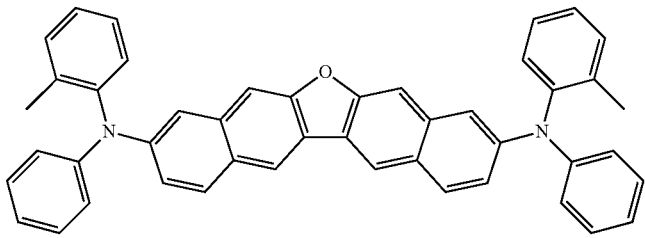

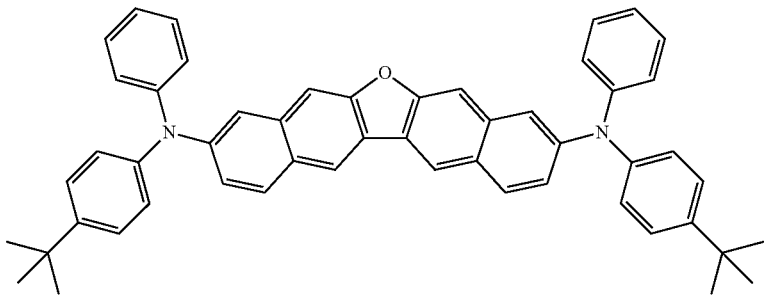

-continued
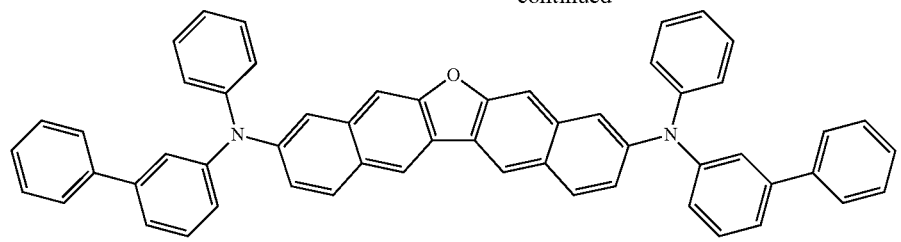
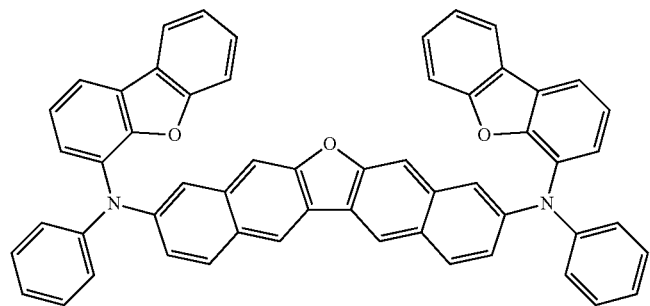
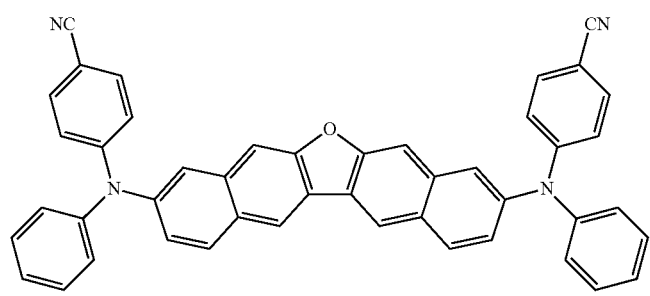
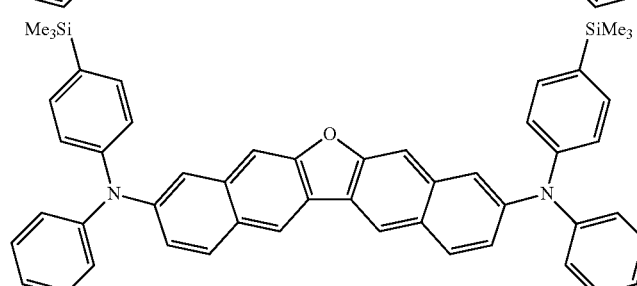
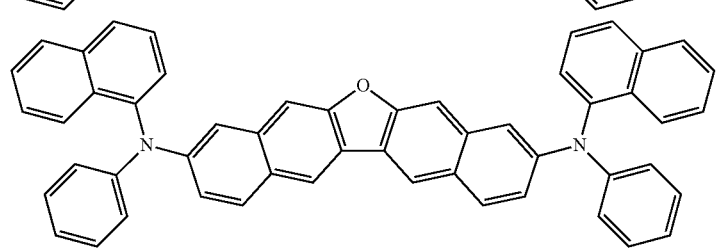
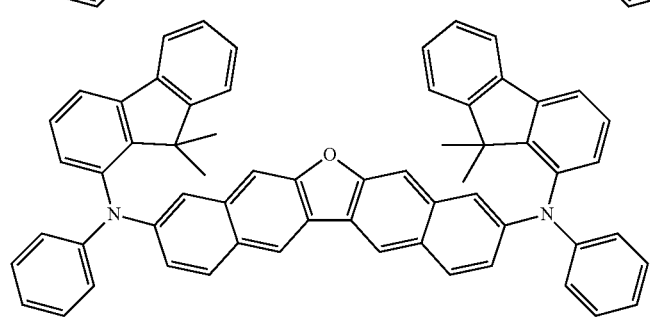

-continued
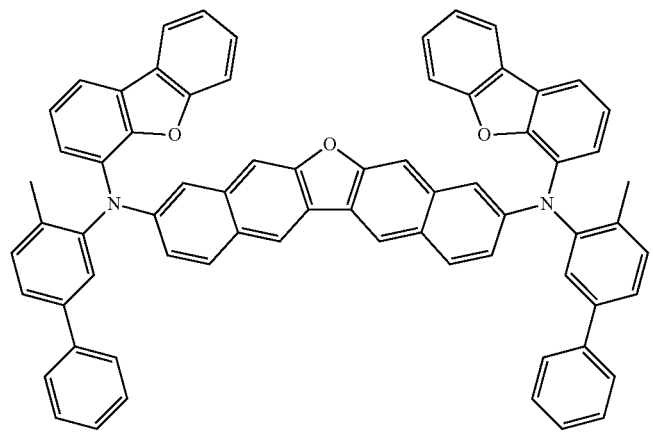
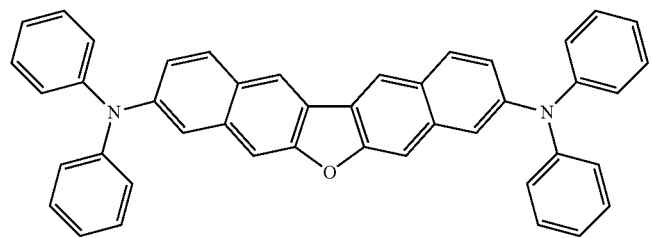
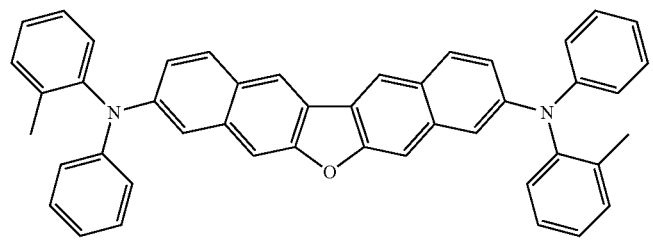
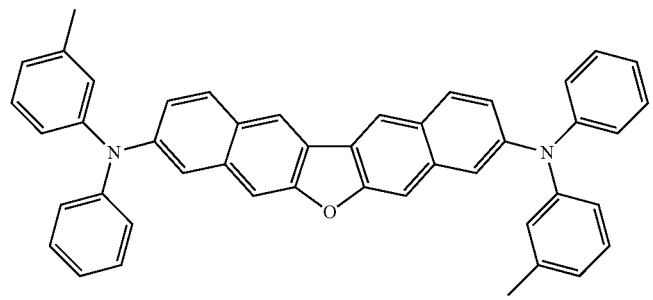
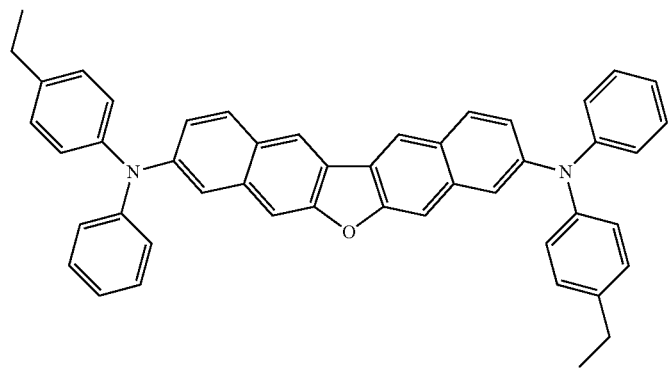

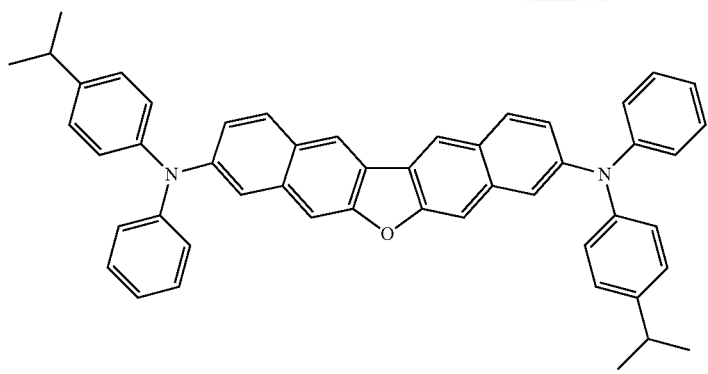
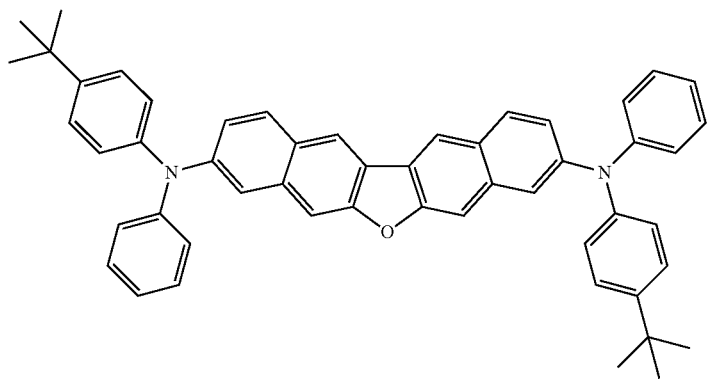
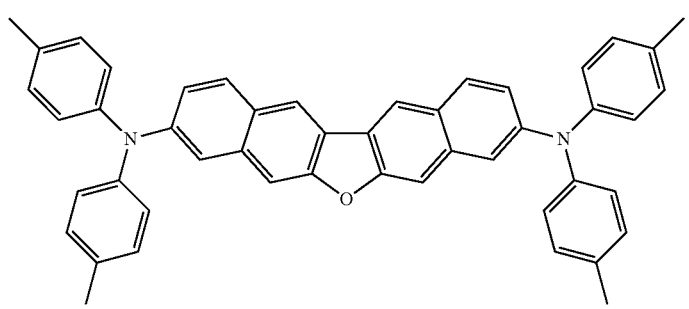
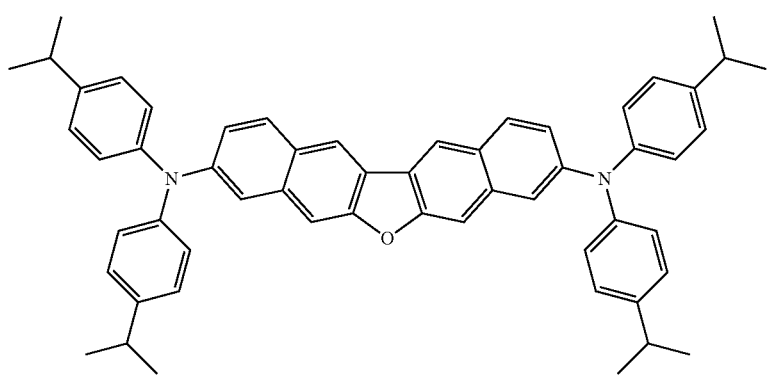

-continued
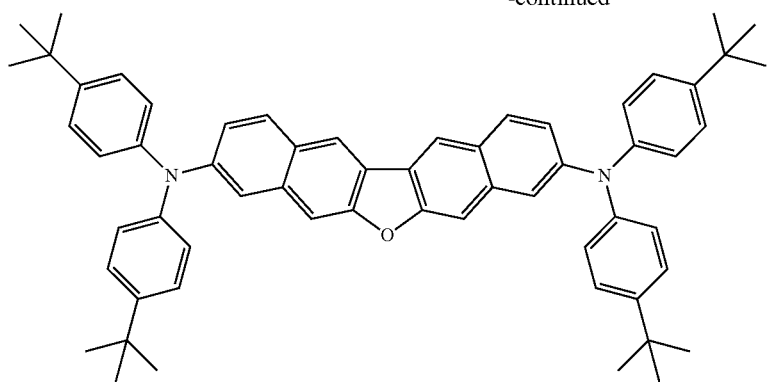
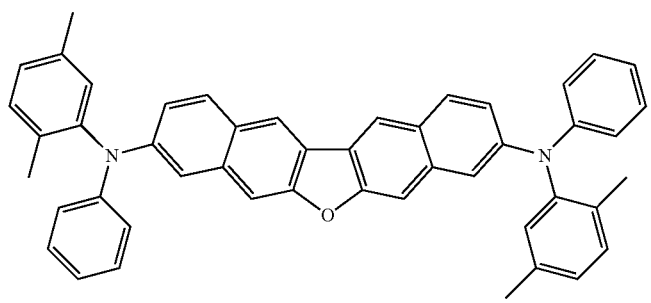
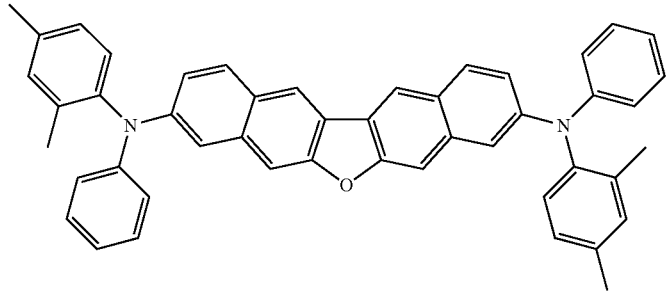
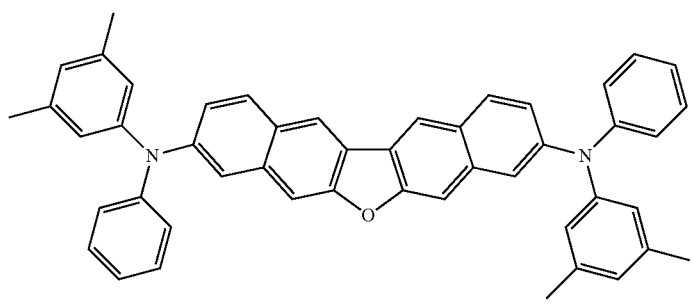
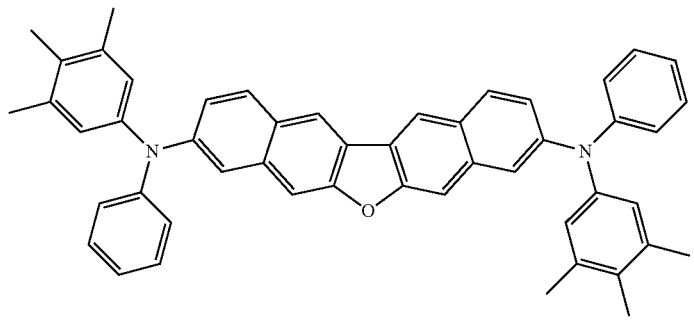

-continued
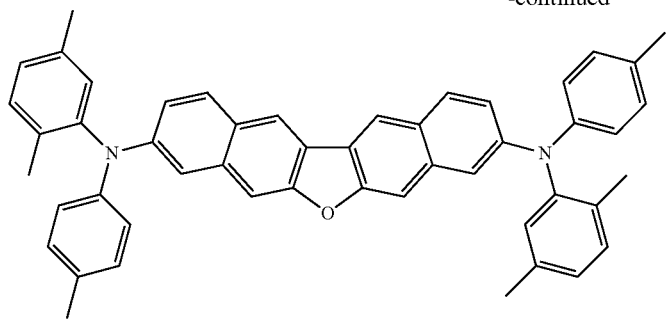
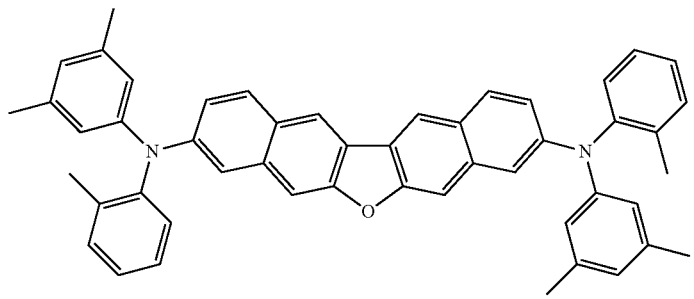
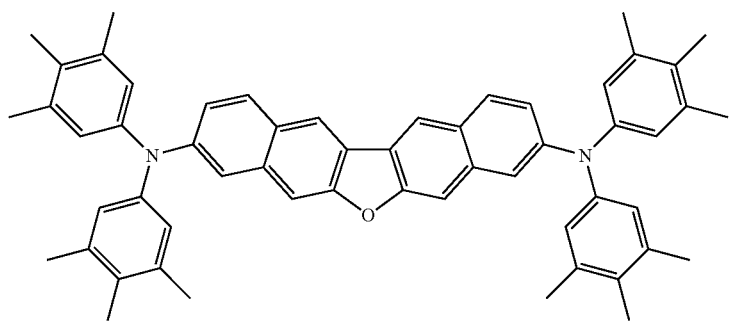
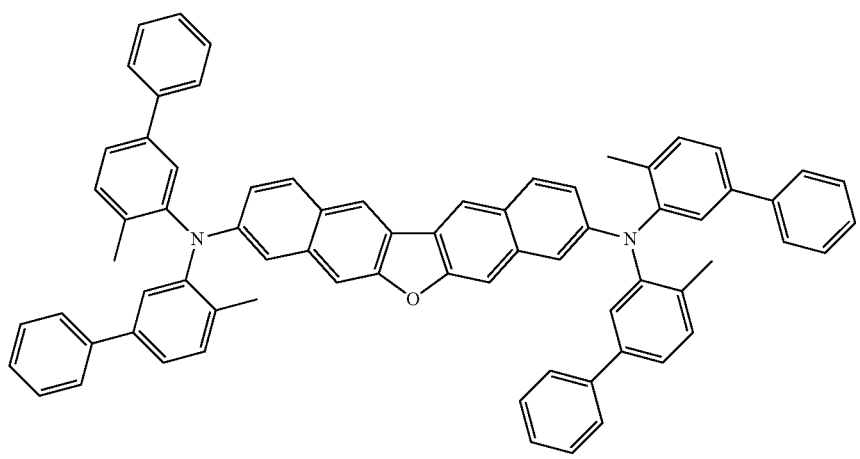

-continued
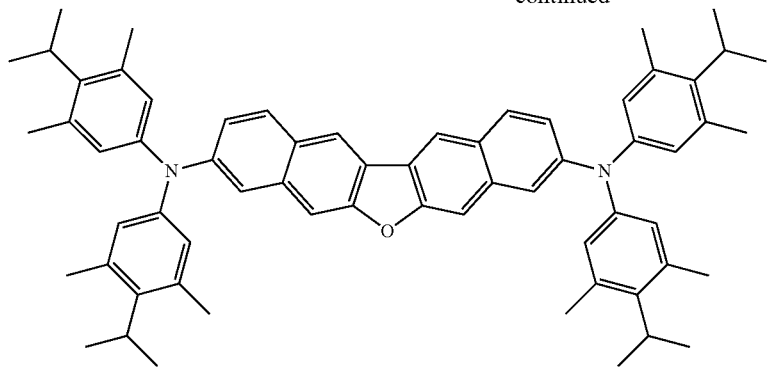
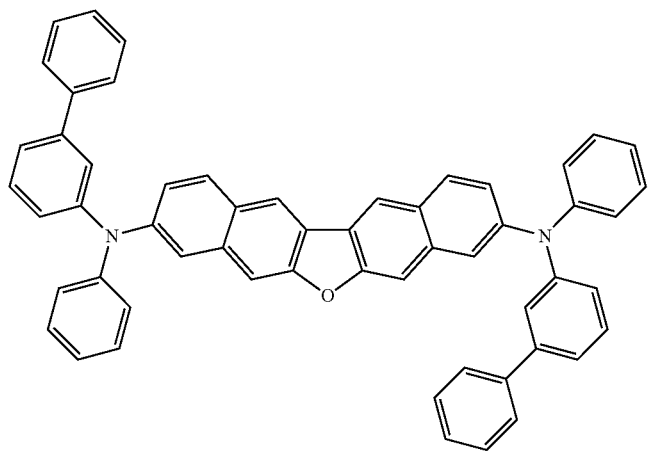
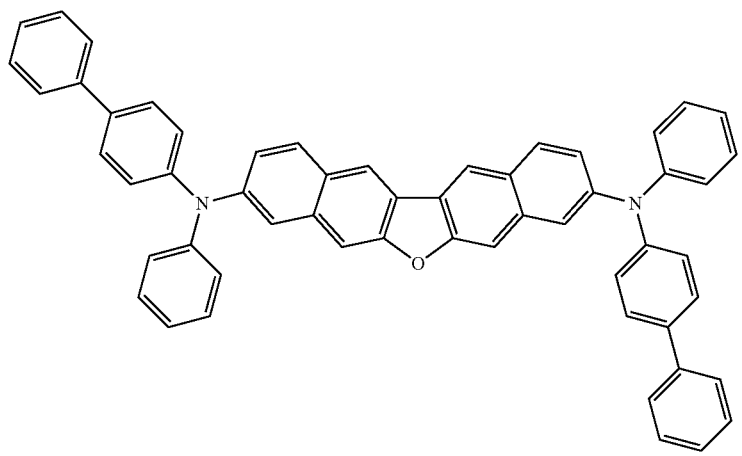
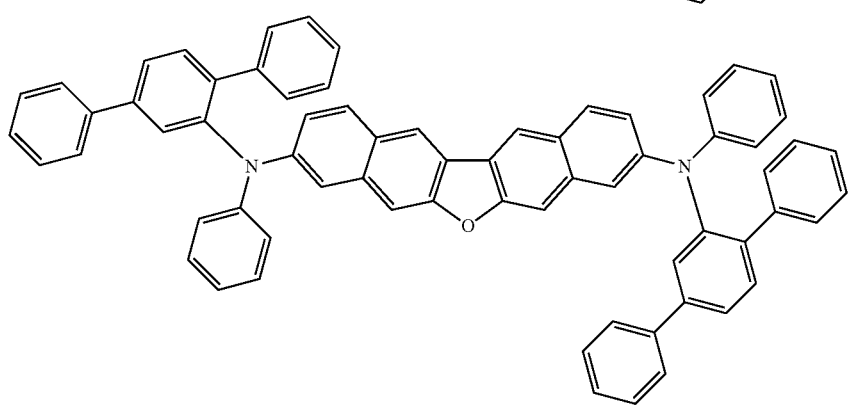

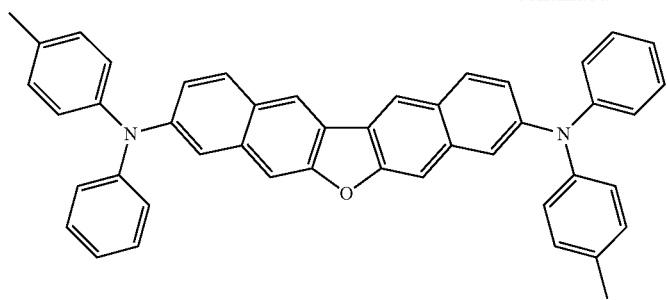
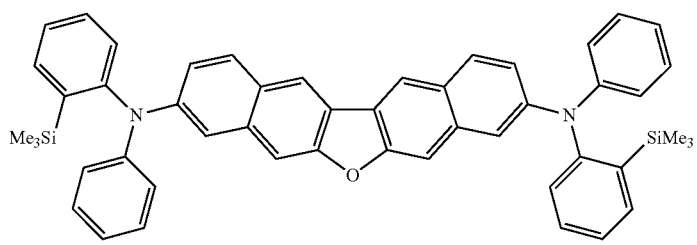
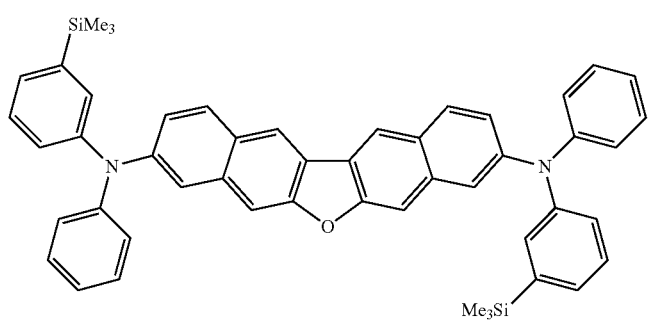
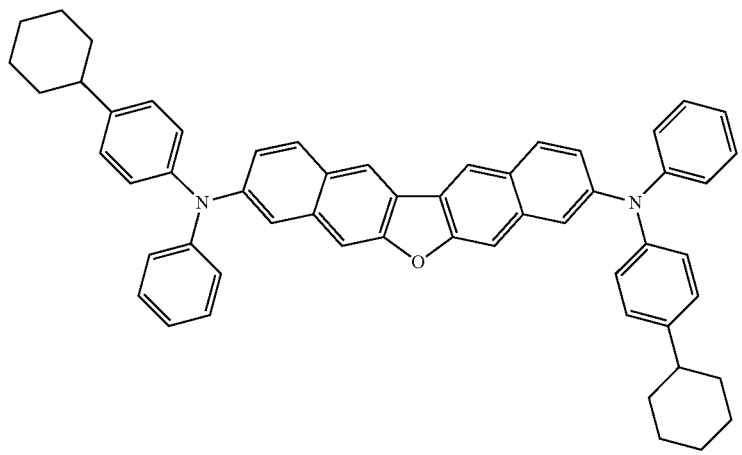
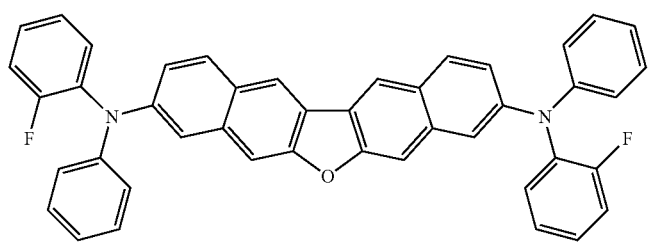

-continued
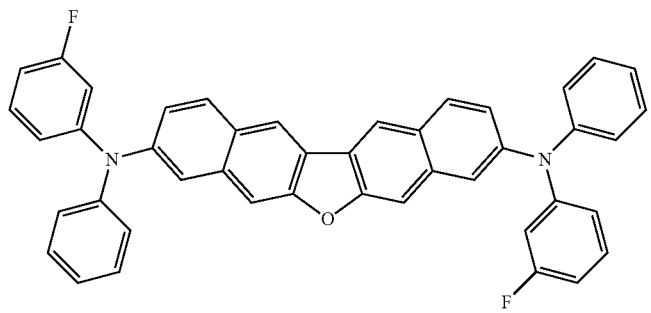
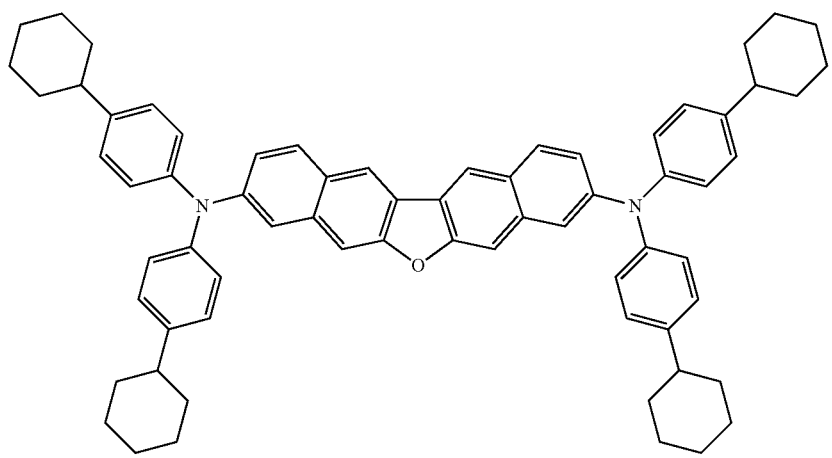
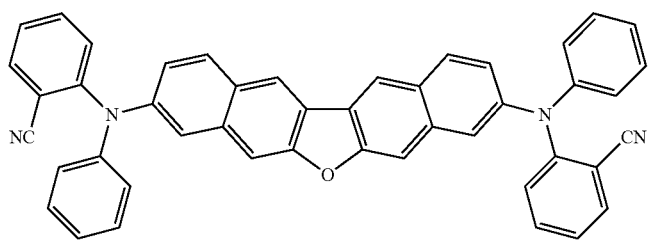
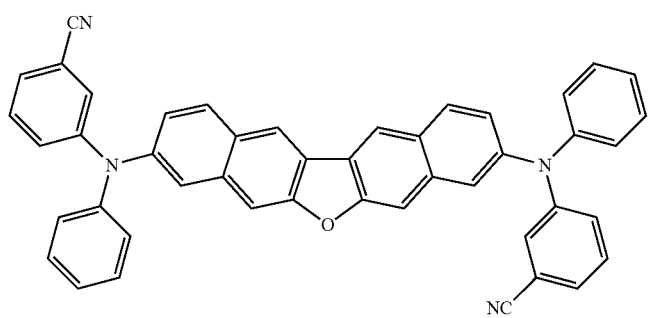
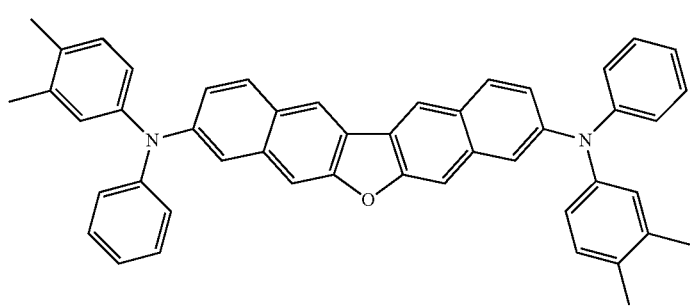

-continued
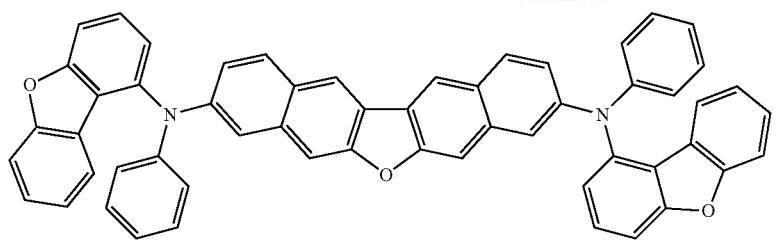
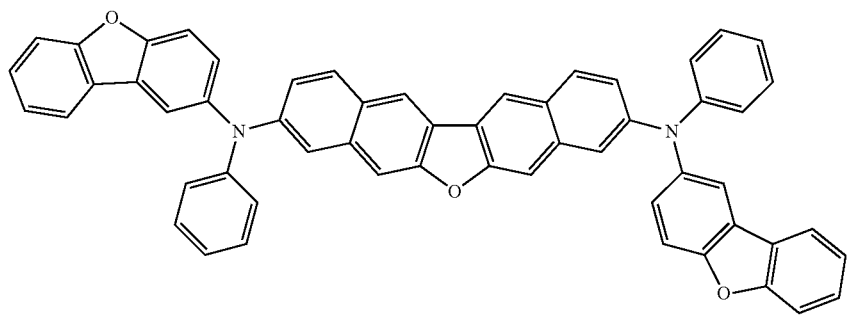
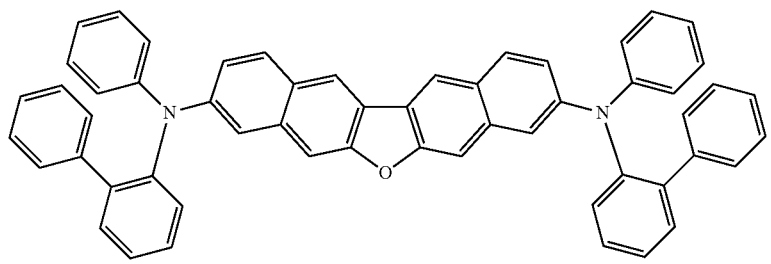
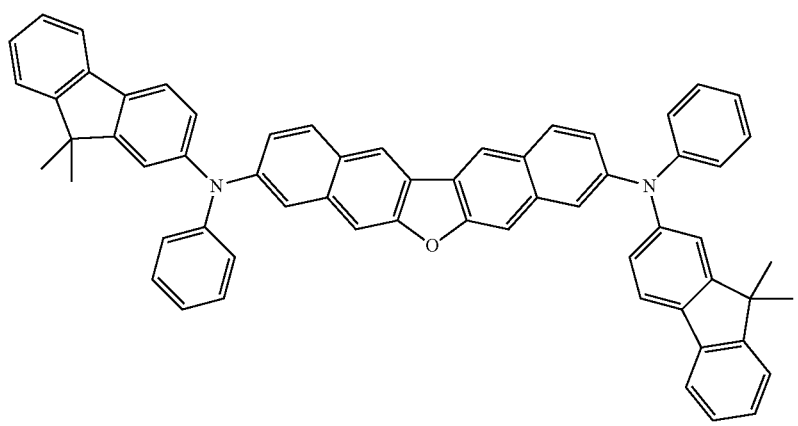

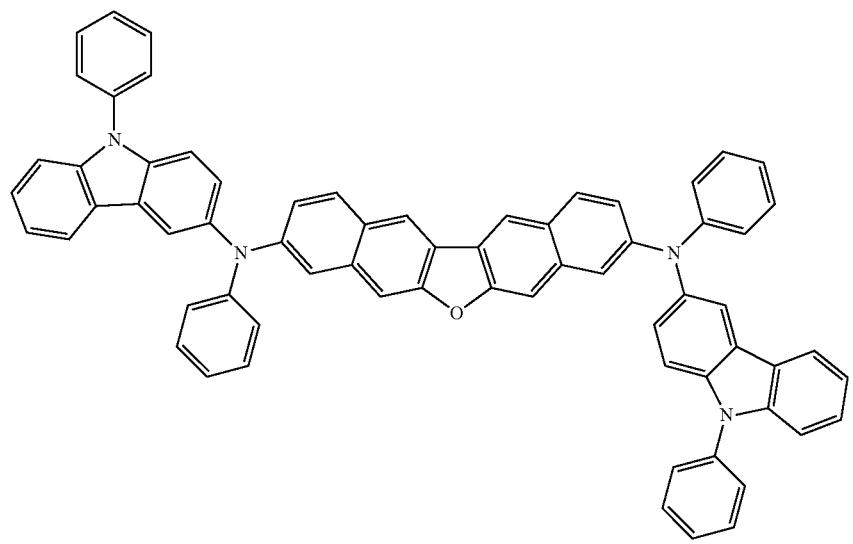
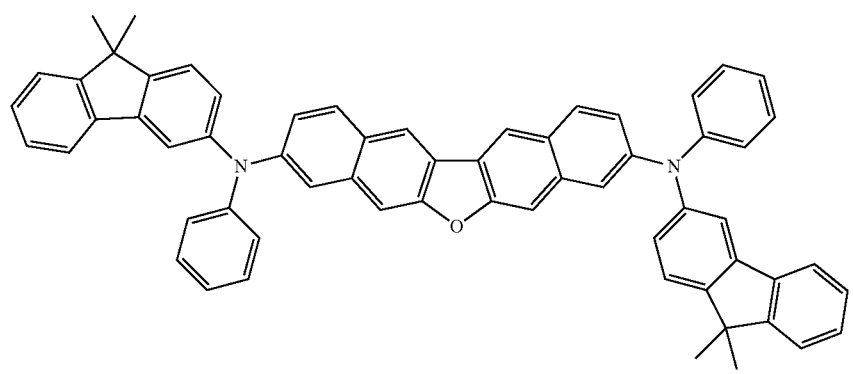
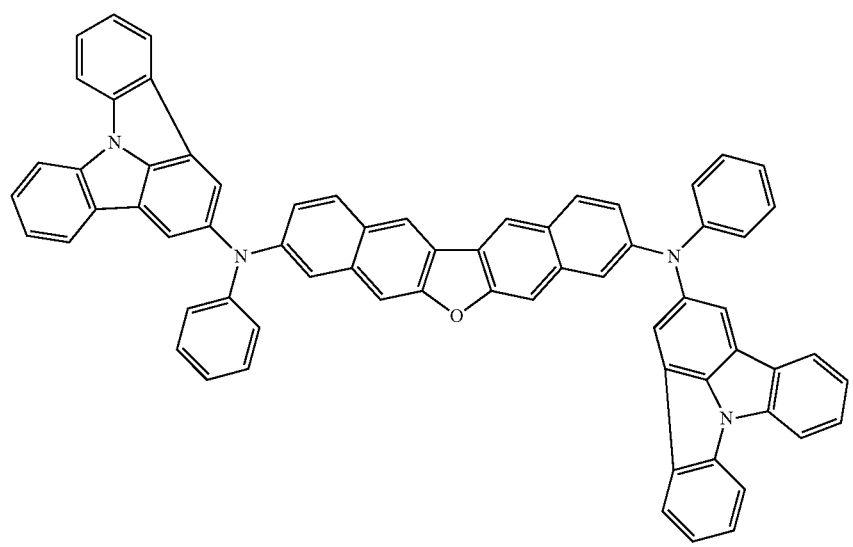

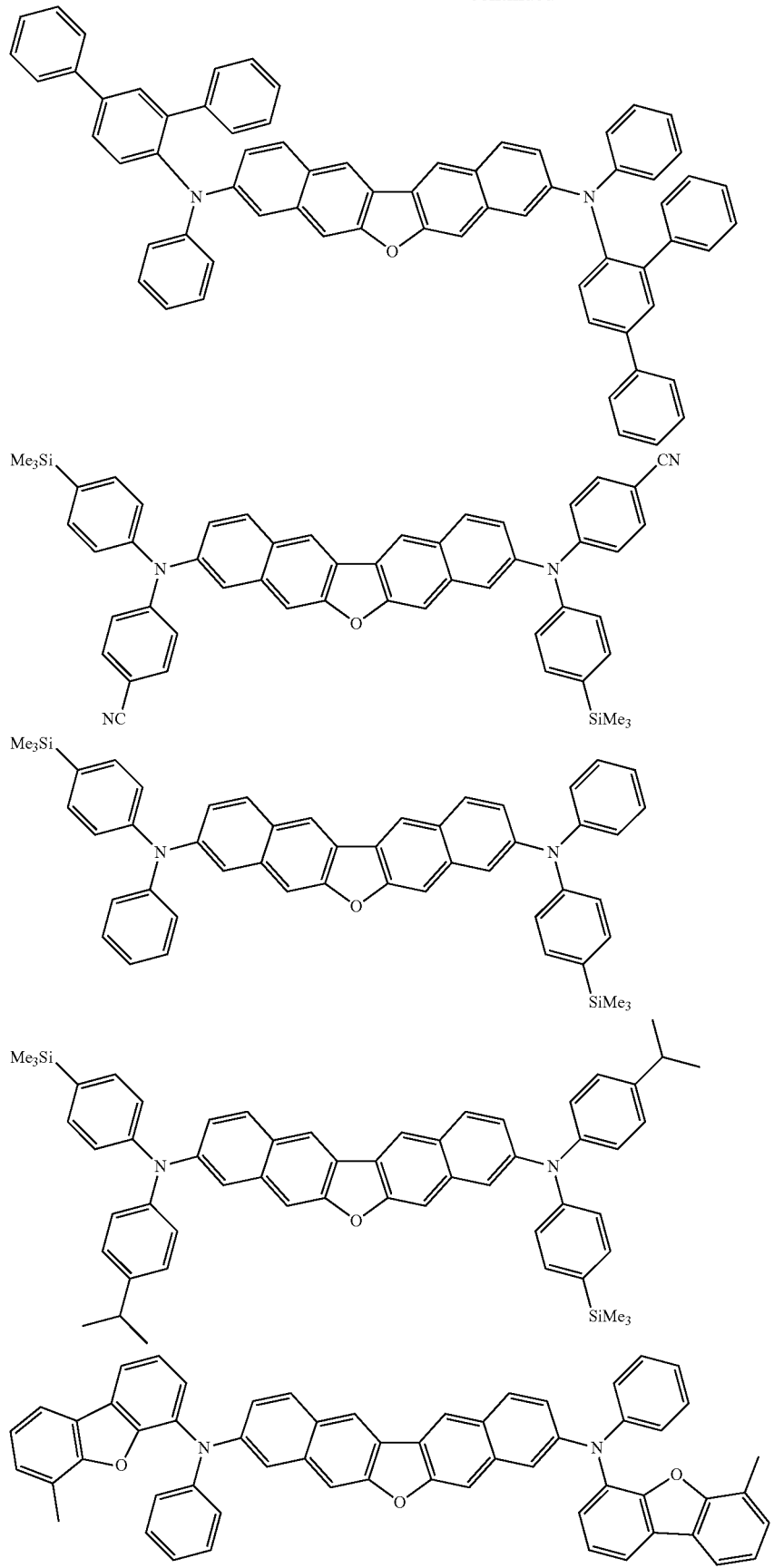

-continued
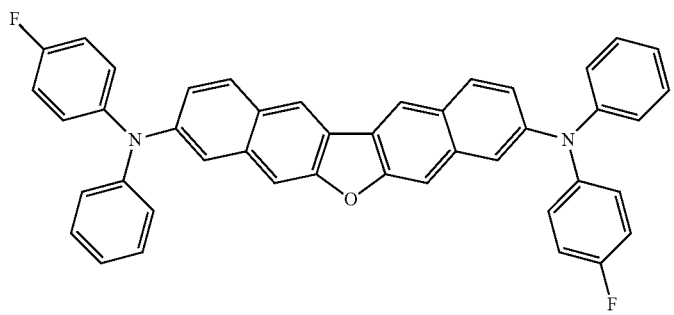
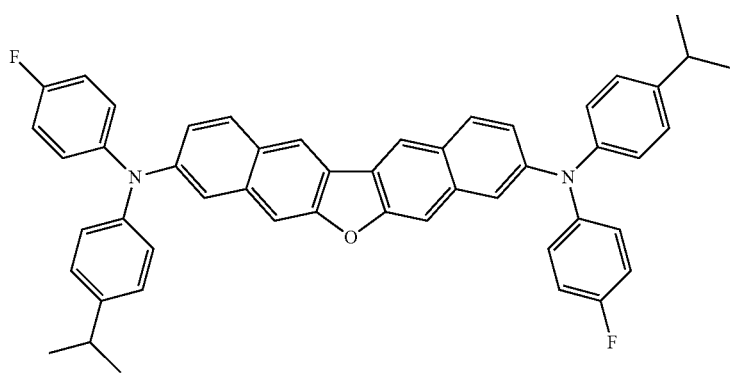
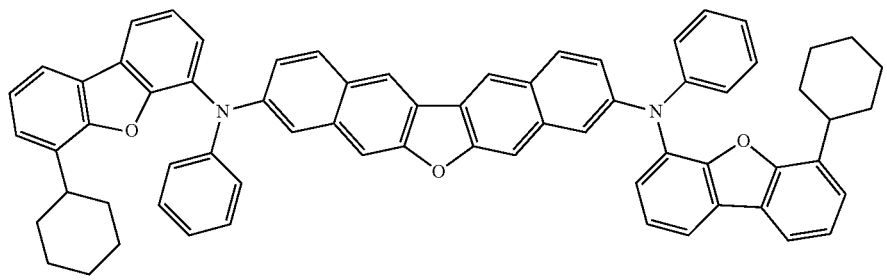
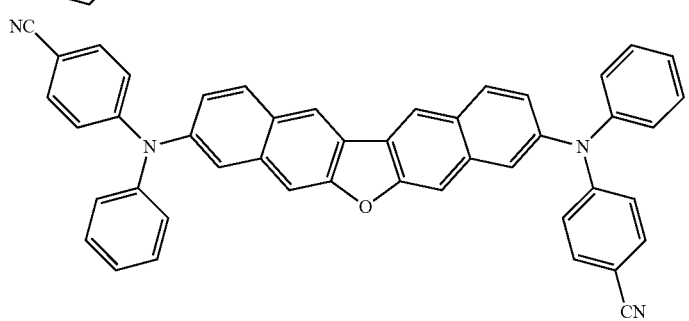
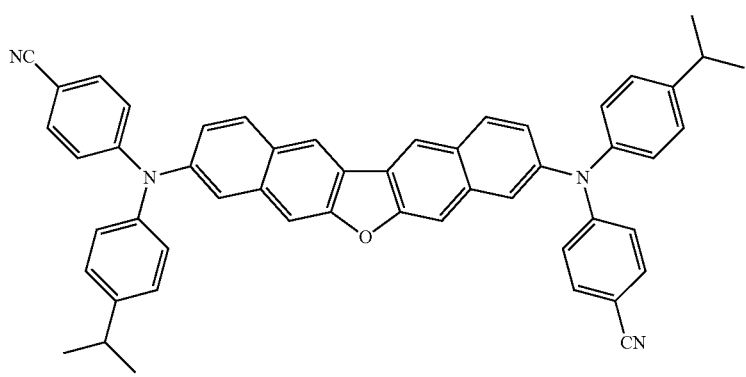

-continued
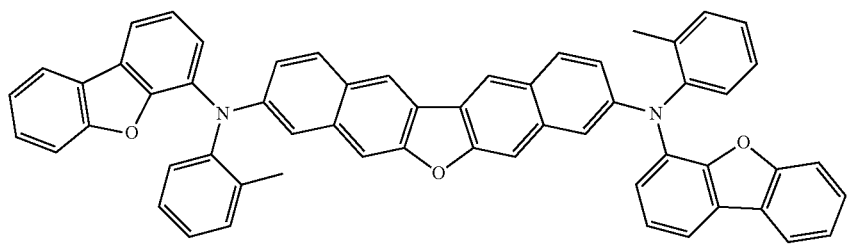
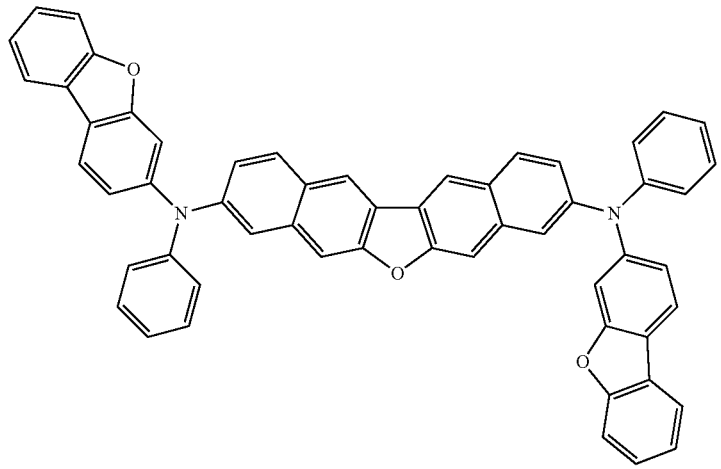
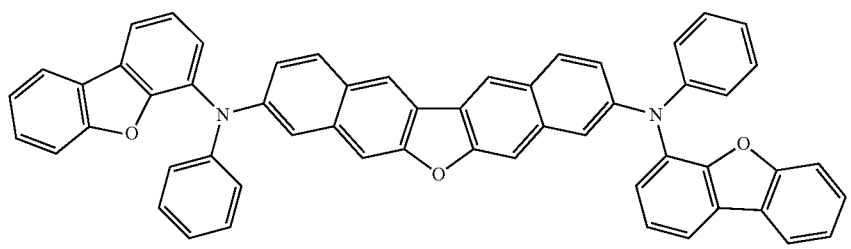
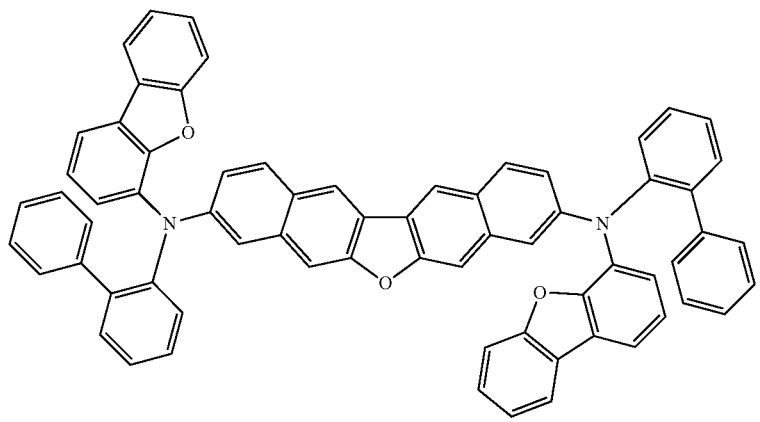
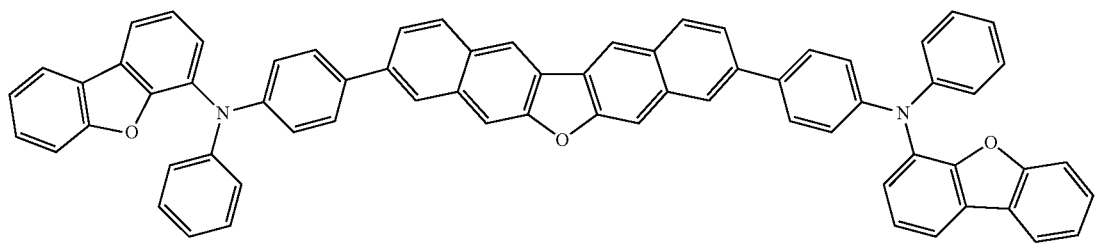

-continued
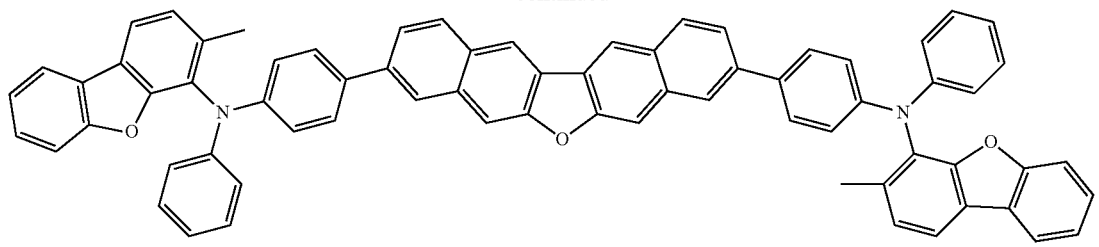
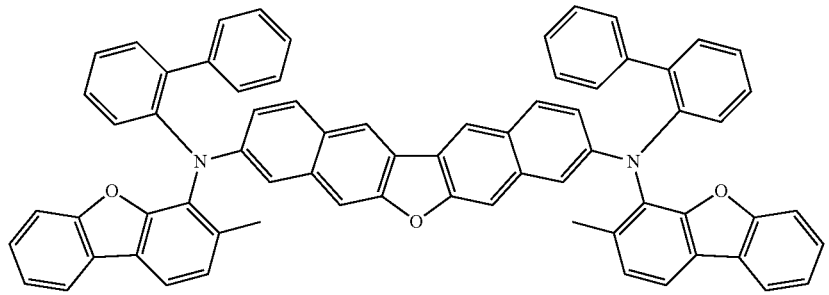
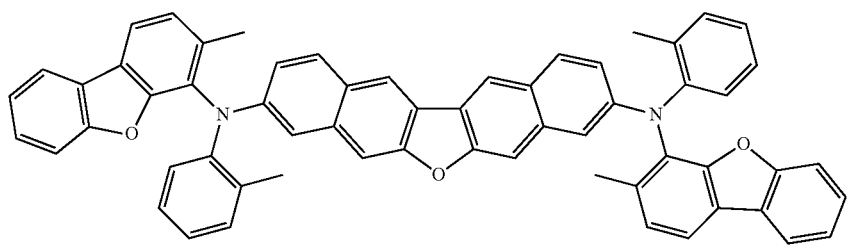
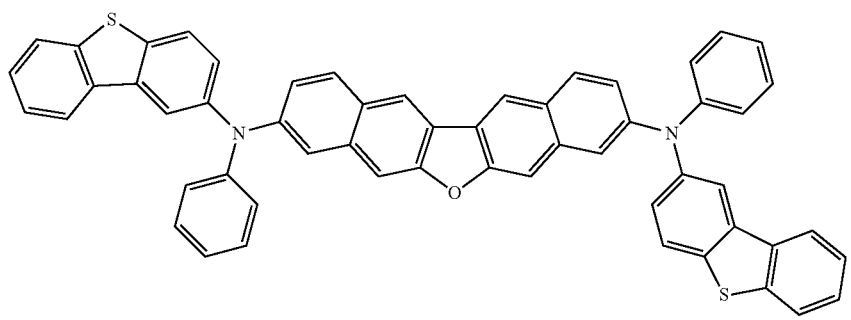
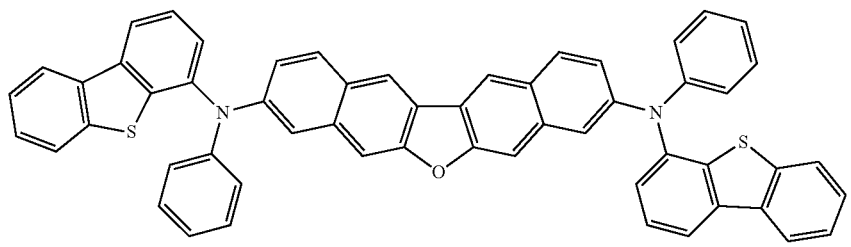
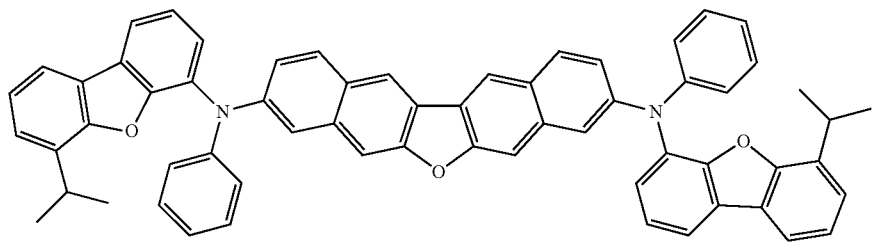

-continued
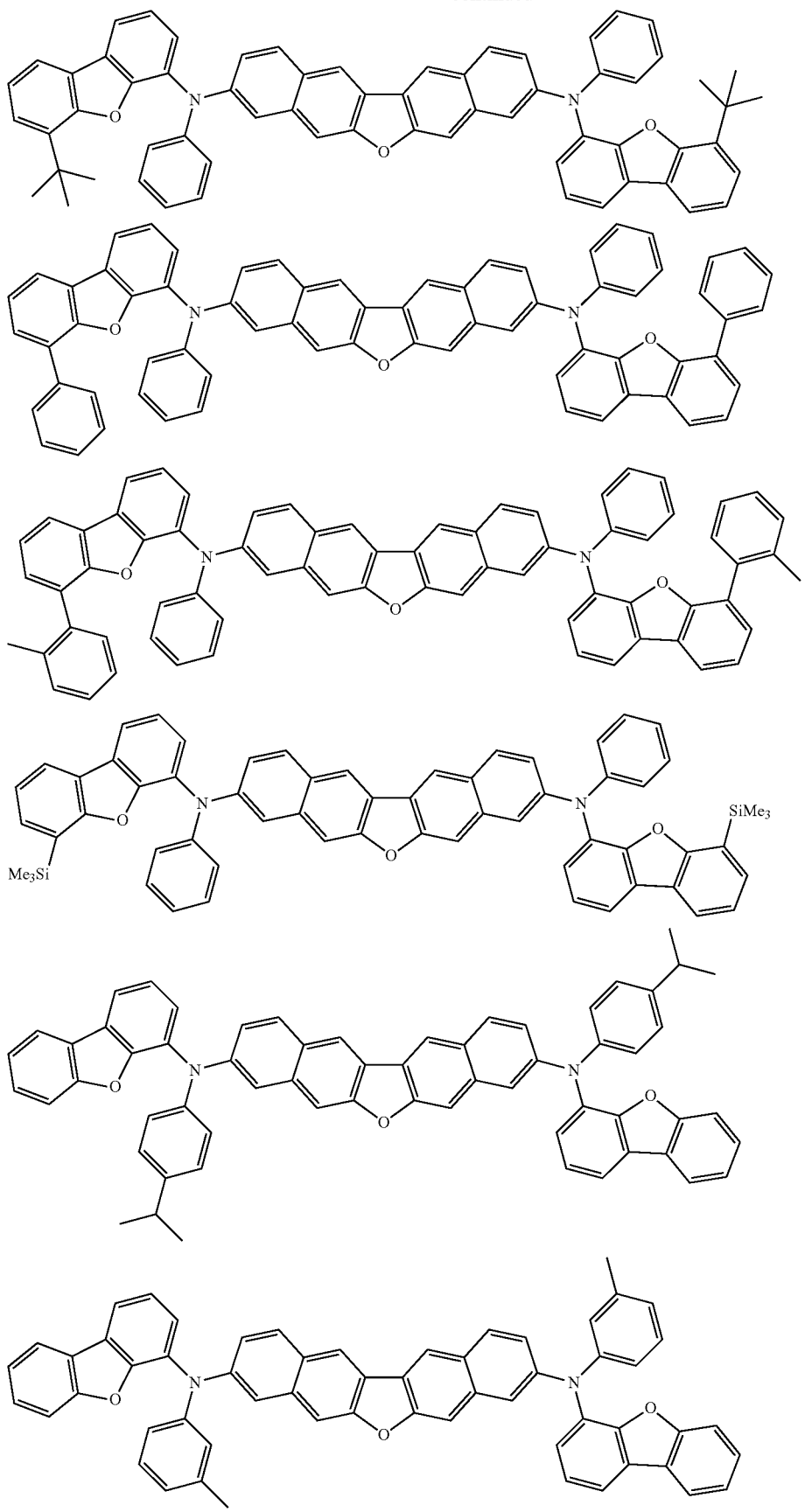

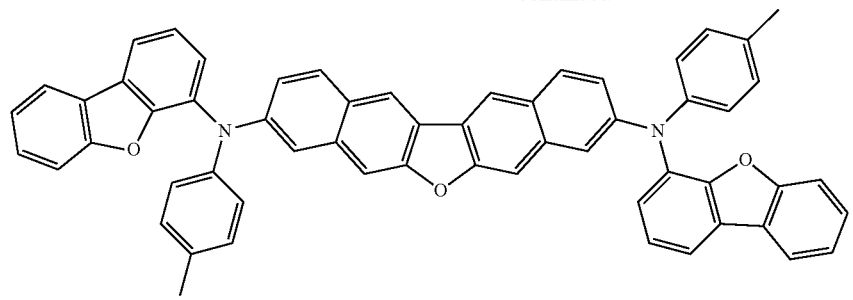
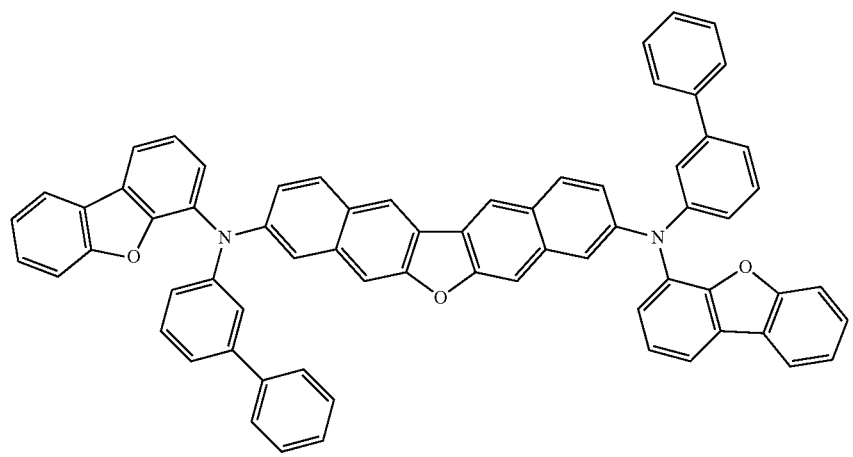
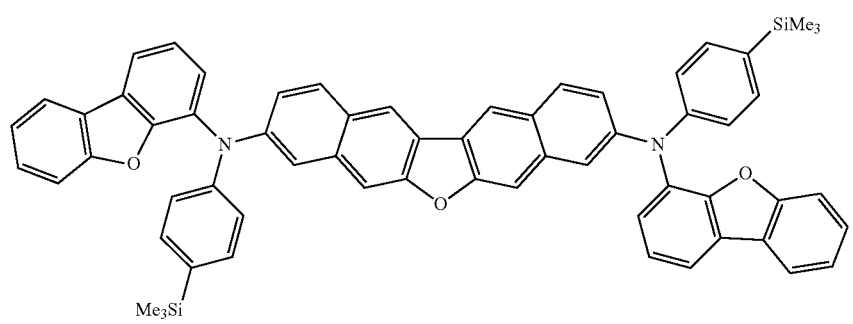
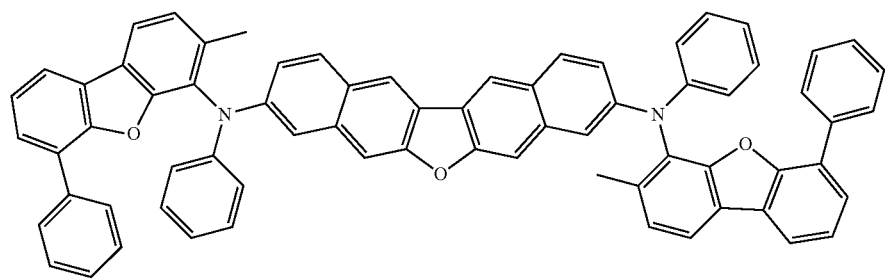

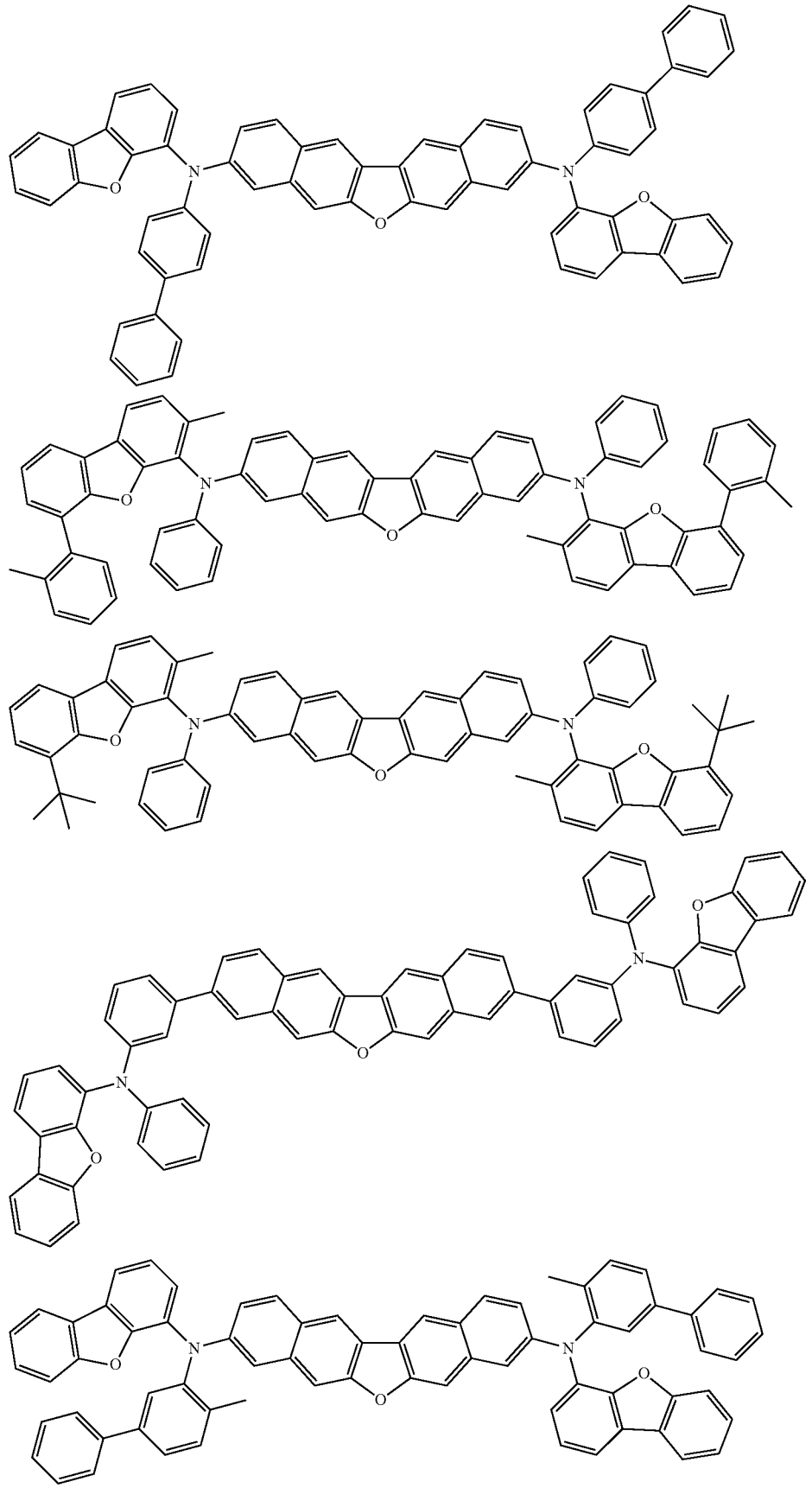

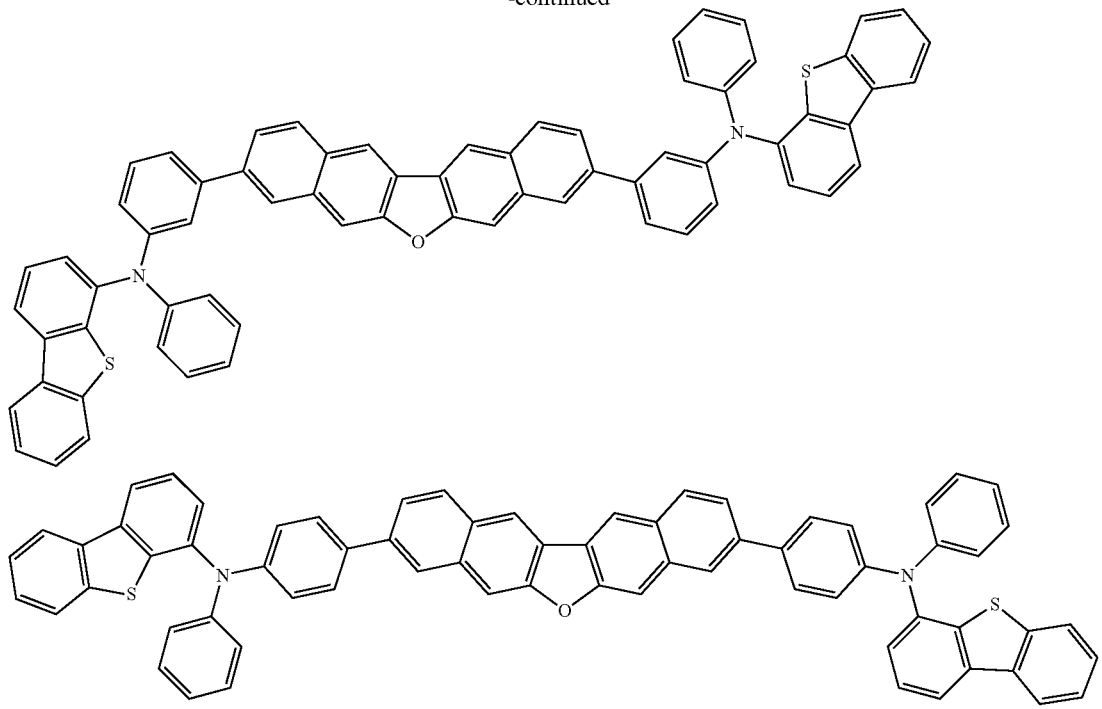

An aspect of the materials for the organic electroluminescence device of the invention comprises the compound as described above.

The first aspect of the organic EL device of the invention comprises: a cathode; an anode; and an organic layer provided between the cathode and the anode, wherein the organic layer contains the compound as described above.

The second aspect of the organic EL device of the invention comprises: a cathode; an anode; and an emitting layer provided between the cathode and the anode, wherein the emitting layer contains the compound as described above.

The first aspect and the second aspect of the organic EL device of the invention are collectively referred to as an aspect of the organic EL device of the invention.

By the aspect of the organic EL device of the invention, the photoluminescence quantum yield of the fluorescence can be improved and the half-width can be reduced.

In the first aspect of the organic EL device of the invention, the organic layer may comprise a hole-injecting layer, a hole-transporting layer, an emitting layer, an electron-injecting layer, an electron-transporting layer, and the like. Preferably, one or more layers selected from the group consisting of a hole-injecting layer, a hole-transporting layer, an emitting layer, an electron-injecting layer, and an electron-transporting layer comprises the compound as described above. The emitting layer may comprise a compound represented by the following formula (11).

In the second aspect of the organic EL device of the invention, it is preferable that the emitting layer further comprise a compound represented by the following formula (11):

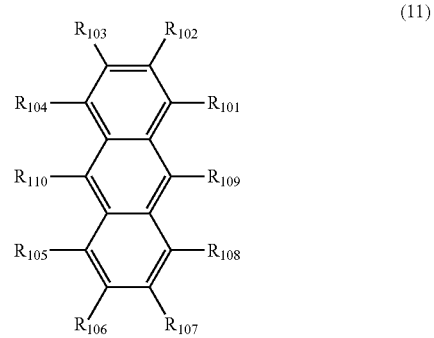

(11)

wherein in the formula (11), except for $R_{101}$ to $R_{110}$ that forms the after-mentioned ring, $R_{101}$ to $R_{110}$ are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted ring aralkyl group including 7 to 50 carbon atoms, —Si($R_{121}$)($R_{122}$)($R_{123}$), —C(=O)$R_{124}$, —COO$R_{125}$, —N($R_{126}$)($R_{127}$), a halogen atom, a cyano group, a nitro group, a substituted or unsubstituted aryl group including 6 to 50 ring carbon atoms, a substituted or unsubstituted heterocyclic group including 5 to 50 ring atoms, or a group represented by -$L_{101}$-$Ar_{101}$;

one or more pair (preferably 1 to 3 pair) of two or more (preferably 2 to 3) adjacent among $R_{101}$ to $R_{110}$ may form a saturated or unsaturated ring (preferably a saturated or unsaturated, substituted or unsubstituted 5-membered ring or 6-membered ring, more preferably a benzene ring);

$R_{121}$ to $R_{127}$ are independently a hydrogen atom, a substituted or unsubstituted alkyl group including 1 to 50 carbon atoms, a substituted or unsubstituted aryl group including 6 to 50 ring carbon atoms, or a substituted or unsubstituted heterocyclic group including 5 to 50 ring atoms;

provided that at least one of $R_{101}$ to $R_{110}$ is a group represented by -$L_{101}$-$Ar_{101}$; $L_{101}$ is a single bond, a substituted or unsubstituted arylene group including 6 to 30 ring carbon atoms, or a substituted or unsubstituted heteroarylene group including 5 to 30 ring atoms; $Ar_{101}$ is a substituted or unsubstituted aryl group including 6 to 50 ring carbon atoms, or a substituted or unsubstituted heterocyclic group including 5 to 50 ring atoms; when two or more $L_{101}$s are present, two or more $L_{101}$s may be the same as or different from each other; when two or more $Ar_{101}$s are present, two or more $Ar_{101}$s may be the same as or different from each other; and when two or more $R_{121}$s to $R_{127}$s are present, each of two or more $R_{121}$s to $R_{127}$s may be the same as or different from each other.

Hereinafter, the term of "one or more pair of two or more adjacent among $R_{101}$ to $R_{110}$ may form a saturated or unsaturated ring" will be described.

The term of "one pair of two or more adjacent among $R_{101}$ to $R_{110}$" is, for example, a combination of $R_{101}$ and $R_{102}$, $R_{102}$ and $R_{103}$, $R_{103}$ and $R_{104}$, $R_{105}$ and $R_{106}$, $R_{106}$ and $R_{107}$, $R_{107}$ and $R_{108}$, $R_{108}$ and $R_{109}$, $R_{101}$ and $R_{102}$ and $R_{103}$, and the like.

The term of "a saturated or unsaturated ring" is a ring formed by carbon atom to which $R_{101}$ is bonded, carbon atom to which $R_{102}$ is bonded, and two or more arbitrary elements when the ring is formed, for example, by $R_{101}$ and $R_{102}$. Specifically, in the case where the ring is formed by $R_{101}$ and $R_{102}$, and when an unsaturated ring is formed by a carbon atom to which $R_{101}$ is bonded, a carbon atom to which $R_{102}$ is bonded, and four carbon atoms, the ring formed with $R_{101}$ and $R_{102}$ is a benzene ring.

The term of "arbitrary elements" is preferably C element, N element, O element, and S element. In arbitrary elements (e.g., for C element or N element), atomic bonding that is not involved in the ring formation may be terminated with hydrogen atom or the like.

The term of "two or more arbitrary elements" is preferably 3 or more and 12 or less arbitrary elements, and more preferably 3 or more and 5 or less.

For example, $R_{101}$ and $R_{102}$ may form a ring, while $R_{105}$ and $R_{106}$ may form a ring at the same time. In this case, the compound represented by the formula (11) is, for example, a compound represented by the following formula (11A).

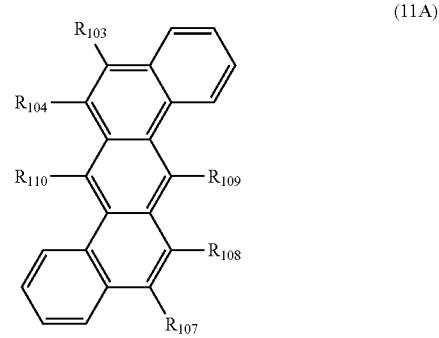

(11A)

$R_{101}$ to $R_{110}$ are preferably independently a hydrogen atom, a substituted or unsubstituted alkyl group including 1 to 50 carbon atoms, a substituted or unsubstituted aryl group including 6 to 50 ring carbon atoms, a substituted or unsubstituted heterocyclic group including 5 to 50 ring atoms, or a group represented by -$L_{101}$-$Ar_{101}$.

$R_{101}$ to $R_{110}$ are more preferably independently a hydrogen atom, a substituted or unsubstituted aryl group including 6 to 50 ring carbon atoms, a substituted or unsubstituted heterocyclic group including 5 to 50 ring atoms, or a group represented by -$L_{101}$-$Ar_{101}$.

$R_{101}$ to $R_{110}$ are still more preferably independently a hydrogen atom, a substituted or unsubstituted aryl group including 6 to 18 ring carbon atoms, a substituted or unsubstituted heterocyclic group including 5 to 18 ring atoms, or a group represented by -$L_{101}$-$Ar_{101}$.

In the second aspect of an organic EL device of the invention, at least one of $R_{109}$ and $R_{110}$ is preferably a group represented by -$L_{101}$-$Ar_{101}$.

In the second aspect of an organic EL device of the invention, $R_{109}$ and $R_{110}$ are preferably independently a group represented by -$L_{101}$-$Ar_{101}$.

In the second aspect of an organic EL device of the invention, the compound (11) is preferably a compound represented by the following formula (12):

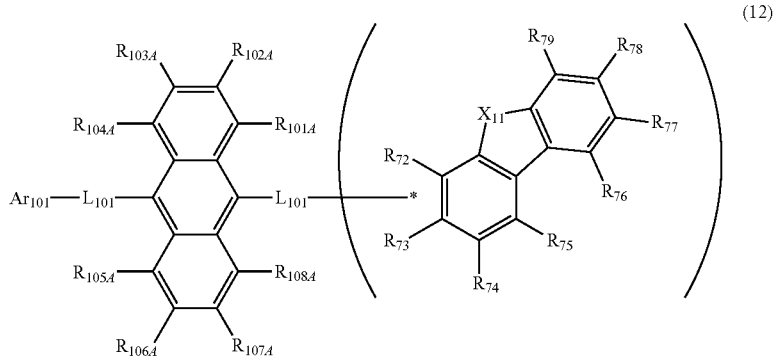

(12)

wherein in the formula (12), an atomic bonding * is bonded to one of $R_{72}$ to $R_{79}$;

$L_{101}$ and $Ar_{101}$ are as defined in the formula (11);

$R_{101A}$ to $R_{108A}$ are independently a hydrogen atom, or a substituted or unsubstituted aryl group including 6 to 50 ring carbon atoms;

$X_{11}$ is O, S, or N($R_{71}$);

$R_{71}$ is a hydrogen atom, a substituted or unsubstituted alkyl group including 1 to 50 carbon atoms, or a substituted or unsubstituted aryl group including 6 to 50 ring carbon atoms;

one of $R_{72}$ to $R_{79}$ is an atomic bonding that is bonded to $L_{101}$;

one or more pair of two or more adjacent among $R_{72}$ to $R_{79}$ that are not bonded to $L_{101}$ may form a substituted or unsubstituted, saturated or unsaturated ring;

$R_{72}$ to $R_{79}$ that are not bonded to $L_{101}$ and do not form the substituted or unsubstituted, saturated or unsaturated ring are independently a hydrogen atom, a substituted or unsubstituted alkyl group including 1 to 50 carbon atoms, or a substituted or unsubstituted aryl group including 6 to 50 ring carbon atoms.

In the second aspect of an organic EL device of the invention, the compound represented by the formula (11) is preferably a compound represented by the following formula (13):

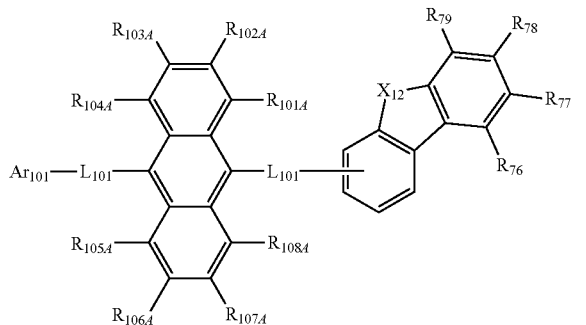

(13)

wherein in the formula (13), $L_{101}$ and $Ar_{101}$ are as defined in the formula (11);

$R_{101A}$ to $R_{108A}$ are as defined in the formula (12);

$R_{76}$ to $R_{79}$ are as defined in the formula (12); and $X_{12}$ is O or S.

In the second aspect of an organic EL device of the invention, the compound represented by the formula (11) is preferably a compound represented by the following formula (14):

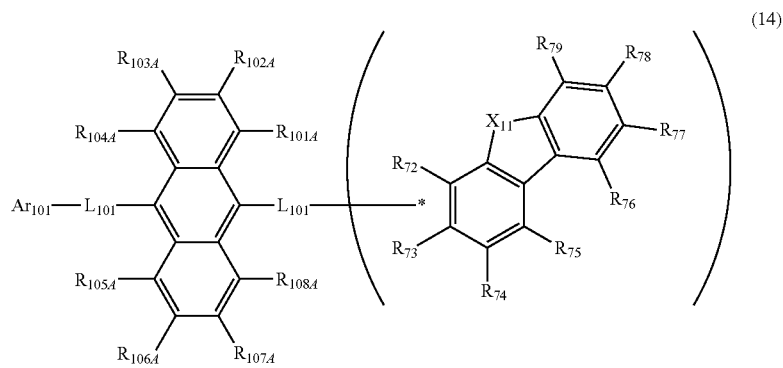

(14)

wherein in the formula (14), the atomic bonding * is bonded to one of $R_{72}$ to $R_{79}$;

$L_{101}$ and $Ar_{101}$ are as defined in the formula (11);

$R_{101A}$ to $R_{108A}$ are as defined in the formula (12);

$X_{11}$ is as defined in the formula (12);

$R_{72}$ to $R_{79}$ are as defined in the formula (12); and provided that any one pair of $R_{76}$ and $R_{77}$, $R_{77}$ and $R_{78}$, and $R_{78}$ and $R_{79}$, is bonded to each other to form a substituted or unsubstituted, saturated or unsaturated ring.

In the second aspect of an organic EL device of the invention, the compound represented by the formula (11) is preferably a compound represented by the following formula (15):

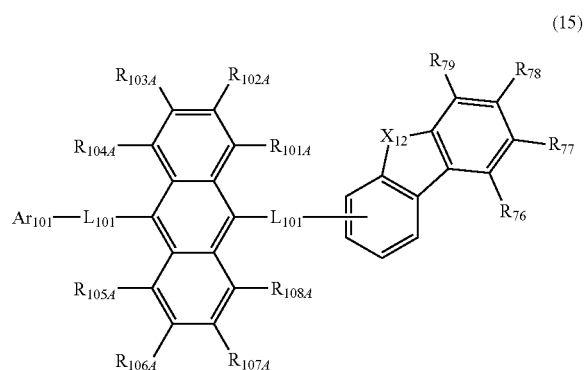

(15)

wherein in the formula (15), $L_{101}$ and $Ar_{101}$ are as defined in the formula (11);

$R_{101A}$ to $R_{108A}$ are as defined in the formula (12);

$X_{12}$ is O or S;

$R_{76}$ to $R_{79}$ are as defined in the formula (12); and provided that any one pair of $R_{76}$ and $R_{77}$, $R_{77}$ and $R_{78}$, and $R_{78}$ and $R_{79}$, is bonded to each other to form a substituted or unsubstituted, saturated or unsaturated ring.

In the second embodiment of an organic EL device of the invention, it is preferable that any one pair of $R_{76}$ and $R_{77}$, $R_{77}$ and $R_{78}$, and $R_{78}$ and $R_{79}$ be bonded to each other to form a ring represented by the following formula (15-1) or (15-2). It is preferred that $R_{76}$ to $R_{79}$ that do not form a ring represented by the formula (15-1) or (15-2) do not form a substituted or unsubstituted, saturated or unsaturated ring:

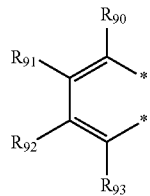
(15-1)

wherein in the formula (16), $L_{101}$ and $Ar_{101}$ are as defined in the formula (11);
$R_{101A}$ to $R_{108A}$ are as defined in the formula (12);
$R_{76}$ to $R_{79}$ are as defined in the formula (12); and
provided that $R_{76}$ and $R_{77}$, $R_{77}$ and $R_{78}$, and $R_{78}$ and $R_{79}$ are not bonded to each other to form a substituted or unsubstituted, saturated or unsaturated ring; and
$X_{12}$ is O or S.

In the second aspect of the organic EL device of the invention, the compound represented by the formula (11) is preferably a compound represented by the following formula (12A):

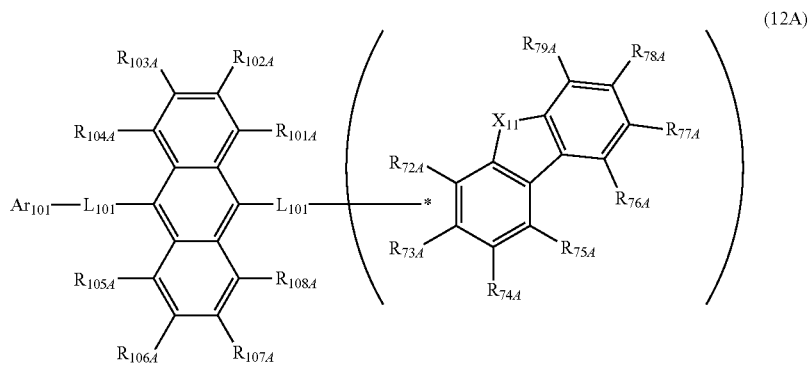
(12A)

-continued

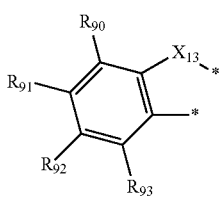
(15-2)

wherein in the formulas (15-1) and (15-2), the two atomic bondings * are independently bonded to one pair of $R_{76}$ and $R_{77}$, $R_{77}$ and $R_{78}$, and $R_{78}$ and $R_{79}$;
$R_{90}$ to $R_{93}$ are independently a hydrogen atom, a substituted or unsubstituted alkyl group including 1 to 50 carbon atoms, or a substituted or unsubstituted aryl group including 6 to 50 ring carbon atoms; and
$X_{13}$ is O or S.

In the second aspect of an organic EL device of the invention, the compound represented by the formula (11) is preferably a compound represented by the following formula (16):

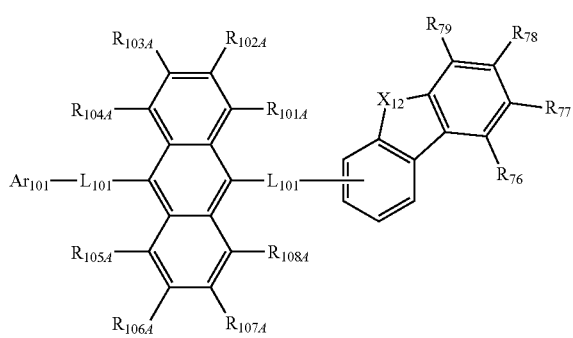
(16)

wherein in formula (12A), the atomic bonding * is bonded to one of $R_{72A}$ to $R_{79A}$;
$L_{101}$ and $Ar_{101}$ are as defined in the formula (11);
$R_{101A}$ to $R_{108A}$ are independently a hydrogen atom, or a substituted or unsubstituted aryl group including 6 to 50 ring carbon atoms;
$X_{11}$ is O, S, or $N(R_{71})$;
$R_{71}$ is a hydrogen atom, a substituted or unsubstituted alkyl group including 1 to 50 carbon atoms, or a substituted or unsubstituted aryl group including 6 to 50 ring carbon atoms;
one or more pair of two or more adjacent among $R_{72A}$ to $R_{79A}$ may form a substituted or unsubstituted, saturated or unsaturated ring, and two adjacent among $R_{72A}$ to $R_{79A}$ form a ring represented by the following formula (12A-1);
$R_{72A}$ to $R_{79A}$ that do not form a substituted or unsubstituted, saturated or unsaturated ring are independently a hydrogen atom, a substituted or unsubstituted alkyl group including 1 to 50 carbon atoms, or a substituted or unsubstituted aryl group including 6 to 50 ring carbon atoms:

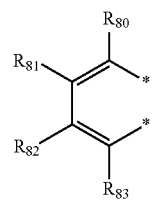
(12A-1)

wherein in the formula (12A-1), each of the two atomic bondings * are bonded to two adjacent among $R_{72A}$ to $R_{79A}$;
one of $R_{80}$ to $R_{83}$ is an atomic bonding that is bonded to $L_{101}$;
$R_{80}$ to $R_{83}$ that are not bonded to $L_{101}$ are independently a hydrogen atom, a substituted or unsubstituted alkyl group including 1 to 50 carbon atoms, or a substituted or unsubstituted aryl group including 6 to 50 ring carbon atoms.

Specific examples of the compound represented by the formula (11) include the following compounds.
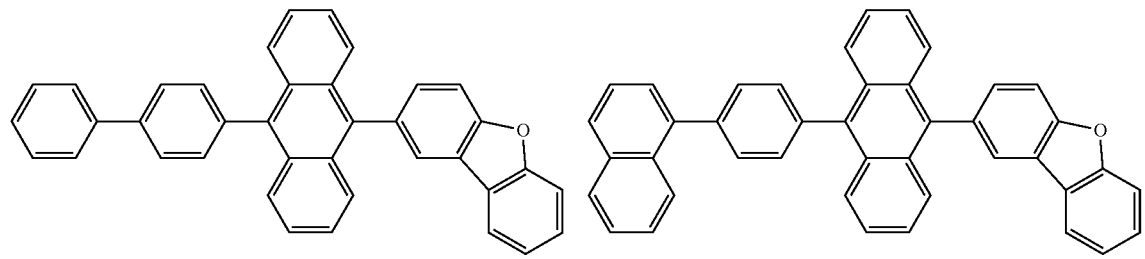
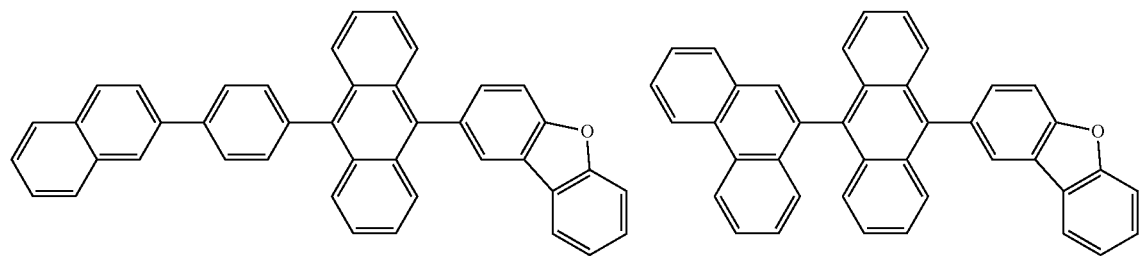
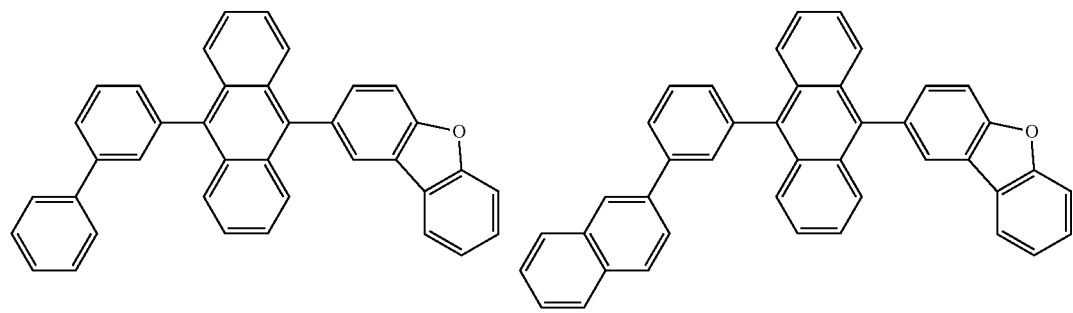
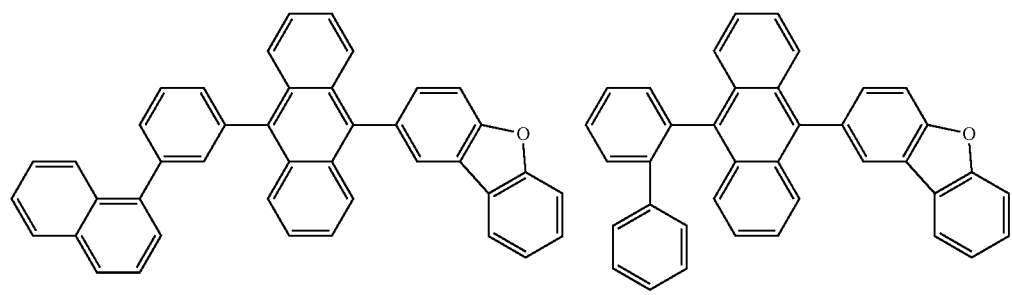
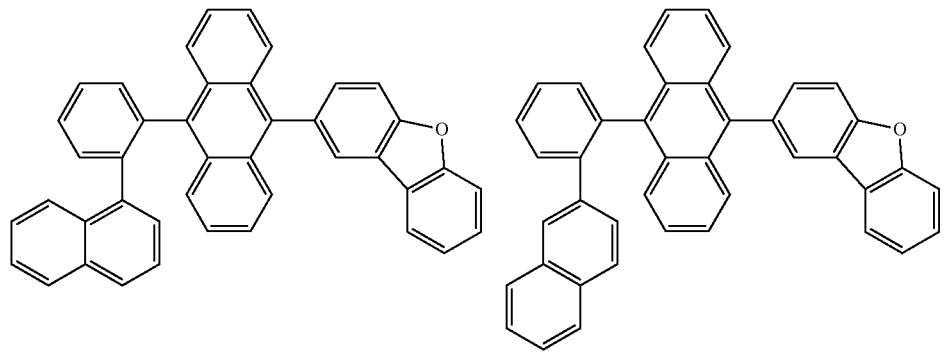

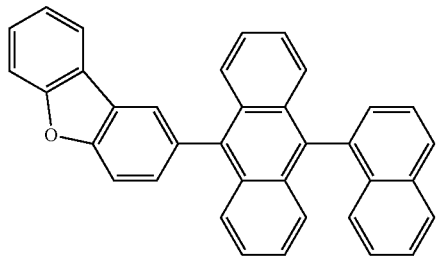
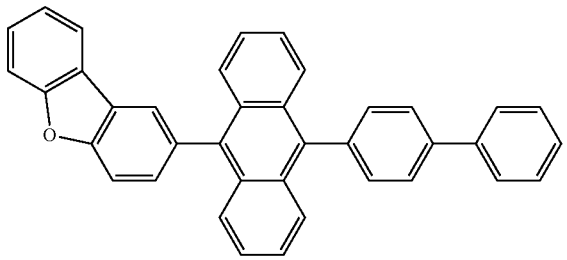
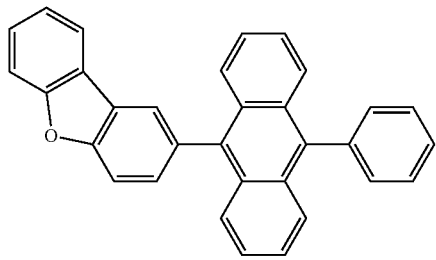
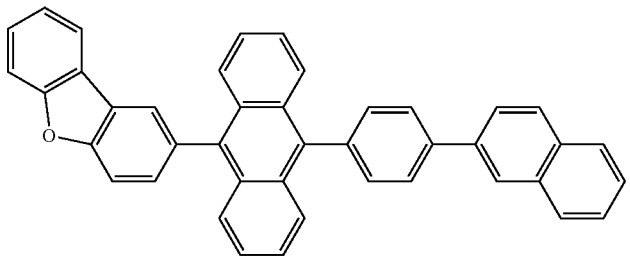
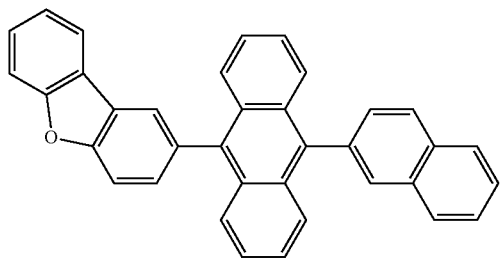
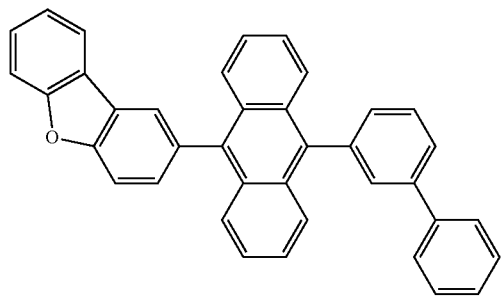
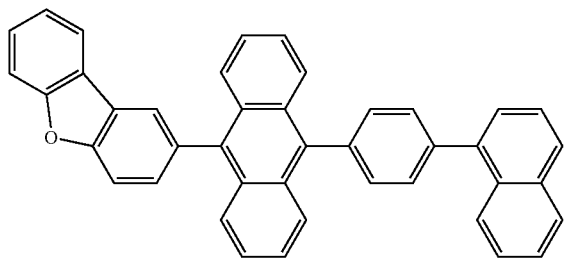
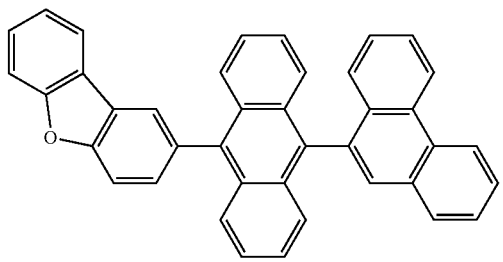
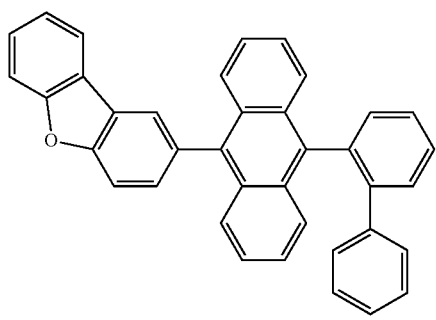
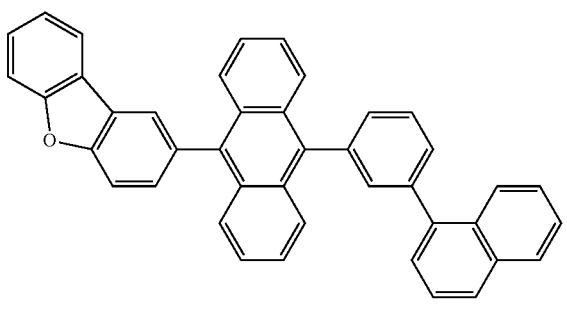

-continued
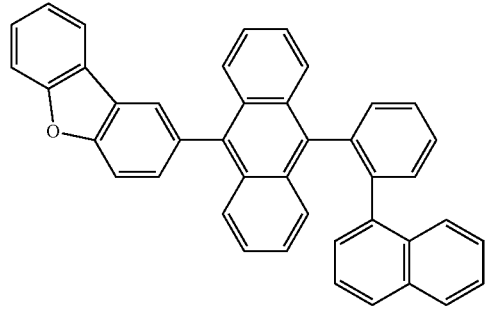
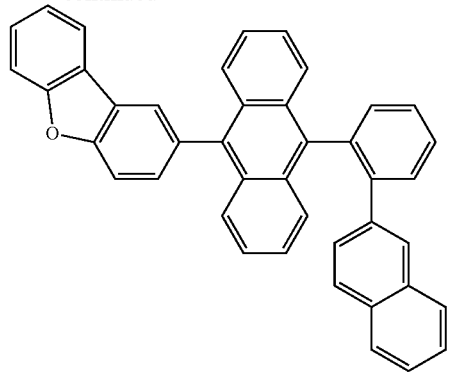
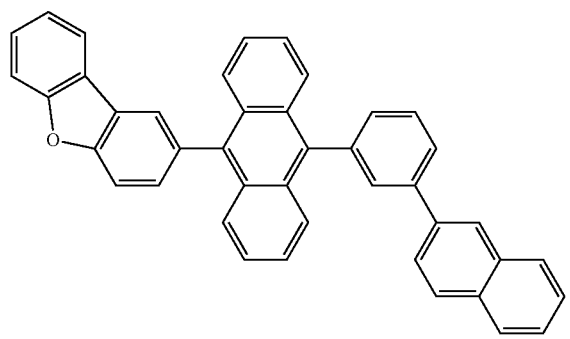
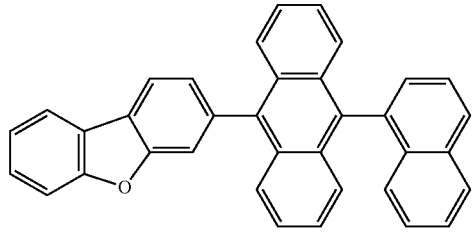
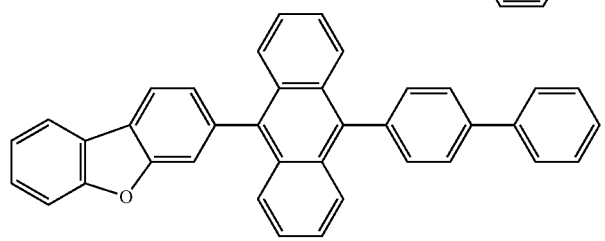
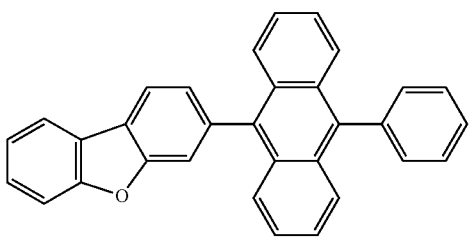
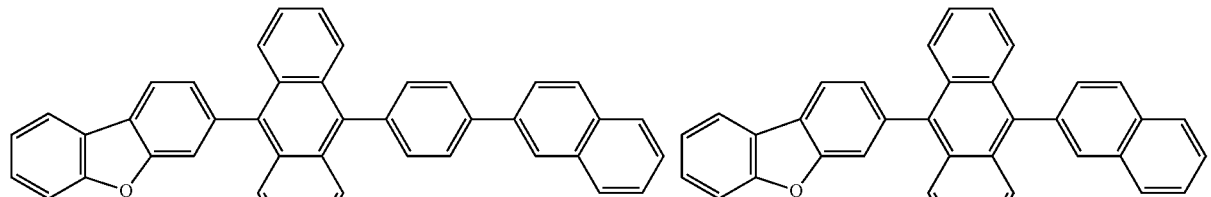
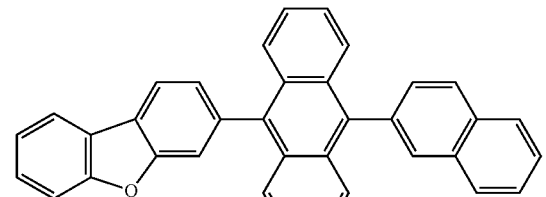
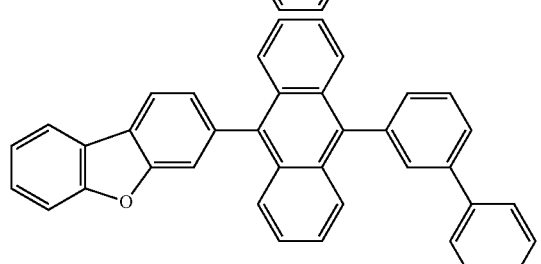
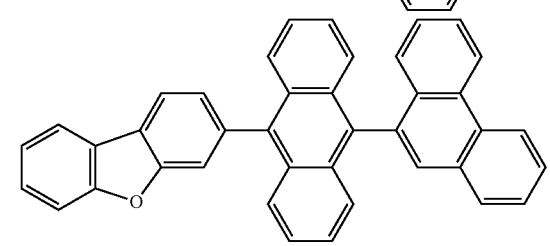
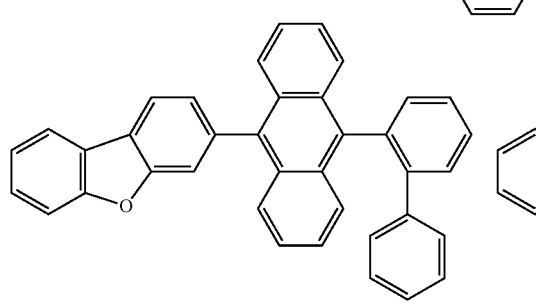
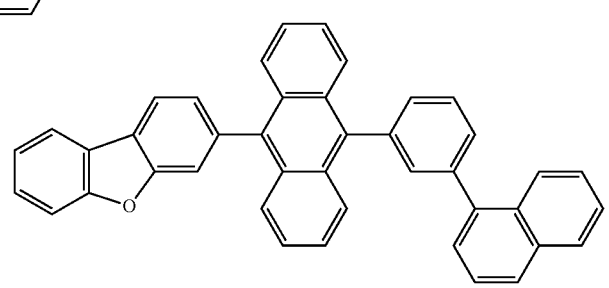

-continued
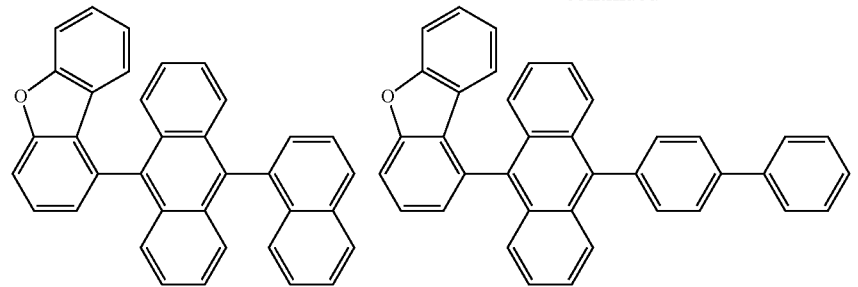
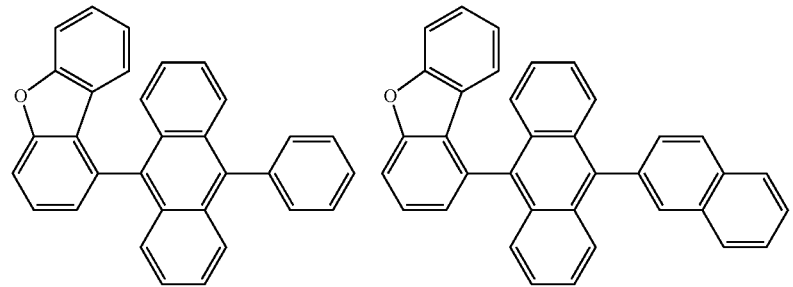
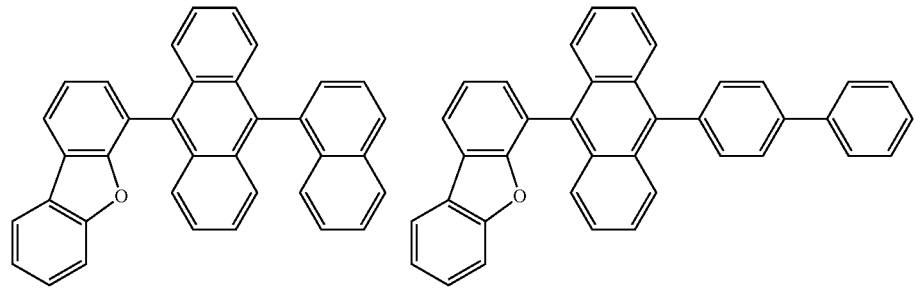
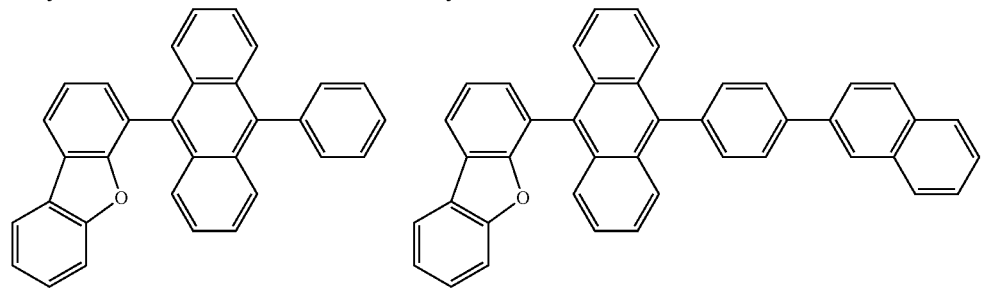
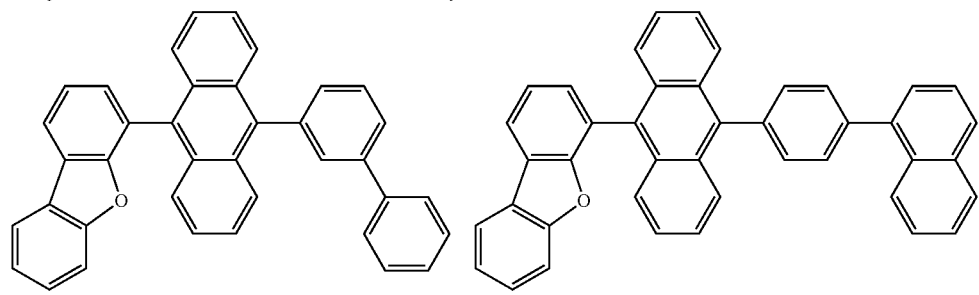
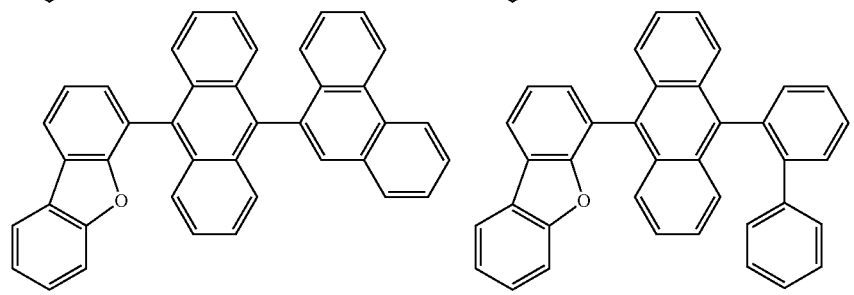

-continued
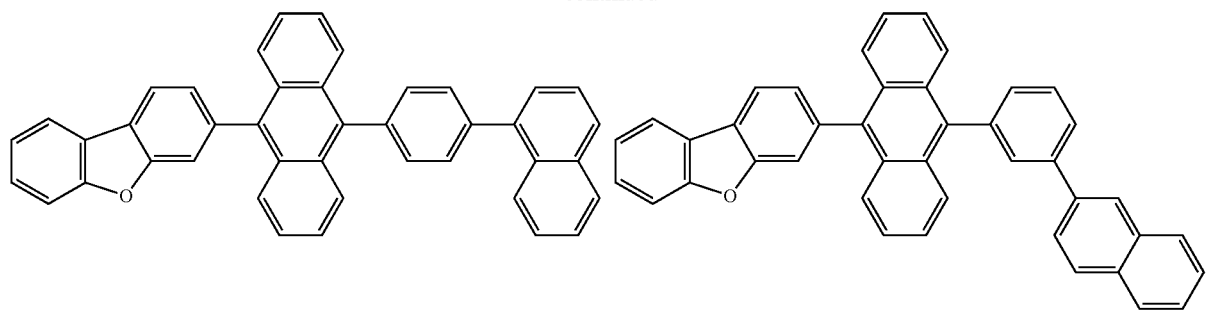
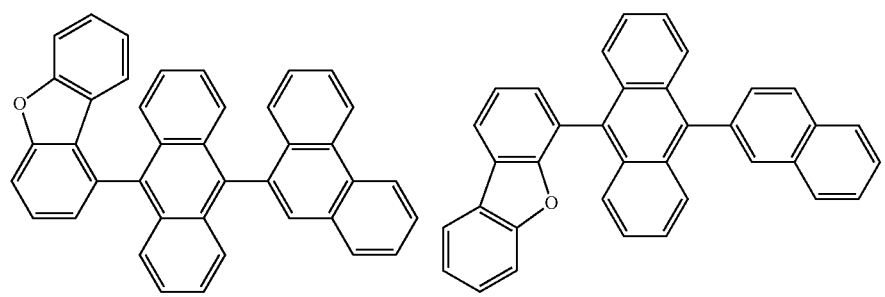
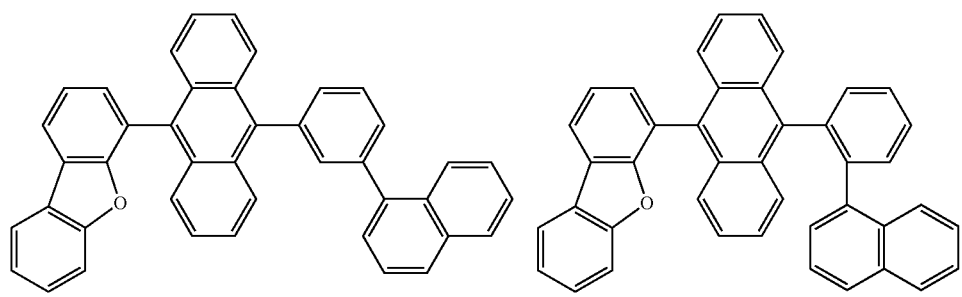
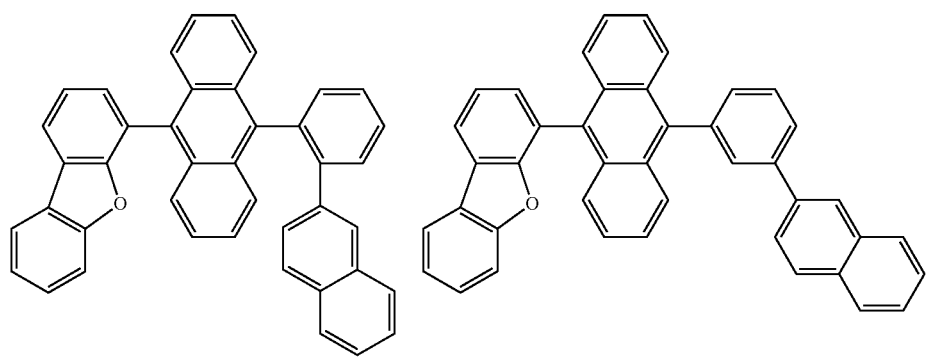
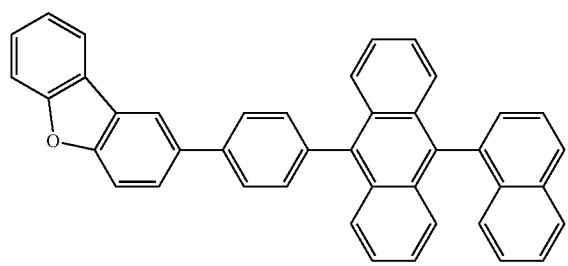

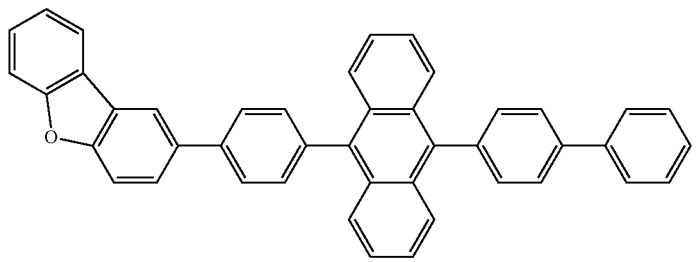
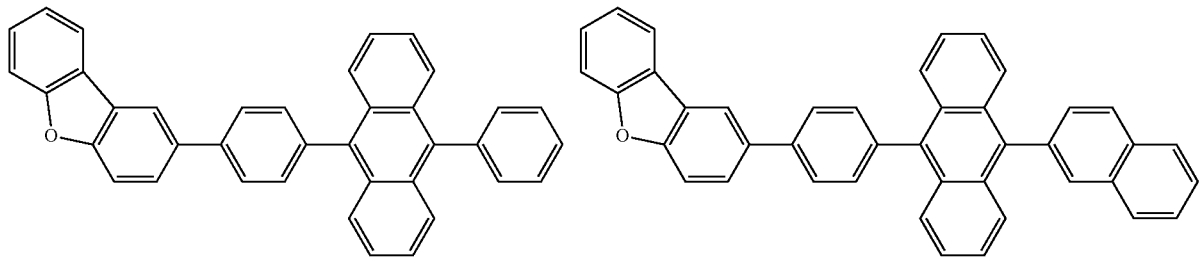
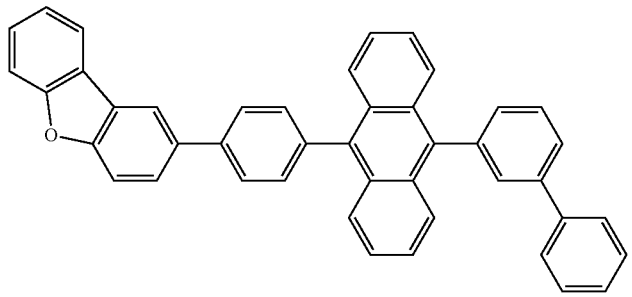
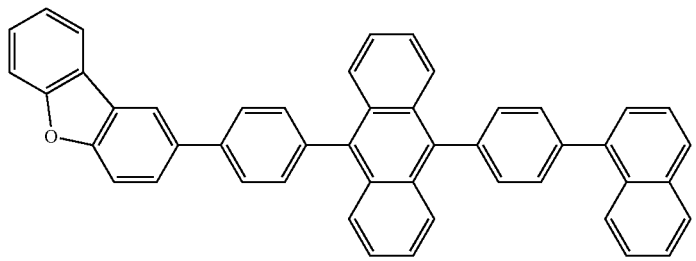
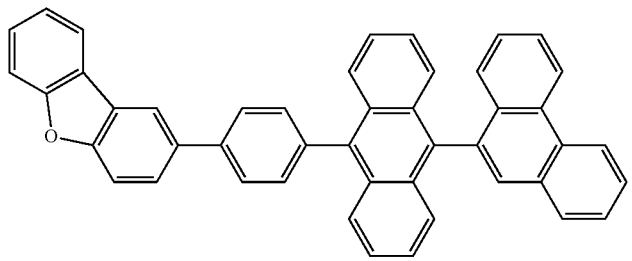
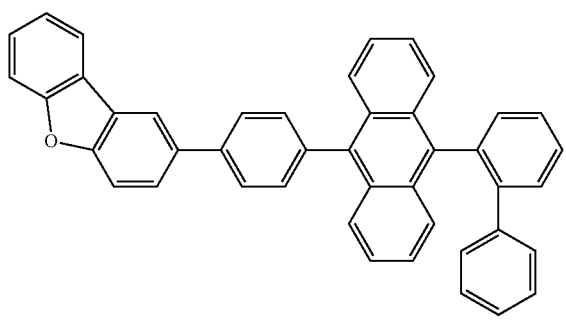

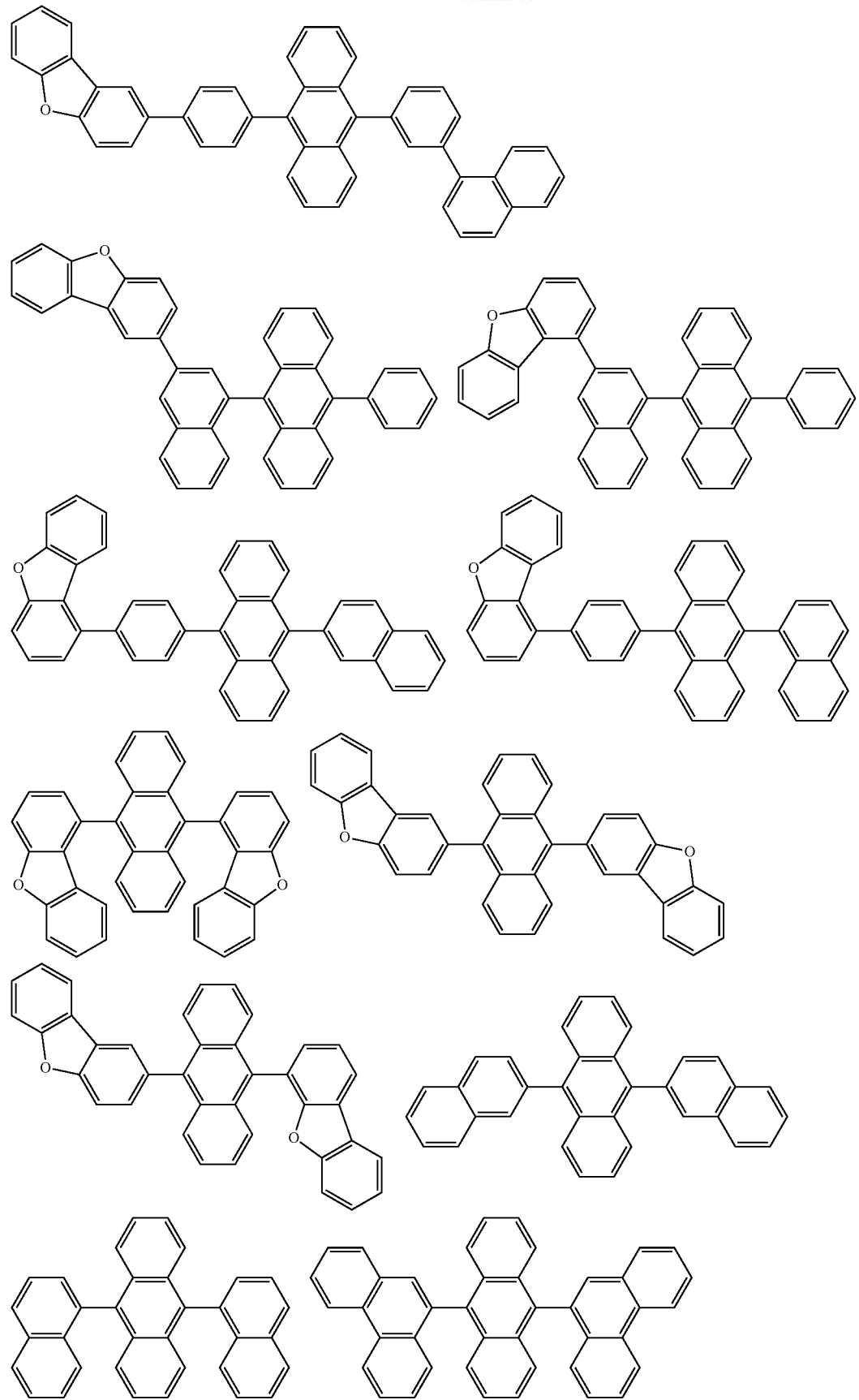

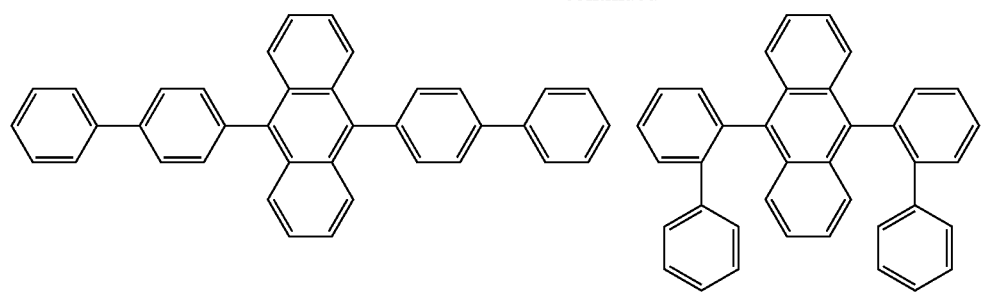
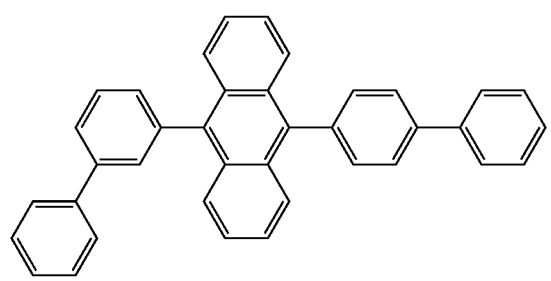
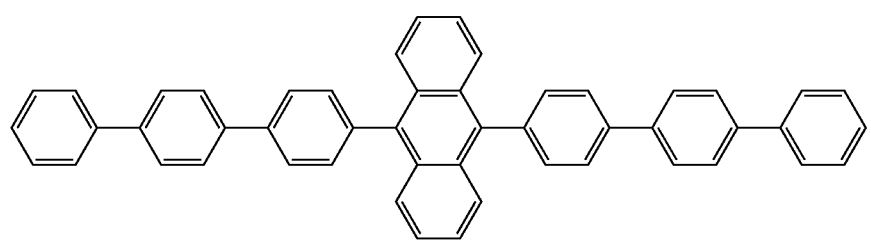
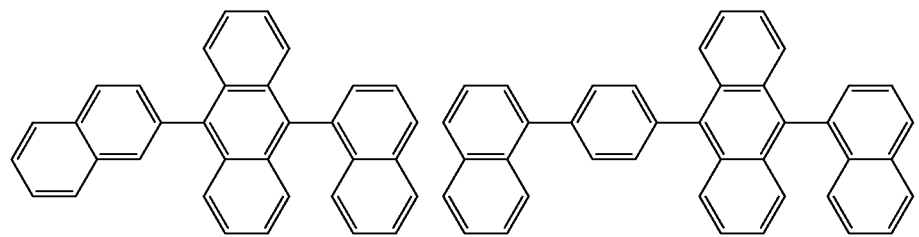
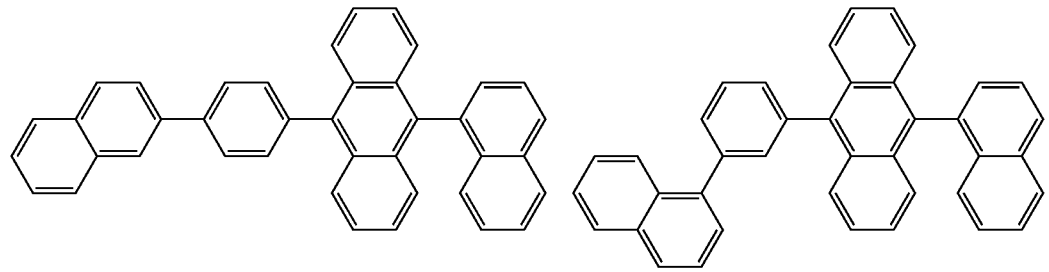
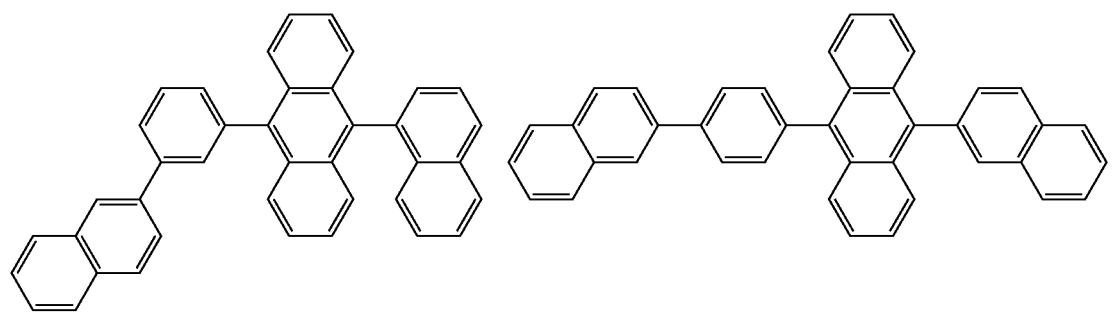

73
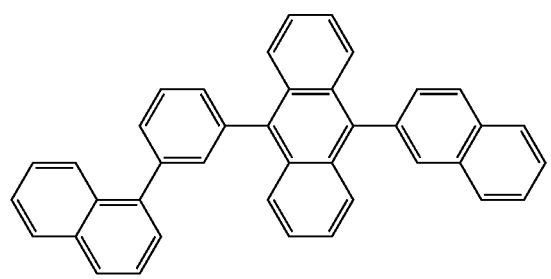
74
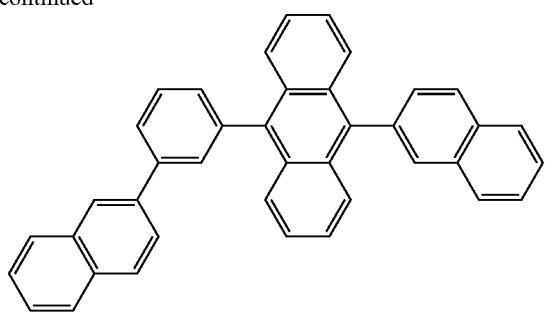
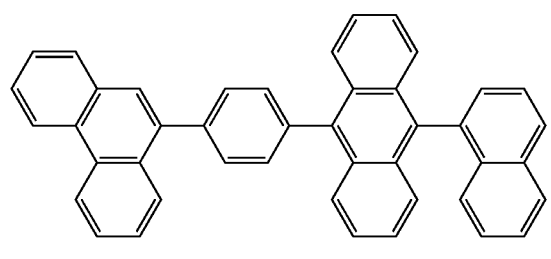
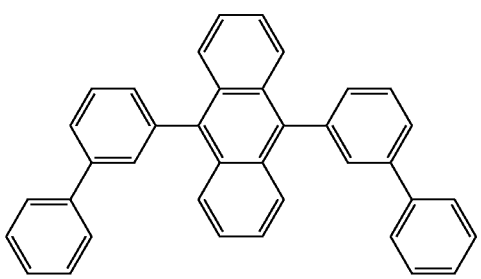
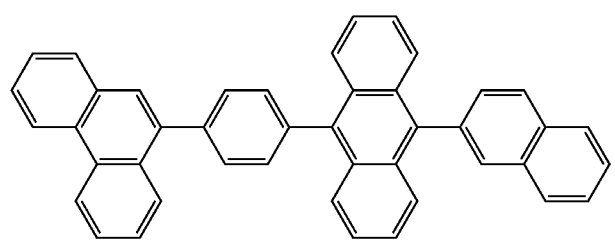
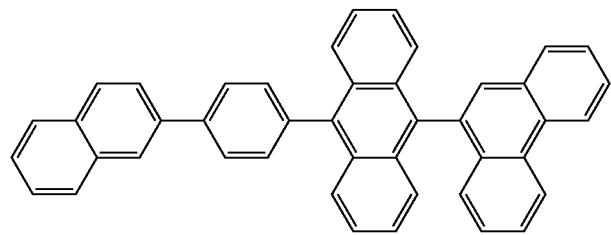
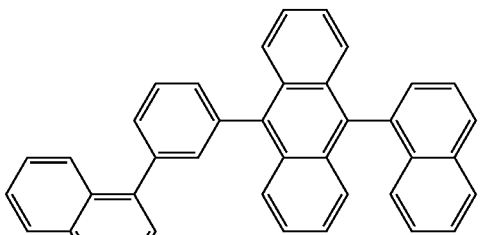
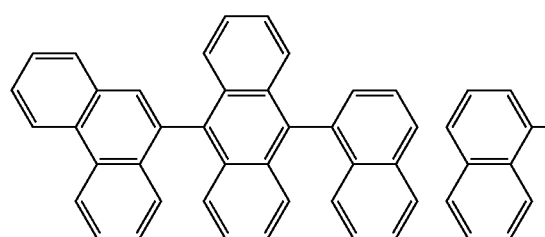
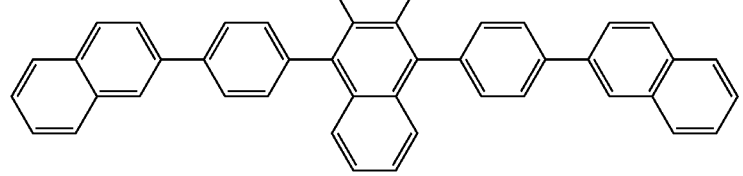

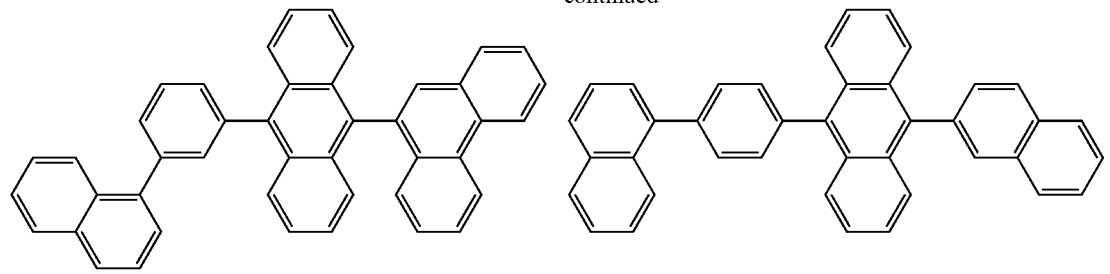
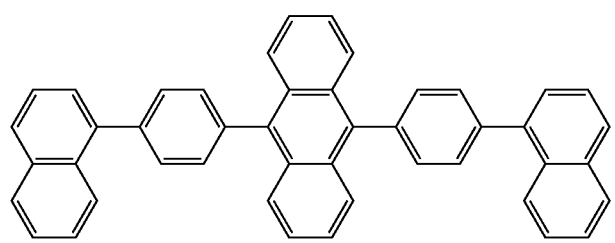
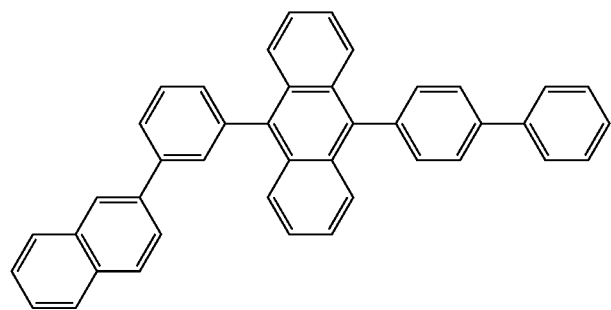
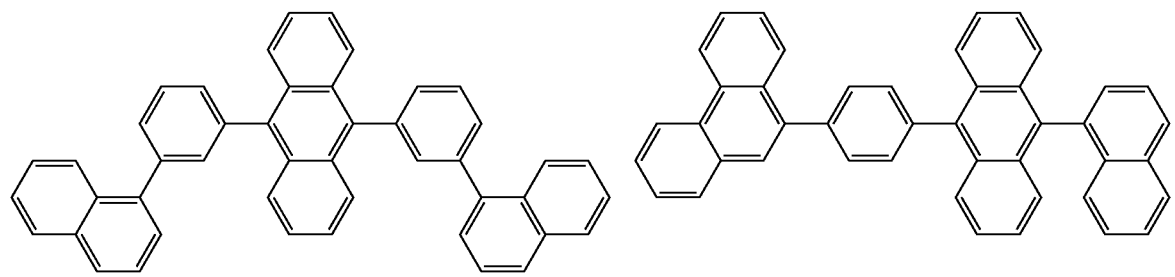
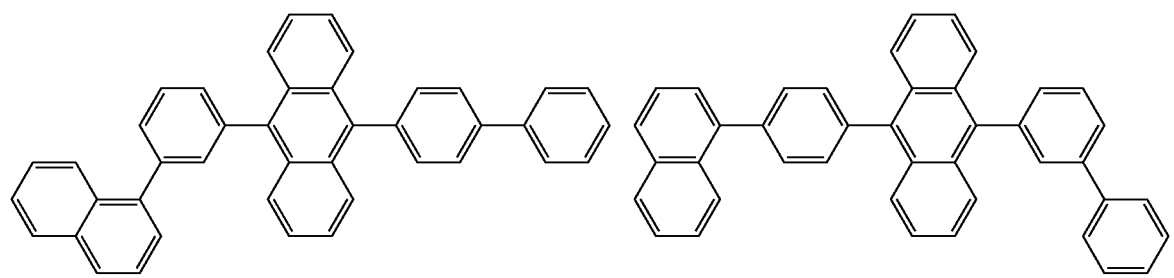

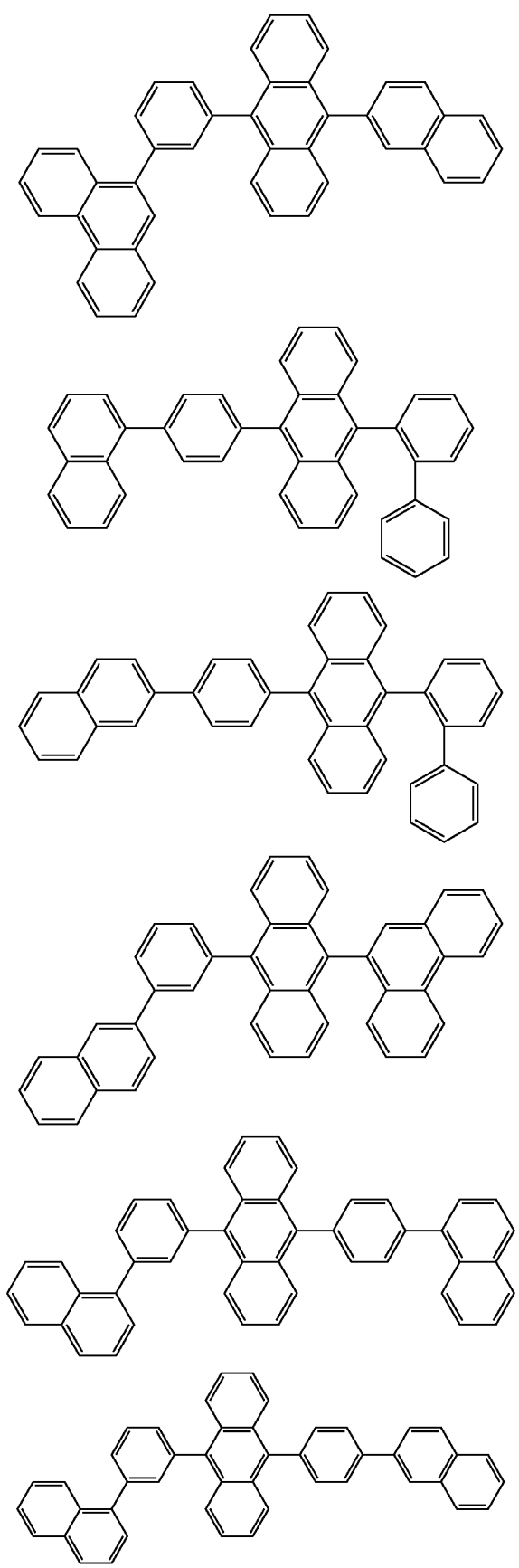
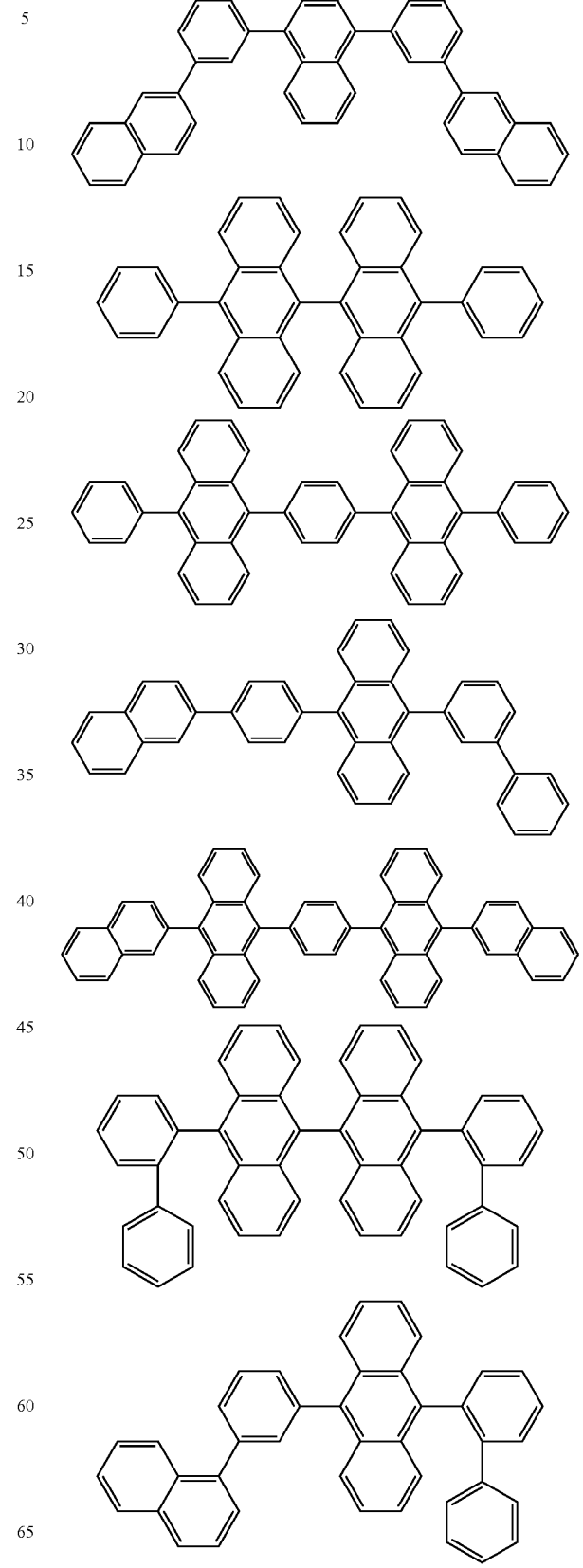

-continued
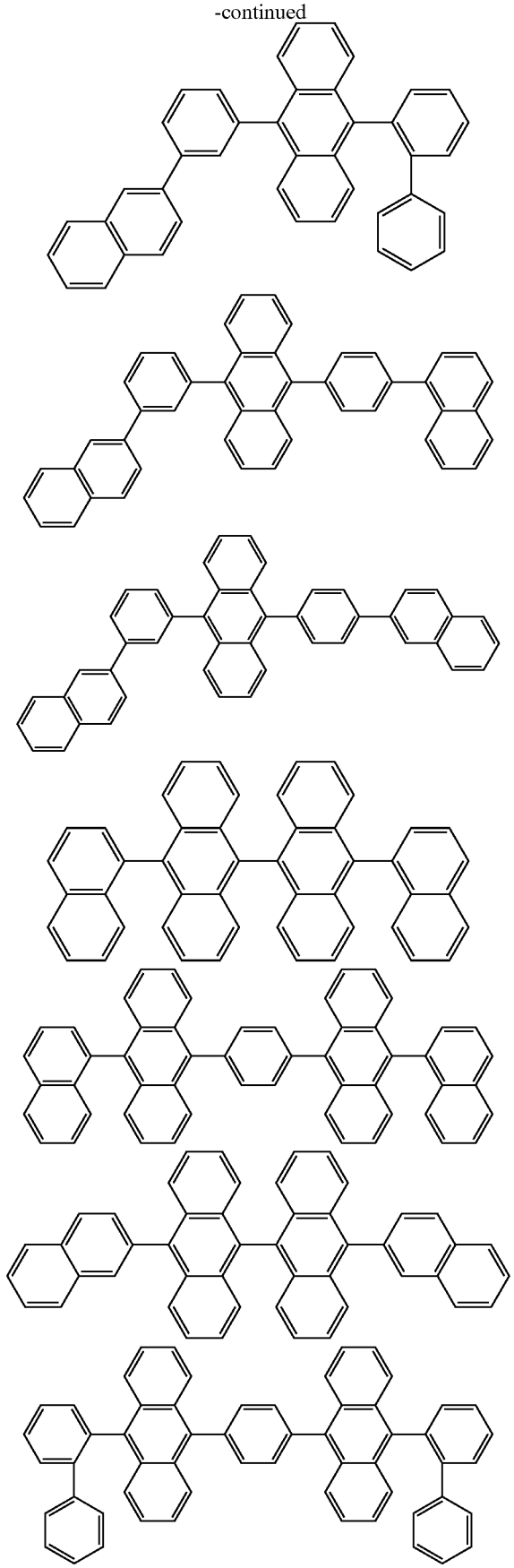
-continued
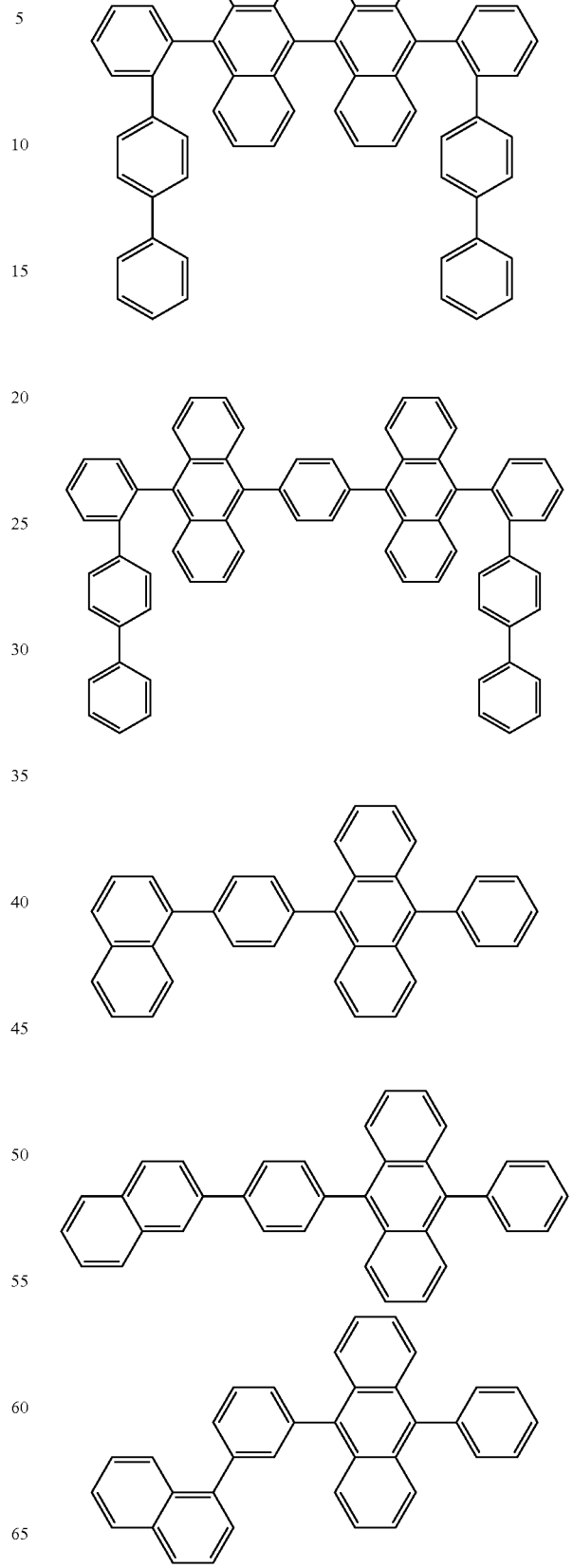

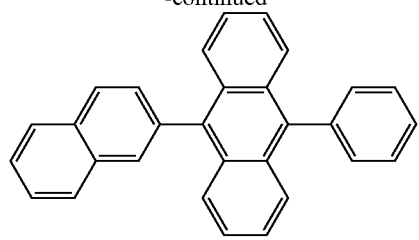
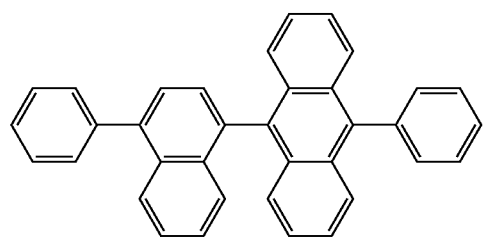
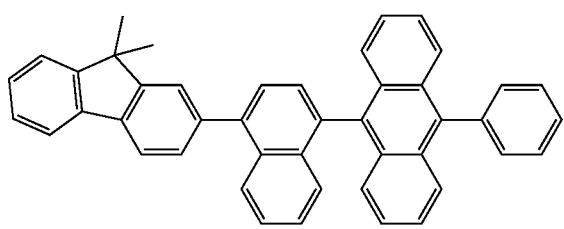
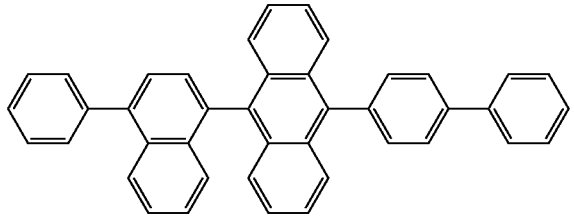
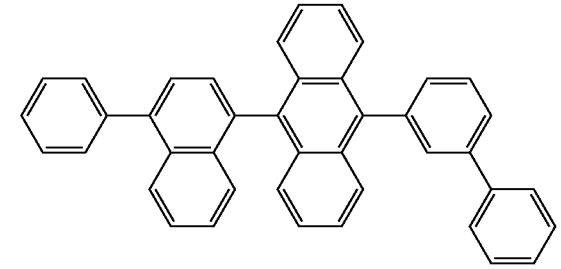
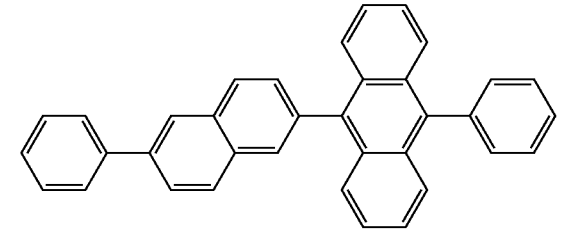
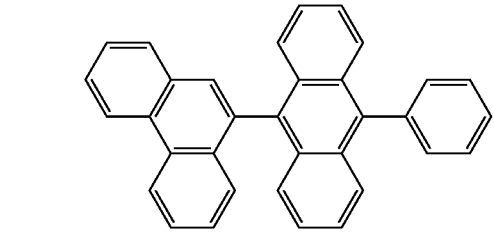
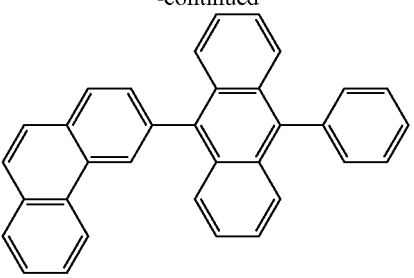
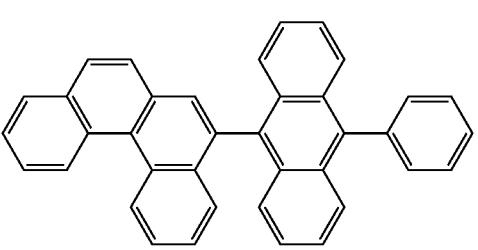
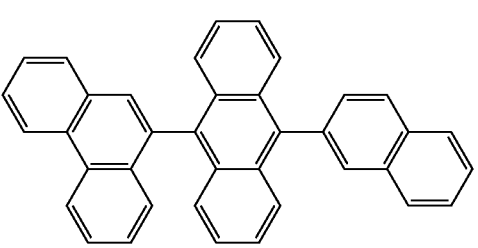
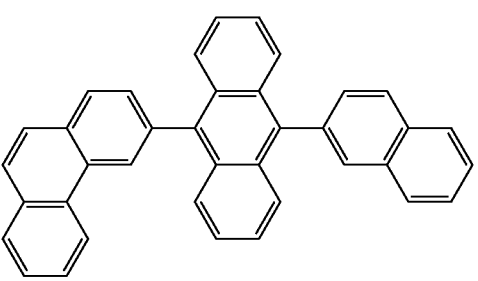
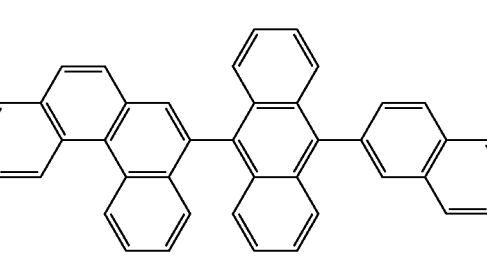
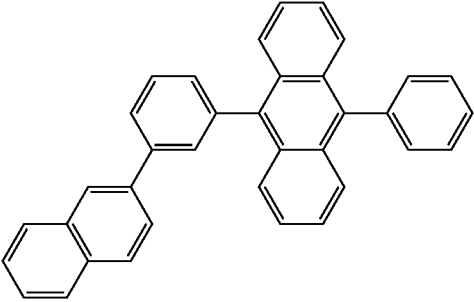

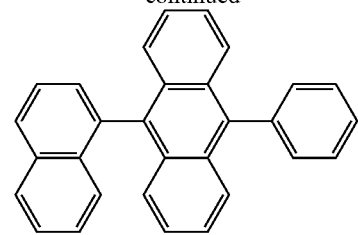
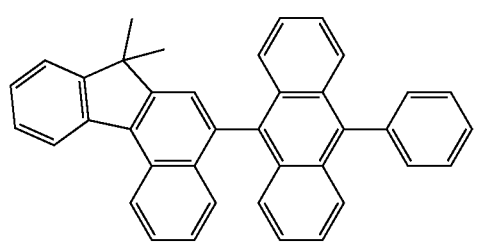
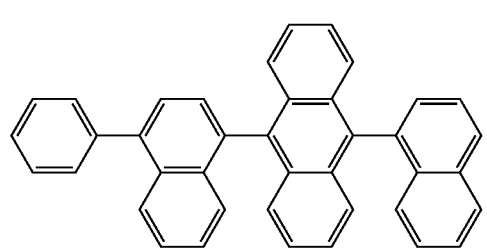
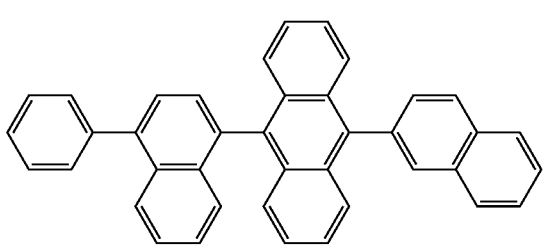
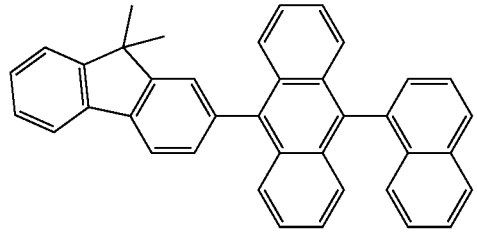
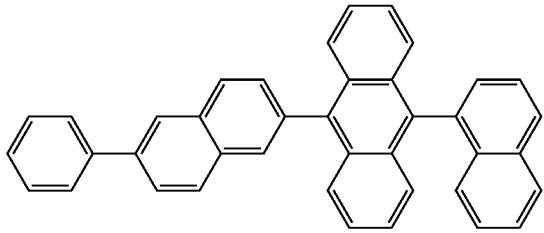
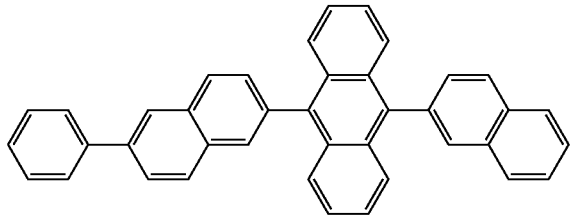
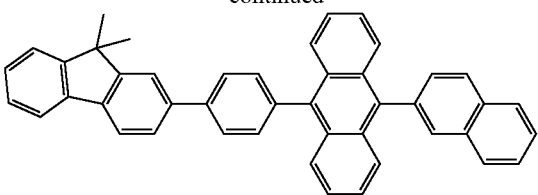
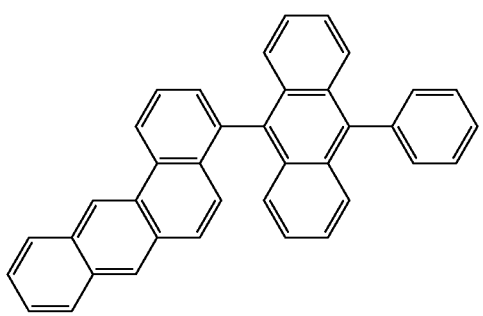
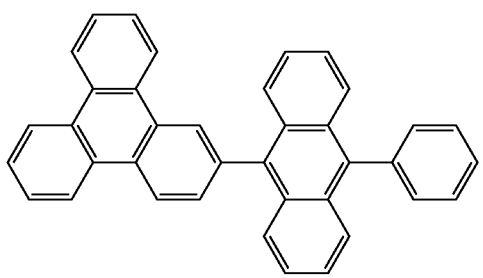
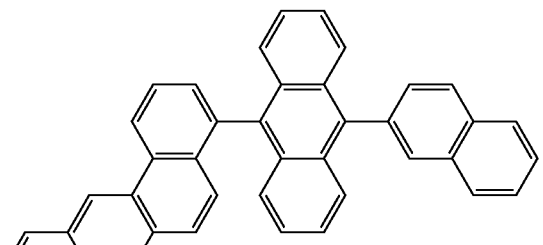
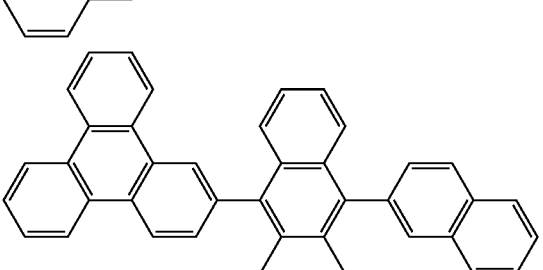
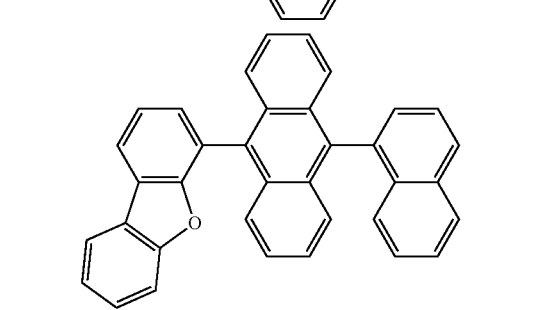

-continued
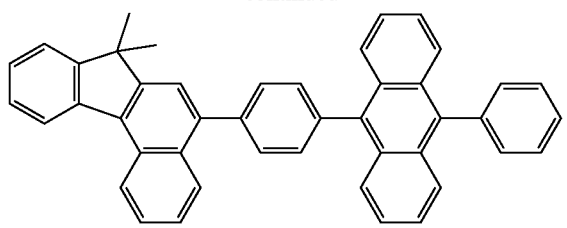
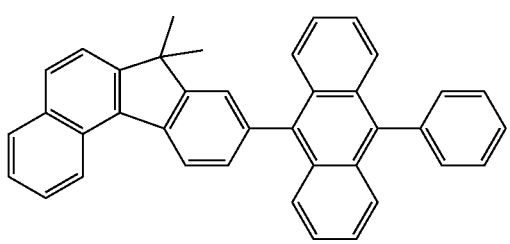
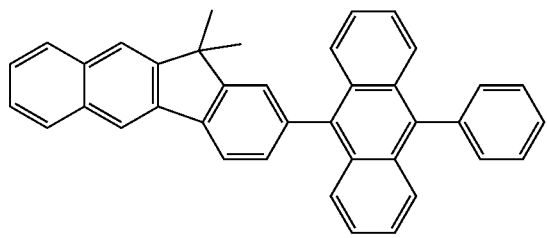
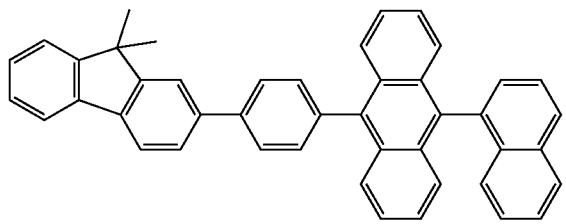
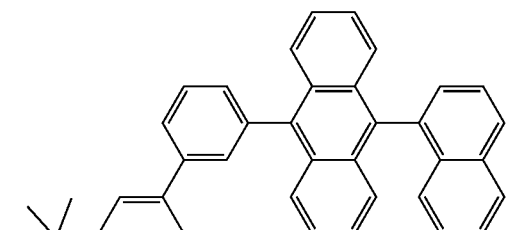
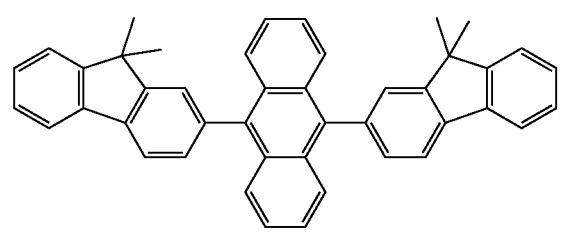
-continued
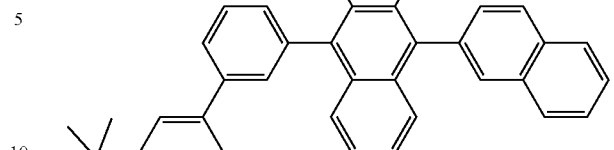
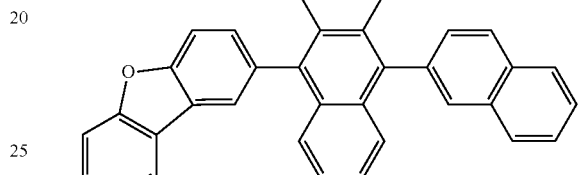
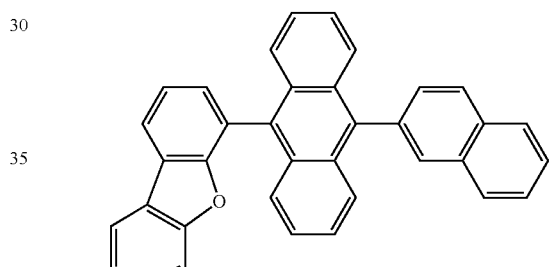
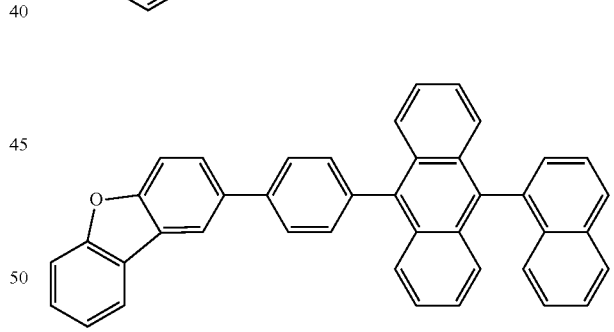
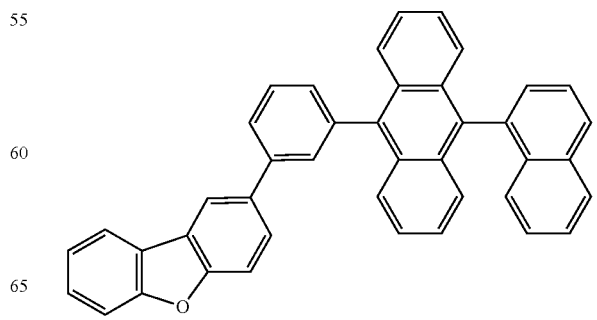

87
-continued
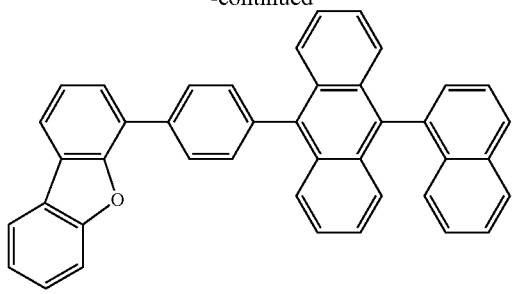
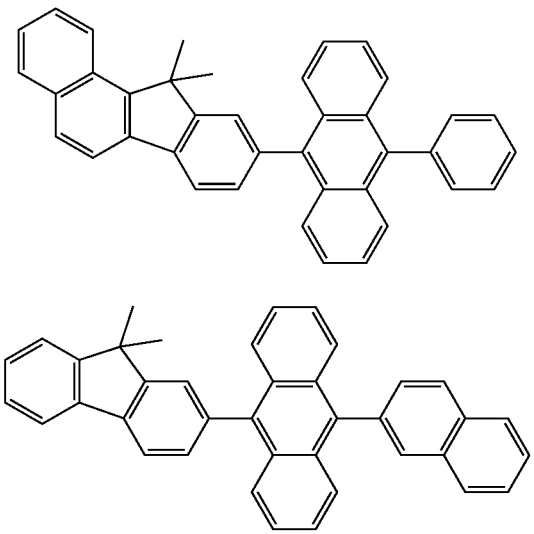
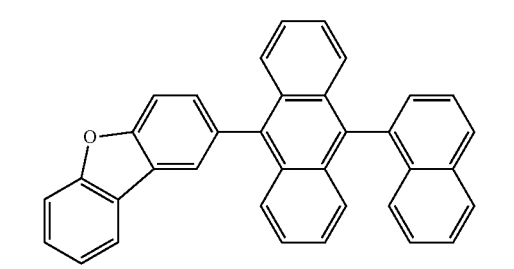
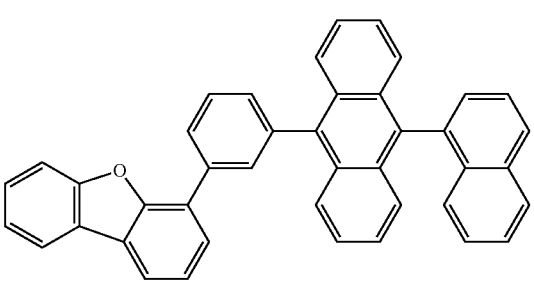
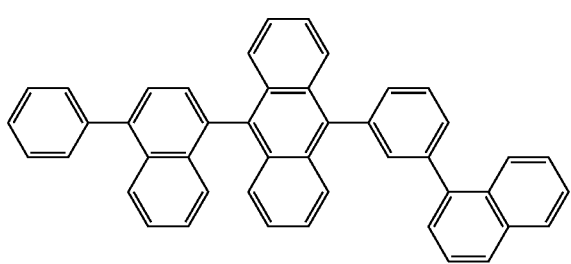
88
-continued
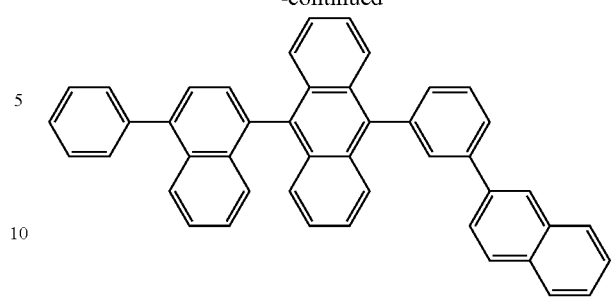
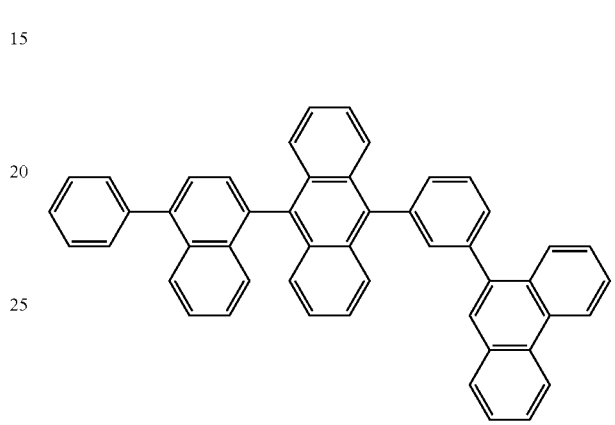
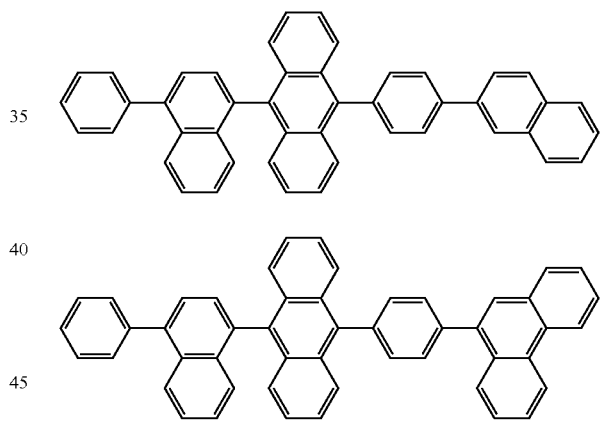
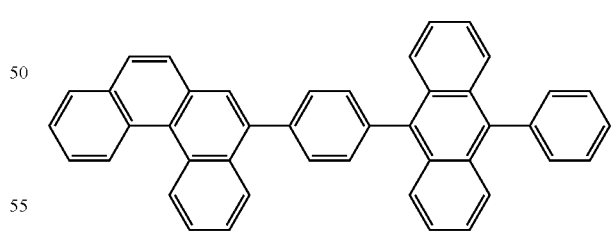
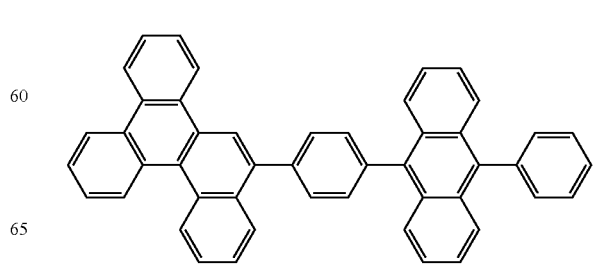

89
-continued
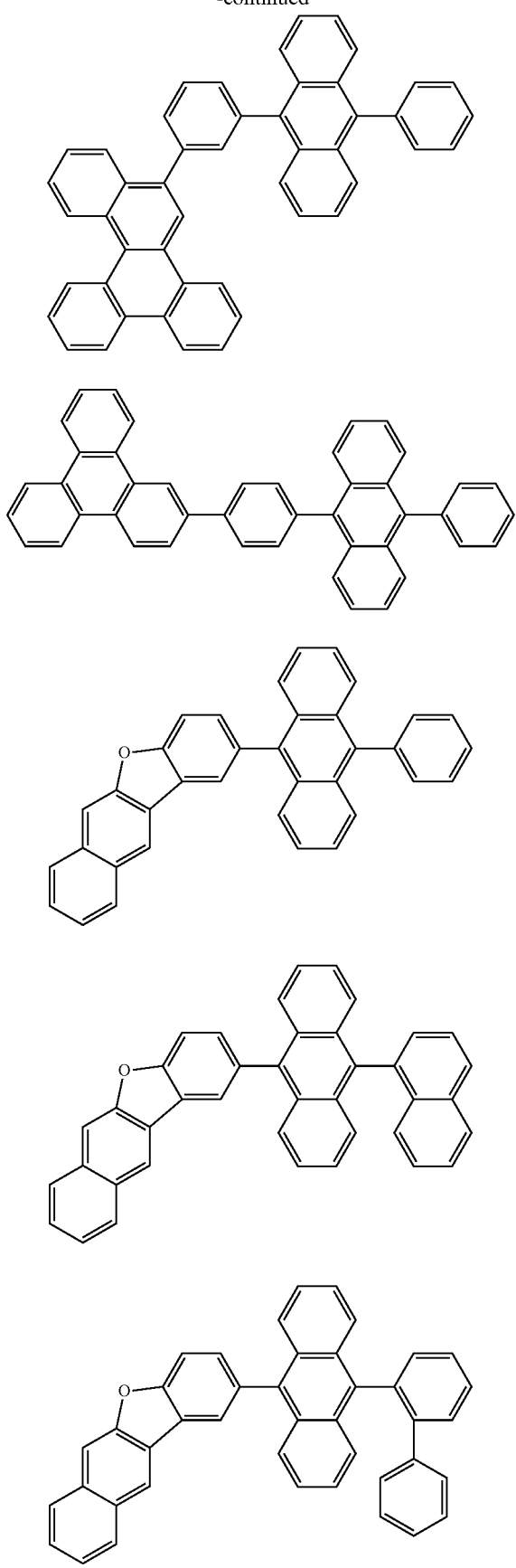
90
-continued
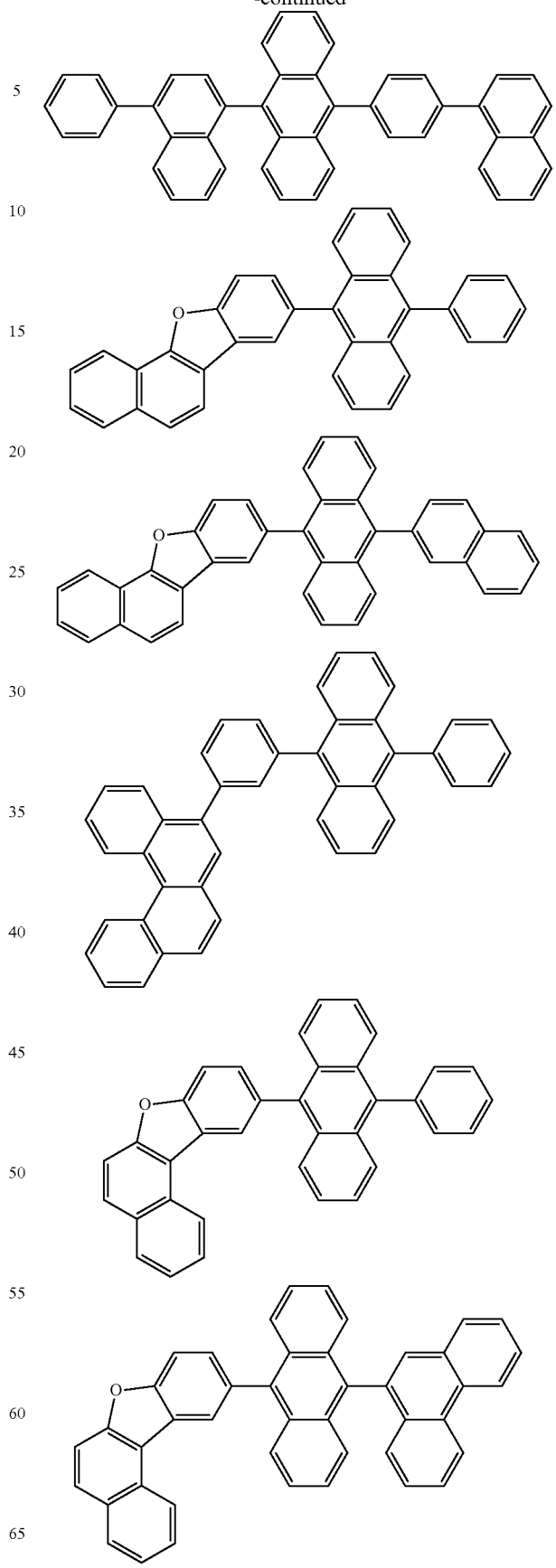

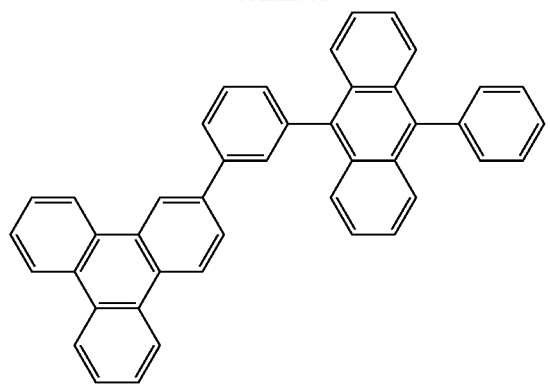
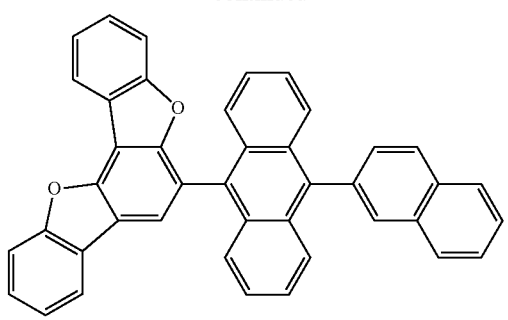
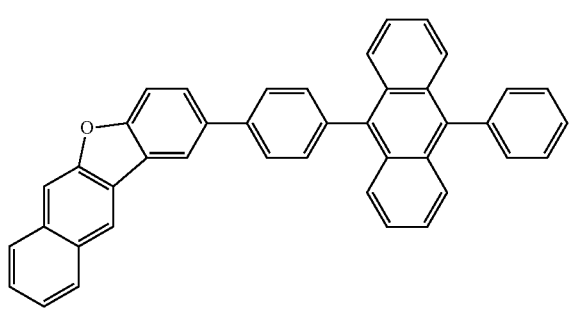
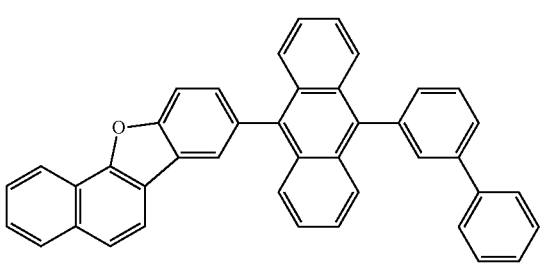
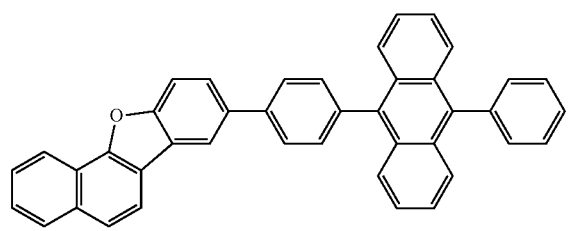
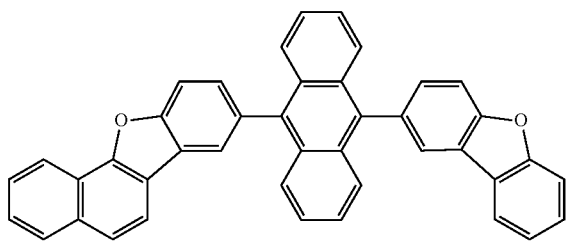
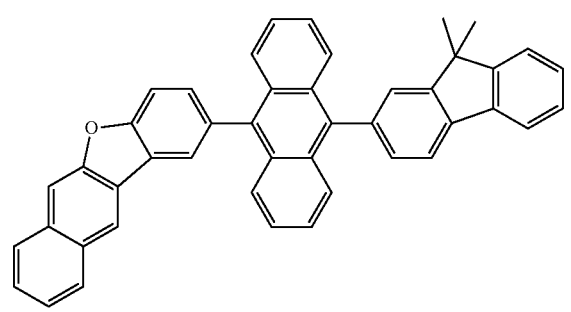
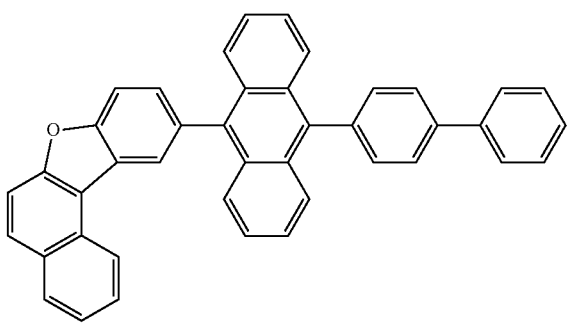
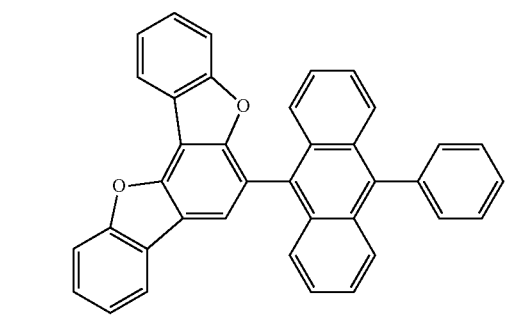
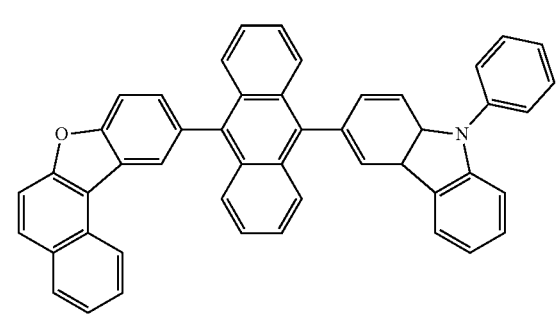

93
-continued
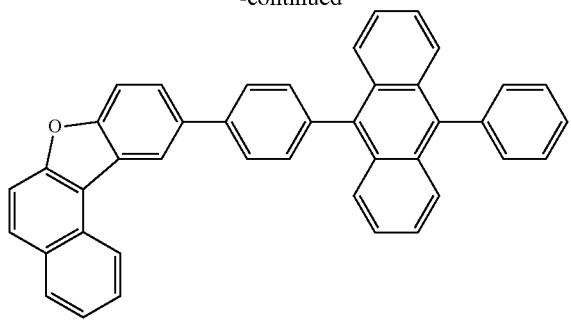
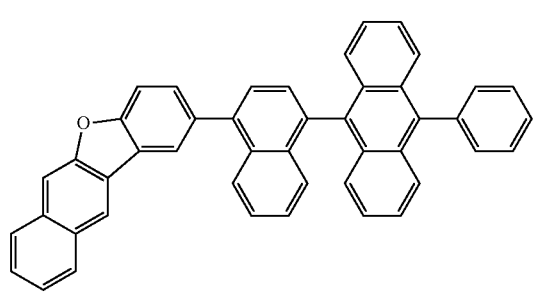
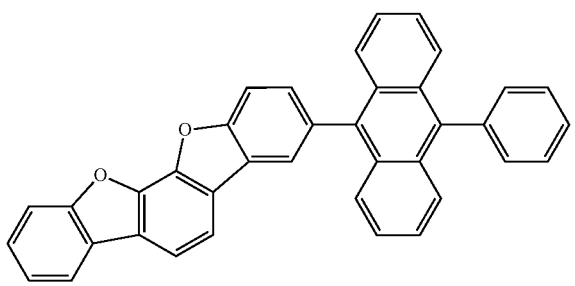
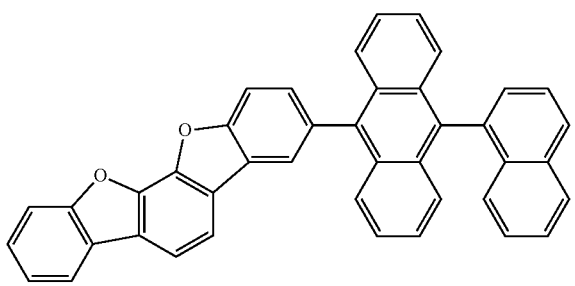
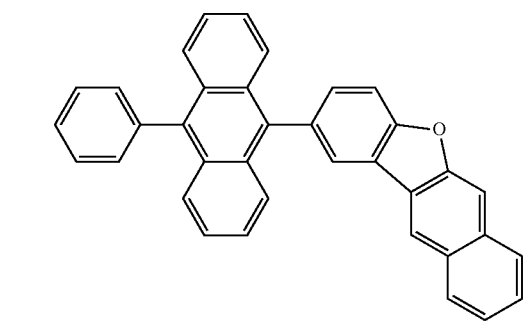
94
-continued
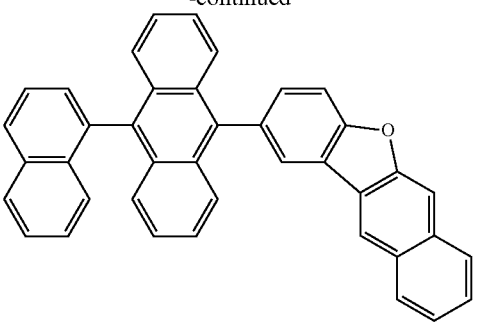
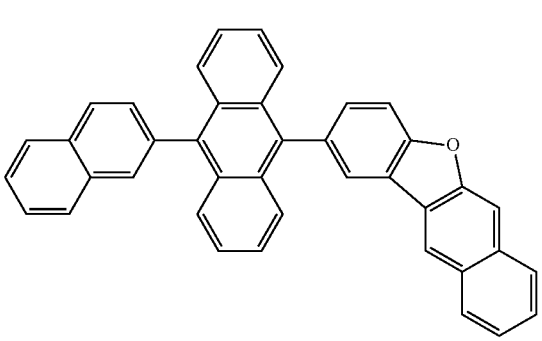
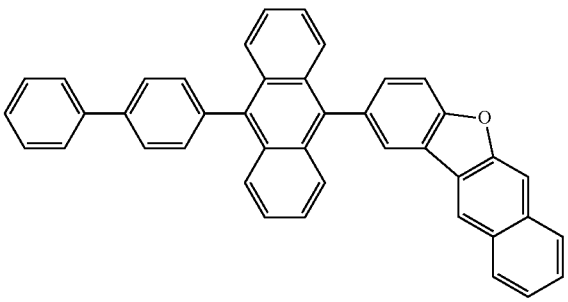
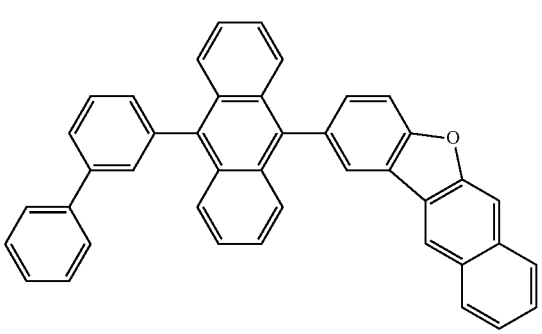
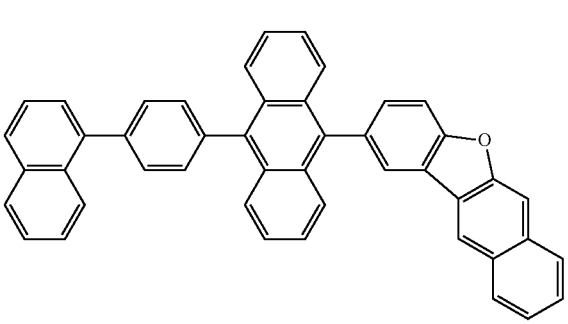

-continued
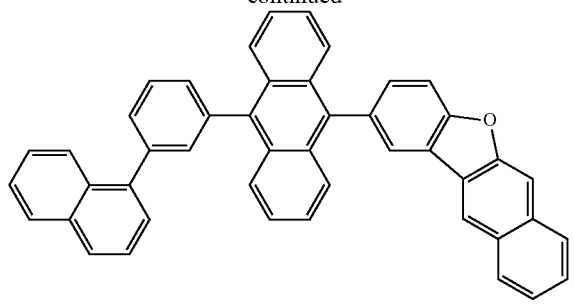
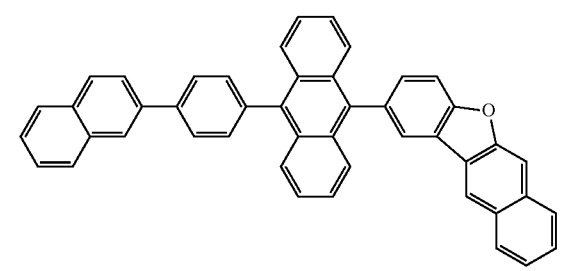
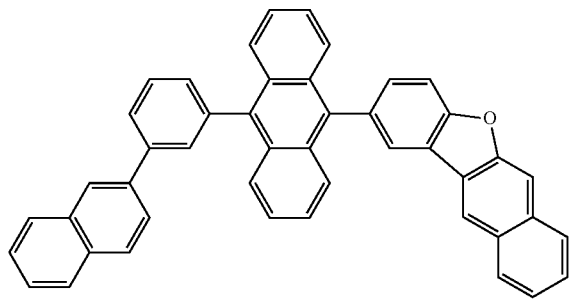
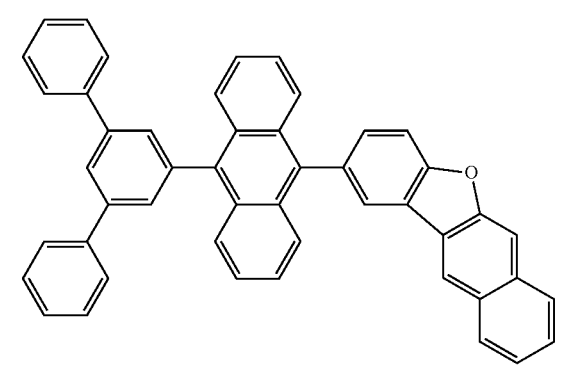
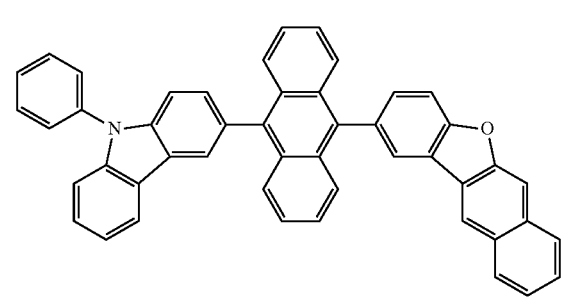
-continued
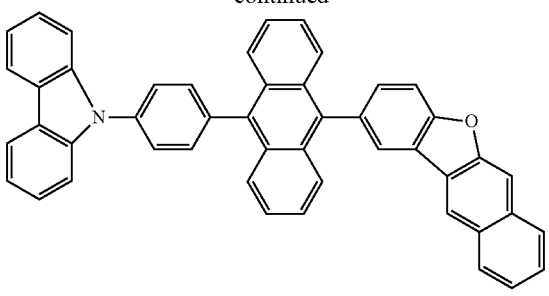
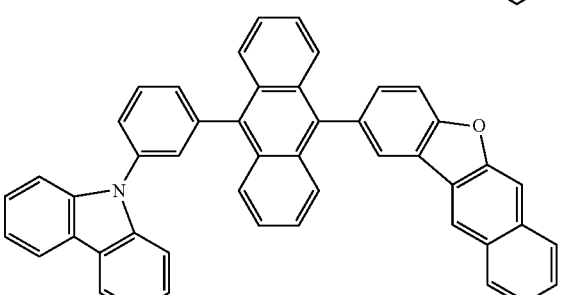
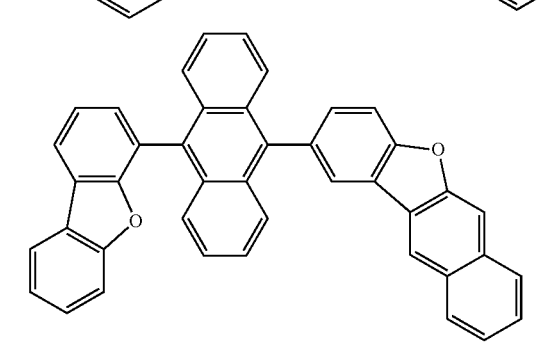
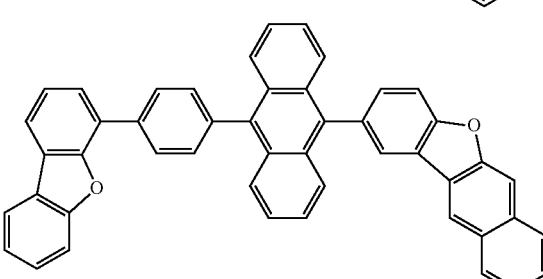
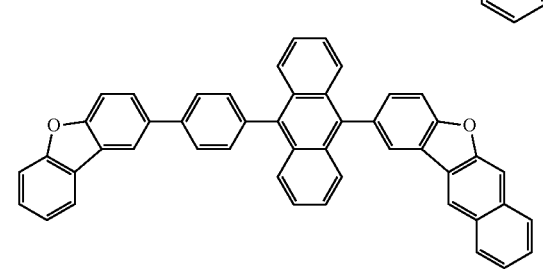
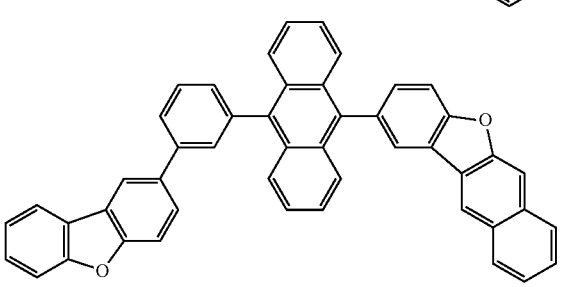

-continued
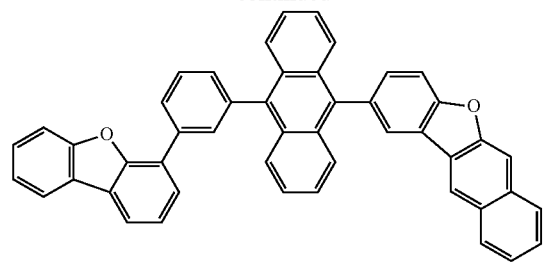
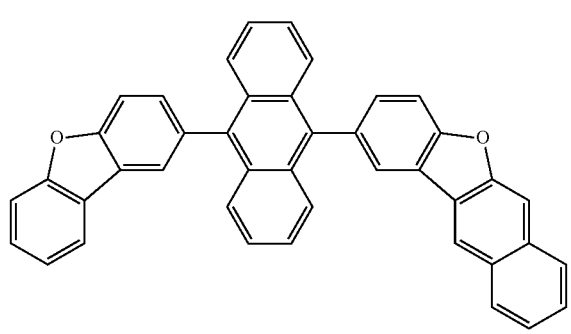
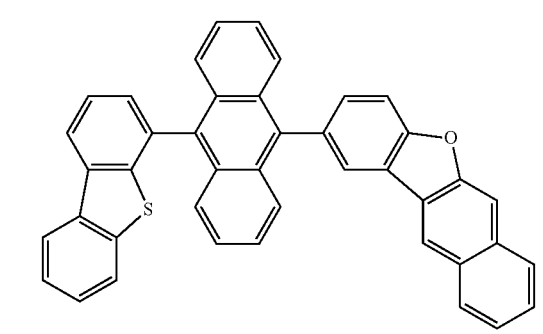
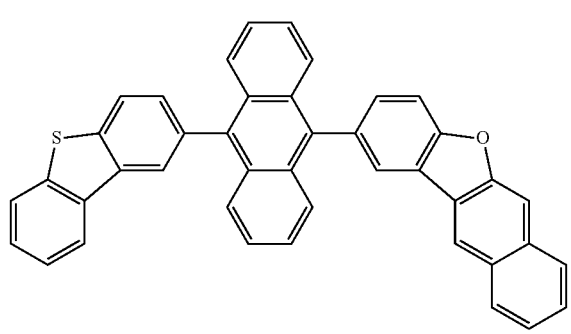
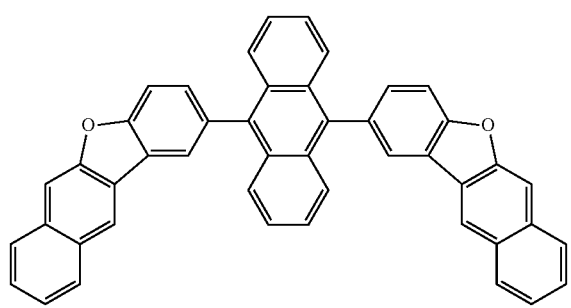
-continued
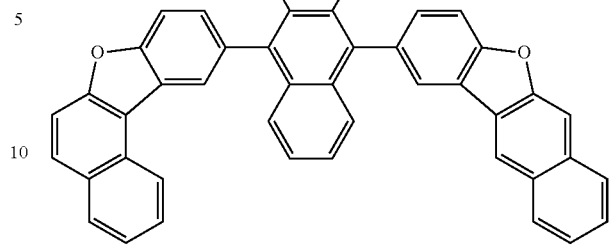
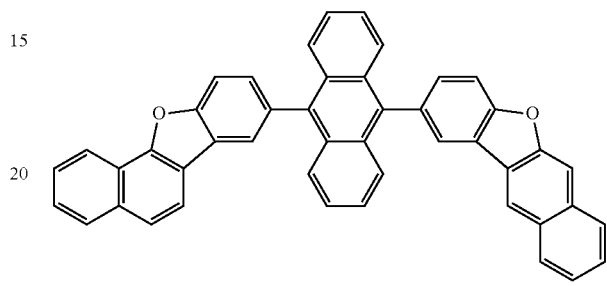
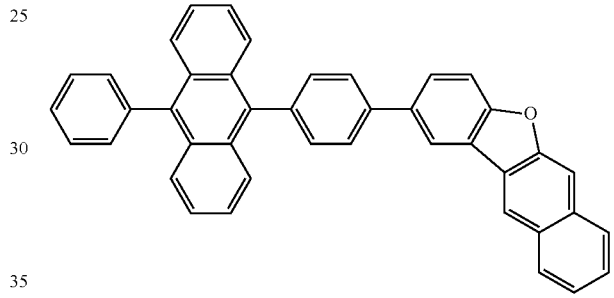
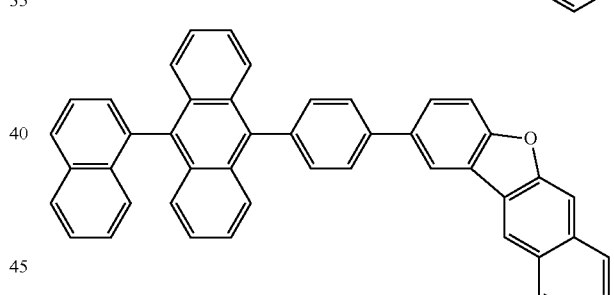
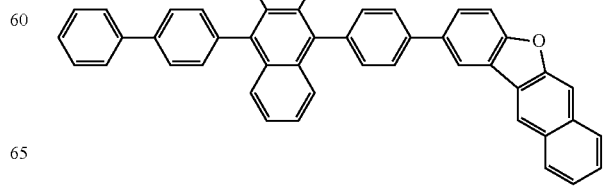

99
-continued
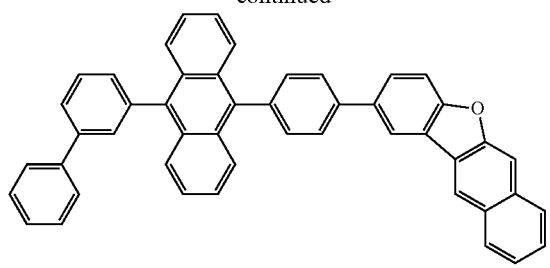
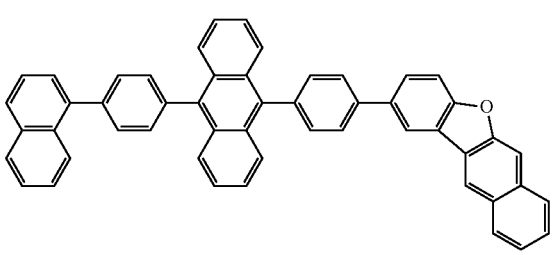
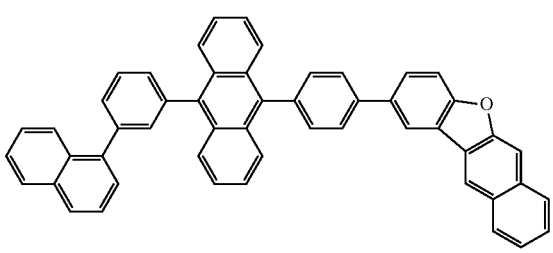
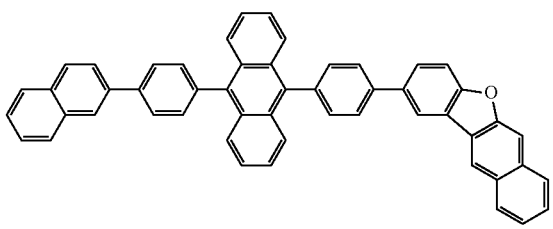
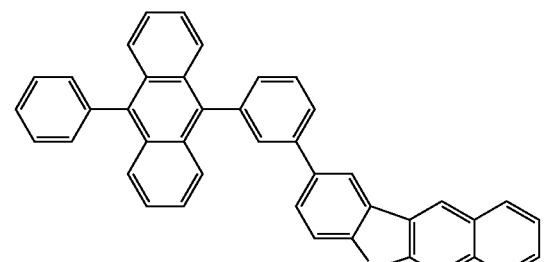
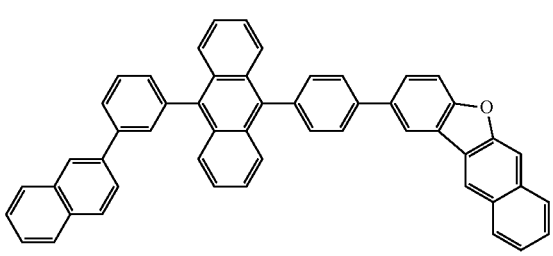
100
-continued
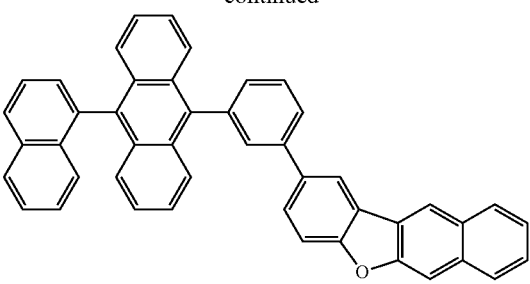
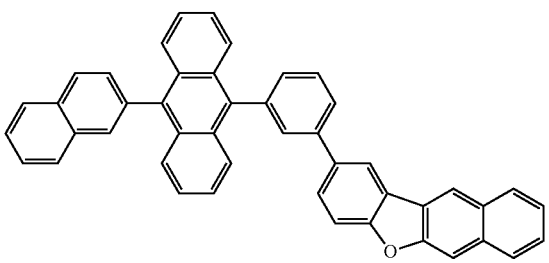
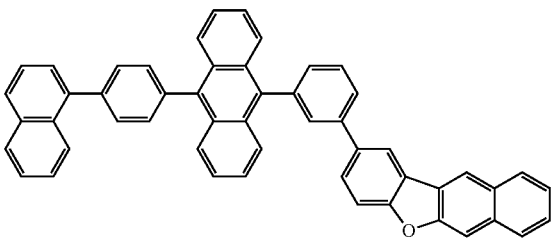
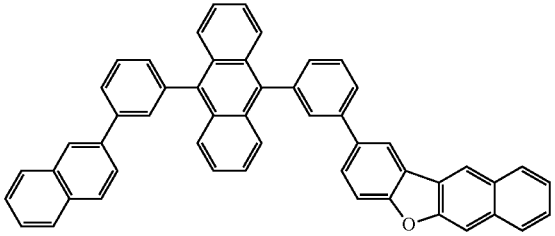
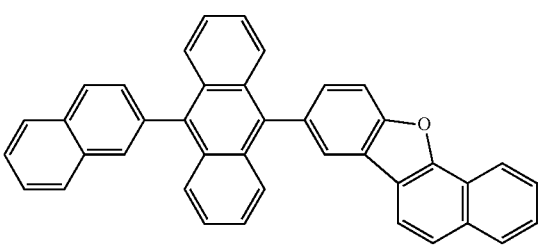
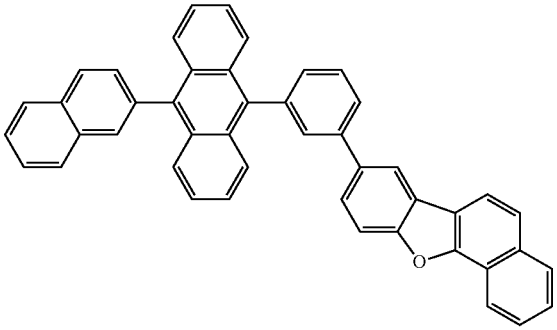

101
-continued
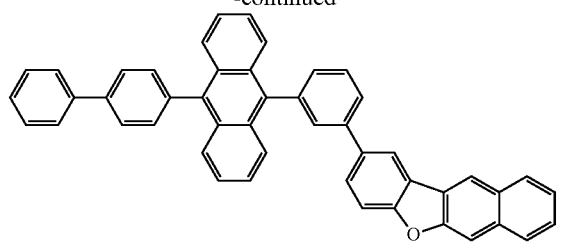
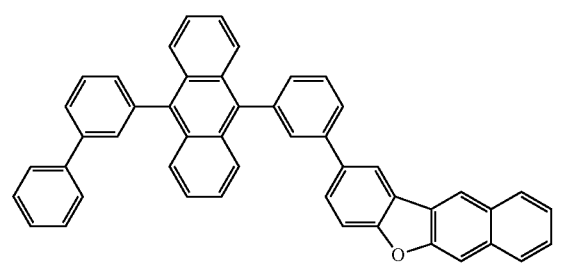
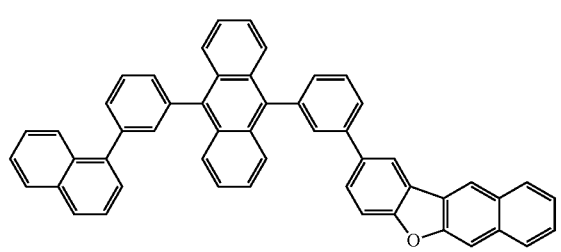
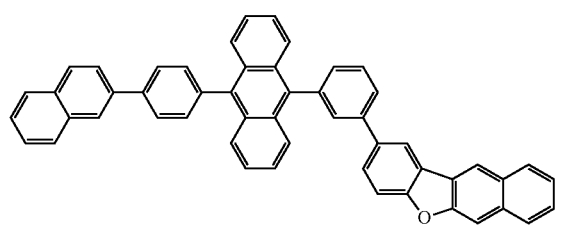
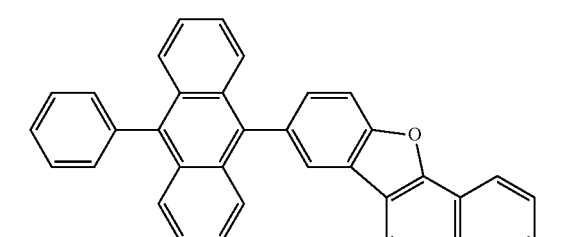
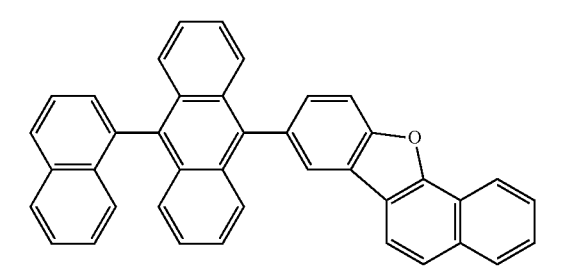
102
-continued
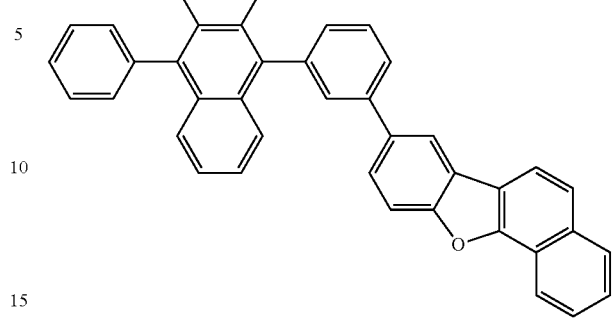
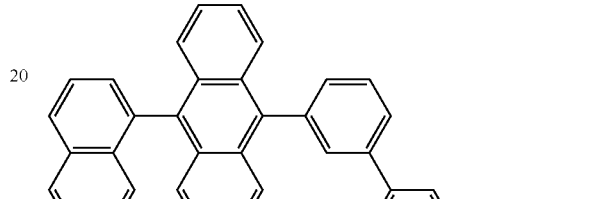
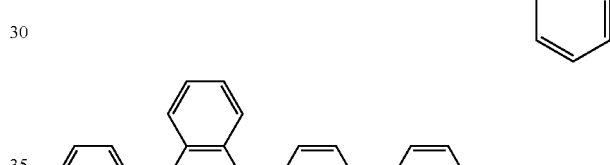
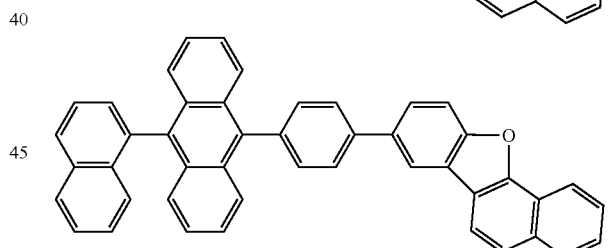
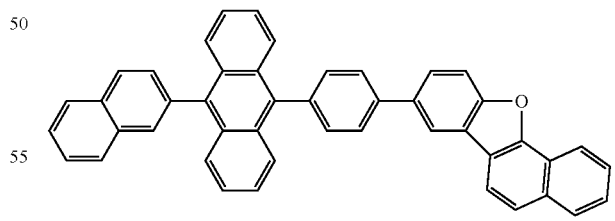
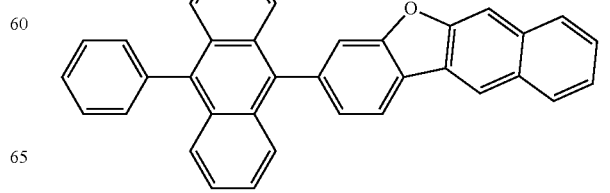

103
-continued
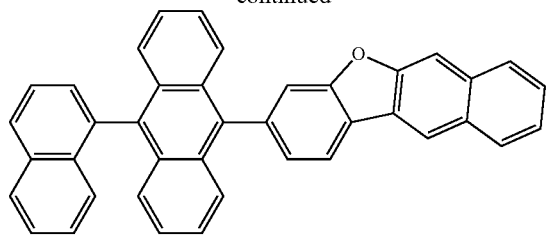
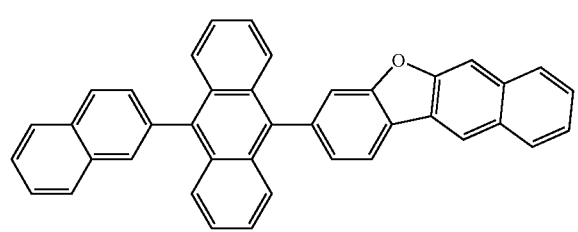
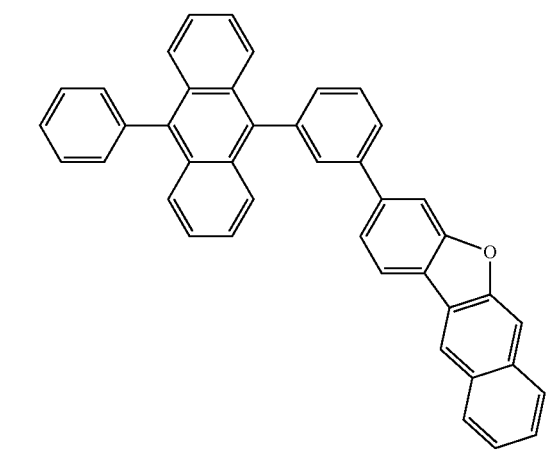
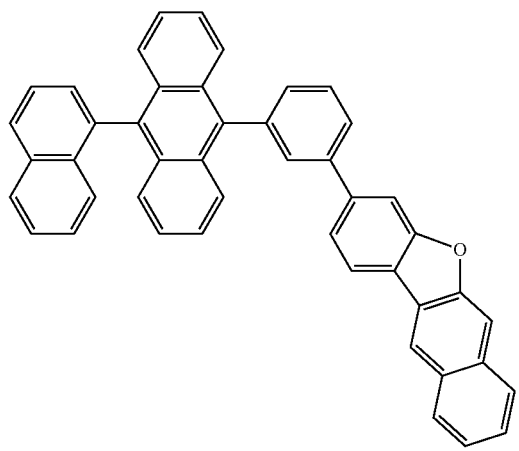
104
-continued
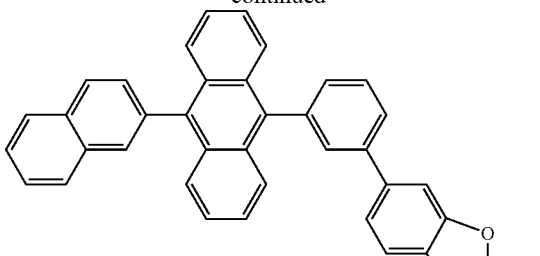
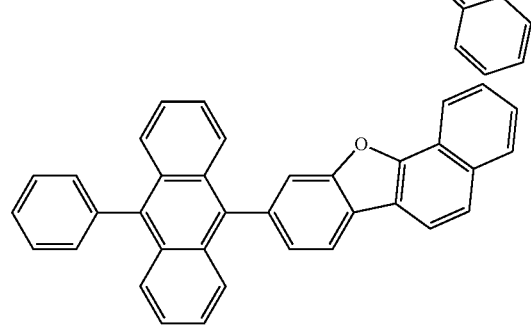
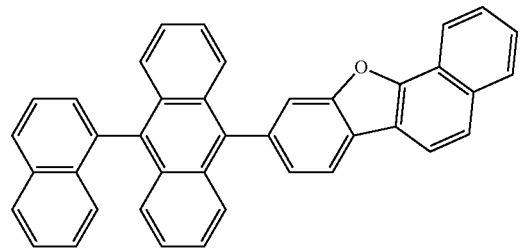
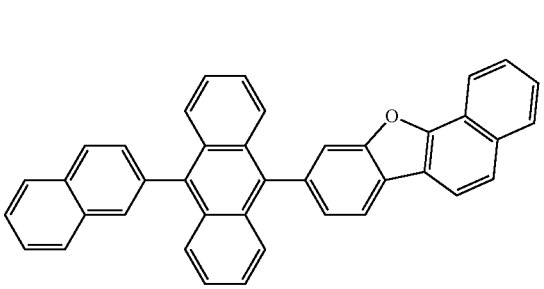
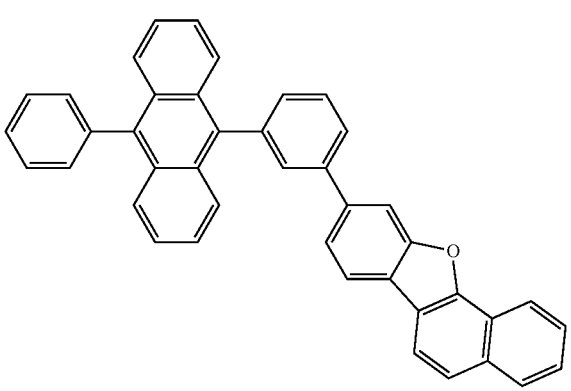

105
-continued
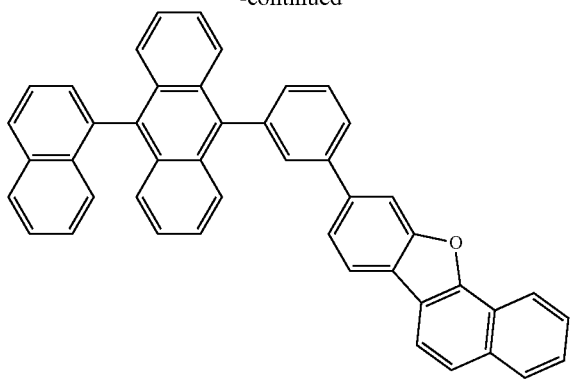
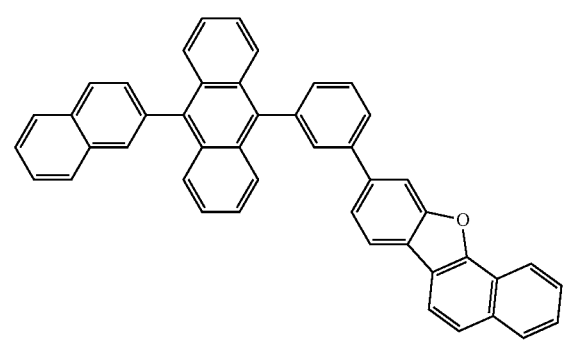
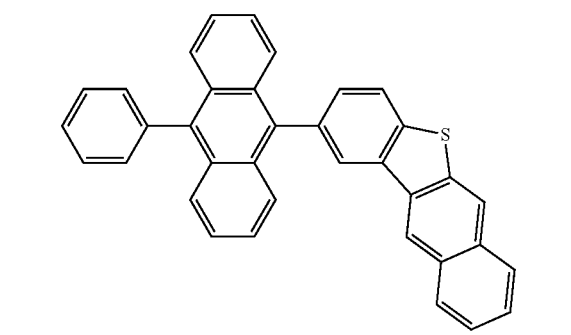
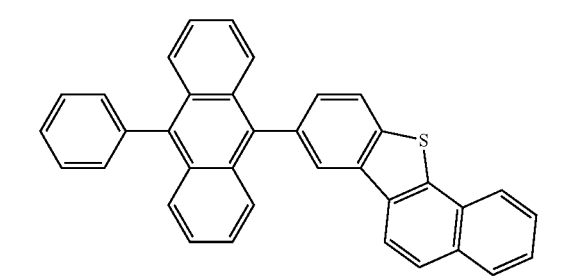
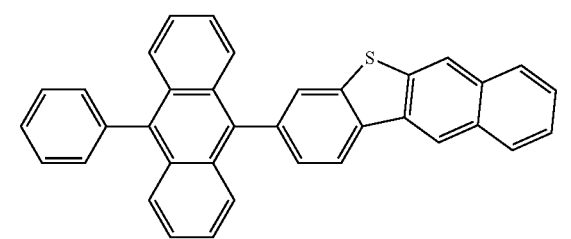
106
-continued
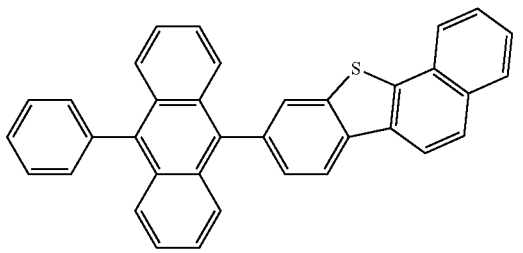
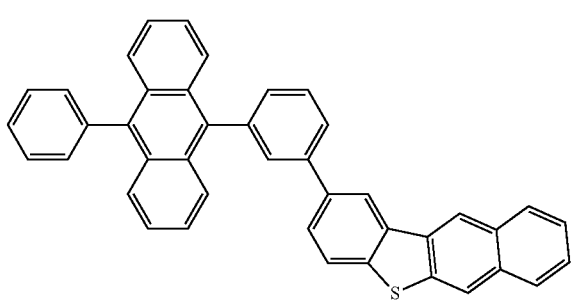
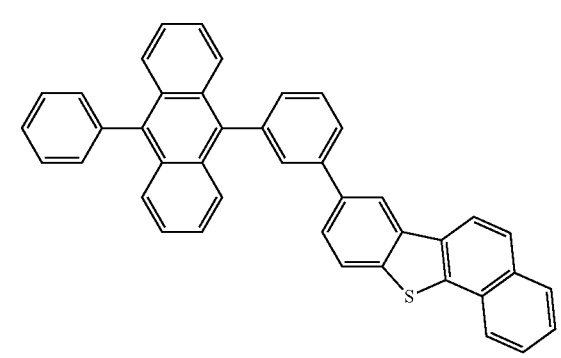
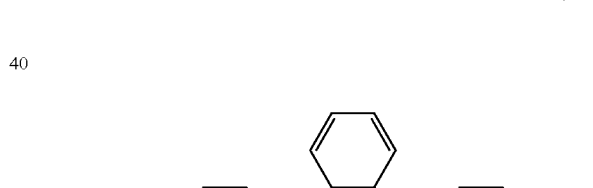
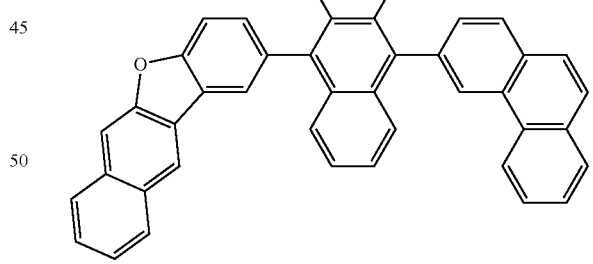
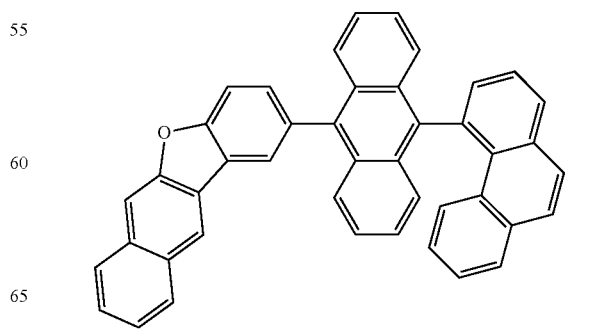

107
-continued
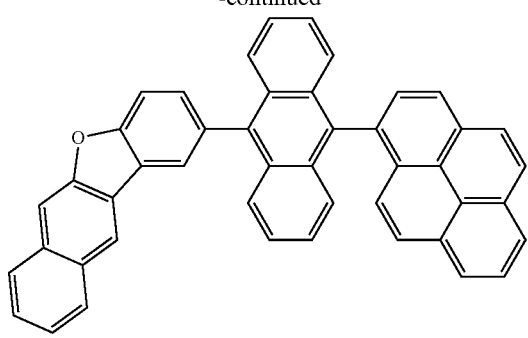
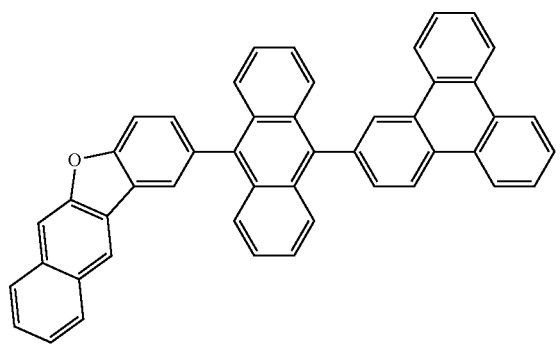
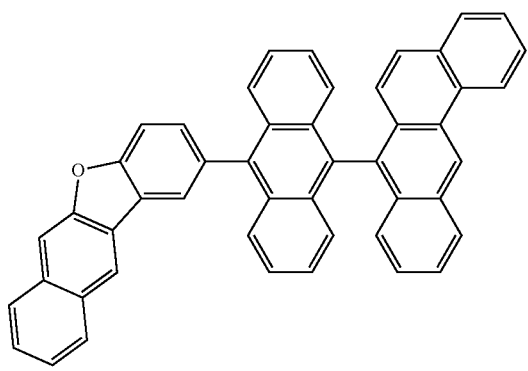
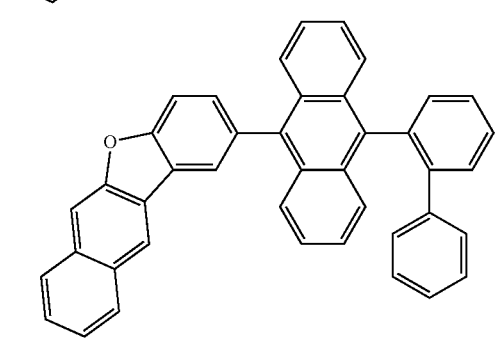
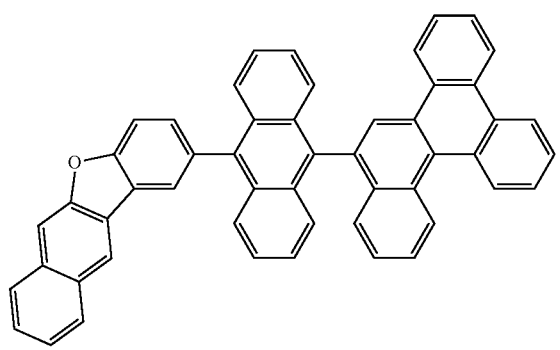
108
-continued
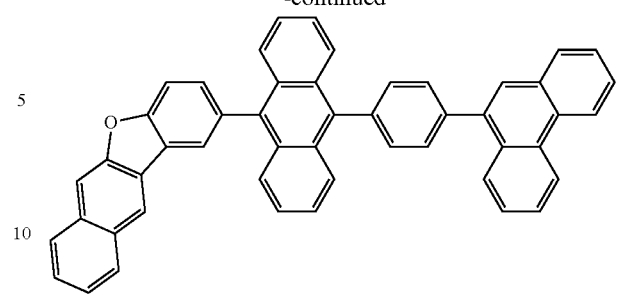
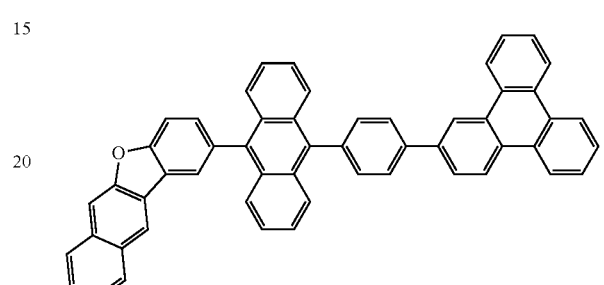
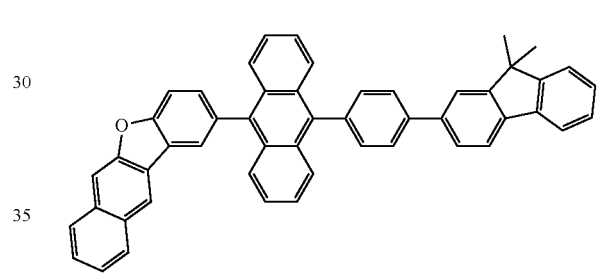
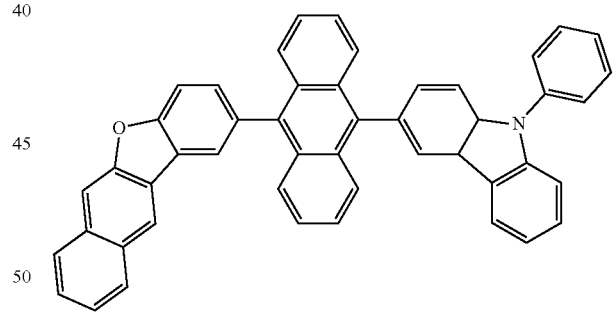
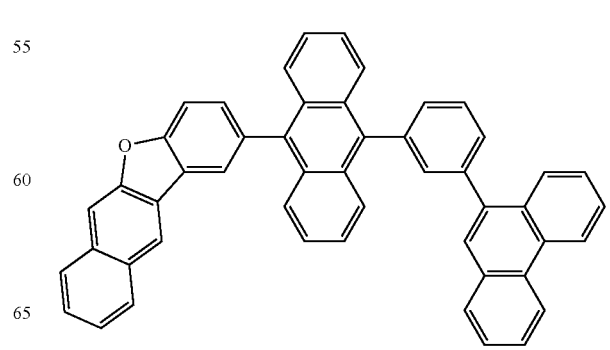

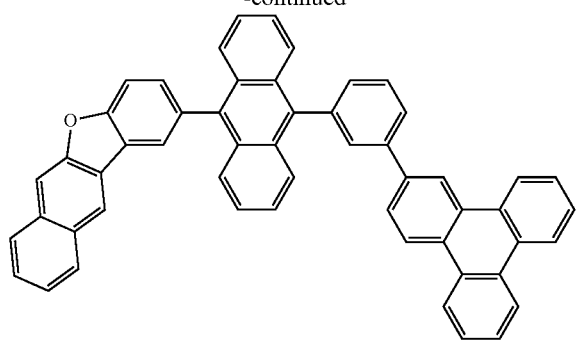
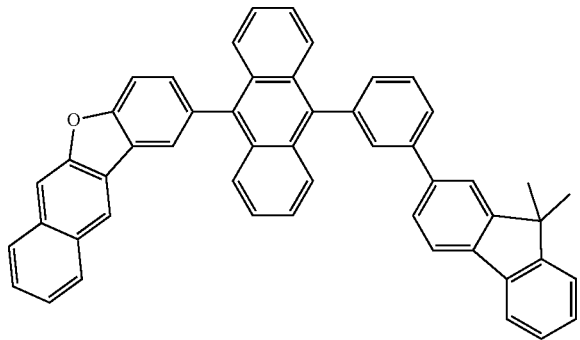
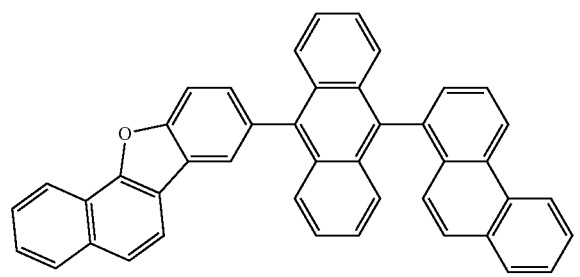
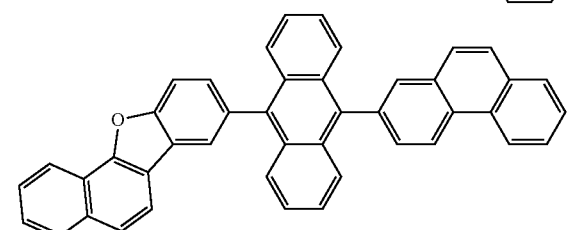
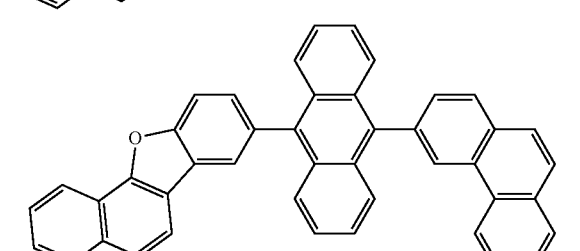
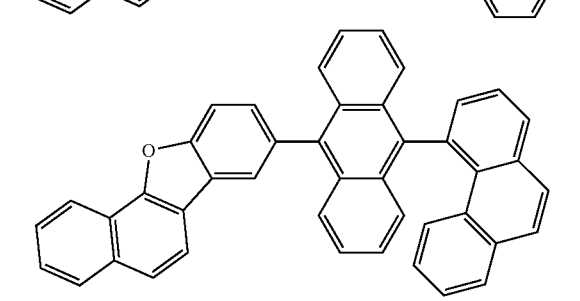
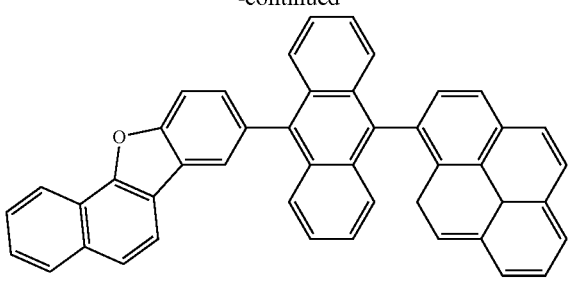
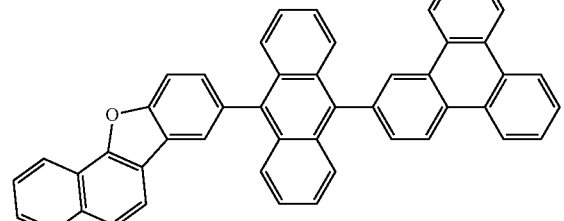
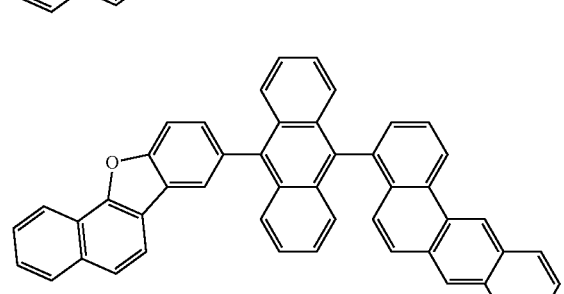
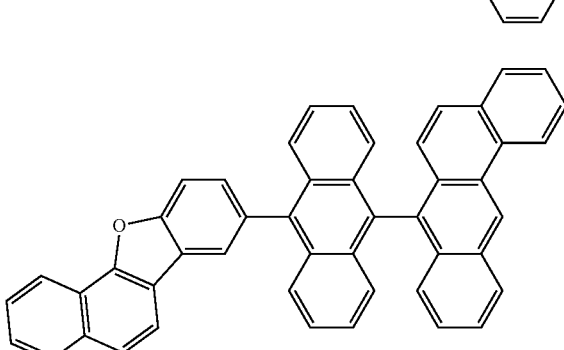
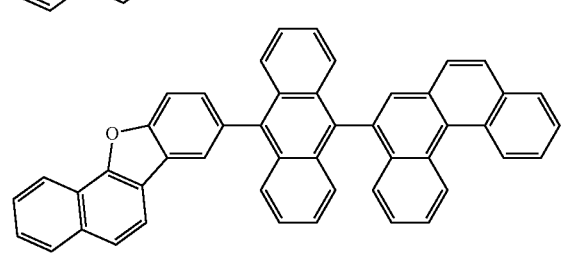
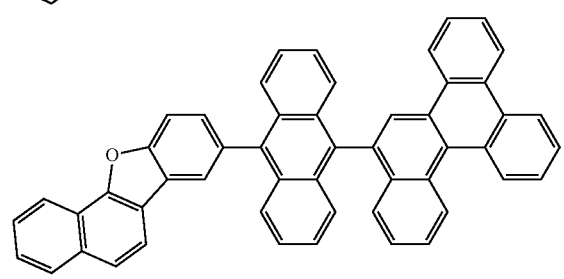

111
-continued
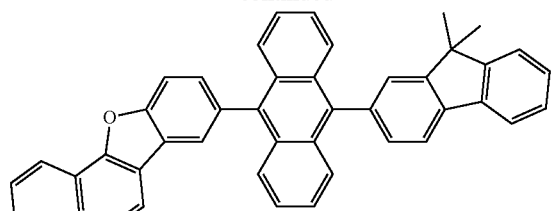
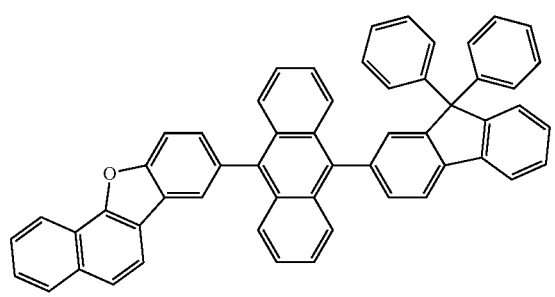
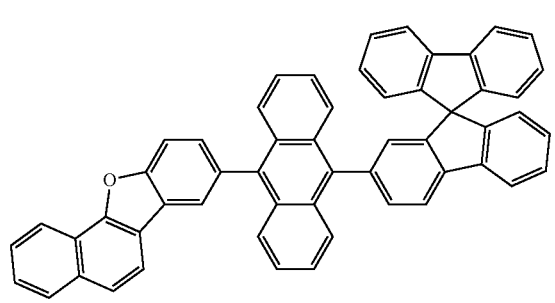
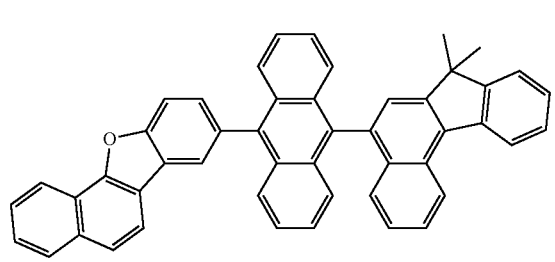
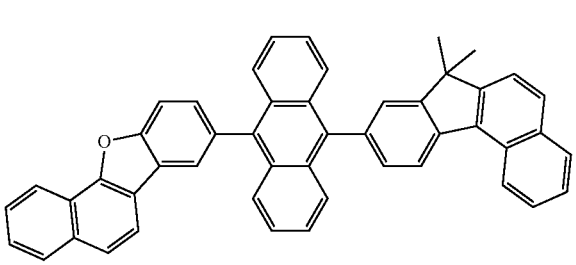
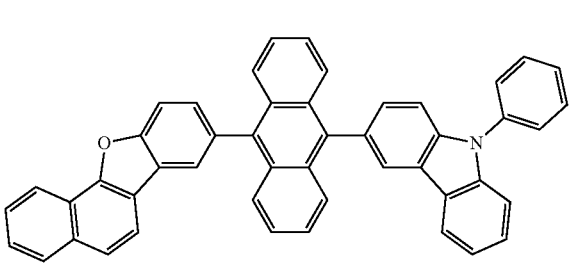
112
-continued
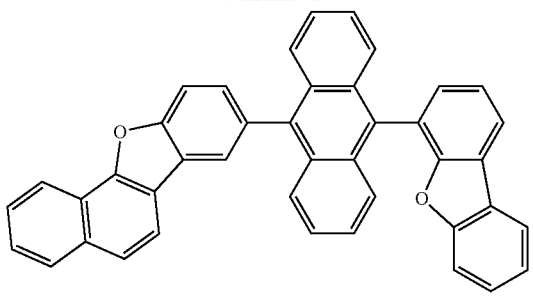
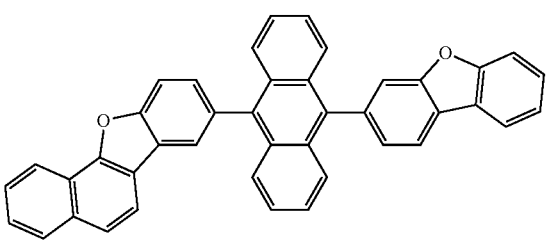
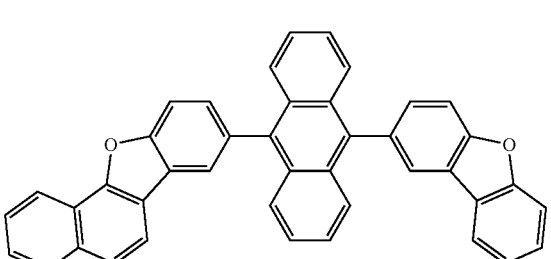
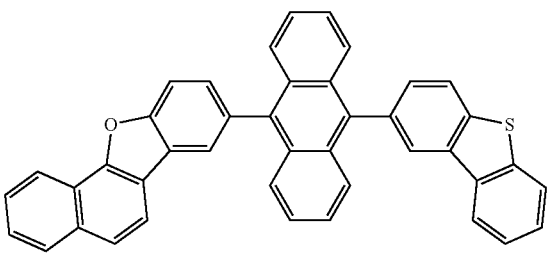
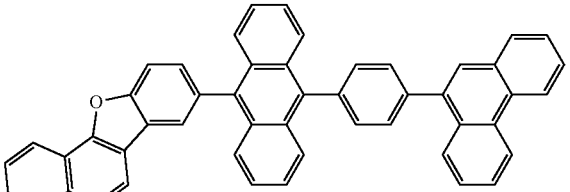
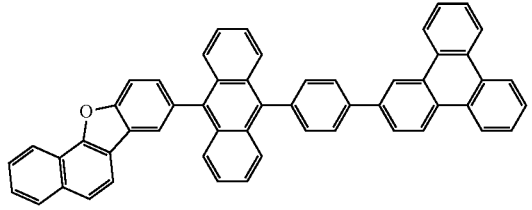
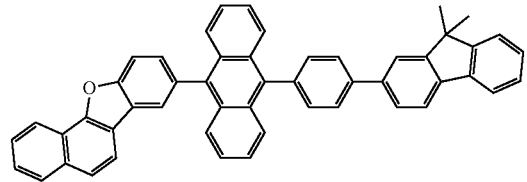

113
-continued
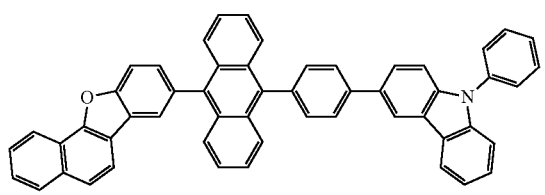
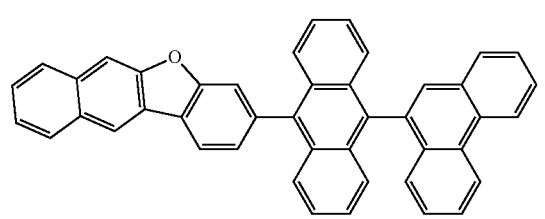
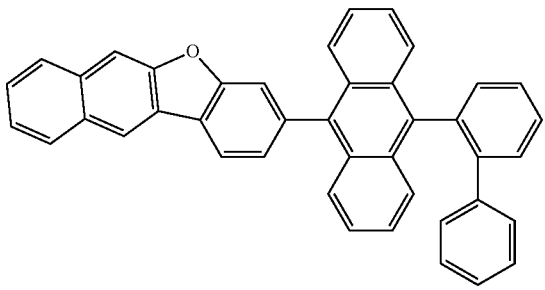
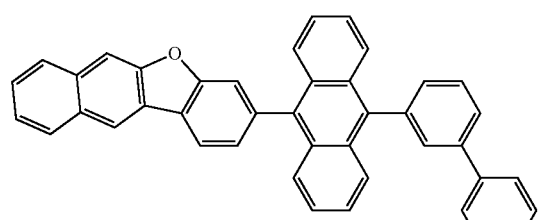
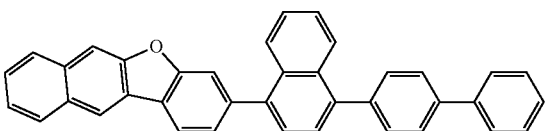
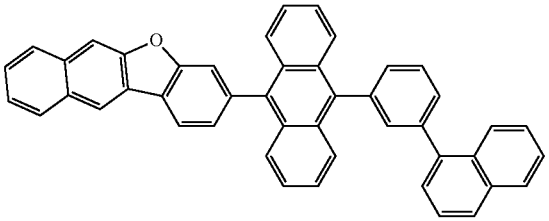
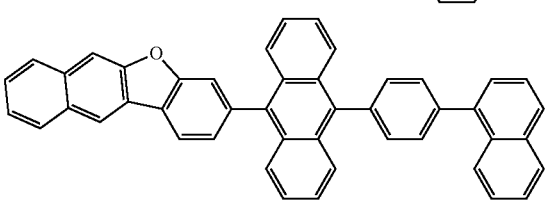
114
-continued
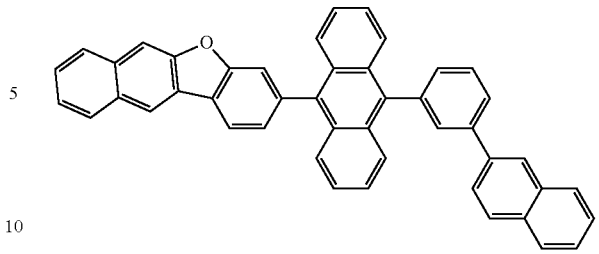
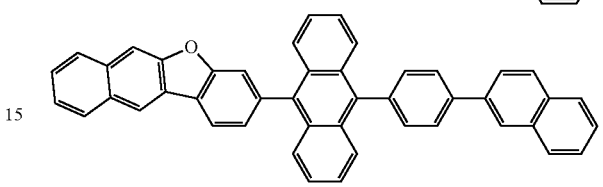
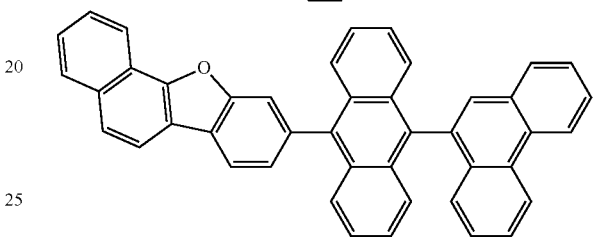
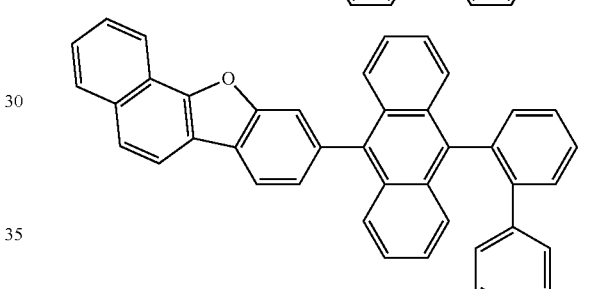
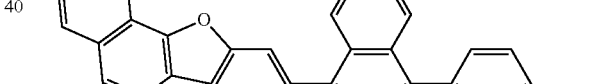
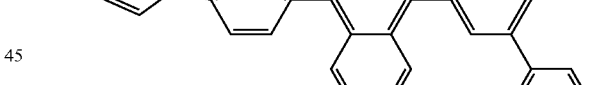
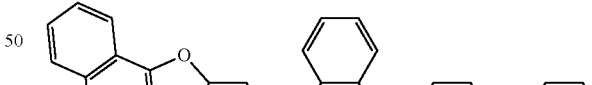
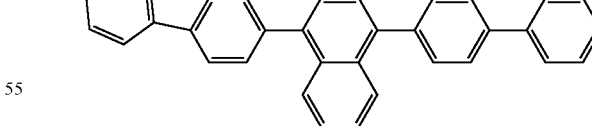
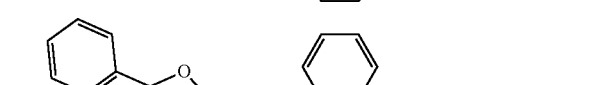
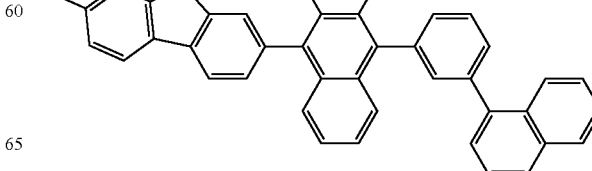

115
-continued
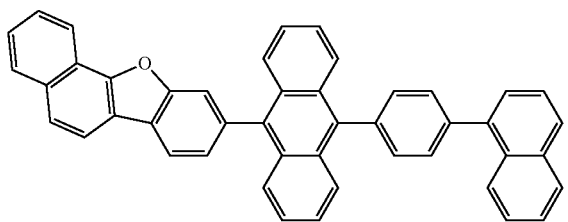
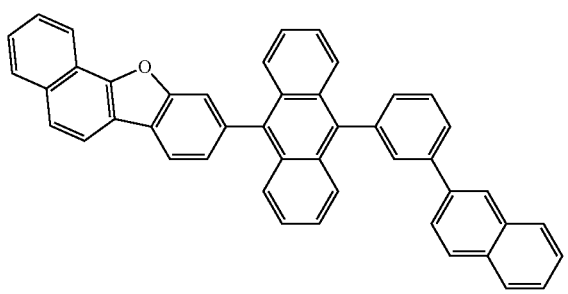
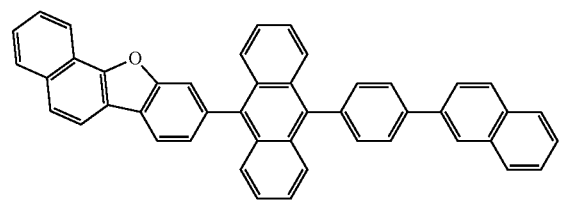
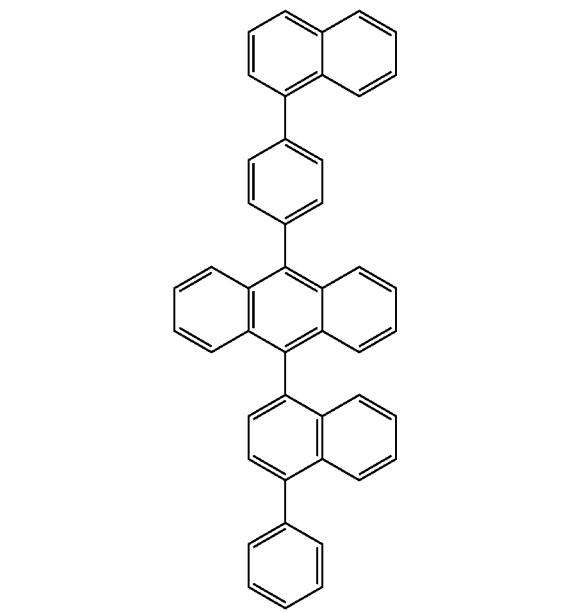
116
-continued
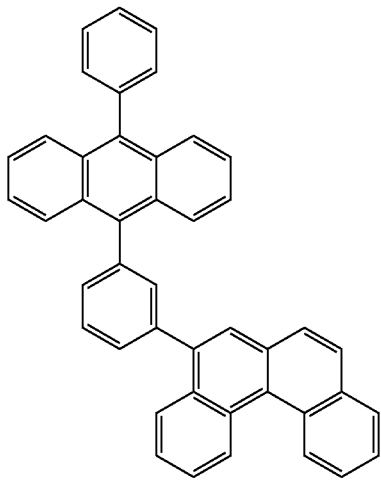
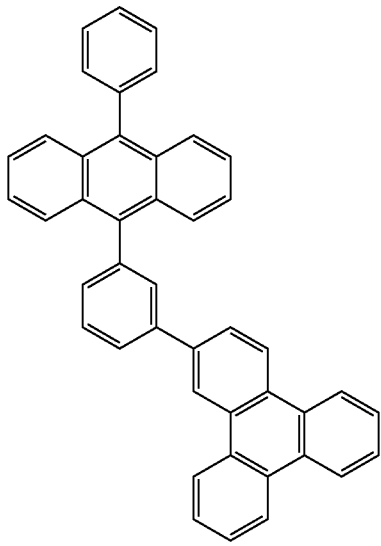
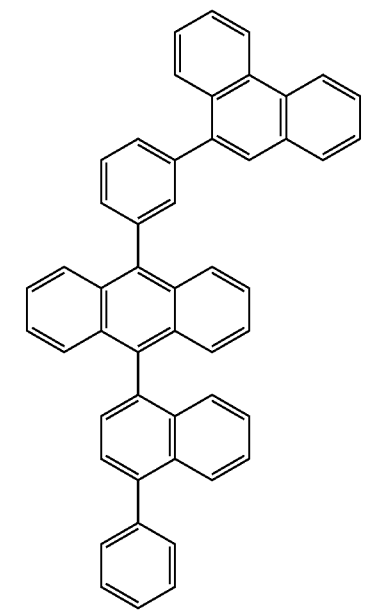

117
-continued
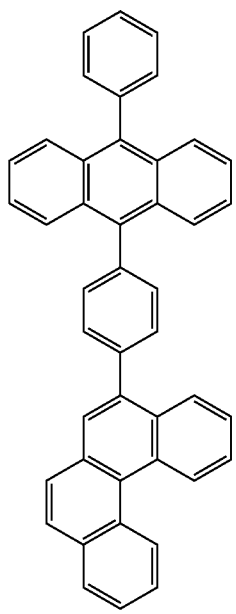
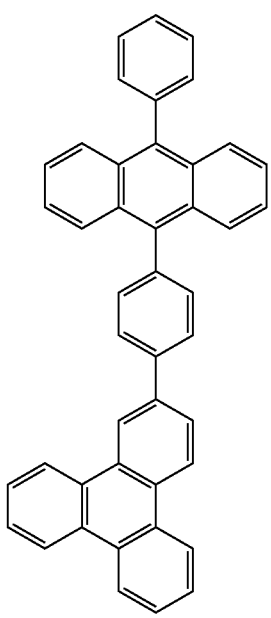
118
-continued
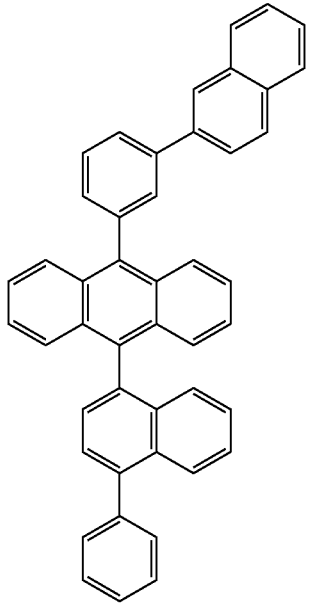
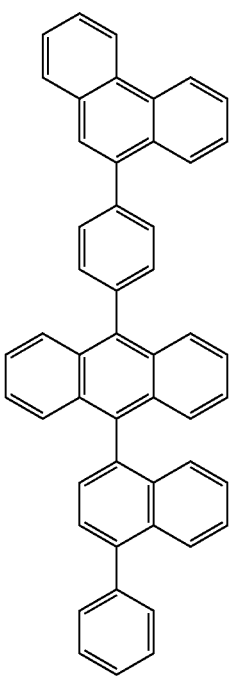

119
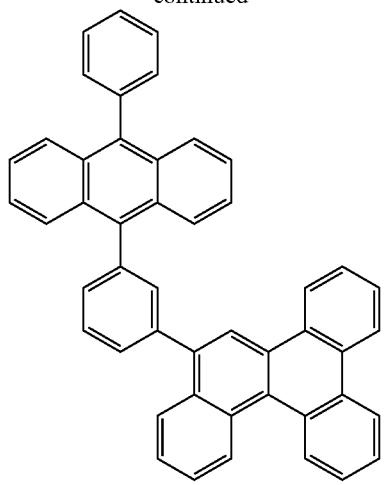
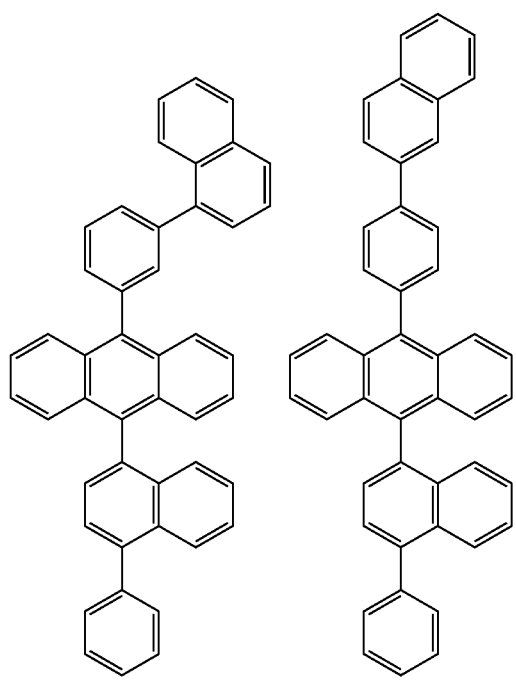
120
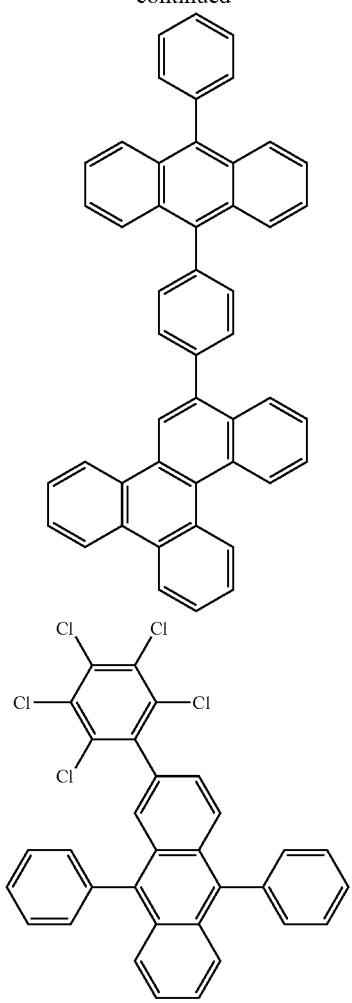
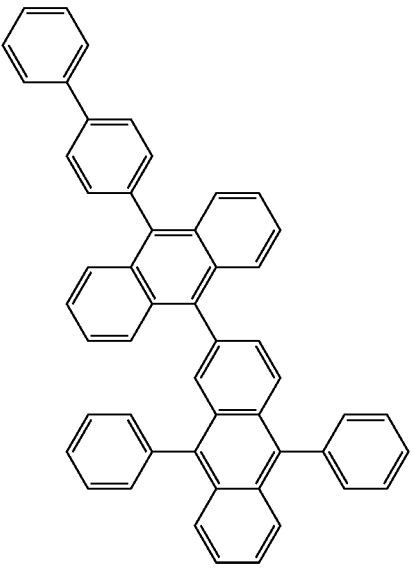

121
-continued
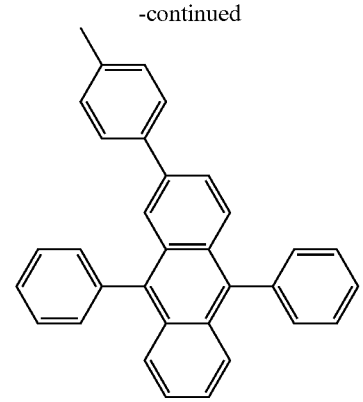
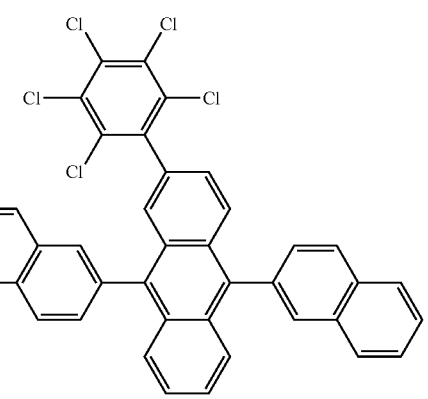
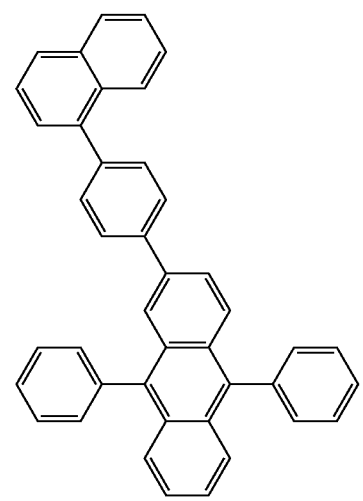
122
-continued
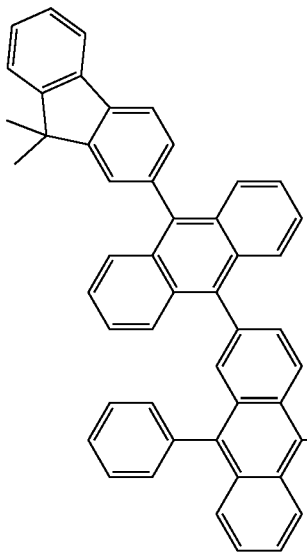
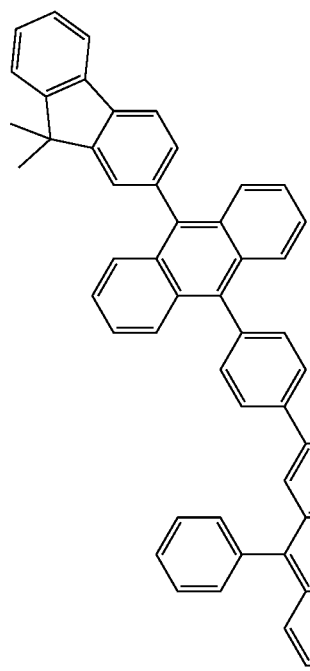
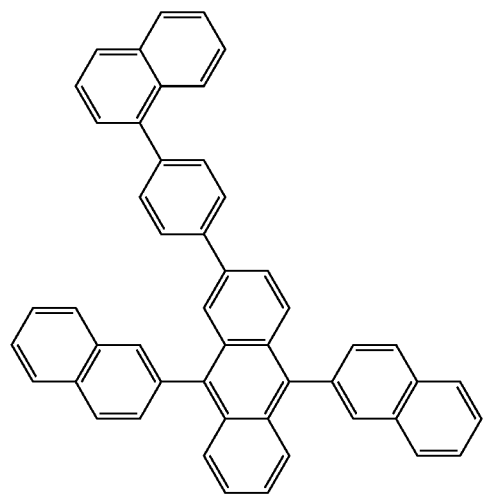

123
-continued
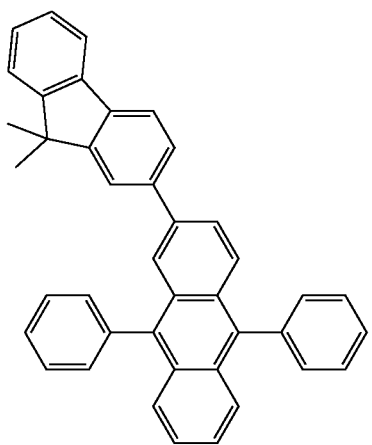
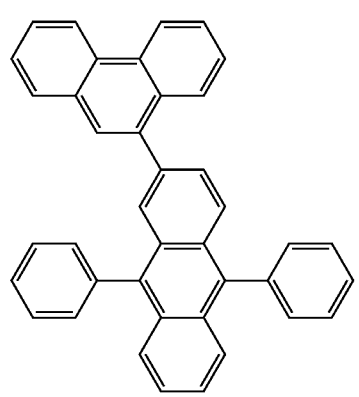
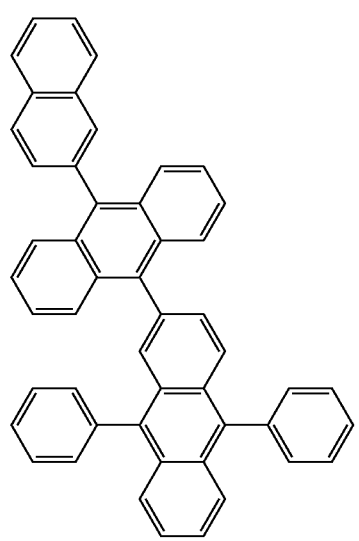
124
-continued
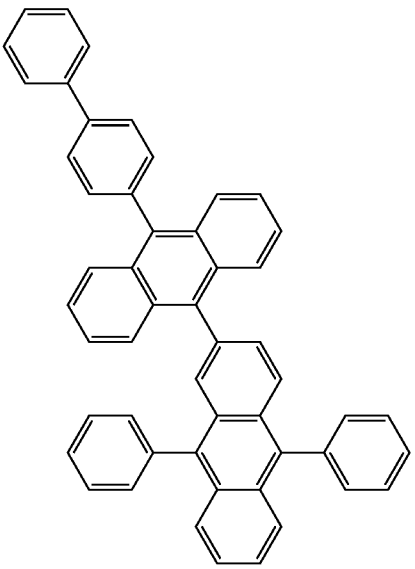
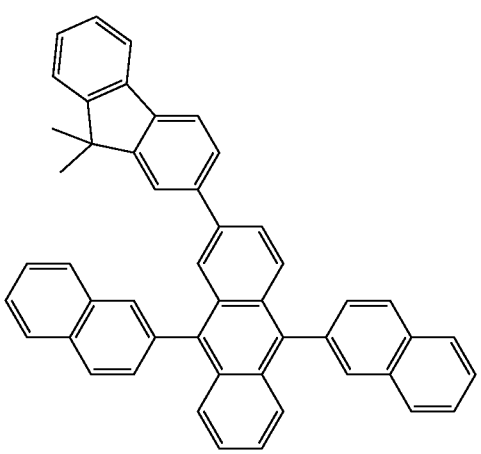
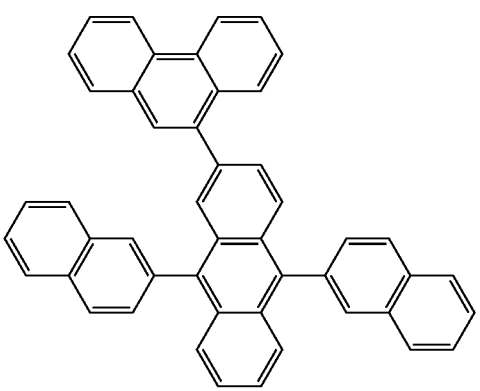

125
-continued
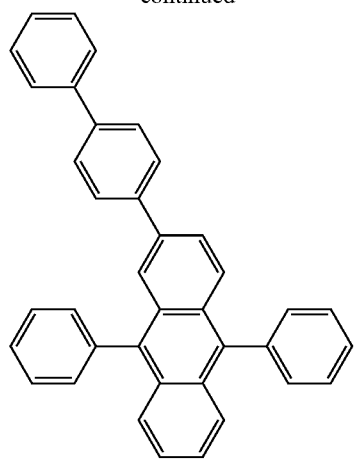
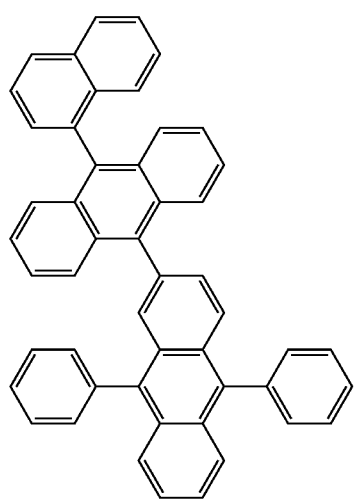
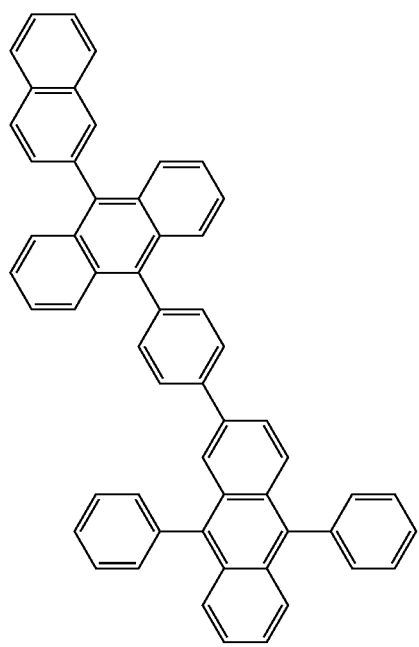
126
-continued
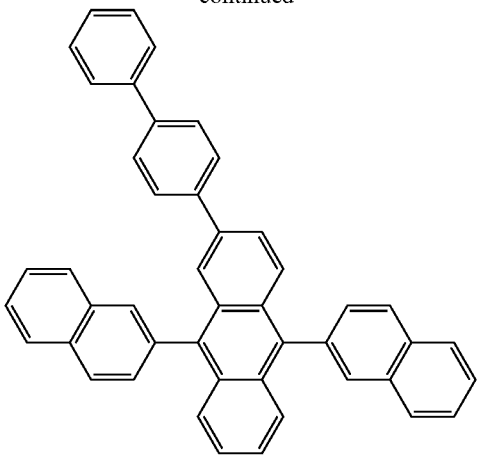
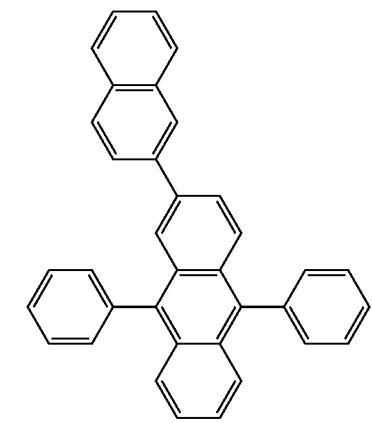
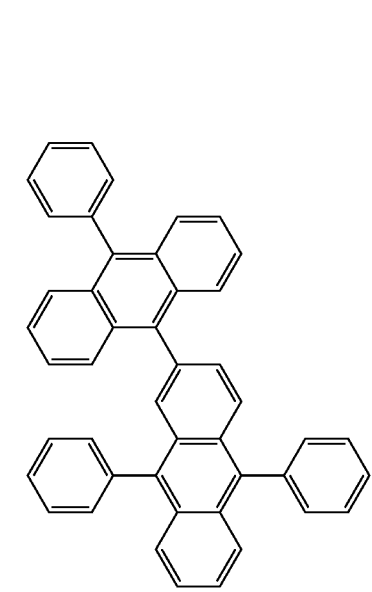

127
-continued
128
-continued
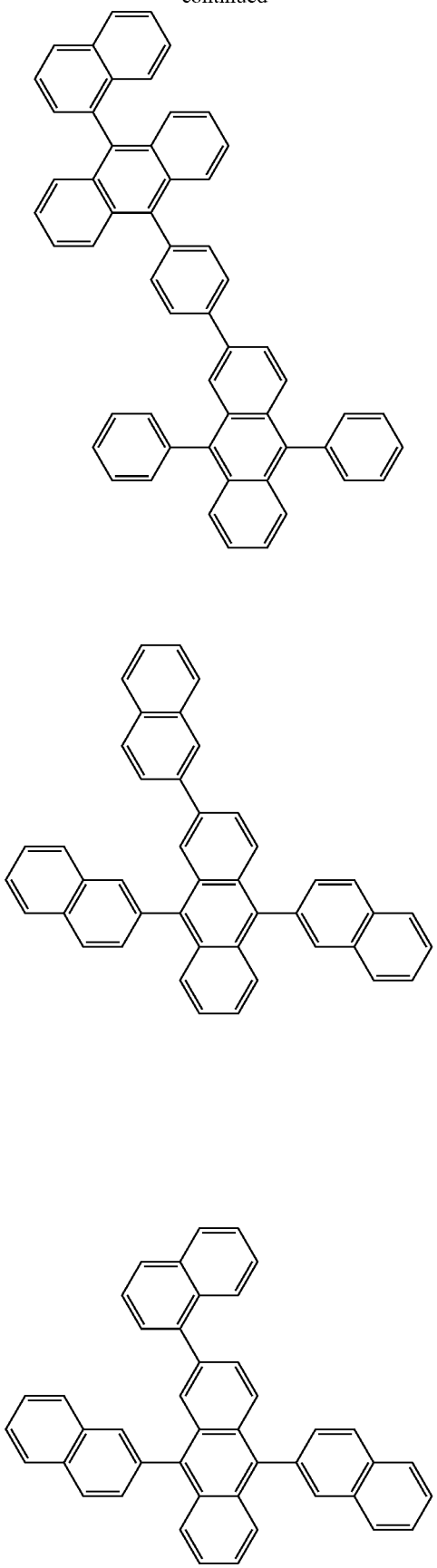
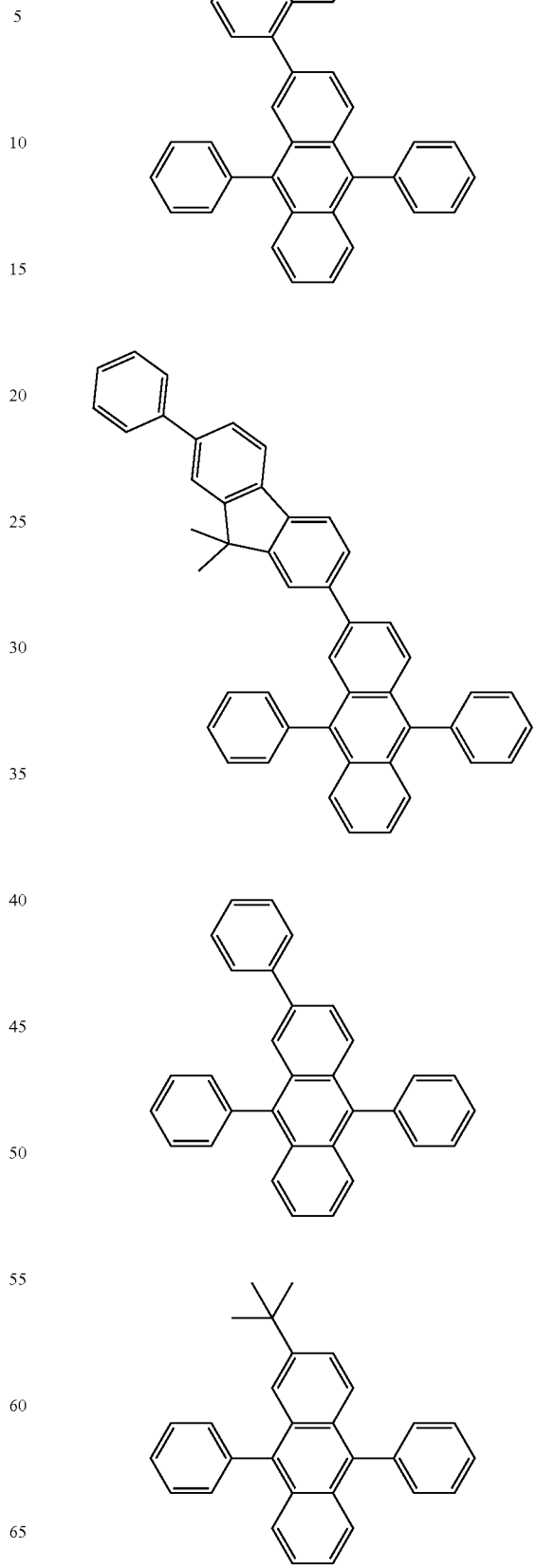

129
-continued
130
-continued
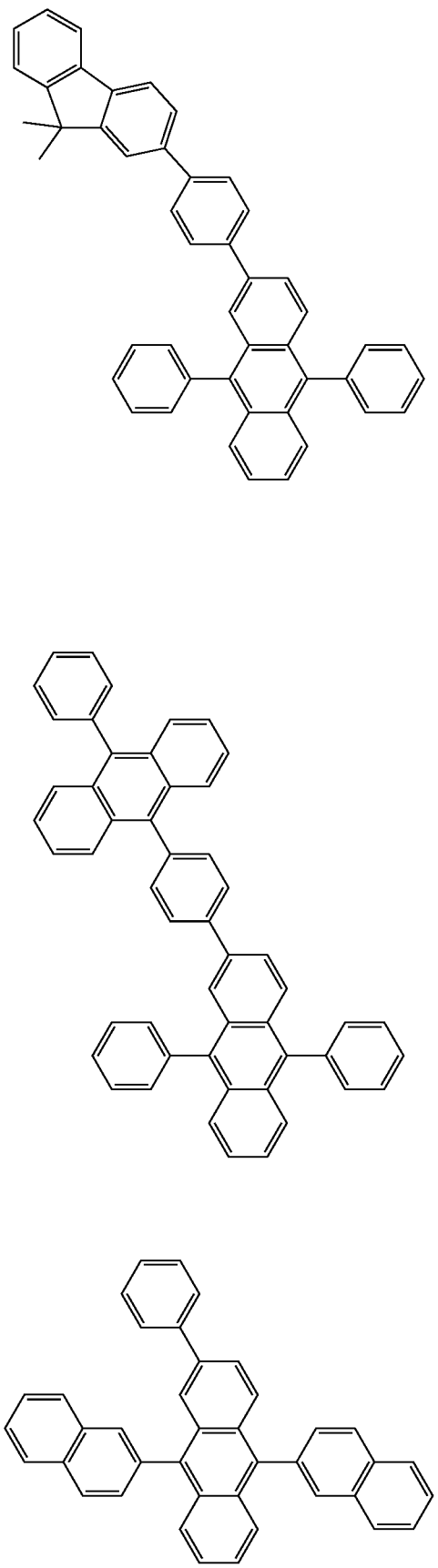
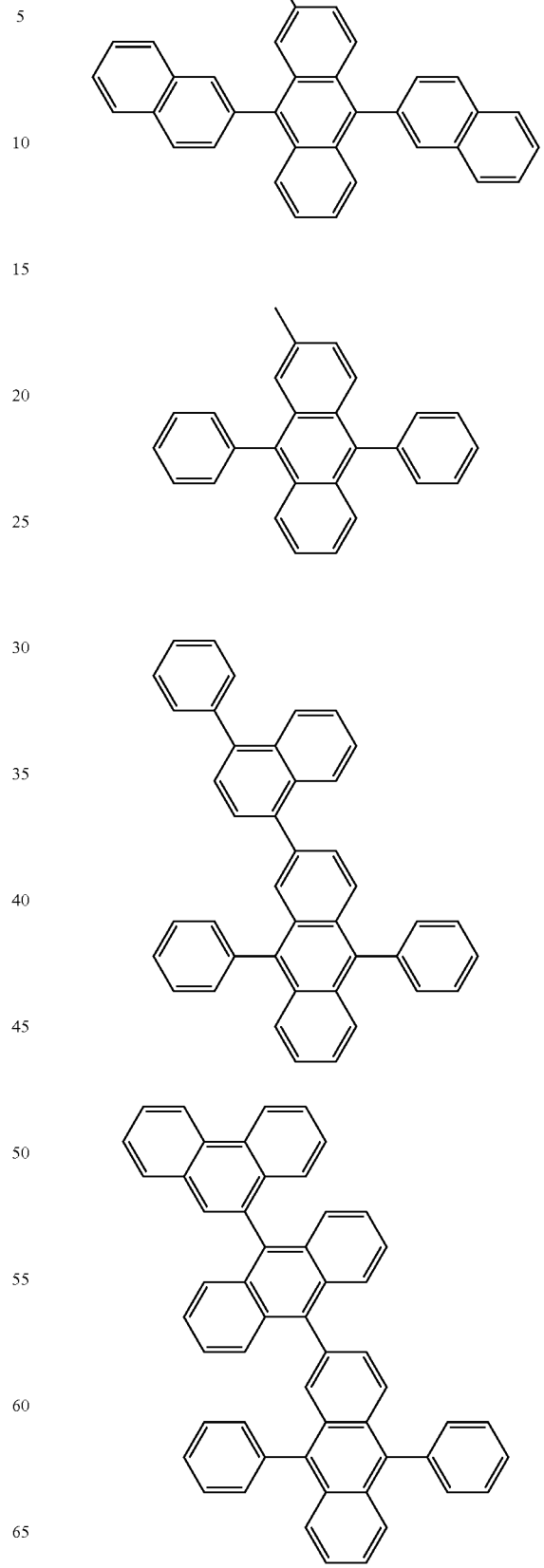

-continued
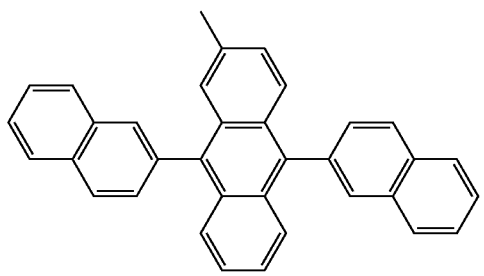
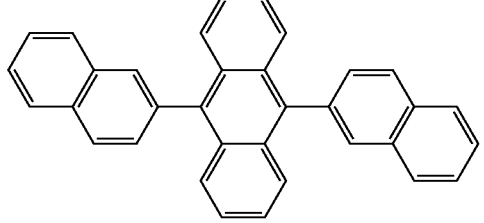
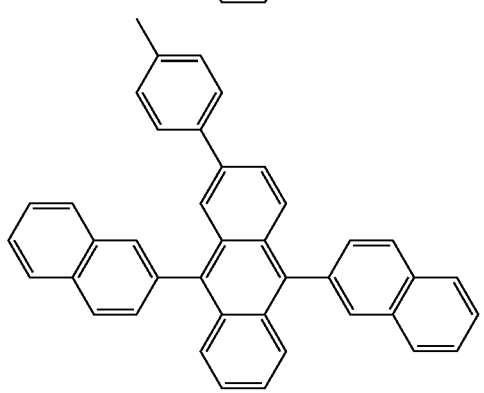
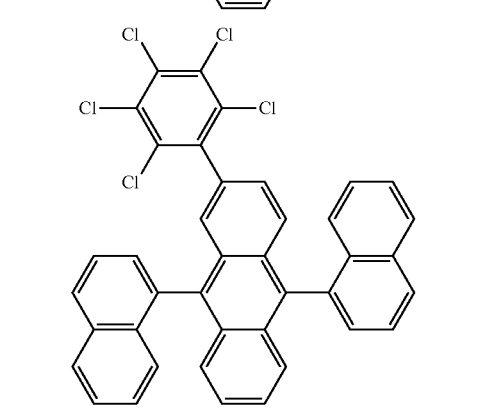
-continued
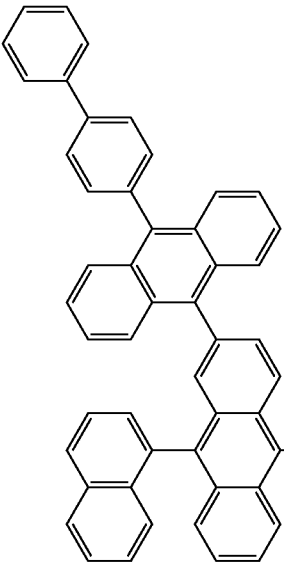

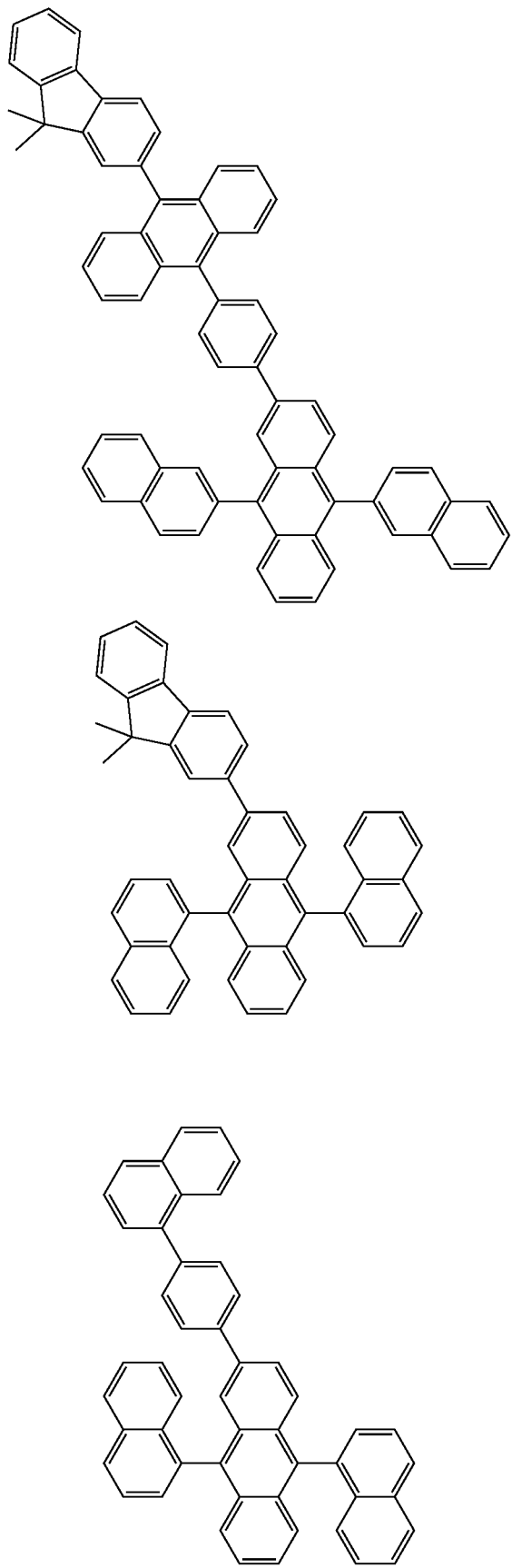
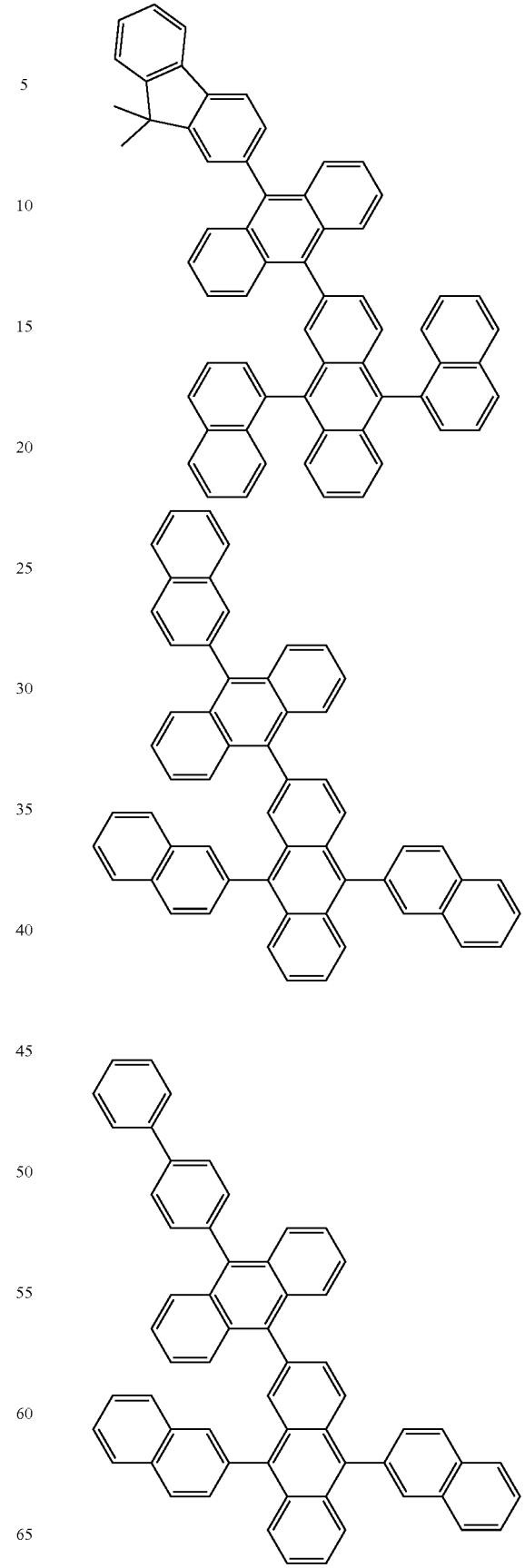

-continued
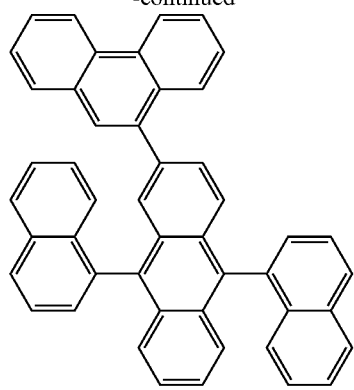
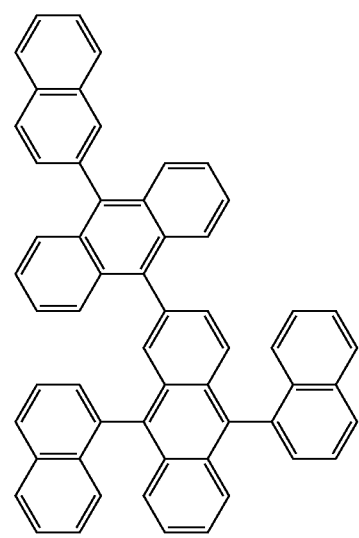
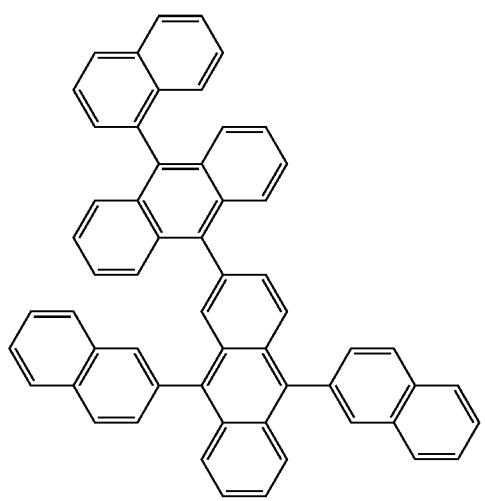
-continued
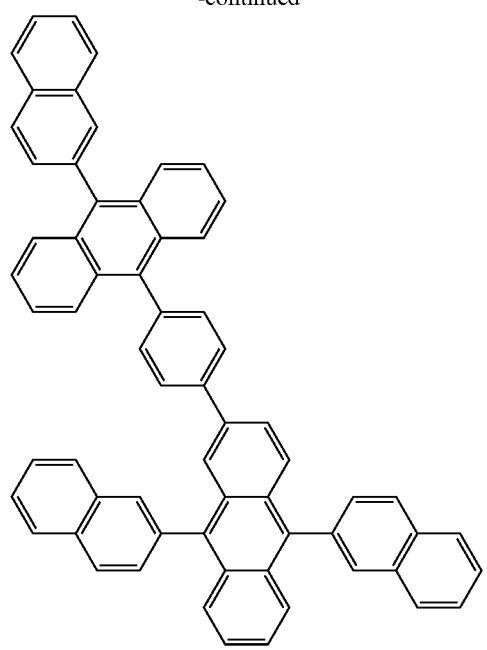
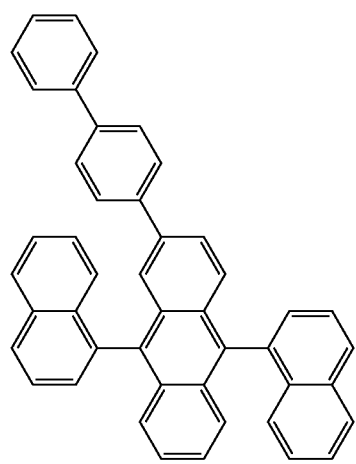
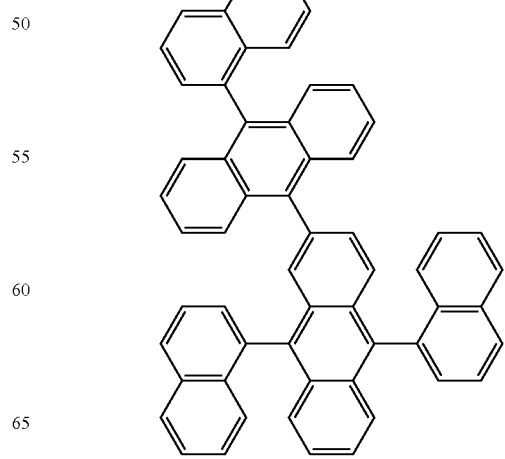

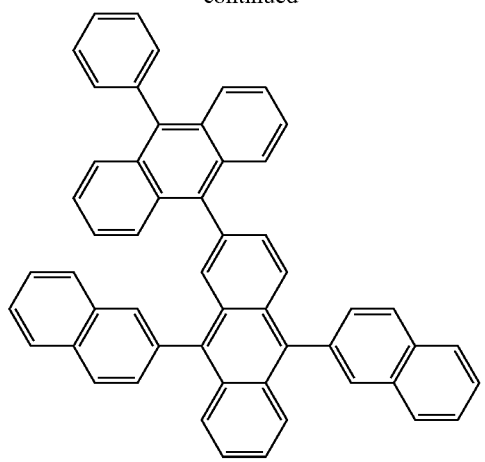
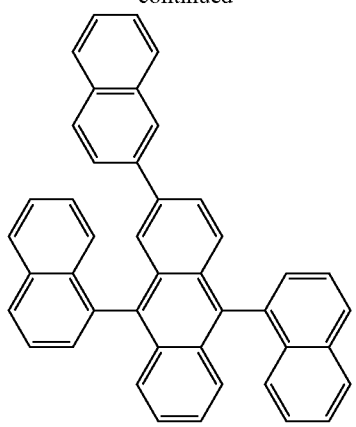
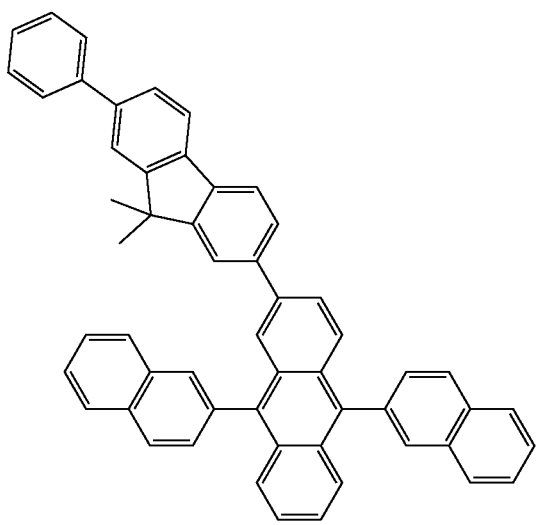
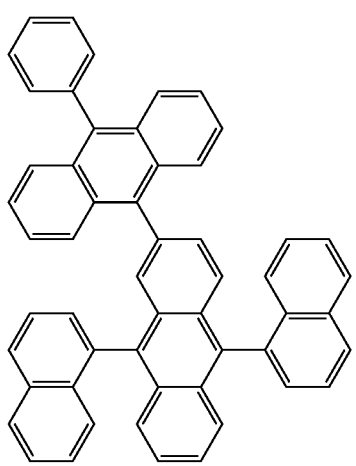
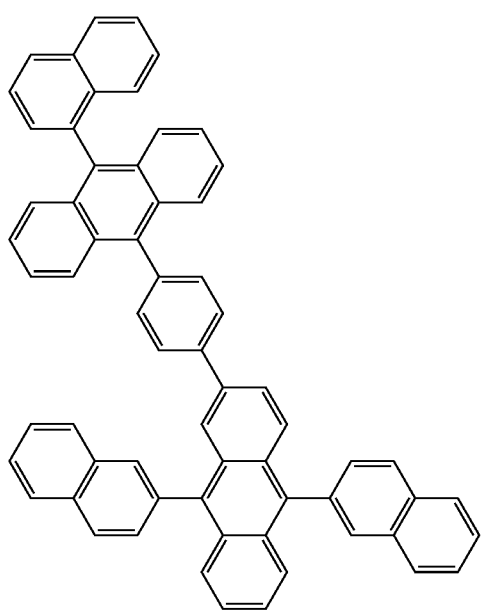
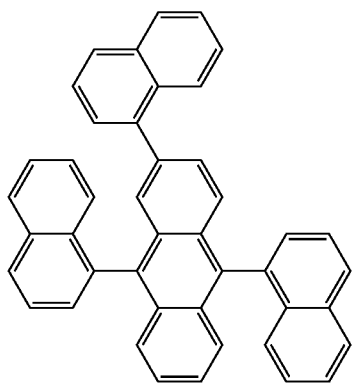

-continued
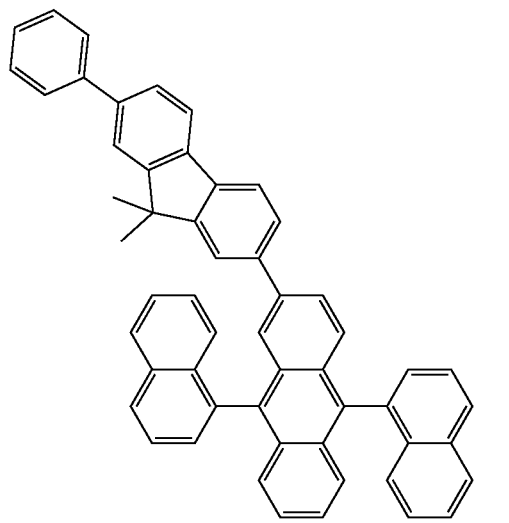
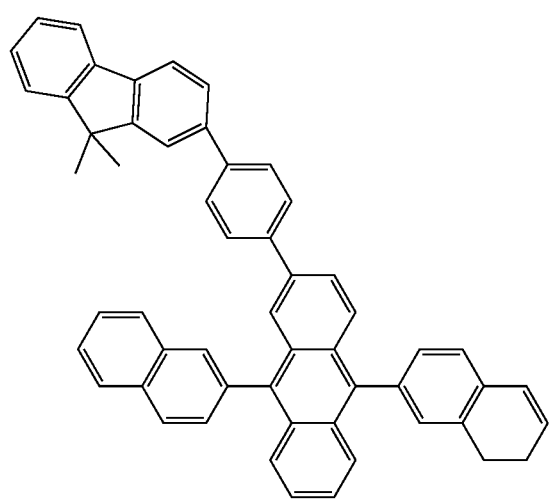
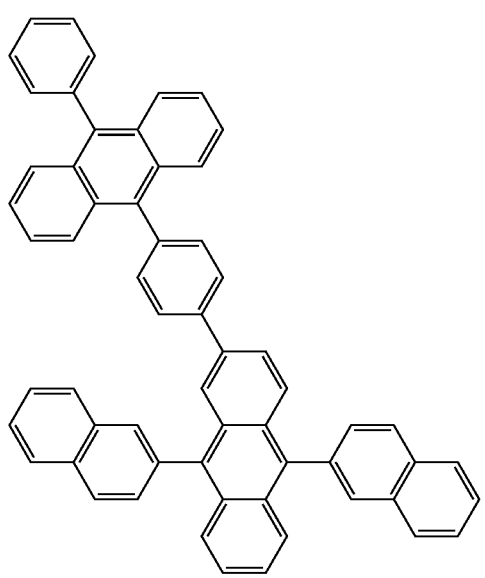
-continued
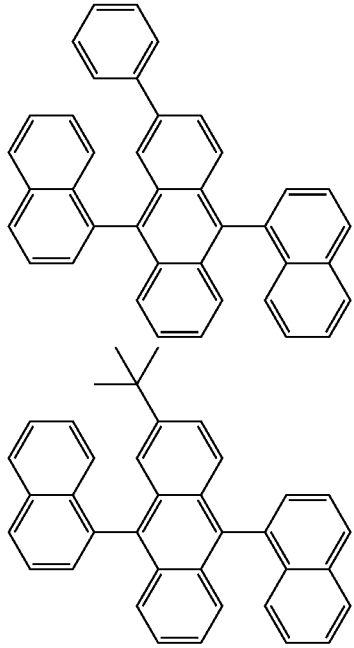
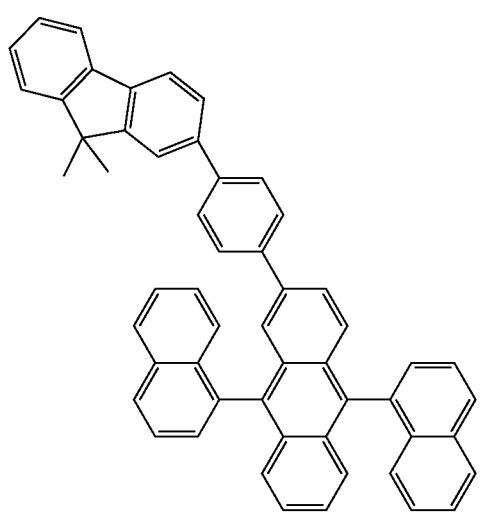
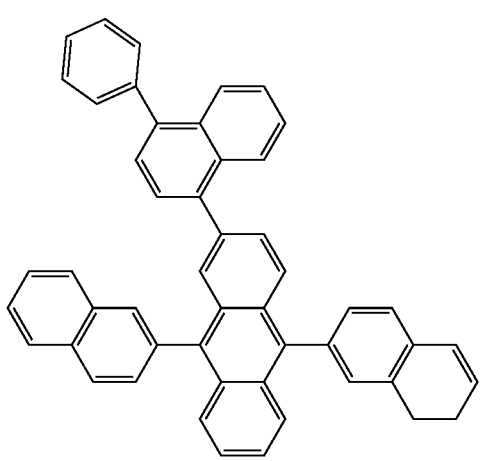

141
-continued
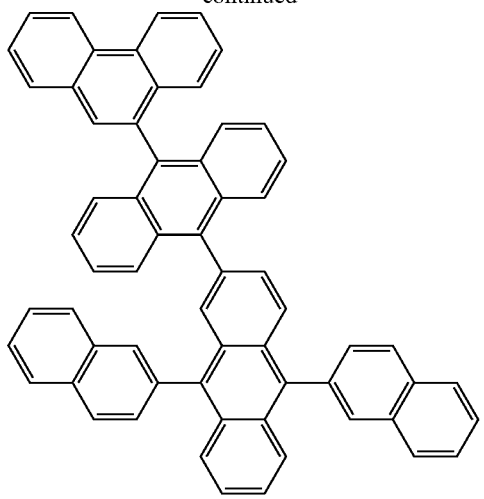
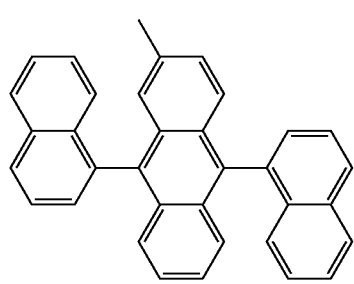
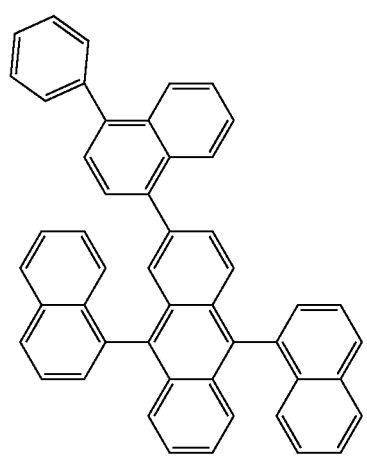
142
-continued
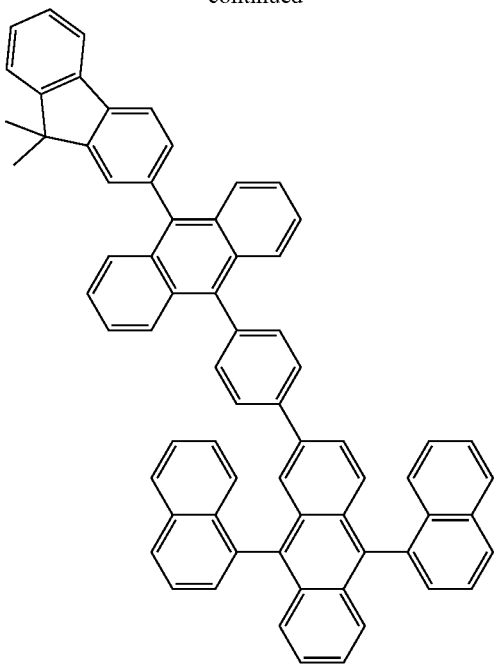
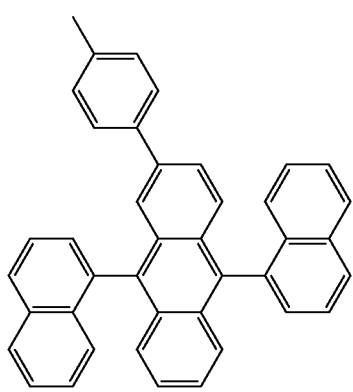
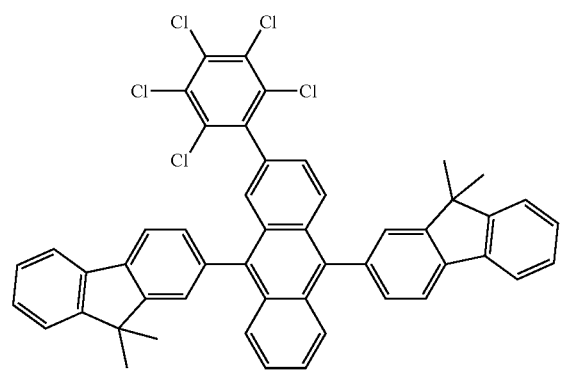

143
-continued
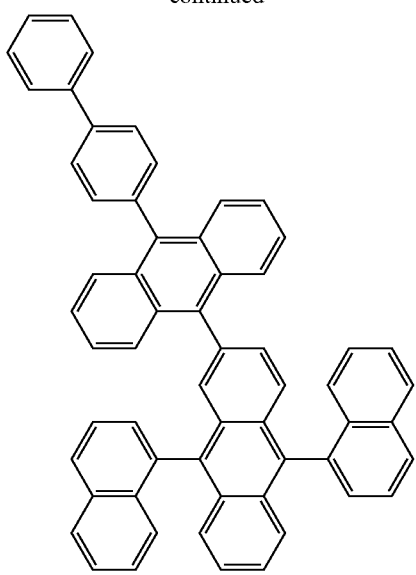
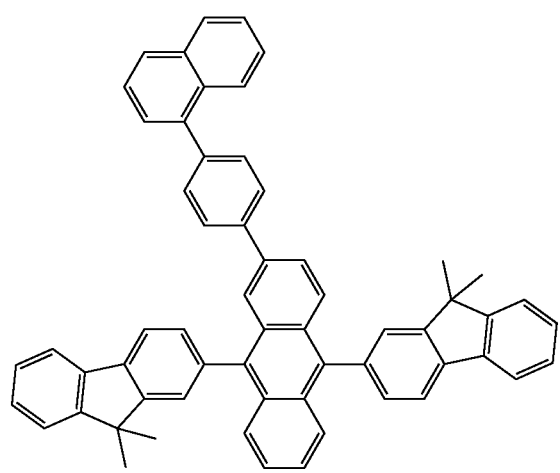
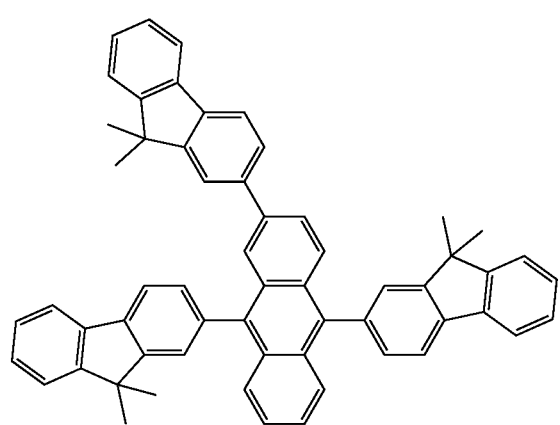
144
-continued
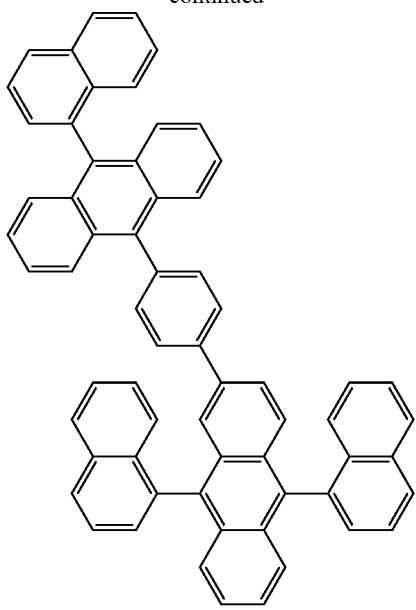
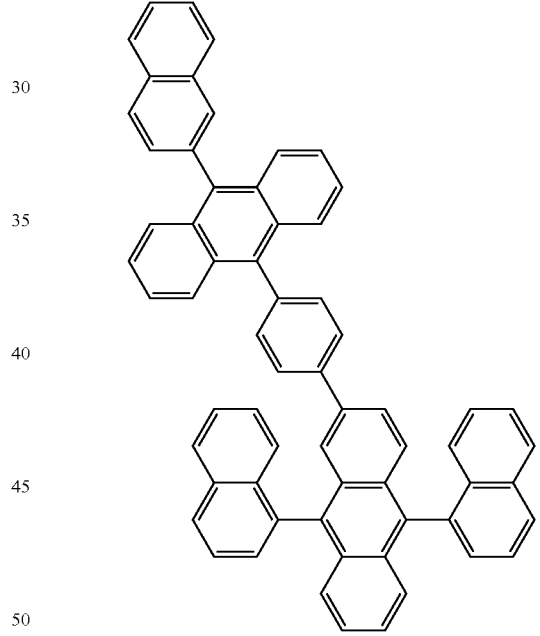
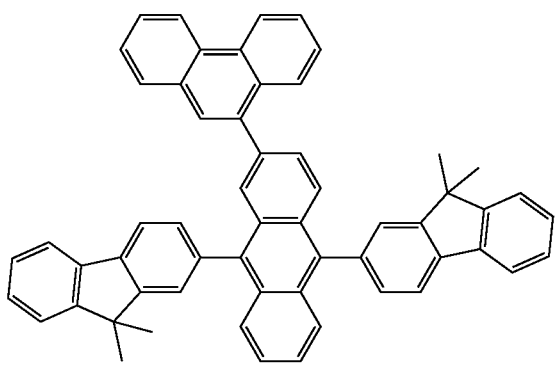

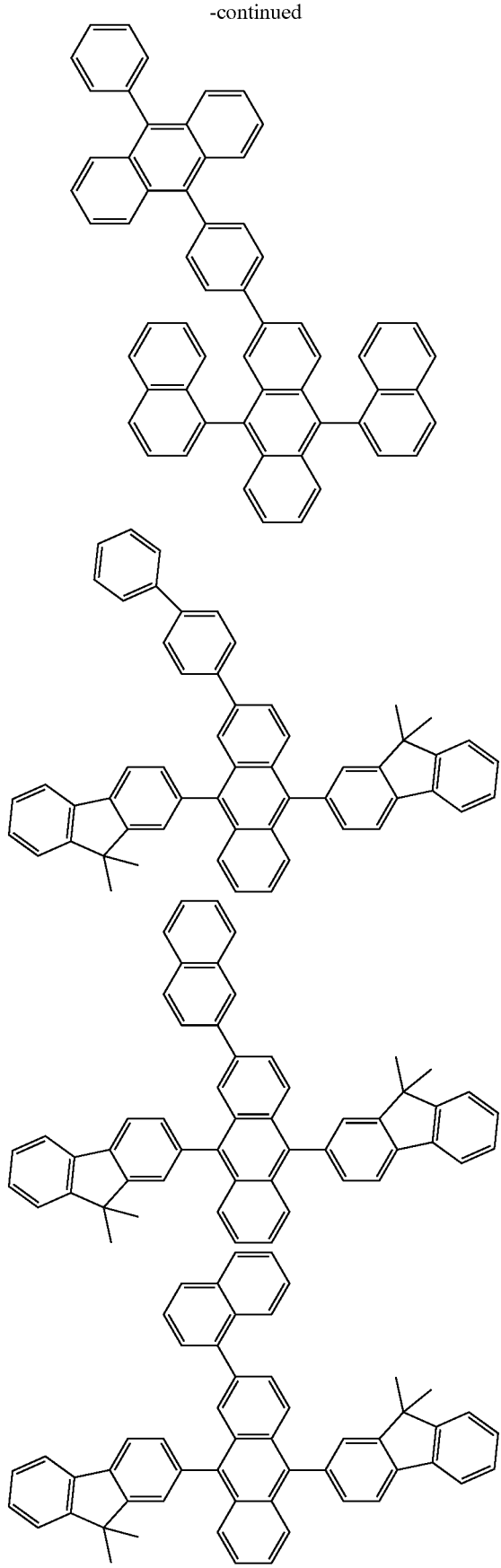
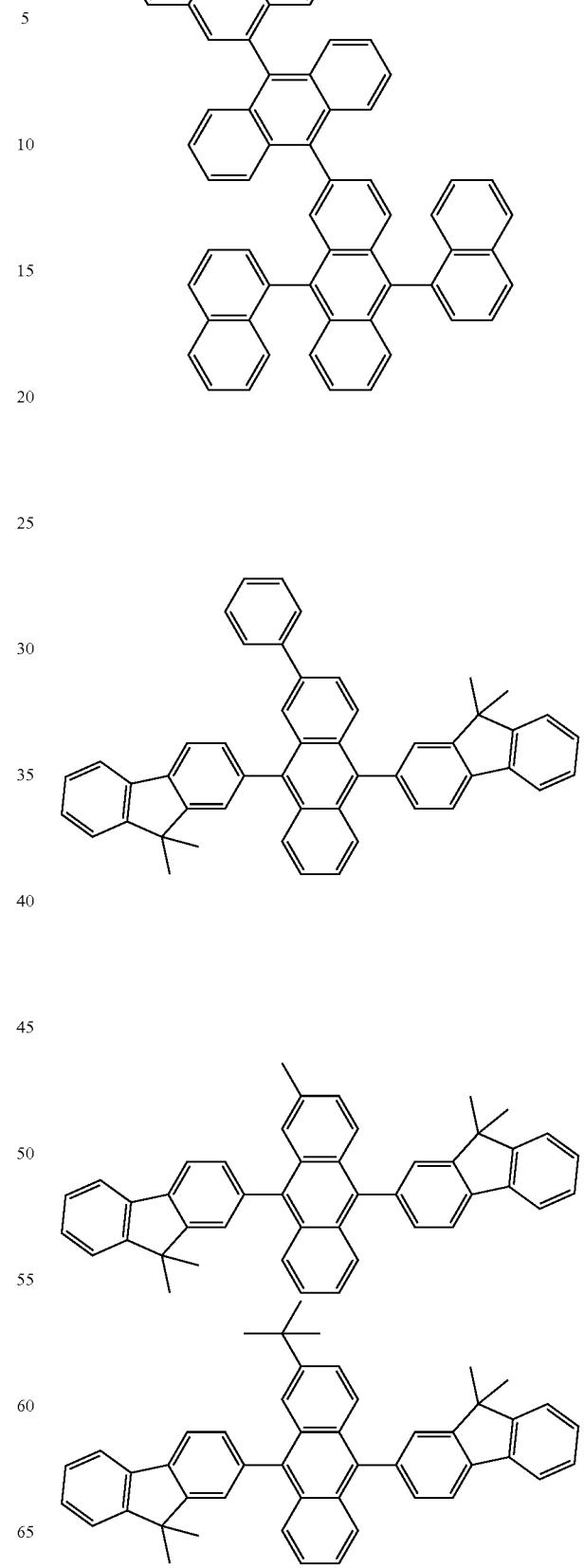

147
-continued
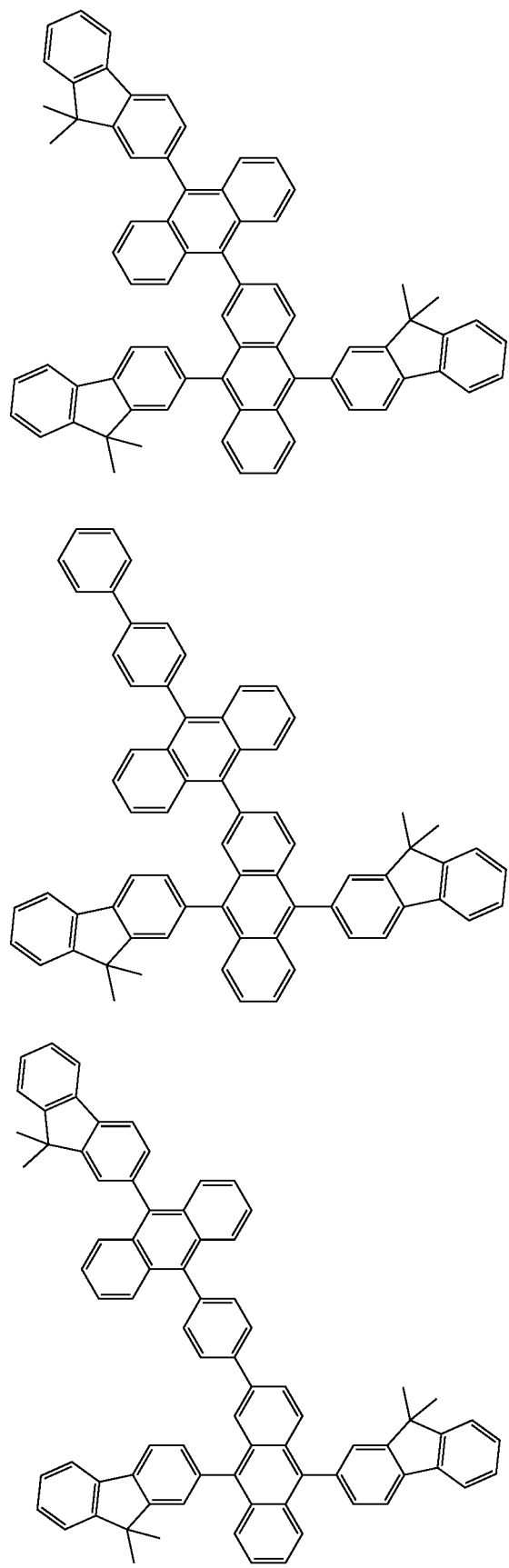
148
-continued
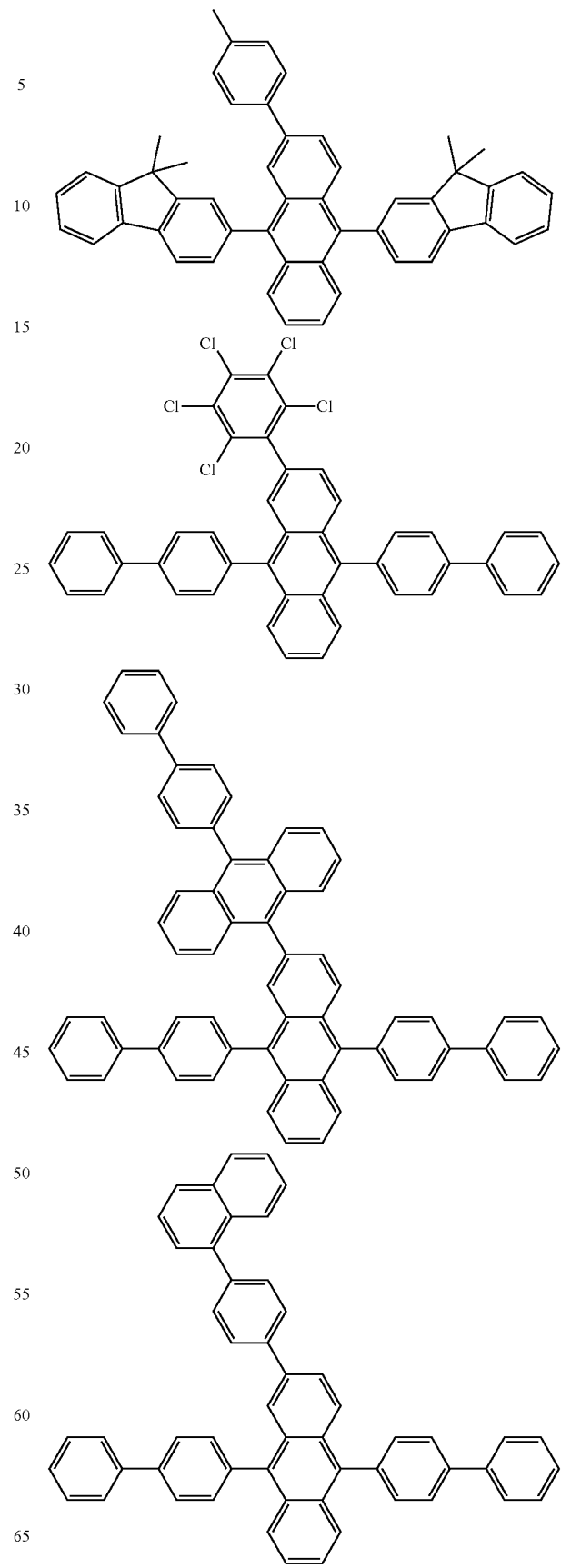

149
-continued
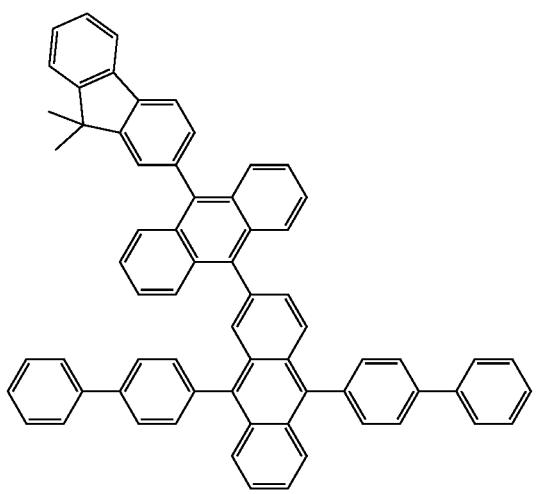
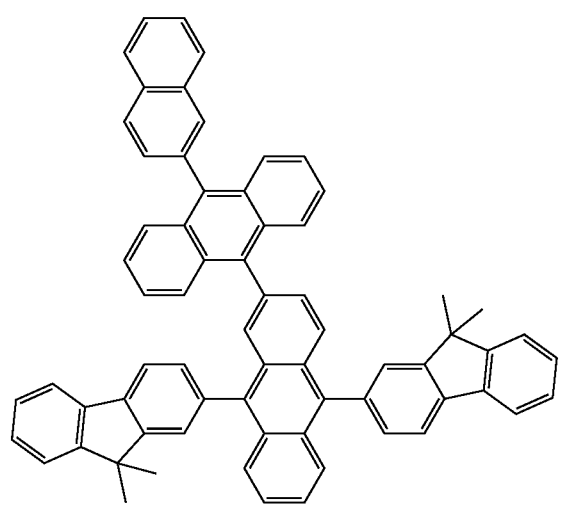
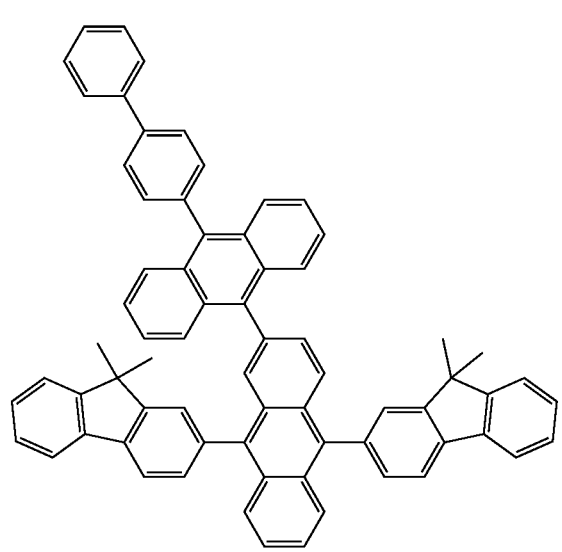
150
-continued
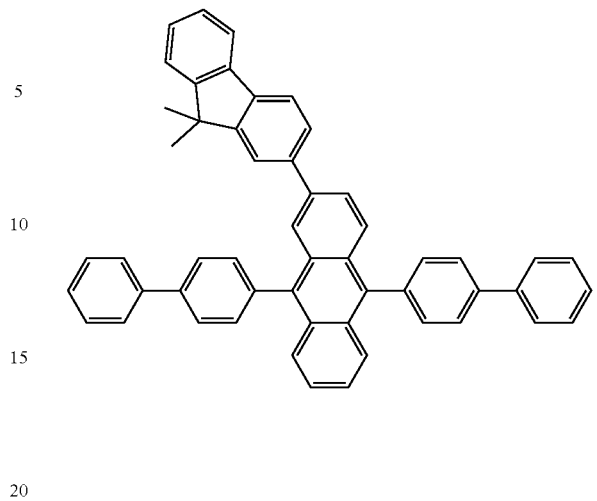
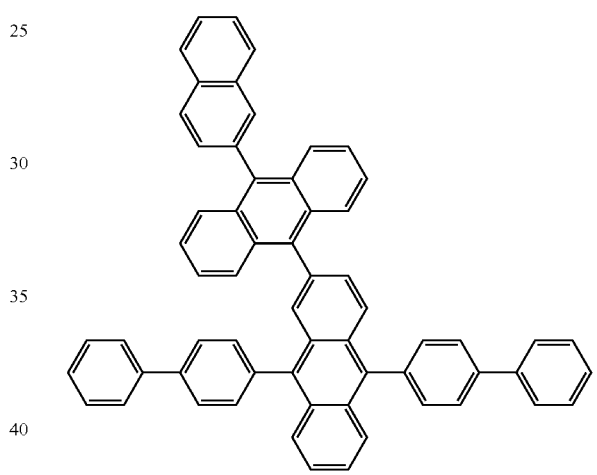
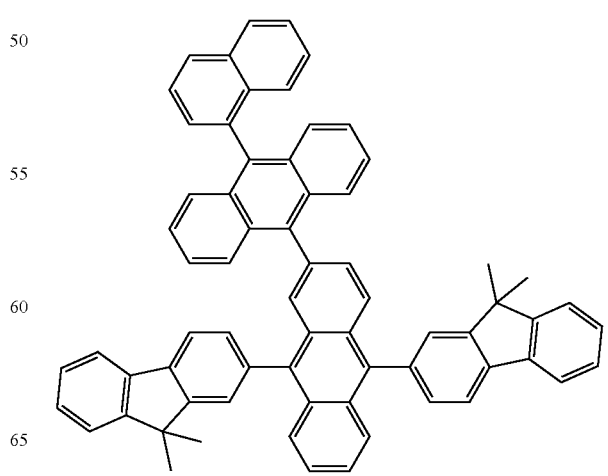

151
-continued
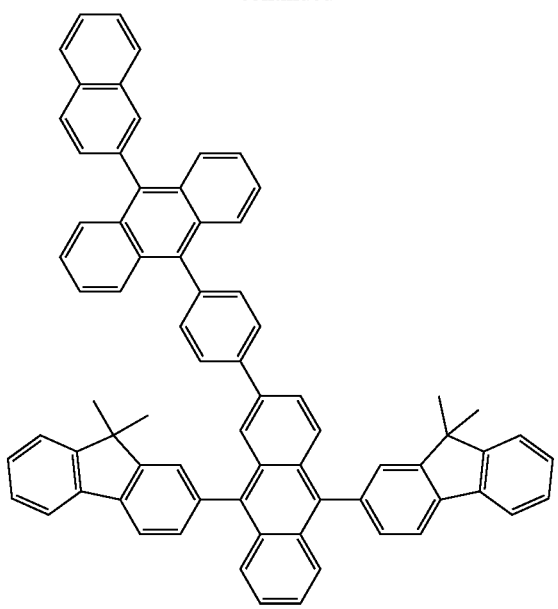
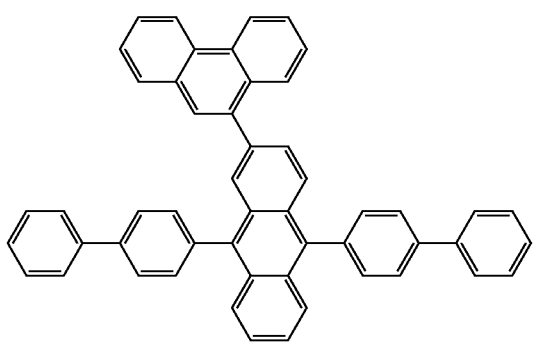
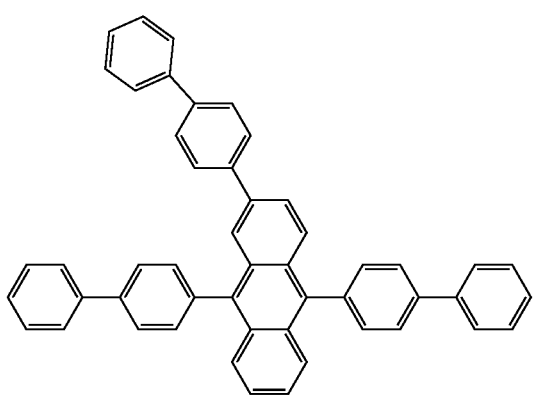
152
-continued
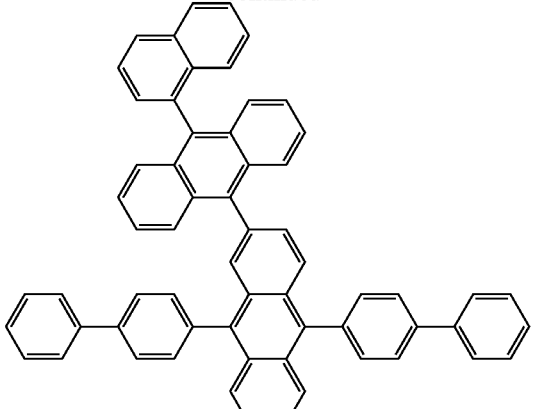
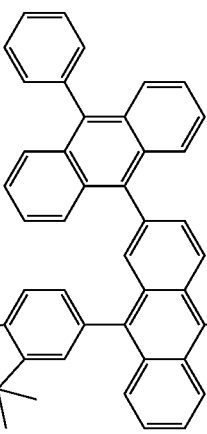
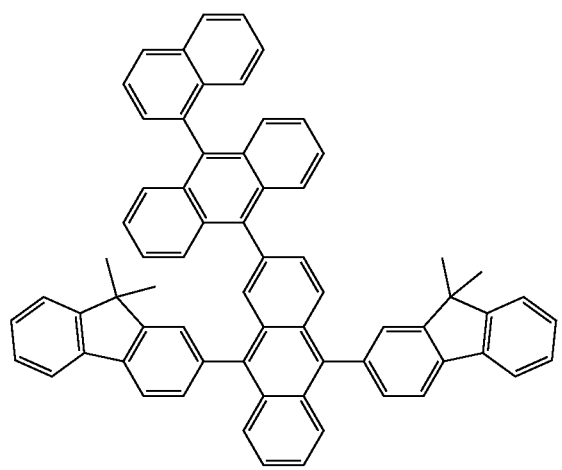

153
-continued
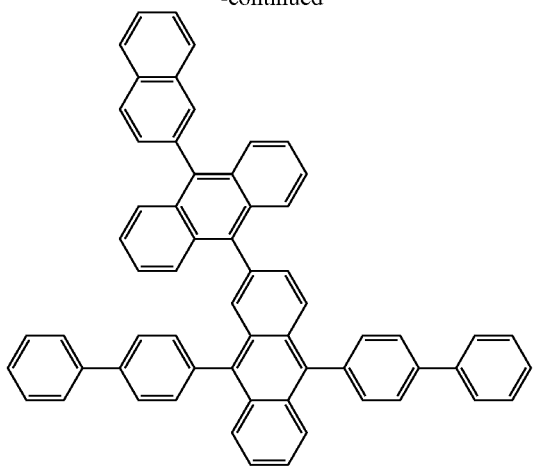
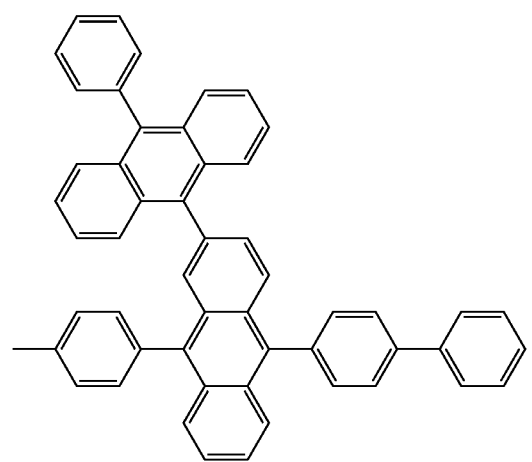
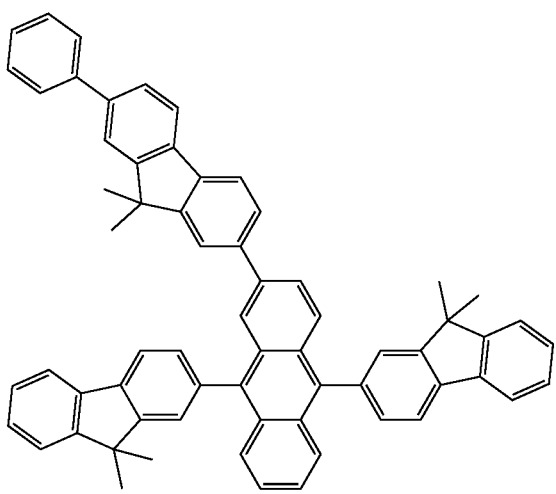
154
-continued
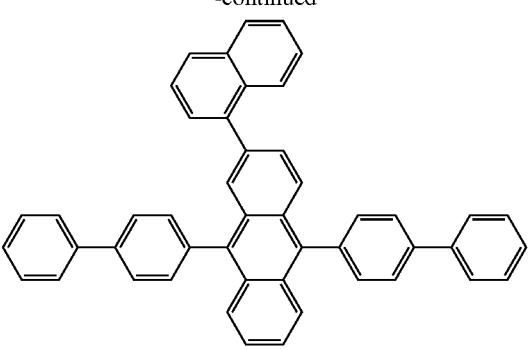
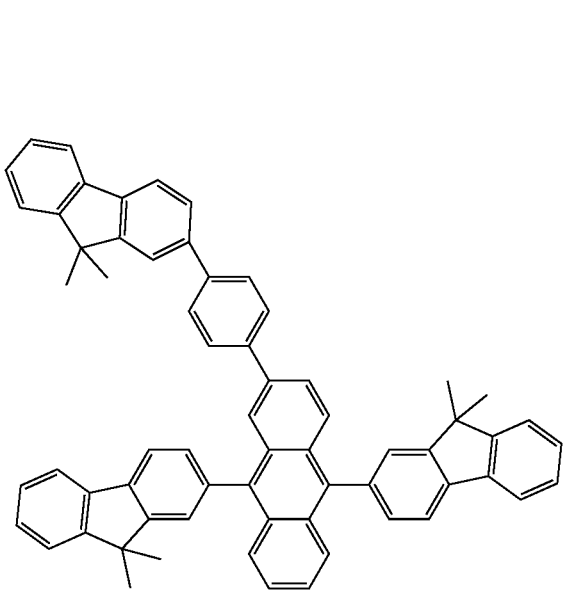

155
-continued
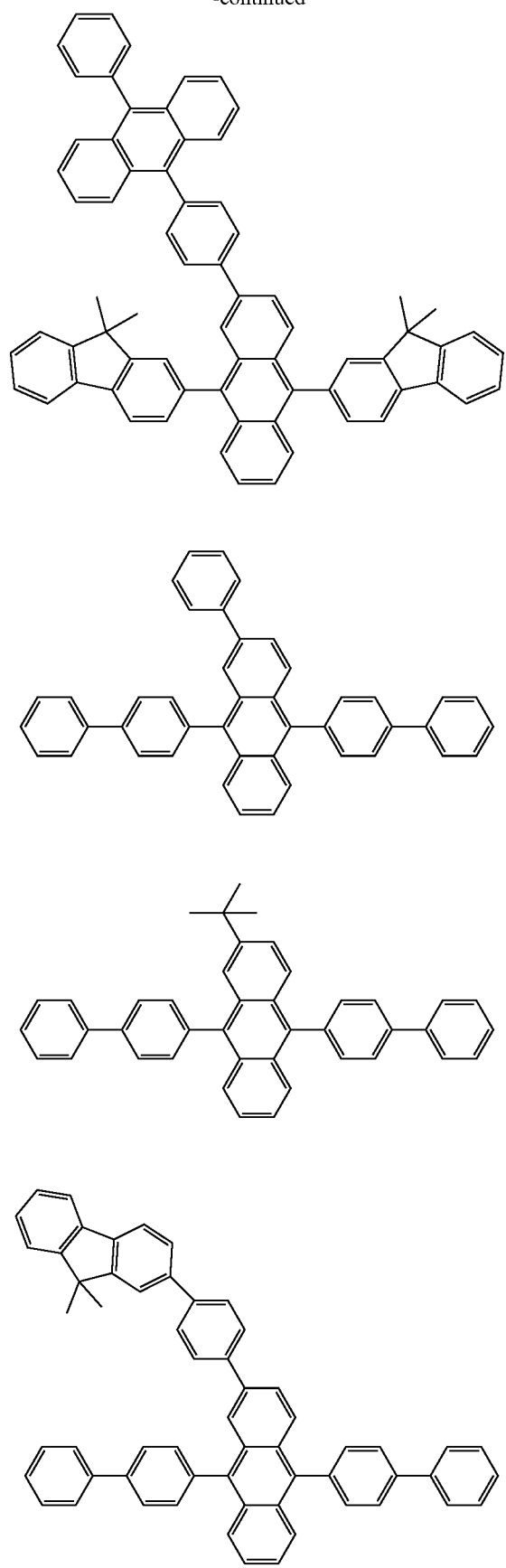
156
-continued
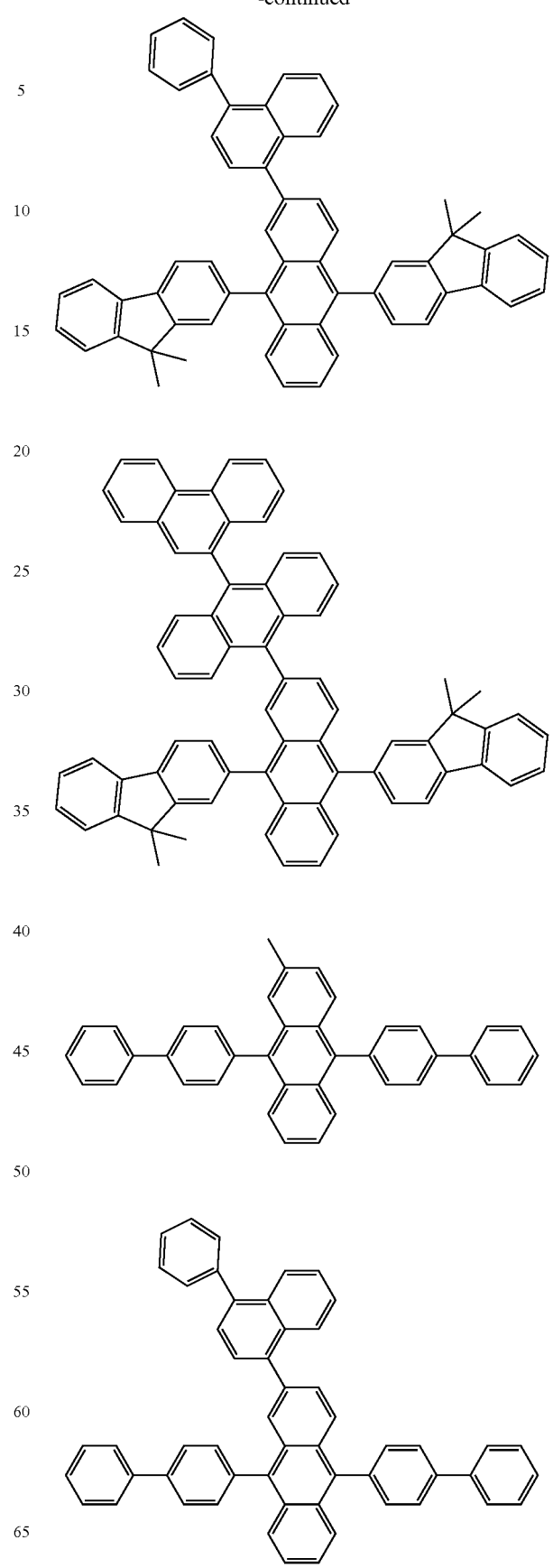

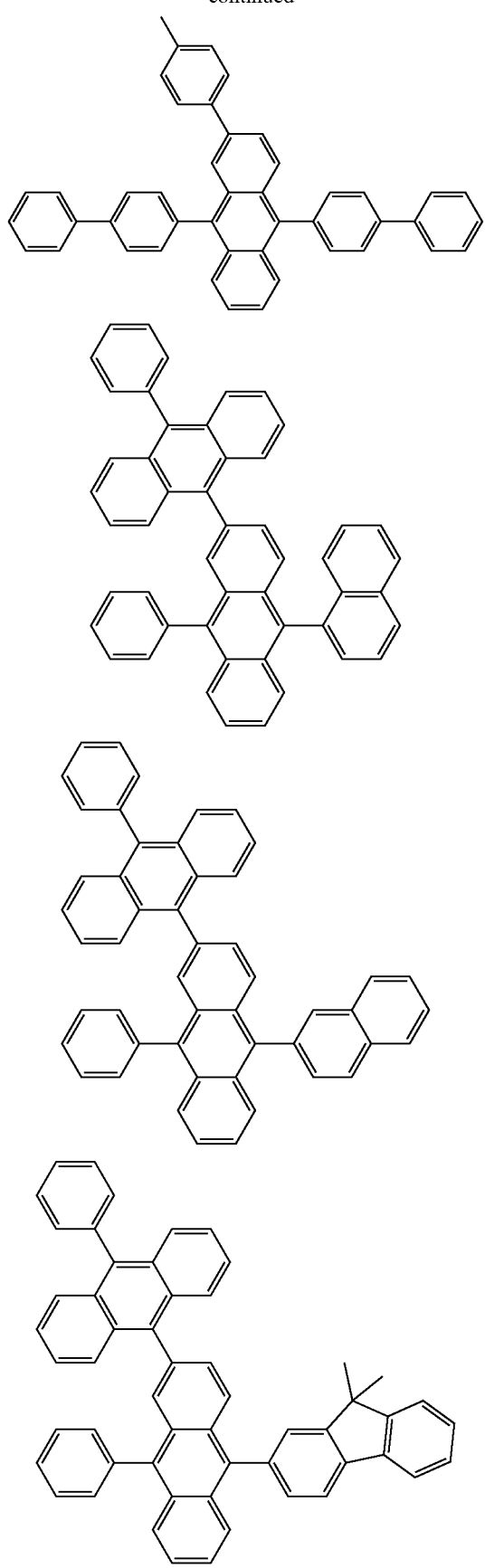
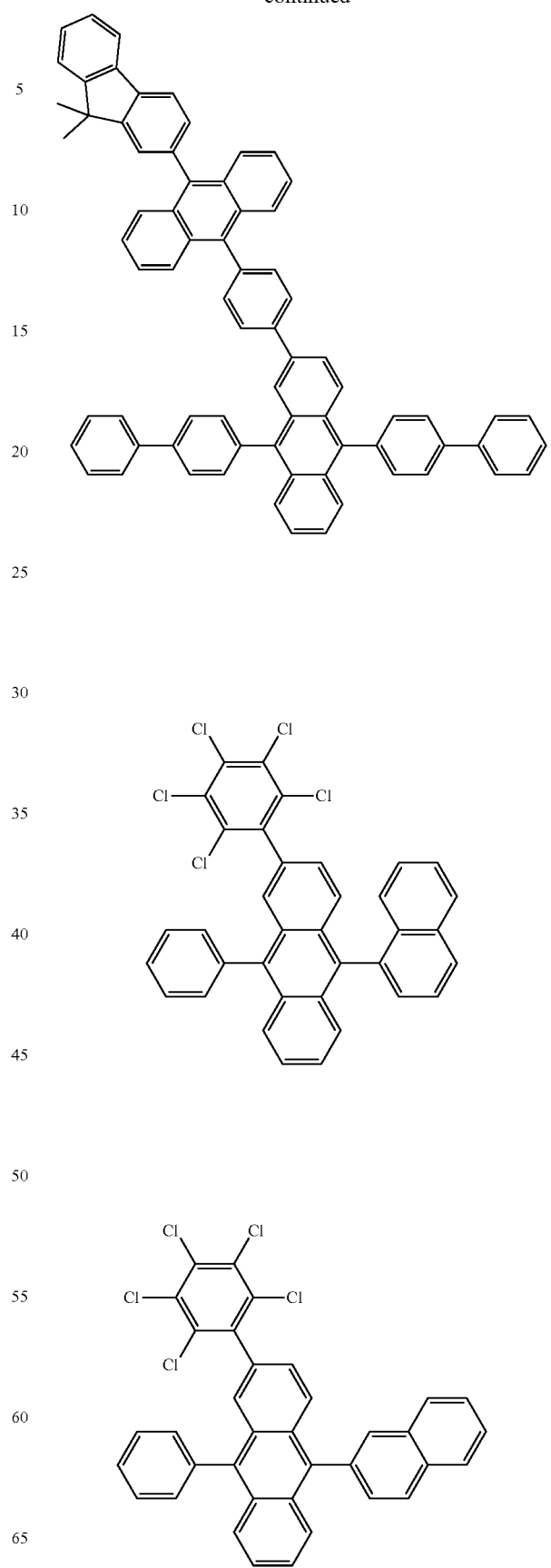

159
-continued
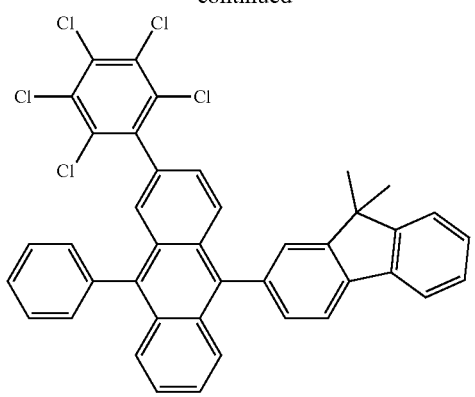
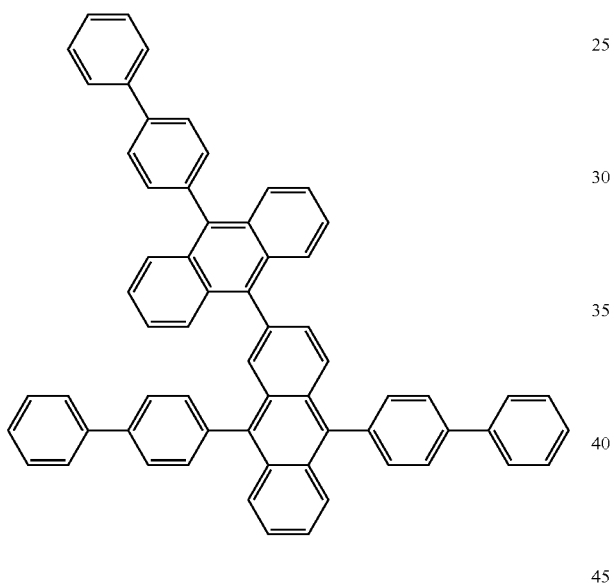
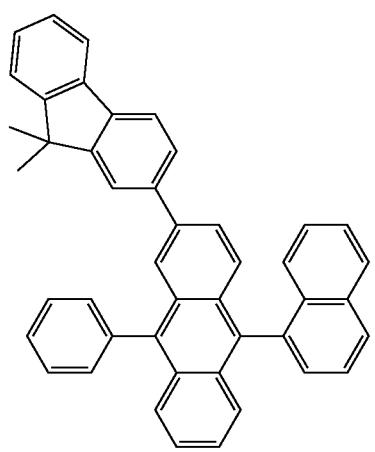
160
-continued
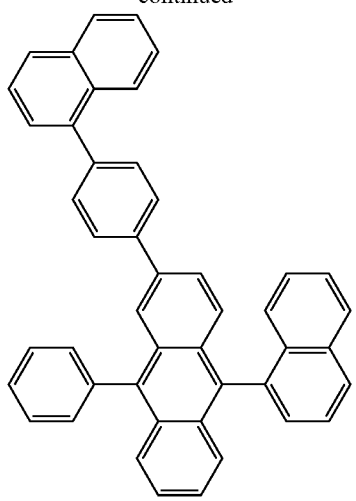
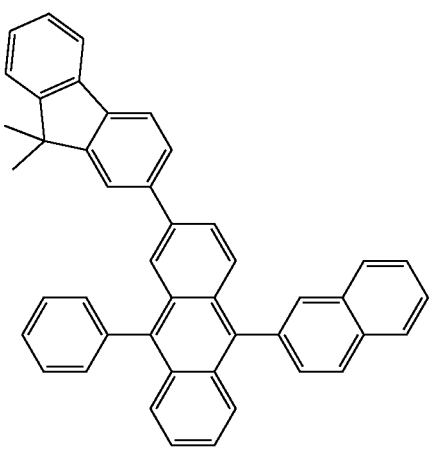

161
-continued
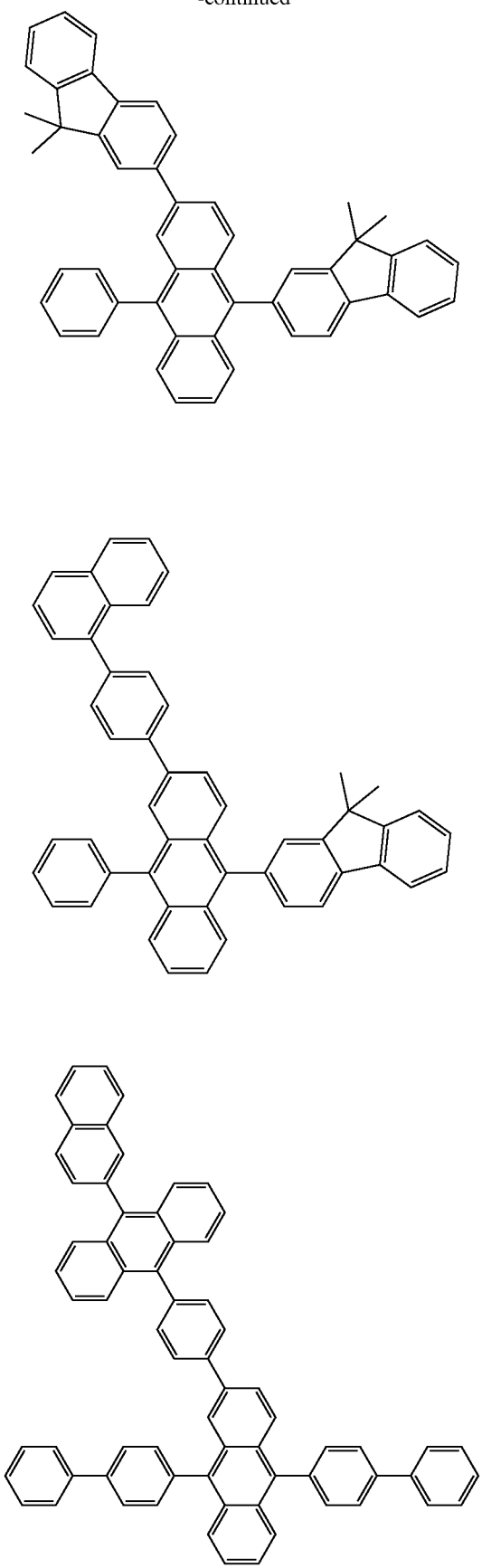
162
-continued
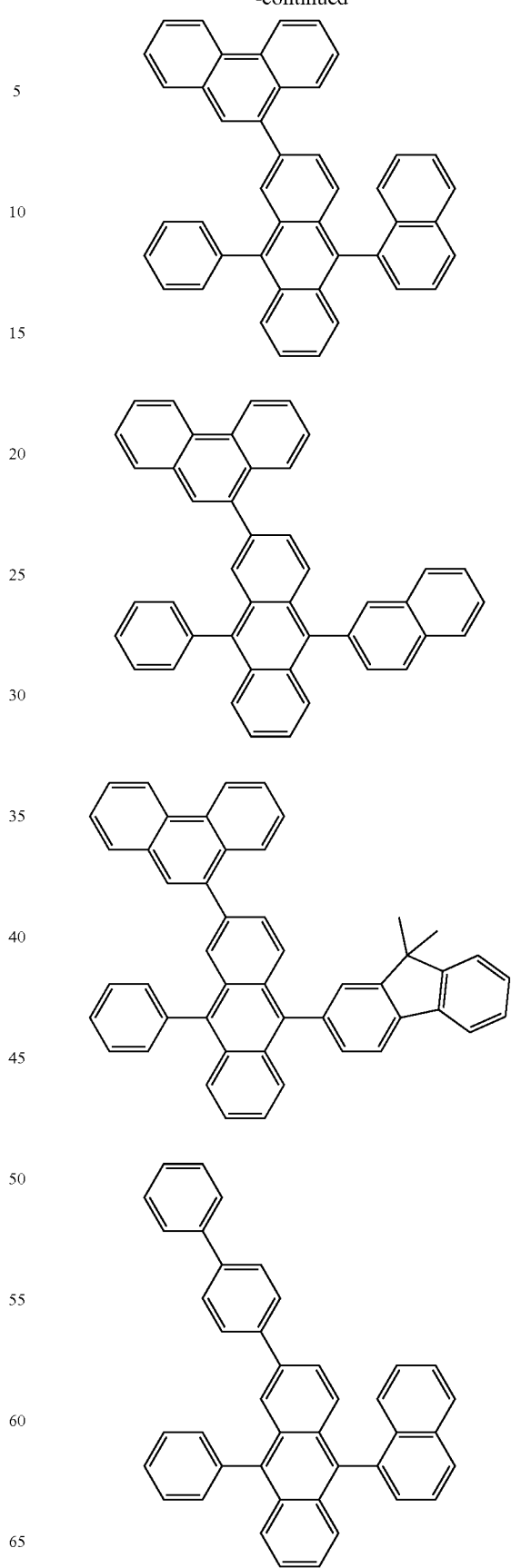

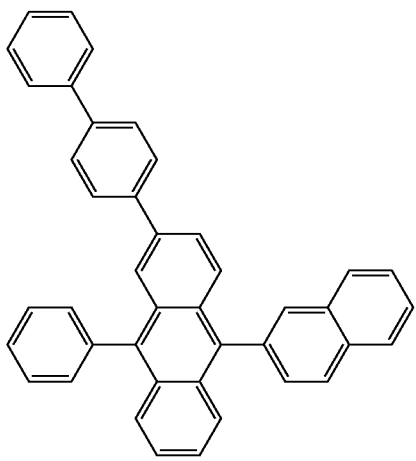
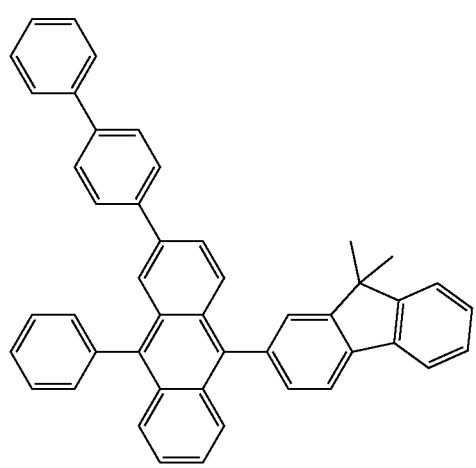
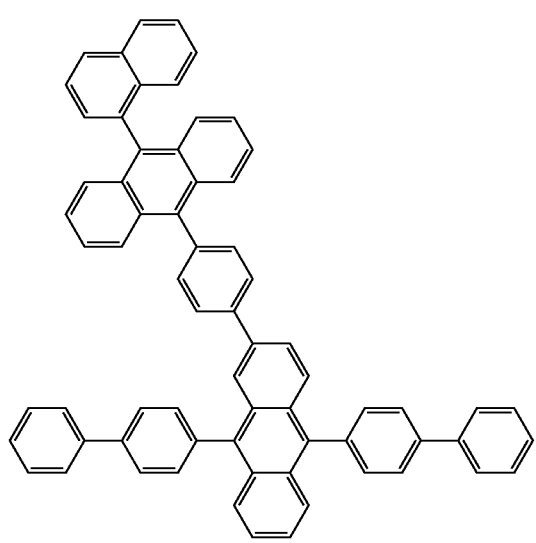
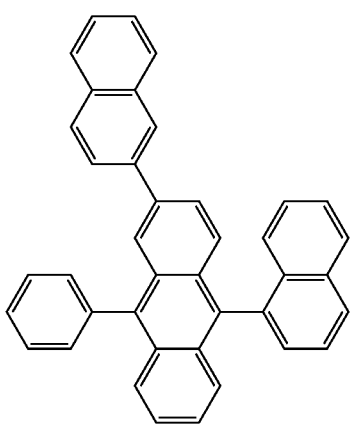
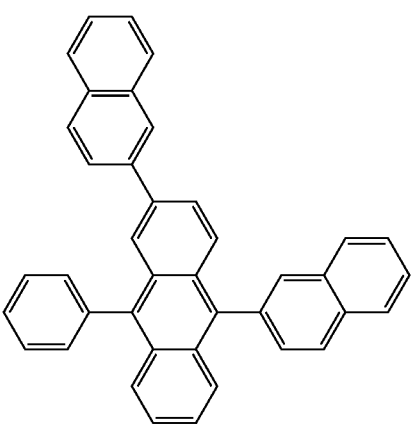
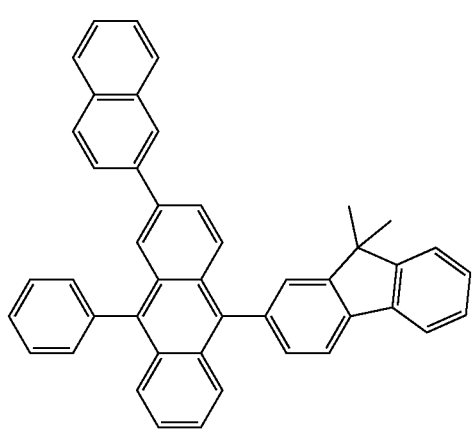

-continued
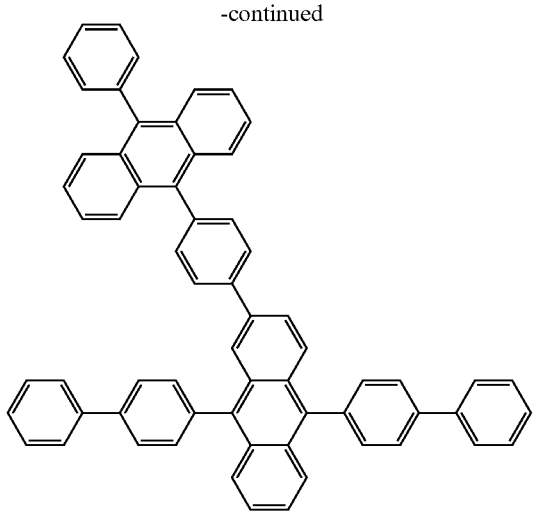
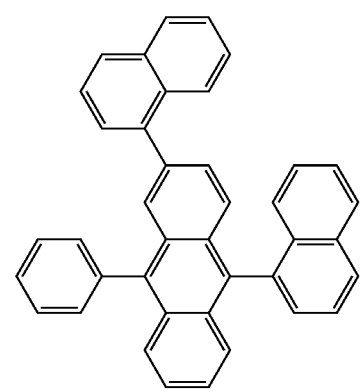
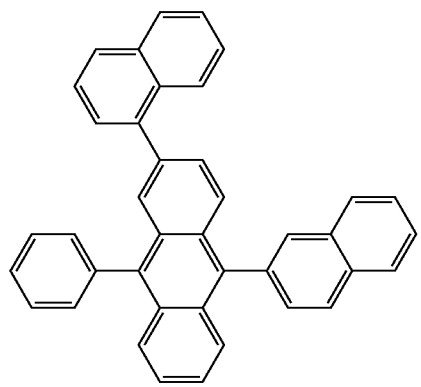
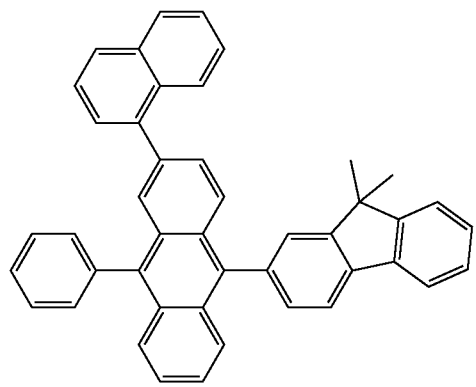
-continued
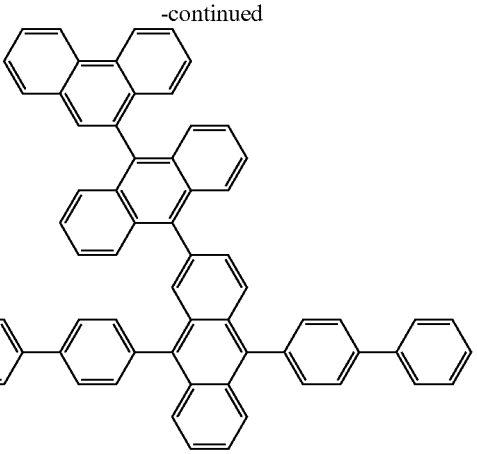
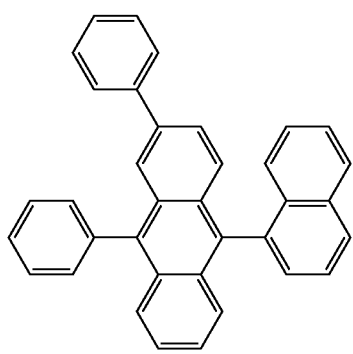
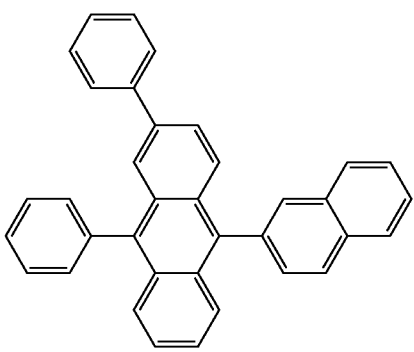
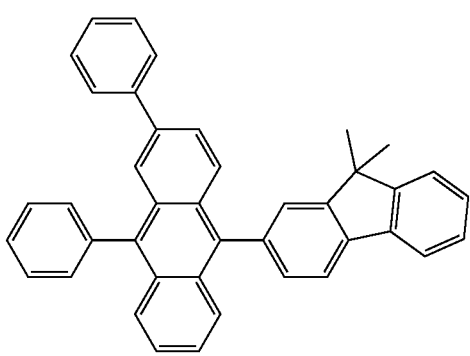

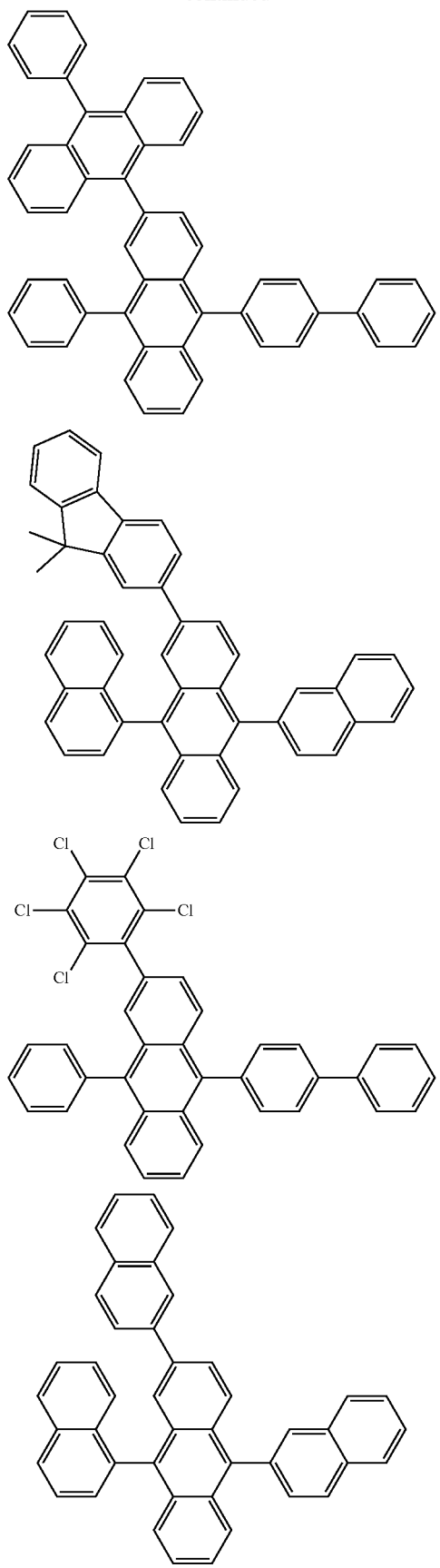
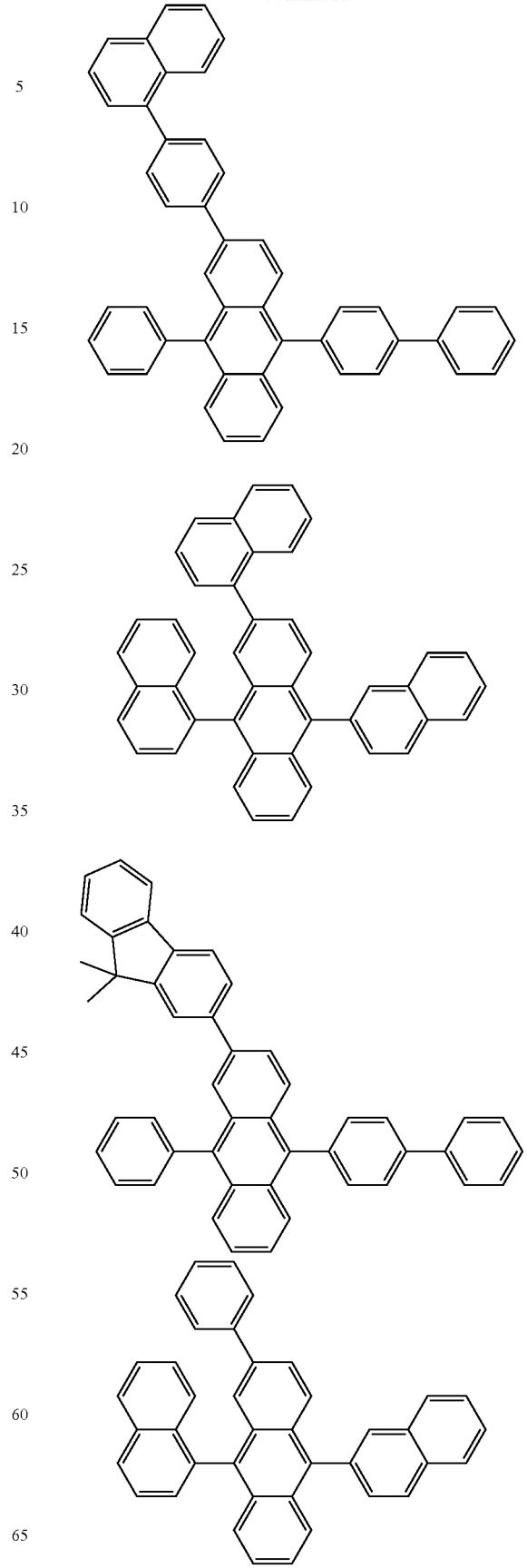

169
-continued
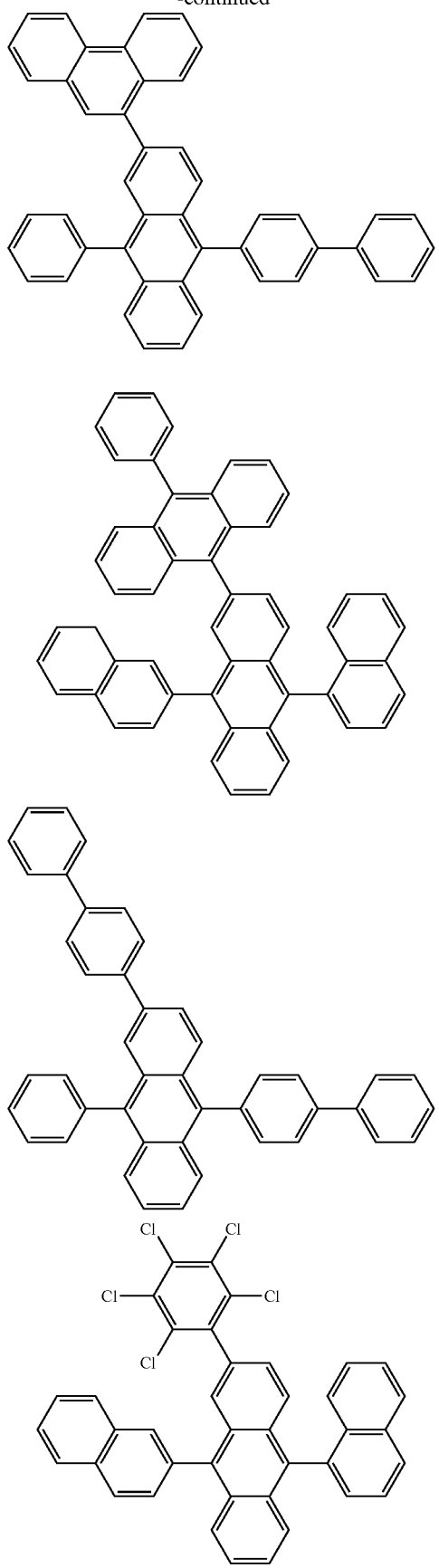
170
-continued
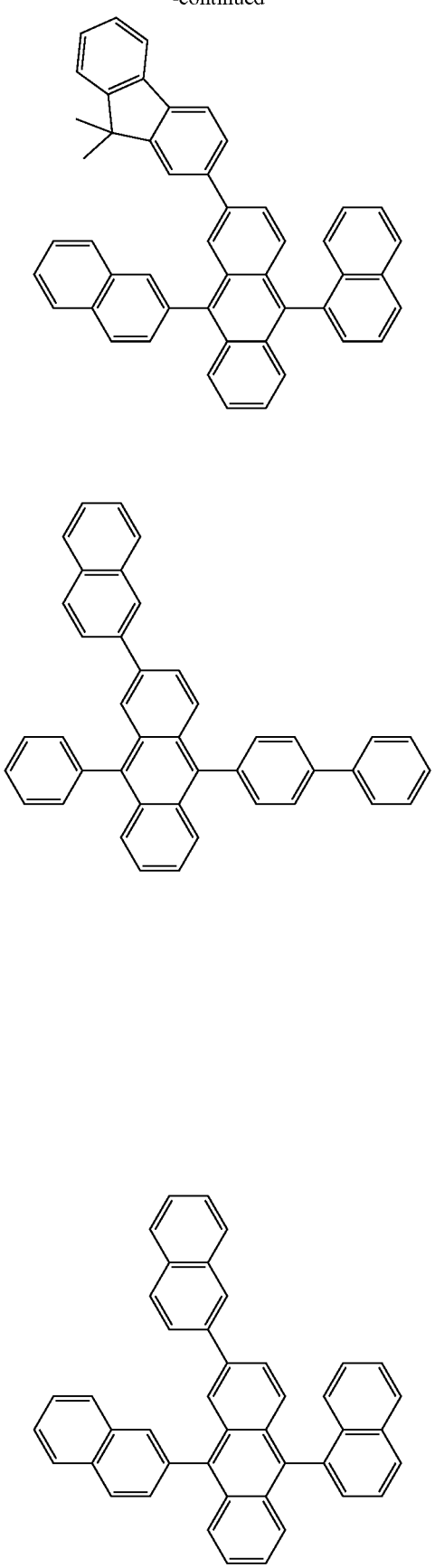

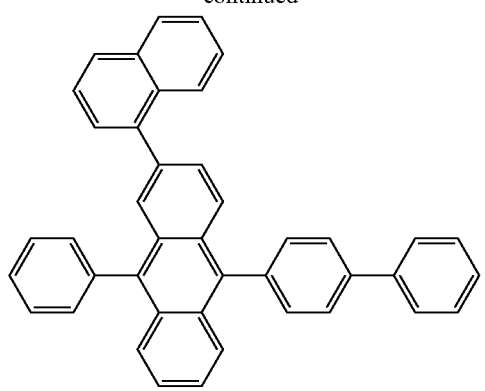
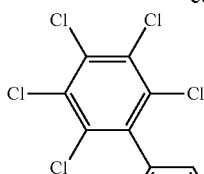
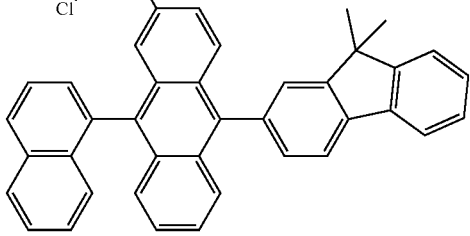
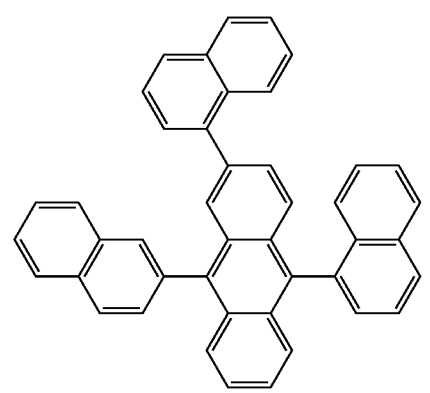
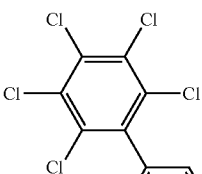
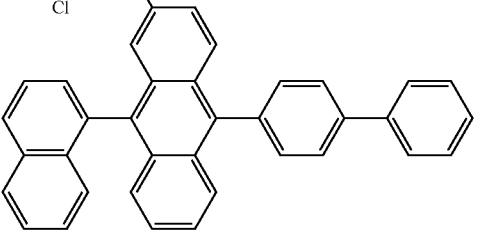
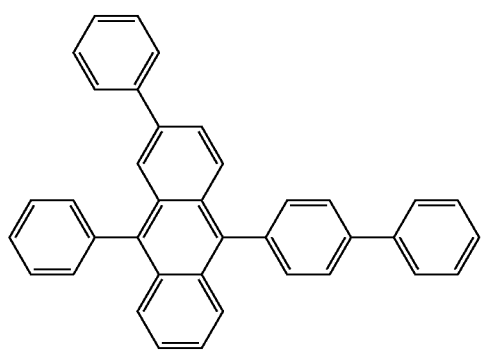
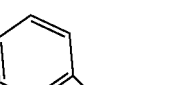
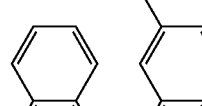
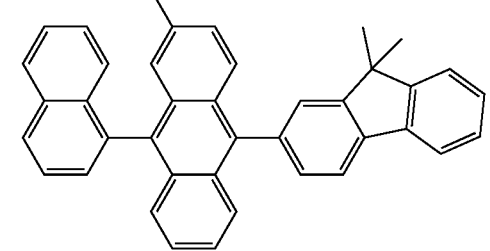
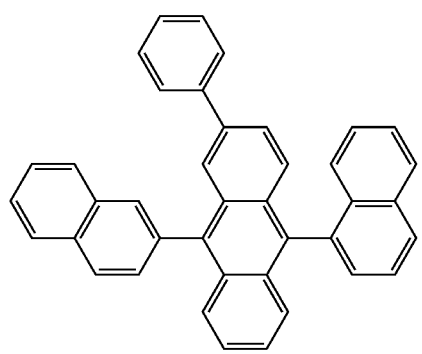
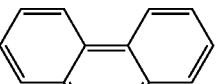
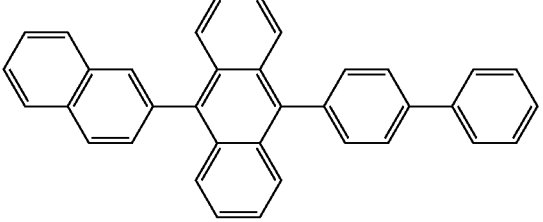

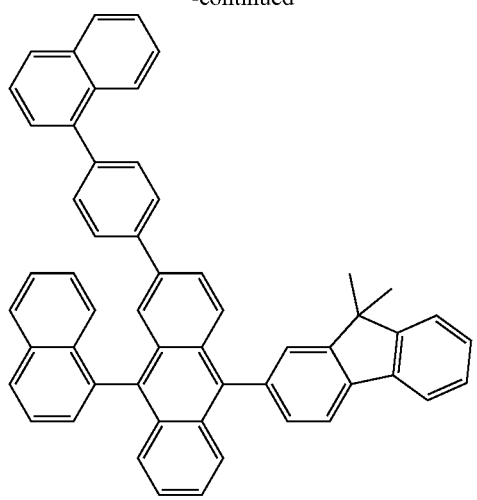
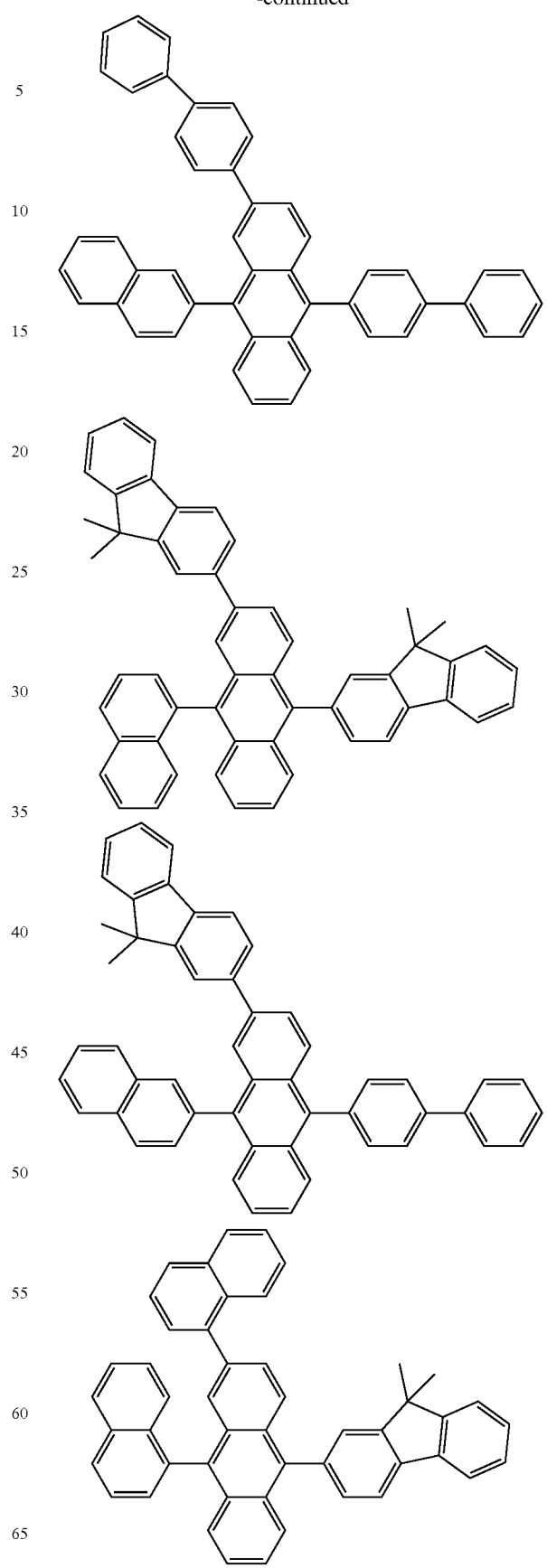

175
-continued
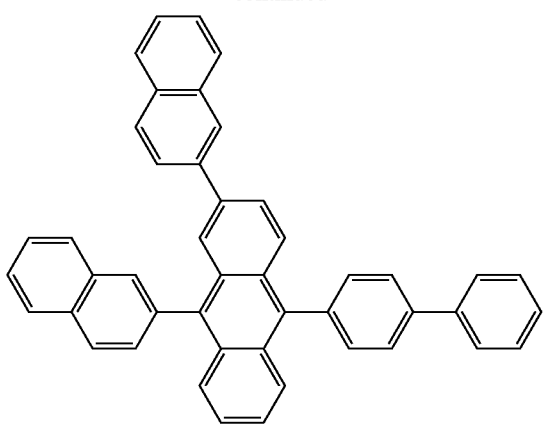
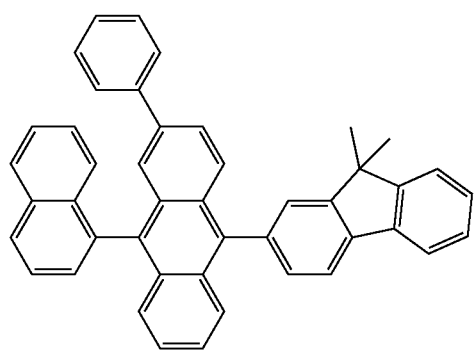
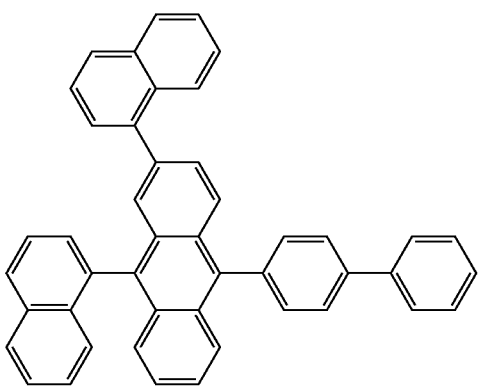
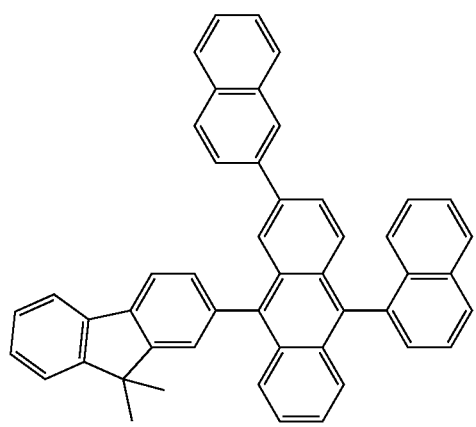
176
-continued
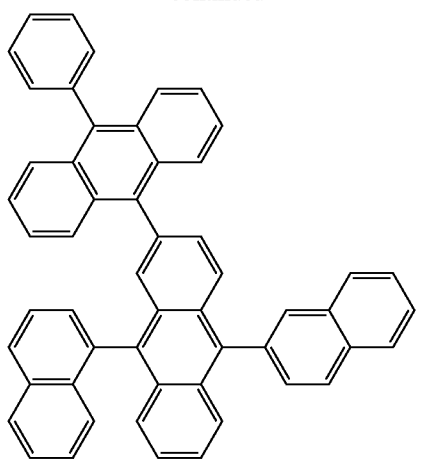
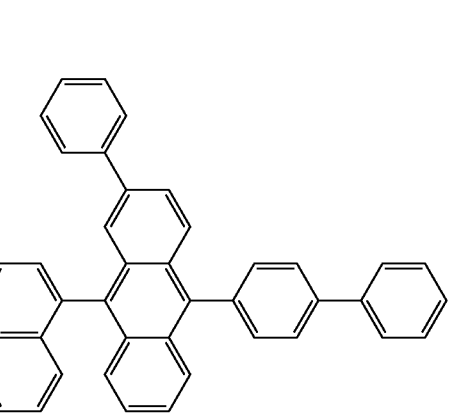
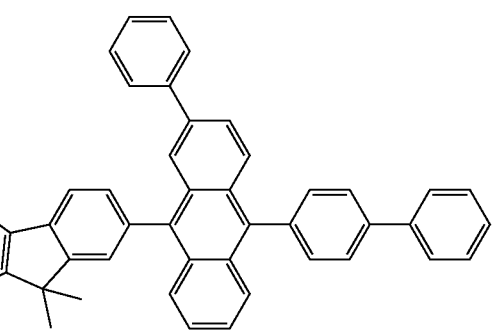
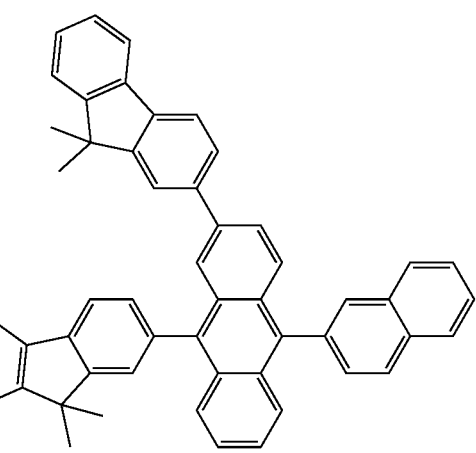

177
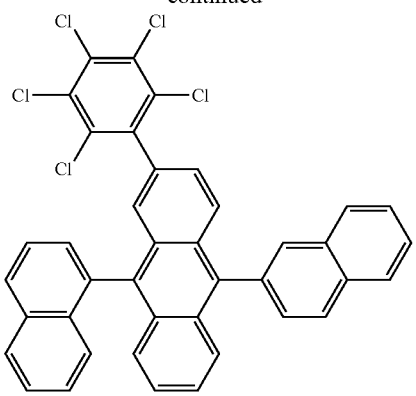
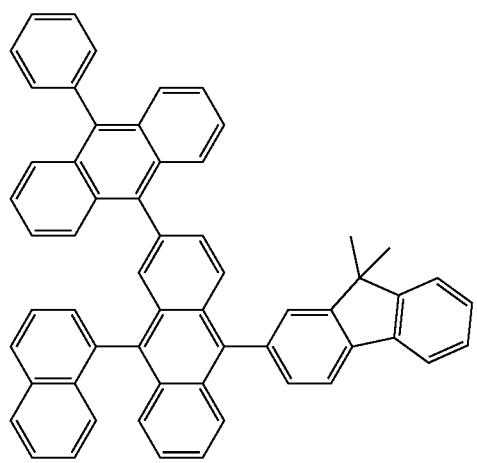
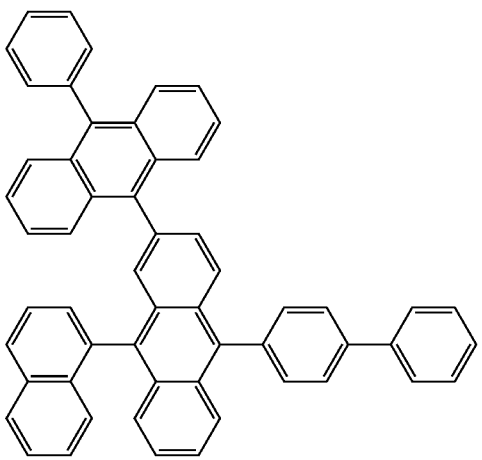
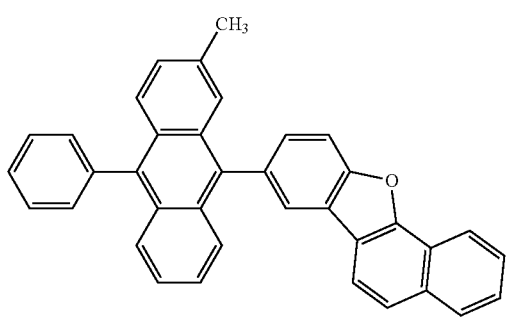
178
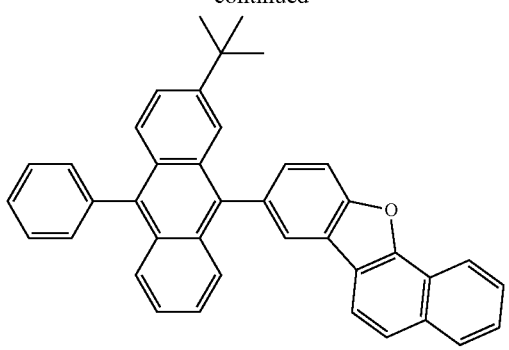
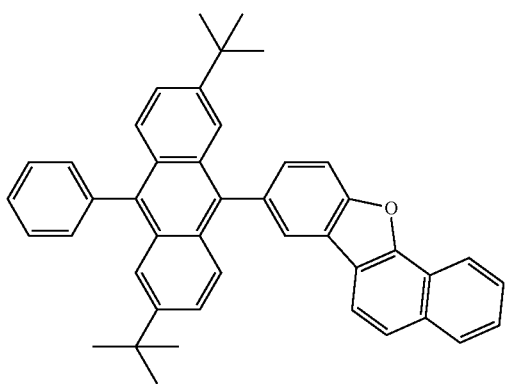
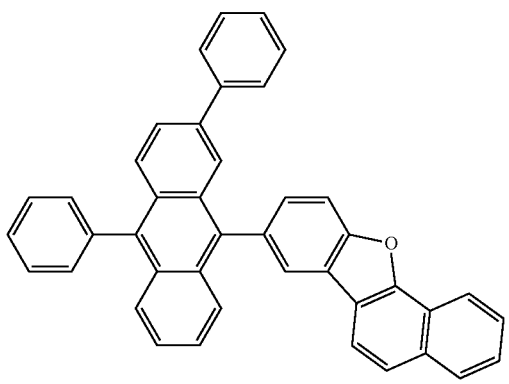
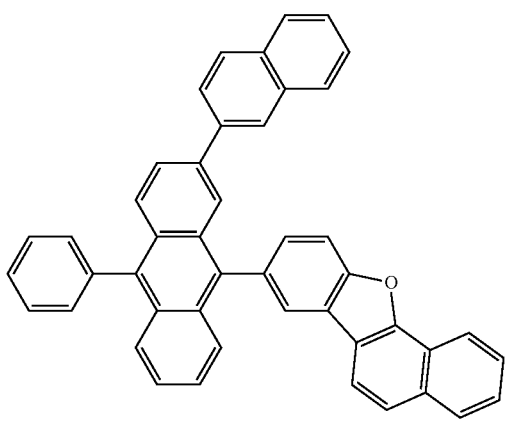

179
-continued
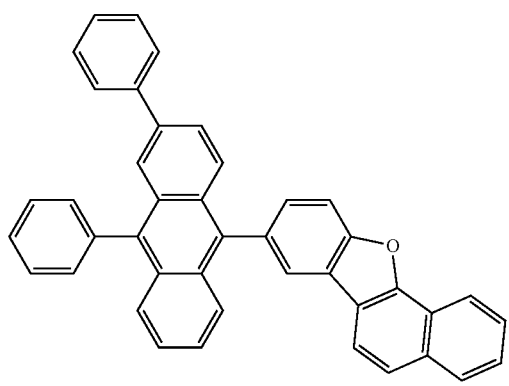
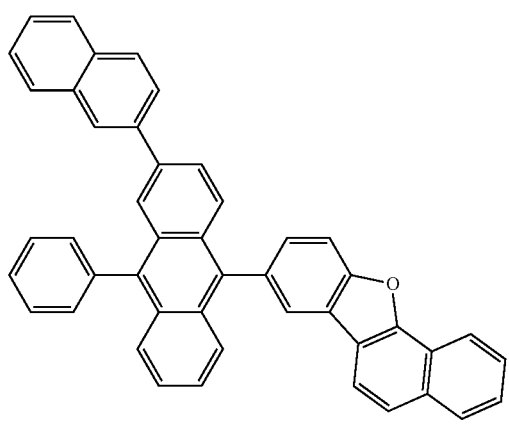
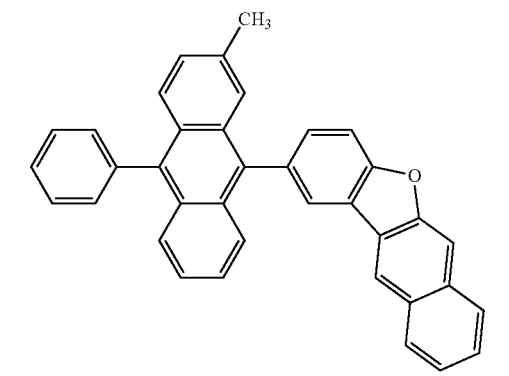
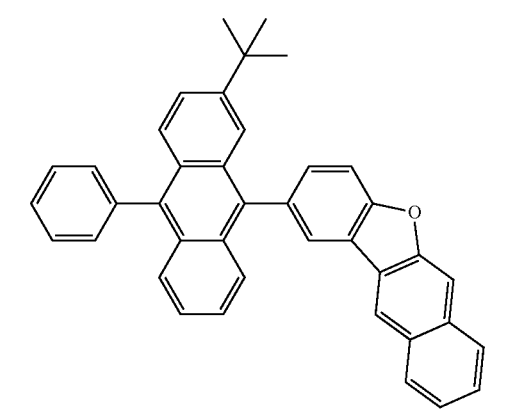
180
-continued
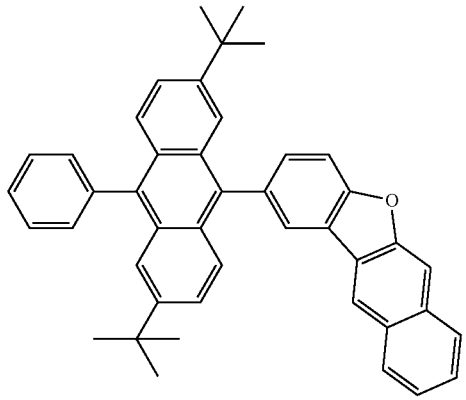
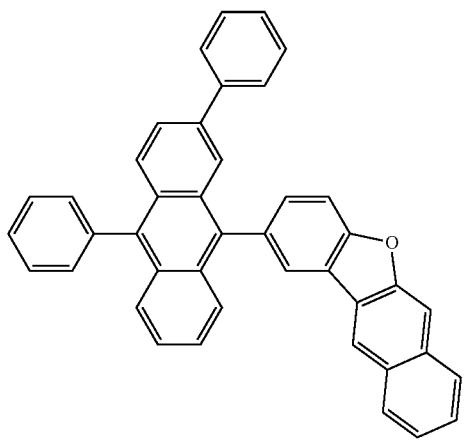
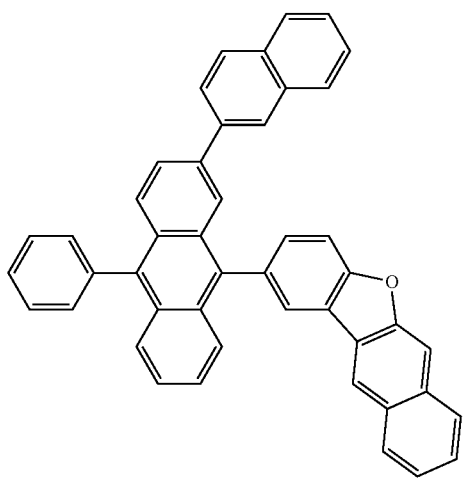

-continued

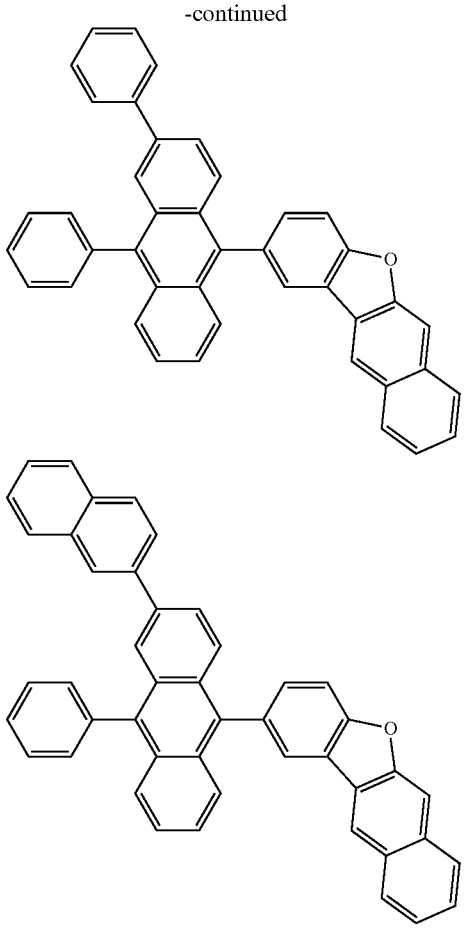

In the second aspect of an organic EL device of the invention, when the emitting layer contains the compound represented by the formula (1) and the compound represented by the formula (11), a content of the compound represented by the formula (1) is preferably 1 mass % or more and 20 mass % or less based on the total mass of the emitting layer.

In the second aspect of an organic EL device of the invention, when the emitting layer contains the compound represented by the formula (1) and the compound represented by the formula (11), a content of the compound represented by the formula (11) is preferably 80 mass % or more and 99 mass % or less based on the total mass of the emitting layer.

In the second aspect of an organic EL device of the invention, the organic EL device preferably comprises a hole-transporting layer between the anode and the emitting layer.

In the second aspect of an organic EL device of the invention, the organic EL device preferably comprises an electron-transporting layer between the cathode and the emitting layer.

Specific examples of a typified device configuration of the organic EL device of the invention include structures such as
(1) an anode/an emitting layer/a cathode,
(2) an anode/a hole-injecting layer/an emitting layer/a cathode,
(3) an anode/an emitting layer/an electron-injecting-transporting layer/a cathode,
(4) an anode/a hole-injecting layer/an emitting layer/an electron-injecting-transporting layer/a cathode,
(5) an anode/an organic semiconductor layer/an emitting layer/a cathode,
(6) an anode/an organic semiconductor layer/an electron barrier layer/an emitting layer/a cathode,
(7) an anode/an organic semiconductor layer/an emitting layer/an adhesion improving layer/a cathode,
(8) an anode/a hole-injecting-transporting layer/an emitting layer/an electron-injecting-transporting layer/a cathode,
(9) an anode/an insulating layer/an emitting layer/an insulating layer/a cathode,
(10) an anode/an inorganic semiconductor layer/an insulating layer/an emitting layer/an insulating layer/a cathode,
(11) an anode/an organic semiconductor layer/an insulating layer/an emitting layer/an insulating layer/a cathode,
(12) an anode/an insulating layer/a hole-injecting-transporting layer/an emitting layer/an insulating layer/a cathode, and
(13) an anode/an insulating layer/a hole-injecting-transporting layer/an emitting layer/an electron-injecting-transporting layer/a cathode.

Among the above-described structures, the configuration of (8) is preferably used, but the device configuration of the organic EL device is not limited thereto.

The emitting layer may be a phosphorescent emitting layer, or a fluorescent emitting layer, or may include a plurality of emitting layers. When the organic EL device comprises the plurality of emitting layers, the organic EL device may comprise a space layer between the respective emitting layers for the purpose of preventing excitons generated in the phosphorescent emitting layer from diffusing into the fluorescent emitting layer.

The FIGURE shows a schematic configuration of one example of the organic EL device in an embodiment of the invention.

The organic EL device 1 comprises a transparent substrate 2, an anode 3, a cathode 4, and an organic thin film layer 10 disposed between the anode 3 and the cathode 4.

The organic thin film layer 10 comprised the above-mentioned emitting layer 5, but may comprise a hole-injecting-transporting layer 6 and the like between the emitting layer 5 and the anode 3, and an electron-injecting-transporting layer 7 and the like between the emitting layer 5 and the cathode 4.

Further, the electron barrier layer may be provided on a side of the anode 3 of the emitting layer 5, and a hole barrier layer may be provided on a side of the cathode 4 of the emitting layer 5, respectively.

By these device configurations, electrons and holes can be confined in the emitting layer 5 to enhance generation probability of the excitons in the emitting layer 5.

Moreover, the "hole-injecting-transporting layer" in this specification means "at least one of the hole-injecting layer and the hole-transporting layer", and the "electron-injecting-transporting layer" in this specification means "at least one of the electron-injecting layer and the electron-transporting layer".

A substrate is used as a support of an emitting device. As the substrate, glass, quartz, plastics or the like can be used, for example. Further, a flexible substrate may be used. A term "flexible substrate" means a bendable (flexible) substrate, and specific examples thereof include a plastic substrate formed of polycarbonate or polyvinyl chloride.

For the anode formed on the substrate, metal, alloy, an electrically conductive compound, a mixture thereof or the like, each having a large work function (specifically 4.0 eV or more), is preferably used. Specific examples include indium oxide-tin oxide (ITO: Indium Tin Oxide), indium oxide-tin oxide containing silicon or silicon oxide, indium oxide-zinc oxide, indium oxide containing tungsten oxide or zinc oxide, graphene, and the like. In addition thereto, specific examples thereof include gold (Au), platinum (Pt), a nitride of a metallic material (for example, titanium nitride) and the like.

The hole-injecting layer is a layer containing a material having high hole-injection properties. As the material having high hole-injection properties, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, aromatic amine compound, a ladder-based compound such as fluorene derivative, or a polymer compound (oligomer, dendrimer, polymer, or the like) can also be used.

The hole-transporting layer is a layer containing a material having high hole-transporting properties. For the hole-transporting layer, an aromatic amine compound, a carbazole derivative, an anthracene derivative, or the like can be used. A polymer compound such as poly(N-vinylcarbazole) (abbreviation: PVK) and poly(4-vinyltriphenylamine) (abbreviation: PVTPA) can also be used. However, a material other than the above-described materials may be used as long as the material has higher transporting properties of holes in comparison with electrons. It should be noted that the layer containing the material having high hole-transporting properties may be formed into not only a monolayer, but also a layer in which two or more layers formed of the above-described materials are stacked.

The electron-transporting layer is a layer containing a material having a high electron-transporting properties. For the electron-transporting layer, 1) a metallic complex such as a lithium complex, an aluminum complex, a beryllium complex, or a zinc complex; 2) a heteroaromatic compound such as an imidazole derivative, a benzimidazole derivative, an azine derivative, a carbazole derivative, or a phenanthroline derivative; and 3) a polymer compound can be used.

The electron-injecting layer is a layer containing a material having a high electron-injecting properties. As the electron-injecting layer, an alkali metal, an alkaline earth metal, or a compound thereof such as lithium (Li), a lithium complex, lithium fluoride (LiF), cesium fluoride (CsF), calcium fluoride ($CaF_2$), lithium oxide ($LiO_x$), or the like can be used.

For the cathode, a metal, an alloy, an electrically conductive compound, a mixture thereof, or the like, having a small work function (specifically, 3.8 eV or less) is preferably used. Specific examples of such a cathode material include an element belonging to group 1 or group 2 of the periodic table of the elements, namely, alkali metal such as lithium (Li) and cesium (Cs), alkaline earth metal such as magnesium (Mg), and alloy containing the metal thereof (for example, MgAg and AlLi).

In one aspect of the organic EL device of the invention, a method for forming each layer is not limited. A conventionally-known method for forming each layer according to a vacuum deposition process, a spin coating process or the like can be used. Each layer such as the emitting layer can be formed by a known method such as a vacuum deposition process, a molecular beam deposition process (MBE process), or an application process such as a dipping process, a spin coating process, a casting process, a bar coating process and a roll coating process, using a solution prepared by dissolving the material in the solvent.

In an aspect of an organic EL device of the invention, the thickness of each layer is not particularly limited, but generally, the thickness of each layer is preferably several nanometers to 1 micrometer in order to suppress defects such as pinholes, suppress applied voltages to be low, and improve luminous efficiency.

The organic EL device of the invention can be used for a display component such as an organic EL panel module, a display apparatus such as a TV, a cellular phone, or a personal computer, and an electronic appliance such as a light emitting device such as a light, a vehicular lamp, or the like.

EXAMPLES

Next, the invention will be described in more detail by referring to Examples and Comparative Examples, but the invention is not limited in any way to the description of these Examples.

Example 1

(Synthesis of Compound 6)

Me represents a methyl group. TfO represents a trifluoromethylsulfonyloxy group.

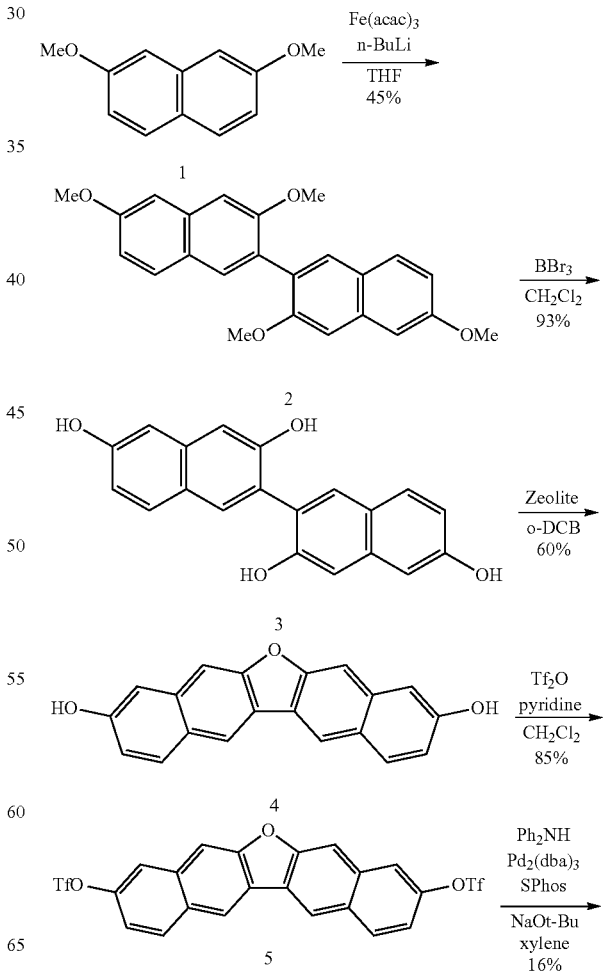

-continued

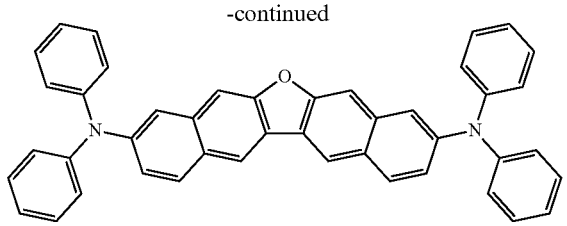

6

Under an argon atmosphere, 10 g (53.1 mmol) of 2,7-dimethoxynaphthalene (Compound 1) was dissolved in 200 mL of tetrahydrofuran (THF). To this solution, 36.5 mL of 1.6 mol/L n-butyllithium (n-BuLi) in hexane was added dropwise at −10° C. After completion of the dropwise addition, 20.6 g (58.4 mmol, 1.1 eq.) of iron(III)acetylacetonate (Fe(acac)$_3$) was added while stirring at −10° C. for 2 hours. After completion of the addition, the temperature of the solution was elevated to room temperature, and was stirred for 4 hours after the elevation of the temperature. After stirring, the solution was left to stand overnight.

After standing overnight, the precipitated solid was filtered through celite and washed with hexane. The resulting residue was purified using column chromatography (100% toluene) and washed with hexane to obtain 4.42 g of a white solid (yield: 45%).

The molecular weight of Compound 2 was 374.43, and the mass spectrum of the obtained white solid indicated m/e (mass-to-charge ratio)=374. By this fact, it was confirmed that the white solid is Compound 2.

Under an argon atmosphere, 4.35 g (11.6 mmol) of Compound 2 obtained above was dissolved in 40 mL of methylene chloride. To this solution, 48.8 mL of 1 mol/L boron tribromide (BBr$_3$) in methylene chloride was added dropwise at −10° C. After completion of the dropwise addition, the solution was stirred at room temperature for 4 hours, and then left to stand overnight.

The reaction solution, which was left to stand overnight, was added to ice water and the precipitated solid was collected by filtration. The resulting solid was purified by column chromatography (100% ethyl acetate) to obtain 3.45 g of a brown solid (yield: 93%).

The molecular weight of Compound 3 is 318.32, and the mass spectrum of the obtained brown solid indicated m/e=318. By this fact, it was confirmed that the brown solid is Compound 3.

Under an argon atmosphere, 3.1 g (9.7 mmol) of Compound 3 obtained above, 1.24 g of zeolite HSZ-360HUA (Zeolite, manufactured by Tosoh Corporation), and 180 mL of o-dichlorobenzene (o-DCB) were mixed and stirred at 160° C. for 6 hours. After stirring, the mixture was cooled to room temperature and left to stand overnight.

After standing overnight, the precipitated solid was collected by filtration and washed with methanol. The resulting solid was extracted with tetrahydrofuran to obtain 1.74 g of a brown solid (yield: 60%).

The molecular weight of Compound 4 is 300.31, and the mass spectrum of the obtained brown solid indicated m/e=300. By this fact, it was confirmed that the brown solid is Compound 4.

Under an argon atmosphere, 1.5 g (5.0 mmol) of Compound 4, 10 mL of pyridine and 25 mL of methylene chloride were mixed, and 2.1 mL (12.5 mmol) of triflate (Tf$_2$O) anhydride was added dropwise to the mixture at 0° C. After completion of the dropwise addition, the mixture was stirred at room temperature for 1 hour, methanol was added thereto, the reaction was stopped, and a reaction solution was obtained.

Water was added to the obtained reaction solution, and methylene chloride was removed by vacuum concentration to precipitate a solid. The precipitated solid was collected by filtration and washed with methanol to obtain 2.6 g of a white solid (yield: 86%).

The molecular weight of Compound 5 is 566.45, and the mass spectrum of the obtained white solid indicated m/e=566. By this fact, it was confirmed that the white solid is Compound 5.

Under an argon atmosphere, Compound 5 obtained above (50 mg, 0.089 mmol), diphenylamine (Ph$_2$NH) (30 mg, 0.18 mmol), tris(dibenzylideneacetone)dipalladium (0) (Pd$_2$(dba)$_3$) (3 mg, 0.003 mmol), 2-dicyclohexylphosphino-2',6'-dimethoxybiphenyl (SPhos) (6 mg, 0.015 mmol), and sodium t-butoxide (NaOt-Bu) (34 mg, 0.35 mmol) were added to xylene (5 mL), and refluxed under heating for 3 days. After completion of the reflux under heating, toluene and water were added thereto, organic phase was extracted, and the obtained organic phase was concentrated to obtain oil.

The resulting oil was purified using high-performance liquid chromatography to obtain 9.0 mg of a yellow solid (yield: 16%).

The molecular weight of Compound 6 is 602.72, and the mass spectrum of the obtained yellow solid indicated m/e=602. By this fact, it was confirmed that the yellow solid is Compound 6.

Compounds within the scope of the invention can be synthesized by using known alternative reactions or raw materials suitable for the object to follow the above reaction.

(Preparation of Toluene Solution)

The obtained Compound 6 was dissolved in toluene to be a concentration of 5 μmol/L, to prepare a toluene solution of Compound 6.

(Measurement of Fluorescence Quantum Yield (PLQY))

The PLQY of the obtained toluene solution of Compound 6 was measured using an absolute PL (photoluminescence) quantum yield measuring device Quantaurus-QY (manufactured by Hamamatsu Photonics K.K.). The PLQY of Compound 6 was 91%.

(Measurement of Fluorescence Peak Wavelength (FL-Peak))

The fluorescence peak wavelength of the obtained toluene solution of Compound 6 was measured using a fluorescent spectrofluorometer F-7000 (manufactured by Hitachi High-Technologies Corporation) of a fluorescence spectrophotometer, and it was observed at 420 nm when the toluene solution was excited at 356 nm.

(Measurement of Half Width)

The obtained toluene solution of Compound 6 was placed in a quartz cell and placed on a spectrofluorometer F-7000. By irradiating excitation light at room temperature (300 K) and measuring the fluorescent intensity while changing the wavelength, a photoluminescence spectrum was obtained in which the vertical axis represents the fluorescence intensity and the horizontal axis represents the wavelength.

From the prepared photoluminescence spectrum, the half width of Compound 6 was obtained from the width of the wavelengths at which the fluorescence intensity became 50% of the peak value. The half width was 26 nm.

Comparative Example 1

Toluene solution was prepared and evaluated in the same manner as in Example 1 using the following Comparative Compound 1. The results are shown in Table 1.

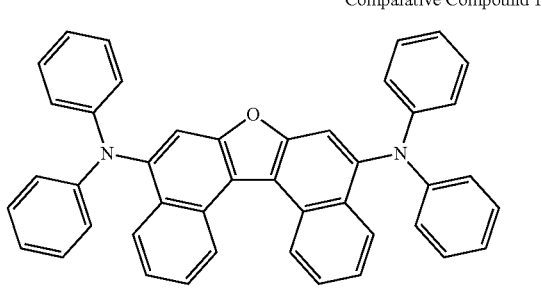

Comparative Compound 1

TABLE 1

| | Compound | PLQY (%) | FL-peak (nm) | Half width (nm) |
|---|---|---|---|---|
| Example 1 | Compound 6 | 85 | 442 | 26 |
| Comparative Example 1 | Comparative Compound 1 | 79 | 456 | 47 |

In Example 1, the value of PLQY was higher and the value of the half width was smaller than those in Comparative Example 1. Further, the fluorescent peak wavelength (FL-peak) in Example 1 was about the same as that in Comparative Example 1.

Examples 2 to 37 and Comparative Examples 2 to 5

(Synthesis of Compound BD-2)

Compound BD-2 was synthesized in the same manner as Compound 6 except that N-phenyl-4-methylaniline was used instead of diphenylamine.

The molecular weight of Compound BD-2 is 630, and the mass spectrum of the obtained yellow solid indicated m/e=631. By this fact, it was confirmed that the yellow solid is Compound BD-2.

(Synthesis of Compound BD-3)

Compound BD-3 was synthesized in the same manner as Compound 6 except that N-phenyl-1,1'-biphenyl-4-amine was used instead of diphenylamine.

The molecular weight of Compound BD-3 is 754, and the mass spectrum of the obtained yellow solid indicated m/e=755. By this fact, it was confirmed that the yellow solid is Compound BD-3.

(Synthesis of Compound BD-4)

Compound BD-4 was synthesized in the same manner as Compound 6 except that N-phenyldibenzofuran-3-amine was used instead of diphenylamine.

The molecular weight of Compound BD-4 is 782, and the mass spectrum of the obtained yellow solid indicated m/e=783. By this fact, it was confirmed that the yellow solid is Compound BD-4.

(Synthesis of Compound BD-5)

Compound BD-5 was synthesized in the same manner as Compound 6 except that N-phenyldibenzofuran-4-amine was used instead of diphenylamine.

The molecular weight of Compound BD-5 is 782, and the mass spectrum of the obtained yellow solid indicated m/e=783. By this fact, it was confirmed that the yellow solid is Compound BD-5.

(Synthesis of Compound BD-6)

Compound BD-6 was synthesized in the same manner as Compound 6 except that N-(4-isopropylphenyl)dibenzofuran-4-amine was used instead of diphenylamine.

The molecular weight of Compound BD-6 is 867, and the mass spectrum of the obtained yellow solid indicated m/e=868. By this fact, it was confirmed that the yellow solid is Compound BD-6.

(Synthesis of Compound BD-7)

Compound BD-7 was synthesized in the same manner as Compound 6 except that N-(2,4-dimethylphenyl)-1,1'-biphenyl-4-amine was used instead of diphenylamine.

The molecular weight of Compound BD-7 is 811, and the mass spectrum of the obtained yellow solid indicated m/e=812. By this fact, it was confirmed that the yellow solid is Compound BD-6.

(Synthesis of Compound BD-8)

Compound BD-8 was synthesized in the same manner as Compound 6 except that N-(4-isopropyl)-3-methyl-1,1'-biphenyl-4-amine was used instead of diphenylamine.

The molecular weight of Compound BD-8 is 867, and the mass spectrum of the obtained yellow solid indicated m/e=868. By this fact, it was confirmed that the yellow solid is Compound BD-8.

(Synthesis of Compound BD-9)

Compound BD-9 was synthesized in the same manner as Compound 6 except that N-(2,4-dimethylphenyl)dibenzofuran-3-amine was used instead of diphenylamine.

The molecular weight of Compound BD-9 is 838, and the mass spectrum of the obtained yellow solid indicated m/e=839. By this fact, it was confirmed that the yellow solid is Compound BD-9.

(Fabrication of Organic EL Device)

A 25 mm×75 mm×1.1 mm-thick glass substrate (manufactured by Geomatic Co., LTD.) with ITO having a thickness of 130 nm as transparent electrode (anode) was subjected to ultrasonic cleaning in isopropyl alcohol for 5 minutes, followed by UV-ozone cleaning for 30 minutes.

The cleaned glass substrate with a transparent electrode was mounted on a substrate holder of a vacuum evaporation device, and Compound HI was deposited on the surface of the glass substrate on which the transparent electrode was formed so as to cover the transparent electrode, thereby forming a Compound HI film having a thickness of 5 nm. The HI film functions as a hole-injecting layer.

Subsequent to the formation of the HI film, Compound HT1 was deposited to form a HT1 film having a thickness of 80 nm on the HI film. The HT1 film functions as a first hole-transporting layer.

Subsequent to the formation of the HT1 film, Compound HT2 was deposited to form a HT2 film having a thickness of 10 nm on the HT1 film. The HT2 film functions as a second hole-transporting layer.

A 25 nm-thick emitting layer was formed on the HT2 film by co-deposition using the combinations of the dopant material (BD) and the host (BH) shown in Table 2 so that the ratio (weight ratio) of the dopant material was 2%.

HBL was deposited on the emitting layer to form an electron-transporting layer having a thickness of 10 nm. ET as an electron-injecting material was deposited on the electron-transporting layer to form an electron-injecting layer having a thickness of 15 nm. LiF was deposited on the electron-injecting layer to form a LiF film having a thickness of 1 nm. Al metal was deposited on the LiF film to form a metal cathode having a thickness of 80 nm.

As described above, an organic EL device was fabricated. The compounds used are shown below.

189 190
BD-2
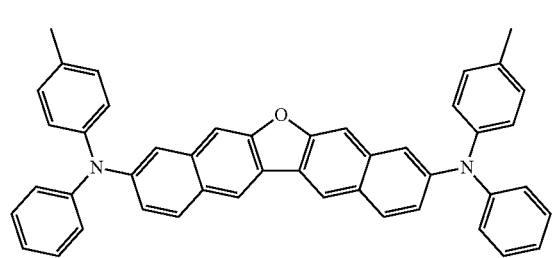
BD-3
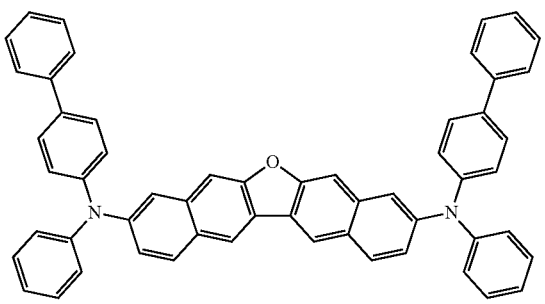
BD-4
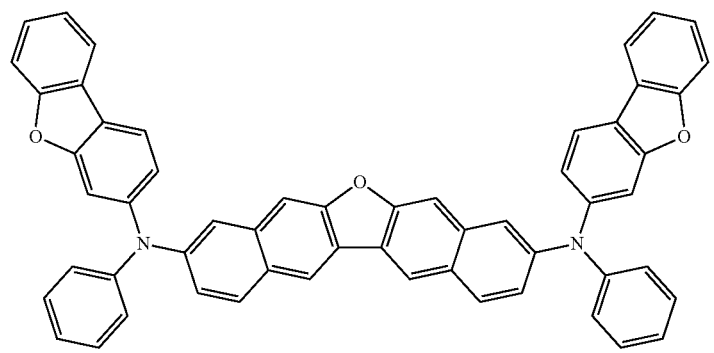
BD-5
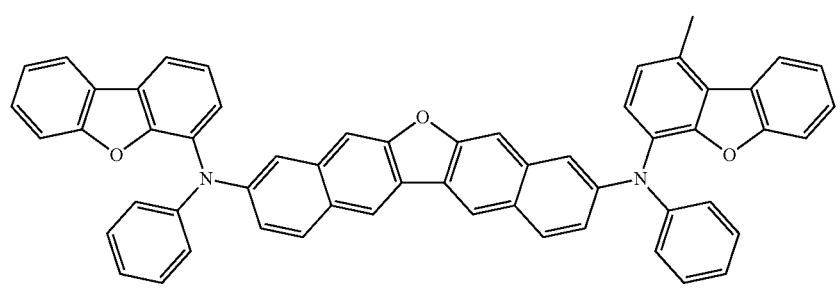
BD-6
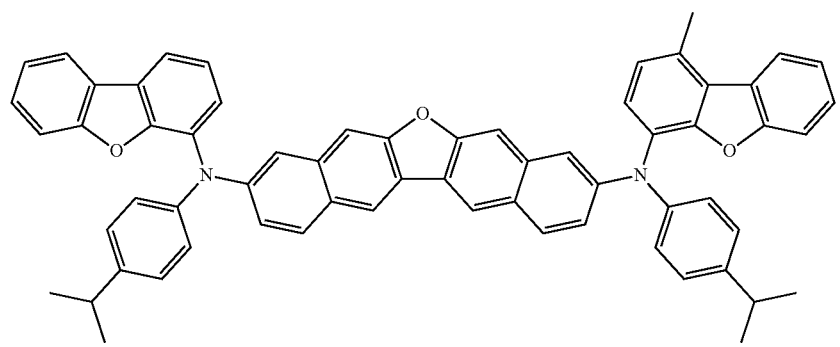
BD-7
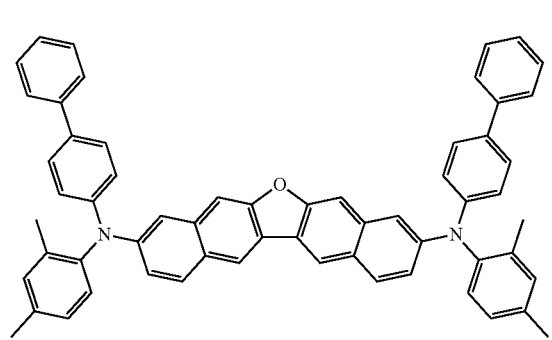
BD-8
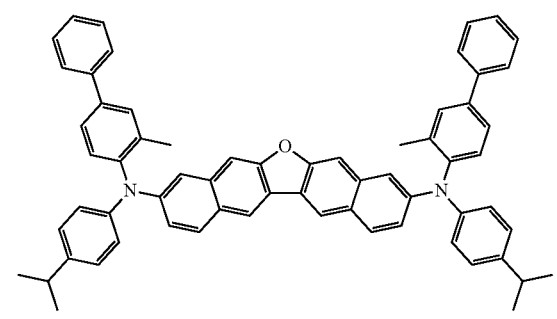

-continued
BD-9
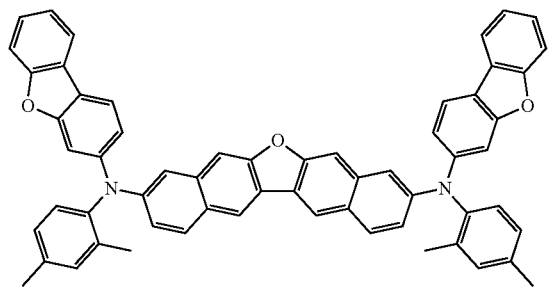
Comparative BD
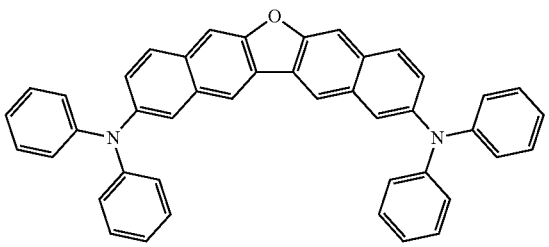
HI
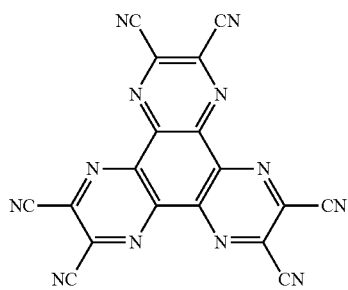
HT1
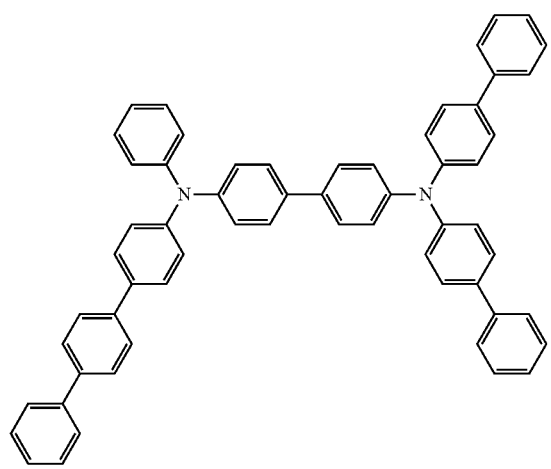
HT2
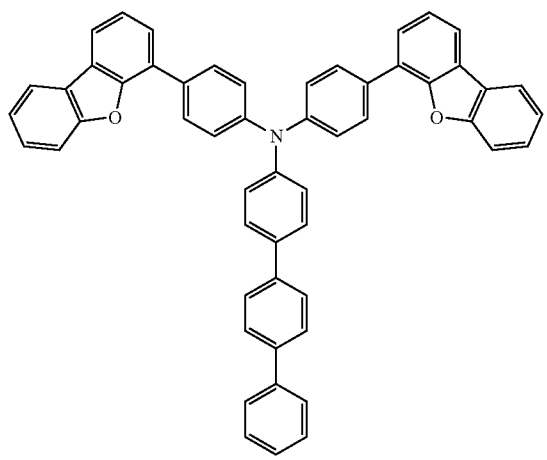
BH-1
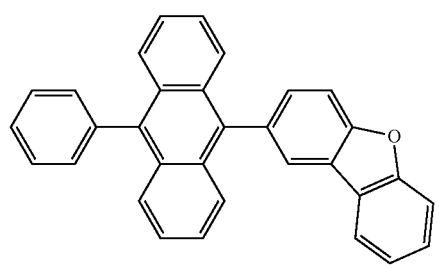
BH-2
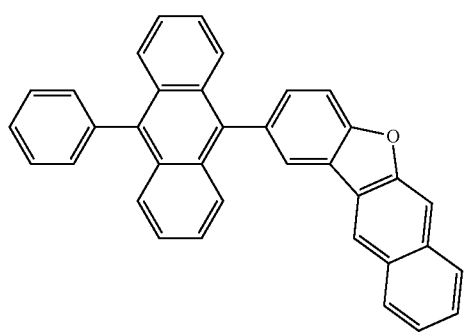
BH-3

-continued
BH-4

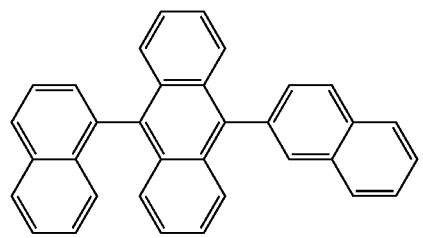

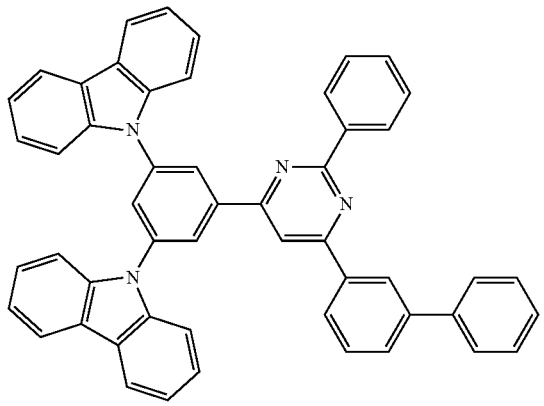

HBL

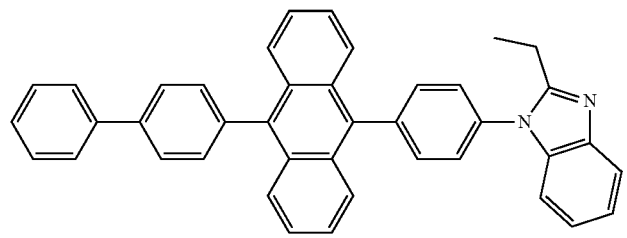

ET (Evaluation of Organic EL Device)

Initial characteristics of the obtained organic EL devices were measured under a condition of DC-constant current 10 mA/cm² driving at room temperature. Voltages were applied to the organic EL devices so that the current densities became 10 mA/cm², and the EL emission spectra were measured by a spectroradiometer CS-1000 (manufactured by Konica Minolta, Inc.). The external quantum efficiency EQE (%) was calculated from the obtained spectral radiance spectrum. The results are shown in Table 2.

The results of the lifetime LT95 (h) obtained by applying voltages to the organic EL devices so that the current densities became 50 mA/cm² and measuring the time until the luminance becomes 95% with respect to the initial luminance are shown in Table 2.

TABLE 2

| | BH | BD | EQE(%) | LT95(h) |
|---|---|---|---|---|
| Example 2 | BH-1 | Compound 6 | 9.3 | 94 |
| Example 3 | | BD-2 | 9.7 | 81 |
| Example 4 | | BD-3 | 9.7 | 115 |
| Example 5 | | BD-4 | 9.4 | 70 |
| Example 6 | | BD-5 | 9.0 | 80 |
| Example 7 | | BD-6 | 8.8 | 87 |
| Example 8 | | BD-7 | 9.7 | 85 |
| Example 9 | | BD-8 | 9.5 | 78 |
| Example 10 | | BD-9 | 8.9 | 95 |
| Comparative Example 2 | | Comparative BD | 7.5 | 58 |
| Example 11 | BH-2 | Compound 6 | 8.0 | 85 |
| Example 12 | | BD-2 | 8.3 | 79 |
| Example 13 | | BD-3 | 8.4 | 98 |
| Example 14 | | BD-4 | 8.1 | 82 |
| Example 15 | | BD-5 | 7.6 | 75 |
| Example 16 | | BD-6 | 7.6 | 77 |
| Example 17 | | BD-7 | 8.1 | 82 |

TABLE 2-continued

| | BH | BD | EQE(%) | LT95(h) |
|---|---|---|---|---|
| Example 18 | | BD-8 | 7.9 | 90 |
| Example 19 | | BD-9 | 7.7 | 88 |
| Comparative Example 3 | | Comparative BD | 6.2 | 55 |
| Example 20 | BH-3 | Compound 6 | 8.2 | 93 |
| Example 21 | | BD-2 | 8.2 | 90 |
| Example 22 | | BD-3 | 8.8 | 102 |
| Example 23 | | BD-4 | 8.4 | 97 |
| Example 24 | | BD-5 | 7.7 | 81 |
| Example 25 | | BD-6 | 7.9 | 72 |
| Example 26 | | BD-7 | 8.5 | 89 |
| Example 27 | | BD-8 | 8.0 | 94 |
| Example 28 | | BD-9 | 8.0 | 85 |
| Comparative Example 4 | | Comparative BD | 6.5 | 62 |
| Example 29 | BH-4 | Compound 6 | 9.2 | 101 |
| Example 30 | | BD-2 | 9.3 | 89 |
| Example 31 | | BD-3 | 9.4 | 135 |
| Example 32 | | BD-4 | 9.1 | 83 |
| Example 33 | | BD-5 | 8.9 | 86 |
| Example 34 | | BD-6 | 8.5 | 97 |
| Example 35 | | BD-7 | 9.6 | 113 |
| Example 36 | | BD-8 | 9.2 | 104 |
| Example 37 | | BD-9 | 8.5 | 95 |
| Comparative Example 5 | | Comparative BD | 7.1 | 76 |

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. A compound represented by the following formula (2):

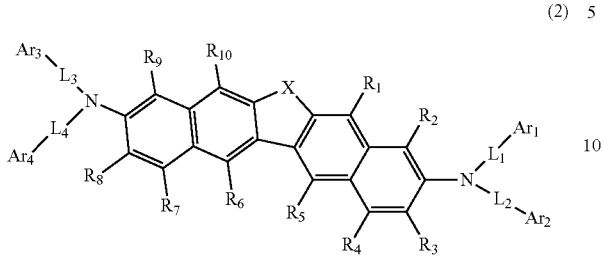

(2)

wherein in the formula (2), $R_1$ to $R_{10}$ are independently a hydrogen atom;

X is an oxygen atom;

$Ar_1$ to $Ar_4$ are independently selected from the group consisting of a substituted or unsubstituted phenyl group, a substituted or unsubstituted biphenylyl group, and a substituted or unsubstituted naphthyl group;

$L_1$ to $L_4$ are independently a single bond or a substituted or unsubstituted arylene group including 6 to 12 ring carbon atoms; and the substituent in the case of "substituted or unsubstituted" is independently an alkyl group having 1 to 5 carbon atoms.

2. The compound according to claim 1, represented by the following formula (3):

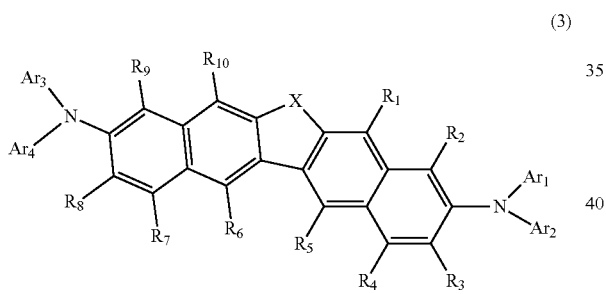

(3)

wherein in the formula (3), $R_1$ to $R_{10}$, X and $Ar_1$ to $Ar_4$ are as defined in the formula (2).

3. The compound according to claim 1, wherein $Ar_1$ to $Ar_4$ are independently a substituted or unsubstituted phenyl group.

4. The compound according to claim 1, which is a material for an organic electroluminescence device.

5. A material for an organic electroluminescence device comprising the compound according to claim 1.

6. An organic electroluminescence device comprising:
a cathode;
an anode; and
an organic layer provided between the cathode and the anode,
wherein the organic layer comprises the compound according to claim 1.

7. An organic electroluminescence device comprising:
a cathode;
an anode; and
an emitting layer provided between the cathode and the anode,
wherein the emitting layer comprises the compound according to claim 1.

8. The organic electroluminescence device according to claim 7, wherein the emitting layer further comprises a compound represented by the following formula (11):

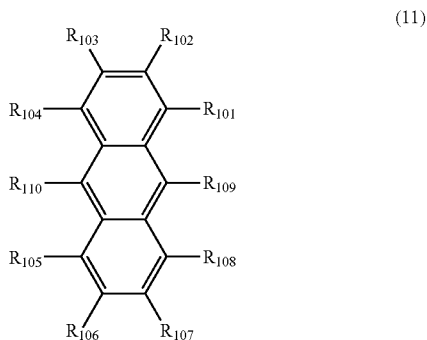

(11)

wherein in the formula (11), except for the case where $R_{101}$ to $R_{110}$ that forms a ring, as described later, $R_{101}$ to $R_{110}$ are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si $(R_{121})(R_{122})(R_{123})$, —C(=O)$R_{124}$, —COO$R_{125}$, —N($R_{126}$)($R_{127}$), a halogen atom, a cyano group, a nitro group, a substituted or unsubstituted aryl group including 6 to 50 ring carbon atoms, a substituted or unsubstituted heterocyclic group including 5 to 50 ring atoms, or a group represented by -$L_{101}$-$Ar_{101}$;

one or more pair of two or more adjacent among $R_{101}$ to $R_{110}$ may form a saturated or unsaturated ring;

$R_{121}$ to $R_{127}$ are independently a hydrogen atom, a substituted or unsubstituted alkyl group including 1 to 50 carbon atoms, a substituted or unsubstituted aryl group including 6 to 50 ring carbon atoms, or a substituted or unsubstituted heterocyclic group including 5 to 50 ring atoms;

provided that at least one of $R_{101}$ to $R_{110}$ is a group represented by -$L_{101}$-$Ar_{101}$; $L_{101}$ is a single bond, a substituted or unsubstituted arylene group including 6 to 30 ring carbon atoms, or a substituted or unsubstituted heteroarylene group including 5 to 30 ring atoms; $Ar_{101}$ is a substituted or unsubstituted aryl group including 6 to 50 ring carbon atoms, or a substituted or unsubstituted heterocyclic group including 5 to 50 ring atoms; when two or more $L_{101}$s are present, two or more $L_{101}$s may be the same as or different from each other; when two or more $Ar_{101}$s are present, two or more $Ar_{101}$s may be the same as or different from each other; and when two or more $R_{121}$s to $R_{127}$s are present, each of two or more $R_{121}$s to $R_{127}$s may be the same as or different from each other.

9. The organic electroluminescence device as according to claim 8, wherein at least one of $R_{109}$ and $R_{110}$ is a group represented by -$L_{101}$-$Ar_{101}$.

10. The organic electroluminescence device according to claim 8, wherein $R_{109}$ and $R_{110}$ are independently a group represented by -$L_{101}$-$Ar_{101}$.

11. The organic electroluminescence device according to claim 8, wherein the compound represented by the formula (11) is represented by the following formula (12),

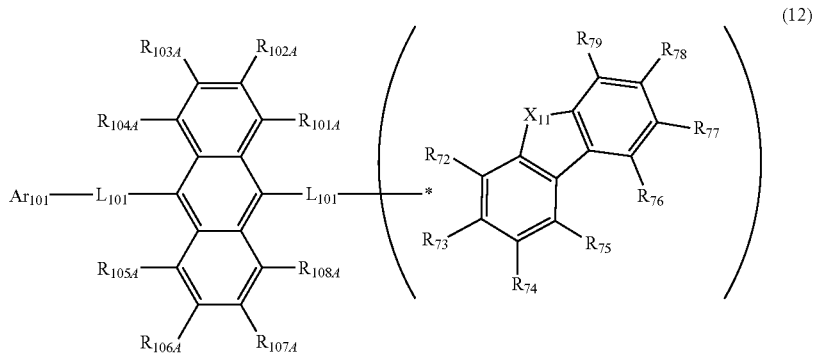

(12)

wherein in the formula (12), an atomic bonding * is bonded to one of $R_{72}$ to $R_{79}$; $L_{101}$ and $Ar_{101}$ are as defined in the formula (11);

$R_{101A}$ to $R_{108A}$ are independently a hydrogen atom, or a substituted or unsubstituted aryl group including 6 to 50 ring carbon atoms;

$X_{11}$ is O, S, or $N(R_{71})$;

$R_{71}$ is a hydrogen atom, a substituted or unsubstituted alkyl group including 1 to 50 carbon atoms, or a substituted or unsubstituted aryl group including 6 to 50 ring carbon atoms;

one of $R_{72}$ to $R_{79}$ is an atomic bonding that is bonded to $L_{101}$;

one or more pair of two or more adjacent among $R_{72}$ to $R_{79}$ that are not bonded to $L_{101}$ may form a substituted or unsubstituted, saturated or unsaturated ring;

$R_{72}$ to $R_{79}$ that are not bonded to $L_{101}$ and do not form the substituted or unsubstituted, saturated or unsaturated ring are independently a hydrogen atom, a substituted or unsubstituted alkyl group including 1 to 50 carbon atoms, or a substituted or unsubstituted aryl group including 6 to 50 ring carbon atoms.

12. The organic electroluminescence device according to claim 11, wherein the compound represented by the formula (11) is represented by the following formula (13):

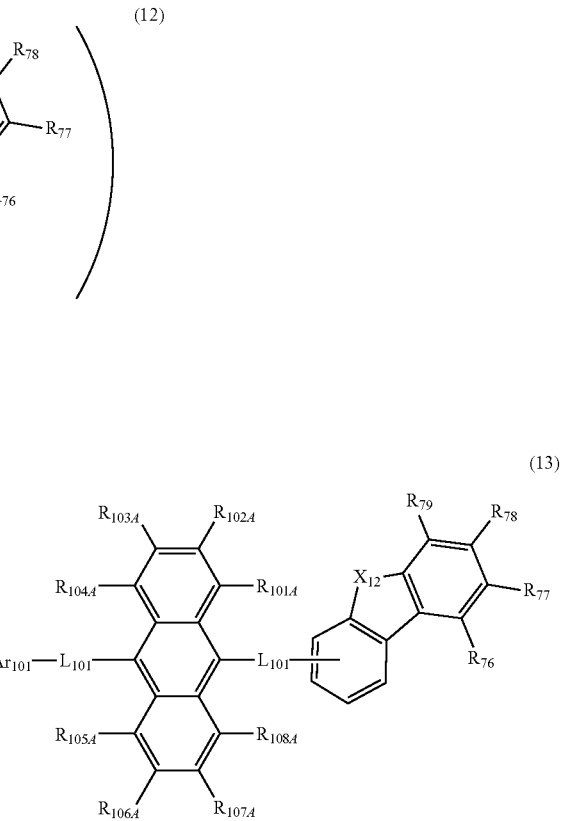

(13)

wherein in the formula (13), $L_{101}$ and $Ar_{101}$ are as defined in the formula (11);

$R_{101A}$ to $R_{108A}$ are as defined in the formula (12);

$R_{76}$ to $R_{79}$ are as defined in the formula (12); and $X_{12}$ is O or S.

13. The organic electroluminescence device as according to claim 11, wherein the compound represented by the formula (11) is represented by the following formula (14):

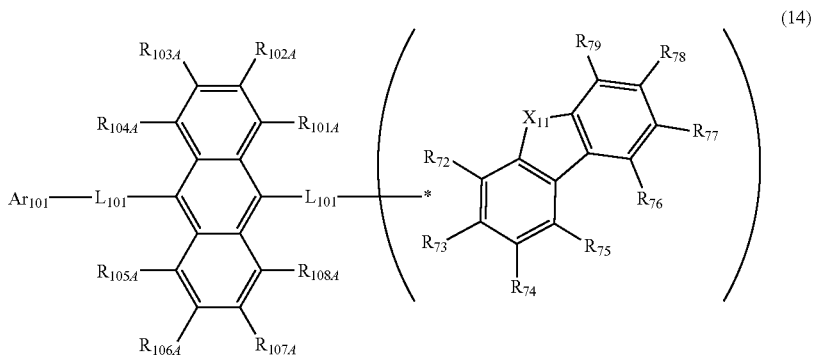

(14)

wherein in the formula (14), the atomic bonding * is bonded to one of $R_{72}$ to $R_{79}$;

$L_{101}$ and $Ar_{101}$ are as defined in the formula (11);

$R_{101A}$ to $R_{108A}$ are as defined in the formula (12);

$X_{11}$ is as defined in the formula (12);

$R_{72}$ to $R_{79}$ are as defined in the formula (12); and provided that any one pair of $R_{76}$ and $R_{77}$, $R_{77}$ and $R_{78}$, and $R_{78}$ and $R_{79}$, is bonded to each other to form a substituted or unsubstituted, saturated or unsaturated ring.

14. The organic electroluminescence device according to claim 11, wherein the compound represented by the formula (11) is represented by the following formula (15):

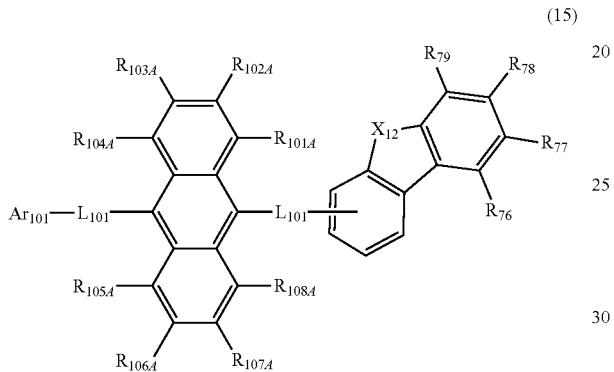

(15)

wherein in the formula (15), $L_{101}$ and $Ar_{101}$ are as defined in the formula (11);

$R_{101A}$ to $R_{108A}$ are as defined in the formula (12);

$X_{12}$ is O or S;

$R_{76}$ to $R_{79}$ are as defined in the formula (12); and provided that any one pair of $R_{76}$ and $R_{77}$, $R_{77}$ and $R_{78}$, and $R_{78}$ and $R_{79}$, is bonded to each other to form a substituted or unsubstituted, saturated or unsaturated ring.

15. The organic electroluminescence device according to claim 13, wherein any one pair of $R_{76}$ and $R_{77}$, $R_{77}$ and $R_{78}$, and $R_{78}$ and $R_{79}$ is bonded to each other to form a ring represented by the following formula (15-1) or (15-2), and $R_{76}$ to $R_{79}$ that do not form a ring represented by the formula (15-1) or (15-2) do not form a substituted or unsubstituted, saturated or unsaturated ring:

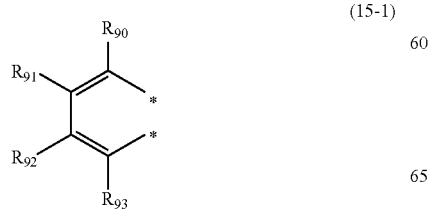

(15-1)

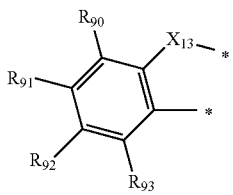

(15-2)

wherein in the formulas (15-1) and (15-2), the two atomic bondings * are independently bonded to one pair of $R_{76}$ and $R_{77}$, $R_{77}$ and $R_{78}$, and $R_{78}$ and $R_{79}$;

$R_{90}$ to $R_{93}$ are independently a hydrogen atom, a substituted or unsubstituted alkyl group including 1 to 50 carbon atoms, or a substituted or unsubstituted aryl group including 6 to 50 ring carbon atoms; and $X_{13}$ is O or S.

16. The organic electroluminescence device according to claim 11, wherein the compound represented by the formula (11) is represented by the following formula (16):

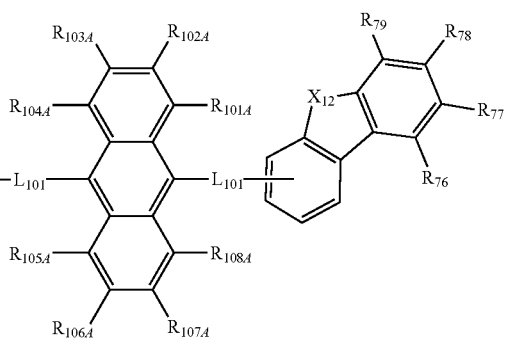

(16)

wherein in the formula (16), $L_{101}$ and $Ar_{101}$ are as defined in the formula (11);

$R_{101A}$ to $R_{108A}$ are as defined in the formula (12);

$R_{76}$ to $R_{79}$ are as defined in the formula (12);

provided that $R_{76}$ and $R_{77}$, $R_{77}$ and $R_{78}$, and $R_{78}$ and $R_{79}$ are not bonded to each other to form a substituted or unsubstituted, saturated or unsaturated ring; and $X_{12}$ is O or S.

17. The organic electroluminescence device according to claim 8, wherein the compound represented by the formula (11) is represented by the following formula (12A):

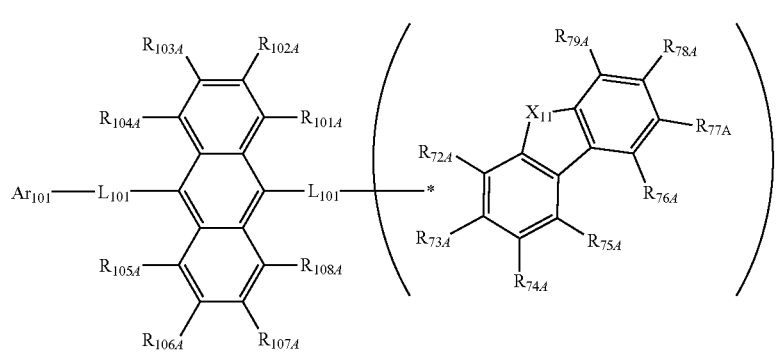

(12A)

wherein in formula (12A), the atomic bonding * is bonded to one of $R_{72A}$ to $R_{79A}$;

$L_{101}$ and $Ar_{101}$ are as defined in the formula (11);

$R_{101A}$ to $R_{108A}$ are independently a hydrogen atom, a substituted or unsubstituted aryl group including 6 to 50 ring carbon atoms;

$X_{11}$ is O, S, or $N(R_{71})$;

$R_{71}$ is a hydrogen atom, a substituted or unsubstituted alkyl group including 1 to 50 carbon atoms, or a substituted or unsubstituted aryl group including 6 to 50 ring carbon atoms;

one or more pair of two or more adjacent among $R_{72A}$ to $R_{79A}$ may form a substituted or unsubstituted, saturated or unsaturated ring, and two adjacent among $R_{72A}$ to $R_{79A}$ form a ring represented by the following formula (12A-1);

$R_{72A}$ to $R_{79A}$ that do not form a substituted or unsubstituted, saturated or unsaturated ring are independently a hydrogen atom, a substituted or unsubstituted alkyl group including 1 to 50 carbon atoms, or a substituted or unsubstituted aryl group including 6 to 50 ring carbon atoms:

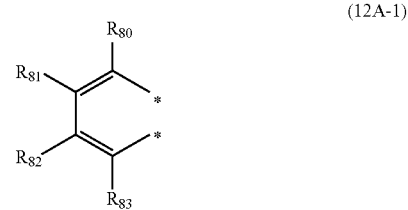

(12A-1)

wherein in the formula (12A-1), each of the two atomic bondings * are bonded to two adjacent among $R_{72A}$ to $R_{79A}$;

one of $R_{80}$ to $R_{83}$ is an atomic bonding that is bonded to $L_{101}$;

$R_{80}$ to $R_{83}$ that are not bonded to $L_{101}$ are independently a hydrogen atom, a substituted or unsubstituted alkyl group including 1 to 50 carbon atoms, or a substituted or unsubstituted aryl group including 6 to 50 ring carbon atoms.

18. The organic electroluminescence device according to claim 7, which further comprises a hole-transporting layer between the anode and the emitting layer.

19. The organic electroluminescence device according to claim 7, which further comprises an electron-transporting layer between the cathode and the emitting layer.

20. An electronic appliance, wherein the organic electroluminescence device according to claim 6 is provided.

* * * * *